US010093740B2

(12) United States Patent
Tamaskovic et al.

(10) Patent No.: US 10,093,740 B2
(45) Date of Patent: Oct. 9, 2018

(54) BISPECIFIC HER2 LIGANDS FOR CANCER THERAPY

(71) Applicant: UNIVERSITAT ZURICH, Zurich (CH)

(72) Inventors: Rastislav Tamaskovic, Rheinfelden (CH); Martin Schwill, Zurich (CH); Andreas Pluckthun, Zurich (CH); Christian Jost, Zurich (CH)

(73) Assignee: Universitat Zurich, Zurich (CH)

( * ) Notice: Subject to any disclaimer, the term of this patent is extended or adjusted under 35 U.S.C. 154(b) by 0 days.

(21) Appl. No.: 14/430,224

(22) PCT Filed: Oct. 14, 2013

(86) PCT No.: PCT/EP2013/071443
§ 371 (c)(1),
(2) Date: Mar. 22, 2015

(87) PCT Pub. No.: WO2014/060365
PCT Pub. Date: Apr. 24, 2014

(65) Prior Publication Data

US 2015/0284463 A1 Oct. 8, 2015

(30) Foreign Application Priority Data

| | | |
|---|---|---|
| Oct. 15, 2012 | (EP) | 12188598 |
| Nov. 7, 2012 | (EP) | 12191673 |
| Nov. 13, 2012 | (EP) | 12192465 |
| Sep. 24, 2013 | (EP) | 13185724 |

(51) Int. Cl.

| | |
|---|---|
| ***C07K 16/46*** | (2006.01) |
| ***A61K 39/395*** | (2006.01) |
| ***C07K 16/28*** | (2006.01) |
| ***C07K 16/32*** | (2006.01) |

(52) U.S. Cl.
CPC .......... *C07K 16/2863* (2013.01); *C07K 16/32* (2013.01); *C07K 2317/22* (2013.01); *C07K 2317/31* (2013.01); *C07K 2317/55* (2013.01); *C07K 2317/56* (2013.01); *C07K 2317/622* (2013.01); *C07K 2317/70* (2013.01); *C07K 2317/73* (2013.01); *C07K 2317/76* (2013.01); *C07K 2317/92* (2013.01); *C07K 2318/00* (2013.01)

(58) Field of Classification Search
CPC ............ C07K 2318/00; C07K 2318/20; C07K 16/2863; C07K 16/466; C07K 2317/31
See application file for complete search history.

(56) References Cited

U.S. PATENT DOCUMENTS

| | | | | |
|---|---|---|---|---|
| 2011/0033460 A1* | 2/2011 | Fendly | C07K 16/32 424/133.1 |
| 2011/0059090 A1* | 3/2011 | Revets et al. | |
| 2012/0309940 A1* | 12/2012 | Fischer | C07K 16/00 530/387.3 |
| 2015/0299265 A1* | 10/2015 | Fiedler | C07K 16/32 514/19.4 |

FOREIGN PATENT DOCUMENTS

WO WO2012/069655 A2 * 5/2012

OTHER PUBLICATIONS

Brand et al., Anticancer Res. 2006; 26:463-70.*
Balmana et al. Ann Oncol 2009; 20(supp 4):iv19-20.*
Steiner D et al:"Efficient Selection of DARPins with Sub-nanomolar Affinities using SRP Phage Display", Journal of Molecular Biology, vol. 382, No. 5, Oct. 24, 2008, pp. 1211-1227.
Zahnd C et al: "Efficient Tumor Targeting with High-Affinity Designed Ankyrin Repeat Proteins: Effects of Affinity and Molecular Size", Cancer Research, vol. 70, No. 4, Feb. 2010, pp. 1595-1605.
Zahnd C. et al: "Supplementary Information for Efficient tumor targeting with high-affinity Designed Ankyrin Repeat Proteins (DARPins): Effects of affinity and molecular size", Cancer Research Feb. 2010(Feb. 2010), Retrieved from the Internet: http://cancerres.aacrjournals.org/content/70/4/1595/suppl/DC1.
Stumpp M T et al:"DARPins: A new generation of protein therapeutics", Drug Discovery Today, vol. 13, No. 15-16, Aug. 1, 2008, pp. 695-701.
Stumpp MT el al: "DARPins:a true alternative to antibodies", Current Opinion in Drug Discovery and Development, vol. 10, No. 2, Mar. 1, 2007, pp. 153-159.
Spiridon C I et al:"Targeting multiple Her-2 epitopes with monoclonal antibodies results inimproved antigrowth activity of a human breast cancer cell line in vitro and in vivo", Clinical Cancer Research, vol. 8, No. 6, Jun. 1, 2002, pp. 1720-1730.

* cited by examiner

*Primary Examiner* — Jessica Hope Roark
(74) *Attorney, Agent, or Firm* — JMB Davis Ben-David

(57) ABSTRACT

The invention relates to a bispecific HER2-targeting agent comprising a.) a first polypeptide ligand that binds to HER2 extracellular domain 1, b.) a second polypeptide ligand that binds to HER2 extracellular domain 4 and c.) a linker covalently attaching said first polypeptide ligand to said second polypeptide ligand.

22 Claims, 34 Drawing Sheets

Specification includes a Sequence Listing.

SEQUENCE LISTING

```
<160> NUMBER OF SEQ ID NOS: 115

<210> SEQ ID NO 1
<211> LENGTH: 197
<212> TYPE: PRT
<213> ORGANISM: Homo sapiens

<400> SEQUENCE: 1

Gln Val Cys Thr Gly Thr Asp Met Lys Leu Arg Leu Pro Ala Ser Pro
1               5                   10                  15

Glu Thr His Leu Asp Met Leu Arg His Leu Tyr Gln Gly Cys Gln Val
            20                  25                  30

Val Gln Gly Asn Leu Glu Leu Thr Tyr Leu Pro Thr Asn Ala Ser Leu
        35                  40                  45

Ser Phe Leu Gln Asp Ile Gln Glu Val Gln Gly Tyr Val Leu Ile Ala
    50                  55                  60

His Asn Gln Val Arg Gln Val Pro Leu Gln Arg Leu Arg Ile Val Arg
65                  70                  75                  80

Gly Thr Gln Leu Phe Glu Asp Asn Tyr Ala Leu Ala Val Leu Asp Asn
                85                  90                  95

Gly Asp Pro Leu Asn Asn Thr Thr Pro Val Thr Gly Ala Ser Pro Gly
            100                 105                 110

Gly Leu Arg Glu Leu Gln Leu Arg Ser Leu Thr Glu Ile Leu Lys Gly
        115                 120                 125

Gly Val Leu Ile Gln Arg Asn Pro Gln Leu Cys Tyr Gln Asp Thr Ile
    130                 135                 140

Leu Trp Lys Asp Ile Phe His Lys Asn Asn Gln Leu Ala Leu Thr Leu
145                 150                 155                 160

Ile Asp Thr Asn Arg Ser Arg Ala Cys His Pro Cys Ser Pro Met Cys
                165                 170                 175

Lys Gly Ser Arg Cys Trp Gly Glu Ser Ser Glu Asp Cys Gln Ser Leu
            180                 185                 190

Thr Arg Thr Val Ala
        195
```

-continued

```
<210> SEQ ID NO 2
<211> LENGTH: 97
<212> TYPE: PRT
<213> ORGANISM: Homo sapiens

<400> SEQUENCE: 2

Val Asn Cys Ser Gln Phe Leu Arg Gly Gln Glu Cys Val Glu Glu Cys
1               5                   10                  15

Arg Val Leu Gln Gly Leu Pro Arg Glu Tyr Val Asn Ala Arg His Cys
            20                  25                  30

Leu Pro Cys His Pro Glu Cys Gln Pro Gln Asn Gly Ser Val Thr Cys
        35                  40                  45

Phe Gly Pro Glu Ala Asp Gln Cys Val Ala Cys Ala His Tyr Lys Asp
    50                  55                  60

Pro Pro Phe Cys Val Ala Arg Cys Pro Ser Gly Val Lys Pro Asp Leu
65                  70                  75                  80

Ser Tyr Met Pro Ile Trp Lys Phe Pro Asp Glu Glu Gly Ala Cys Gln
                85                  90                  95

Pro


<210> SEQ ID NO 3
<211> LENGTH: 302
<212> TYPE: PRT
<213> ORGANISM: Artificial Sequence
<220> FEATURE:
<223> OTHER INFORMATION: a designed akyrin repeat protein domain binding
      the extracellular domain 1 of HER2 and a designed akyrin repeat
      protein domain binding the extracellular domain 4 of HER2
      connected by a glycine/serine peptide linker and with a N-terminal
      His-tag

<400> SEQUENCE: 3

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Phe Tyr Gly Ile
        35                  40                  45

Thr Pro Leu His Leu Ala Ala Ala Tyr Gly His Leu Glu Ile Val Glu
    50                  55                  60

Val Leu Leu Lys His Gly Ala Asp Val Asn Ala His Asp Trp Asn Gly
65                  70                  75                  80

Trp Thr Pro Leu His Leu Ala Ala Lys Tyr Gly His Leu Glu Ile Val
                85                  90                  95

Glu Val Leu Leu Lys His Gly Ala Asp Val Asn Ala Ile Asp Asn Ala
            100                 105                 110

Gly Lys Thr Pro Leu His Leu Ala Ala Ala His Gly His Leu Glu Ile
        115                 120                 125

Val Glu Val Leu Leu Lys Tyr Gly Ala Asp Val Asn Ala Gln Asp Lys
    130                 135                 140

Phe Gly Glu Thr Ala Glu Asp Leu Ala Lys Asp Asn Gly Asn Gln Asp
145                 150                 155                 160

Ile Ala Asp Leu Leu Glu Lys Ala Leu Lys Leu Gly Gly Gly Gly Ser
                165                 170                 175

Arg Ser Asp Leu Gly Lys Lys Leu Leu Glu Ala Ala Arg Ala Gly Gln
            180                 185                 190

Asp Asp Glu Val Arg Ile Leu Met Ala Asn Gly Ala Asp Val Asn Ala
        195                 200                 205
```

```
Lys Asp Glu Tyr Gly Leu Thr Pro Leu Tyr Leu Ala Thr Ala His Gly
    210                 215                 220

His Leu Glu Ile Val Glu Val Leu Leu Lys Asn Gly Ala Asp Val Asn
225                 230                 235                 240

Ala Val Asp Ala Ile Gly Phe Thr Pro Leu His Leu Ala Ala Phe Ile
                245                 250                 255

Gly His Leu Glu Ile Ala Glu Val Leu Leu Lys His Gly Ala Asp Val
            260                 265                 270

Asn Ala Gln Asp Lys Phe Gly Lys Thr Ala Phe Asp Ile Ser Ile Gly
        275                 280                 285

Asn Gly Asn Glu Asp Leu Ala Glu Ile Leu Gln Lys Leu Asn
    290                 295                 300


<210> SEQ ID NO 4
<211> LENGTH: 335
<212> TYPE: PRT
<213> ORGANISM: Artificial Sequence
<220> FEATURE:
<223> OTHER INFORMATION: a designed akyrin repeat protein domain binding
      the extracellular domain 1 of HER2 and a designed akyrin repeat
      protein domain binding the extracellular domain 4 of HER2
      connected by a glycine/serine peptide linker and with a N-terminal
      His-tag

<400> SEQUENCE: 4

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Phe Tyr Gly Ile
        35                  40                  45

Thr Pro Leu His Leu Ala Ala Ala Tyr Gly His Leu Glu Ile Val Glu
    50                  55                  60

Val Leu Leu Lys His Gly Ala Asp Val Asn Ala His Asp Trp Asn Gly
65                  70                  75                  80

Trp Thr Pro Leu His Leu Ala Ala Lys Tyr Gly His Leu Glu Ile Val
                85                  90                  95

Glu Val Leu Leu Lys His Gly Ala Asp Val Asn Ala Ile Asp Asn Ala
            100                 105                 110

Gly Lys Thr Pro Leu His Leu Ala Ala Ala His Gly His Leu Glu Ile
        115                 120                 125

Val Glu Val Leu Leu Lys Tyr Gly Ala Asp Val Asn Ala Gln Asp Lys
    130                 135                 140

Phe Gly Glu Thr Ala Glu Asp Leu Ala Lys Asp Asn Gly Asn Gln Asp
145                 150                 155                 160

Ile Ala Asp Leu Leu Glu Lys Ala Leu Lys Leu Gly Gly Gly Gly Ser
                165                 170                 175

Arg Ser Asp Leu Gly Lys Lys Leu Leu Glu Ala Ala Arg Ala Gly Gln
            180                 185                 190

Asp Asp Glu Val Arg Ile Leu Met Ala Asn Gly Ala Asp Val Asn Ala
        195                 200                 205

Thr Asp Ile His Gly His Thr Pro Leu His Leu Ala Ala Ala Met Gly
    210                 215                 220

His Leu Glu Ile Val Glu Val Leu Leu Lys Asn Gly Ala Asp Val Asn
225                 230                 235                 240

Ala Asn Asp Trp Arg Gly Phe Thr Pro Leu His Leu Ala Ala Leu Asn
```

-continued

```
                245                 250                 255

Gly His Leu Glu Ile Val Glu Val Leu Leu Lys Asn Gly Ala Asp Val
            260                 265                 270

Asn Ala Thr Asp Thr Ala Gly Asn Thr Pro Leu His Leu Ala Ala Trp
        275                 280                 285

Phe Gly His Leu Glu Ile Val Glu Val Leu Leu Lys Asn Gly Ala Asp
    290                 295                 300

Val Asn Ala Gln Asp Lys Phe Gly Lys Thr Ala Phe Asp Ile Ser Ile
305                 310                 315                 320

Asp Asn Gly Asn Glu Asp Leu Ala Glu Ile Leu Gln Lys Leu Asn
                325                 330                 335


<210> SEQ ID NO 5
<211> LENGTH: 298
<212> TYPE: PRT
<213> ORGANISM: Artificial Sequence
<220> FEATURE:
<223> OTHER INFORMATION: a designed akyrin repeat protein domain binding
      the extracellular domain 1 of HER2 and a designed akyrin repeat
      protein domain binding the extracellular domain 4 of HER2
      connected by a glycine/serine peptide linker and with a N-terminal
      His-tag

<400> SEQUENCE: 5

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Asn Ala Ser Asp Arg Asp Gly
            100                 105                 110

His Thr Pro Leu His Leu Ala Ala Arg Glu Gly His Leu Glu Ile Val
        115                 120                 125

Glu Val Leu Leu Lys Asn Gly Ala Asp Val Asn Ala Gln Asp Lys Phe
    130                 135                 140

Gly Lys Thr Ala Phe Asp Ile Ser Ile Asp Asn Gly Asn Glu Asp Leu
145                 150                 155                 160

Ala Glu Ile Leu Gln Lys Leu Gly Gly Gly Gly Ser Arg Ser Asp Leu
                165                 170                 175

Gly Lys Lys Leu Leu Glu Ala Ala Arg Ala Gly Gln Asp Asp Glu Val
            180                 185                 190

Arg Ile Leu Met Ala Asn Gly Ala Asp Val Asn Ala Lys Asp Glu Tyr
        195                 200                 205

Gly Leu Thr Pro Leu Tyr Leu Ala Thr Ala His Gly His Leu Glu Ile
    210                 215                 220

Val Glu Val Leu Leu Lys Asn Gly Ala Asp Val Asn Ala Val Asp Ala
225                 230                 235                 240

Ile Gly Phe Thr Pro Leu His Leu Ala Ala Phe Ile Gly His Leu Glu
                245                 250                 255
```

Ile Ala Glu Val Leu Leu Lys His Gly Ala Asp Val Asn Ala Gln Asp
260 265 270

Lys Phe Gly Lys Thr Ala Phe Asp Ile Ser Ile Gly Asn Gly Asn Glu
275 280 285

Asp Leu Ala Glu Ile Leu Gln Lys Leu Asn
290 295

<210> SEQ ID NO 6
<211> LENGTH: 331
<212> TYPE: PRT
<213> ORGANISM: Artificial Sequence
<220> FEATURE:
<223> OTHER INFORMATION: a designed akyrin repeat protein domain binding the extracellular domain 1 of HER2 and a designed akyrin repeat protein domain binding the extracellular domain 4 of HER2 connected by a glycine/serine peptide linker and with a N-terminal His-tag

<400> SEQUENCE: 6

Met Arg Gly Ser His His His His His His Gly Ser Asp Leu Gly Lys
1 5 10 15

Lys Leu Leu Glu Ala Ala Arg Ala Gly Gln Asp Asp Glu Val Arg Ile
20 25 30

Leu Met Ala Asn Gly Ala Asp Val Asn Ala His Asp Phe Tyr Gly Ile
35 40 45

Thr Pro Leu His Leu Ala Ala Asn Phe Gly His Leu Glu Ile Val Glu
50 55 60

Val Leu Leu Lys His Gly Ala Asp Val Asn Ala Phe Asp Tyr Asp Asn
65 70 75 80

Thr Pro Leu His Leu Ala Ala Asp Ala Gly His Leu Glu Ile Val Glu
85 90 95

Val Leu Leu Lys Tyr Gly Ala Asp Val Asn Ala Ser Asp Arg Asp Gly
100 105 110

His Thr Pro Leu His Leu Ala Ala Arg Glu Gly His Leu Glu Ile Val
115 120 125

Glu Val Leu Leu Lys Asn Gly Ala Asp Val Asn Ala Gln Asp Lys Phe
130 135 140

Gly Lys Thr Ala Phe Asp Ile Ser Ile Asp Asn Gly Asn Glu Asp Leu
145 150 155 160

Ala Glu Ile Leu Gln Lys Leu Gly Gly Gly Gly Ser Arg Ser Asp Leu
165 170 175

Gly Lys Lys Leu Leu Glu Ala Ala Arg Ala Gly Gln Asp Asp Glu Val
180 185 190

Arg Ile Leu Met Ala Asn Gly Ala Asp Val Asn Ala Thr Asp Ile His
195 200 205

Gly His Thr Pro Leu His Leu Ala Ala Ala Met Gly His Leu Glu Ile
210 215 220

Val Glu Val Leu Leu Lys Asn Gly Ala Asp Val Asn Ala Asn Asp Trp
225 230 235 240

Arg Gly Phe Thr Pro Leu His Leu Ala Ala Leu Asn Gly His Leu Glu
245 250 255

Ile Val Glu Val Leu Leu Lys Asn Gly Ala Asp Val Asn Ala Thr Asp
260 265 270

Thr Ala Gly Asn Thr Pro Leu His Leu Ala Ala Trp Phe Gly His Leu
275 280 285

Glu Ile Val Glu Val Leu Leu Lys Asn Gly Ala Asp Val Asn Ala Gln
290 295 300

```
Asp Lys Phe Gly Lys Thr Ala Phe Asp Ile Ser Ile Asp Asn Gly Asn
305                 310                 315                 320

Glu Asp Leu Ala Glu Ile Leu Gln Lys Leu Asn
                325                 330


<210> SEQ ID NO 7
<211> LENGTH: 336
<212> TYPE: PRT
<213> ORGANISM: Artificial Sequence
<220> FEATURE:
<223> OTHER INFORMATION: a designed akyrin repeat protein domain binding
      the extracellular domain 1 of HER2 and a designed akyrin repeat
      protein domain binding the extracellular domain 4 of HER2
      connected by a glycine/serine peptide linker and with a N-terminal
      His-tag

<400> SEQUENCE: 7

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Asn Ala Ser Asp Arg Asp Gly
            100                 105                 110

His Thr Pro Leu His Leu Ala Ala Arg Glu Gly His Leu Glu Ile Val
        115                 120                 125

Glu Val Leu Leu Lys Asn Gly Ala Asp Val Asn Ala Gln Asp Lys Phe
    130                 135                 140

Gly Lys Thr Ala Phe Asp Ile Ser Ile Asp Asn Gly Asn Glu Asp Leu
145                 150                 155                 160

Ala Glu Ile Leu Gln Lys Leu Gly Gly Gly Gly Ser Gly Gly Gly Gly
                165                 170                 175

Ser Arg Ser Asp Leu Gly Lys Lys Leu Leu Glu Ala Ala Arg Ala Gly
            180                 185                 190

Gln Asp Asp Glu Val Arg Ile Leu Met Ala Asn Gly Ala Asp Val Asn
        195                 200                 205

Ala Thr Asp Ile His Gly His Thr Pro Leu His Leu Ala Ala Ala Met
    210                 215                 220

Gly His Leu Glu Ile Val Glu Val Leu Leu Lys Asn Gly Ala Asp Val
225                 230                 235                 240

Asn Ala Asn Asp Trp Arg Gly Phe Thr Pro Leu His Leu Ala Ala Leu
                245                 250                 255

Asn Gly His Leu Glu Ile Val Glu Val Leu Leu Lys Asn Gly Ala Asp
            260                 265                 270

Val Asn Ala Thr Asp Thr Ala Gly Asn Thr Pro Leu His Leu Ala Ala
        275                 280                 285

Trp Phe Gly His Leu Glu Ile Val Glu Val Leu Leu Lys Asn Gly Ala
    290                 295                 300

Asp Val Asn Ala Gln Asp Lys Phe Gly Lys Thr Ala Phe Asp Ile Ser
```

-continued 305 310 315 320

Ile Asp Asn Gly Asn Glu Asp Leu Ala Glu Ile Leu Gln Lys Leu Asn
325 330 335

<210> SEQ ID NO 8
<211> LENGTH: 341
<212> TYPE: PRT
<213> ORGANISM: Artificial Sequence
<220> FEATURE:
<223> OTHER INFORMATION: a designed akyrin repeat protein domain binding the extracellular domain 1 of HER2 and a designed akyrin repeat protein domain binding the extracellular domain 4 of HER2 connected by a glycine/serine peptide linker and with a N-terminal His-tag

<400> SEQUENCE: 8

Met Arg Gly Ser His His His His His His Gly Ser Asp Leu Gly Lys
1 5 10 15

Lys Leu Leu Glu Ala Ala Arg Ala Gly Gln Asp Asp Glu Val Arg Ile
20 25 30

Leu Met Ala Asn Gly Ala Asp Val Asn Ala His Asp Phe Tyr Gly Ile
35 40 45

Thr Pro Leu His Leu Ala Ala Asn Phe Gly His Leu Glu Ile Val Glu
50 55 60

Val Leu Leu Lys His Gly Ala Asp Val Asn Ala Phe Asp Tyr Asp Asn
65 70 75 80

Thr Pro Leu His Leu Ala Ala Asp Ala Gly His Leu Glu Ile Val Glu
85 90 95

Val Leu Leu Lys Tyr Gly Ala Asp Val Asn Ala Ser Asp Arg Asp Gly
100 105 110

His Thr Pro Leu His Leu Ala Ala Arg Glu Gly His Leu Glu Ile Val
115 120 125

Glu Val Leu Leu Lys Asn Gly Ala Asp Val Asn Ala Gln Asp Lys Phe
130 135 140

Gly Lys Thr Ala Phe Asp Ile Ser Ile Asp Asn Gly Asn Glu Asp Leu
145 150 155 160

Ala Glu Ile Leu Gln Lys Leu Gly Gly Gly Gly Ser Gly Gly Gly Gly
165 170 175

Ser Gly Gly Gly Gly Ser Arg Ser Asp Leu Gly Lys Lys Leu Leu Glu
180 185 190

Ala Ala Arg Ala Gly Gln Asp Asp Glu Val Arg Ile Leu Met Ala Asn
195 200 205

Gly Ala Asp Val Asn Ala Thr Asp Ile His Gly His Thr Pro Leu His
210 215 220

Leu Ala Ala Ala Met Gly His Leu Glu Ile Val Glu Val Leu Leu Lys
225 230 235 240

Asn Gly Ala Asp Val Asn Ala Asn Asp Trp Arg Gly Phe Thr Pro Leu
245 250 255

His Leu Ala Ala Leu Asn Gly His Leu Glu Ile Val Glu Val Leu Leu
260 265 270

Lys Asn Gly Ala Asp Val Asn Ala Thr Asp Thr Ala Gly Asn Thr Pro
275 280 285

Leu His Leu Ala Ala Trp Phe Gly His Leu Glu Ile Val Glu Val Leu
290 295 300

Leu Lys Asn Gly Ala Asp Val Asn Ala Gln Asp Lys Phe Gly Lys Thr
305 310 315 320

```
Ala Phe Asp Ile Ser Ile Asp Asn Gly Asn Glu Asp Leu Ala Glu Ile
                325                 330                 335

Leu Gln Lys Leu Asn
            340


<210> SEQ ID NO 9
<211> LENGTH: 346
<212> TYPE: PRT
<213> ORGANISM: Artificial Sequence
<220> FEATURE:
<223> OTHER INFORMATION: a designed akyrin repeat protein domain binding
      the extracellular domain 1 of HER2 and a designed akyrin repeat
      protein domain binding the extracellular domain 4 of HER2
      connected by a glycine/serine peptide linker and with a N-terminal
      His-tag

<400> SEQUENCE: 9

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Asn Ala Ser Asp Arg Asp Gly
            100                 105                 110

His Thr Pro Leu His Leu Ala Ala Arg Glu Gly His Leu Glu Ile Val
        115                 120                 125

Glu Val Leu Leu Lys Asn Gly Ala Asp Val Asn Ala Gln Asp Lys Phe
    130                 135                 140

Gly Lys Thr Ala Phe Asp Ile Ser Ile Asp Asn Gly Asn Glu Asp Leu
145                 150                 155                 160

Ala Glu Ile Leu Gln Lys Leu Gly Gly Gly Gly Ser Gly Gly Gly Gly
                165                 170                 175

Ser Gly Gly Gly Gly Ser Gly Gly Gly Gly Ser Arg Ser Asp Leu Gly
            180                 185                 190

Lys Lys Leu Leu Glu Ala Ala Arg Ala Gly Gln Asp Asp Glu Val Arg
        195                 200                 205

Ile Leu Met Ala Asn Gly Ala Asp Val Asn Ala Thr Asp Ile His Gly
    210                 215                 220

His Thr Pro Leu His Leu Ala Ala Ala Met Gly His Leu Glu Ile Val
225                 230                 235                 240

Glu Val Leu Leu Lys Asn Gly Ala Asp Val Asn Ala Asn Asp Trp Arg
                245                 250                 255

Gly Phe Thr Pro Leu His Leu Ala Ala Leu Asn Gly His Leu Glu Ile
            260                 265                 270

Val Glu Val Leu Leu Lys Asn Gly Ala Asp Val Asn Ala Thr Asp Thr
        275                 280                 285

Ala Gly Asn Thr Pro Leu His Leu Ala Ala Trp Phe Gly His Leu Glu
    290                 295                 300

Ile Val Glu Val Leu Leu Lys Asn Gly Ala Asp Val Asn Ala Gln Asp
305                 310                 315                 320
```

```
Lys Phe Gly Lys Thr Ala Phe Asp Ile Ser Ile Asp Asn Gly Asn Glu
                325                 330                 335

Asp Leu Ala Glu Ile Leu Gln Lys Leu Asn
            340                 345


<210> SEQ ID NO 10
<211> LENGTH: 158
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 10

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ser Asp Tyr Tyr Gly Ile Thr Pro Leu His Leu Ala Ala His Thr Gly
        35                  40                  45

His Leu Glu Ile Val Glu Val Leu Leu Lys His Gly Ala Asp Val Asn
    50                  55                  60

Ala Arg Asn Trp Gly Trp Thr Pro Leu His Leu Ala Ala Met Thr Gly
65                  70                  75                  80

His Leu Glu Ile Val Glu Val Leu Leu Lys Tyr Gly Ala Asp Val Asn
                85                  90                  95

Ala Val Asp Glu Asp Gly Asp Thr Pro Leu His Leu Ala Ala Thr His
            100                 105                 110

Gly His Leu Glu Ile Val Glu Val Leu Leu Lys Tyr Gly Ala Asp Val
        115                 120                 125

Asn Ala Gln Asp Lys Phe Gly Lys Thr Ala Phe Asp Ile Ser Ile Asp
    130                 135                 140

Asn Gly Asn Glu Asp Leu Ala Glu Ile Leu Gln Lys Leu Asn
145                 150                 155


<210> SEQ ID NO 11
<211> LENGTH: 160
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 11

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Trp Tyr Gly Ile Thr Pro Leu His Leu Ala Ala Asp Thr Gly
        35                  40                  45

His Leu Glu Ile Val Glu Val Leu Leu Lys His Gly Ala Asp Val Asn
    50                  55                  60

Ala Phe Asp Ser Tyr Thr Gly His Thr Pro Leu His Leu Ala Ala Gln
65                  70                  75                  80

Lys Gly Gln Leu Glu Ile Val Glu Val Leu Leu Lys Tyr Gly Ala Asp
                85                  90                  95

Val Asn Ala Ile Asp Arg His Gly Lys Thr Pro Leu His Leu Ala Ala
            100                 105                 110
```

```
Leu Met Gly His Leu Glu Ile Val Glu Val Leu Leu Lys Tyr Gly Ala
        115                 120                 125

Asp Val Asn Ala Gln Asp Lys Phe Gly Lys Thr Ala Phe Asp Ile Ser
    130                 135                 140

Ile Asp Asn Gly Asn Glu Asp Leu Ala Glu Ile Leu Gln Lys Leu Asn
145                 150                 155                 160


<210> SEQ ID NO 12
<211> LENGTH: 125
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 12

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ser Asp Phe Tyr Gly Lys Thr Pro Leu His Leu Ala Ala Thr Ile Gly
        35                  40                  45

His Leu Lys Ile Val Glu Val Leu Leu Lys Tyr Gly Ala Asp Val Asn
    50                  55                  60

Ala Thr Asp Trp Gly Asn Thr Pro Leu His Leu Ala Ala Ile Asn Gly
65                  70                  75                  80

His Leu Glu Ile Val Glu Val Leu Leu Lys His Gly Ala Asp Val Asn
                85                  90                  95

Ala Gln Asp Lys Phe Gly Lys Thr Ala Phe Asp Ile Ser Ile Asp Asn
            100                 105                 110

Gly Asn Glu Asp Leu Ala Glu Ile Leu Gln Lys Leu Asn
        115                 120                 125


<210> SEQ ID NO 13
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 13

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Phe His Gly Leu Thr Pro Leu His Leu Ala Ala Gly Met Gly
        35                  40                  45

His Leu Glu Ile Val Glu Val Leu Leu Lys Asn Gly Ala Asp Val Asn
    50                  55                  60

Ala Val Asp Thr Asp Gly Ile Thr Leu Leu His Leu Ala Ala Tyr Tyr
65                  70                  75                  80

Gly His Leu Glu Ile Val Glu Val Leu Leu Lys His Gly Ala Asp Val
                85                  90                  95

Asn Ala His Asp Tyr Ala Gly Ser Thr Pro Leu His Leu Ala Ala Asn
            100                 105                 110

Thr Gly His Leu Glu Ile Val Glu Val Leu Leu Lys Asn Gly Ala Asp
        115                 120                 125
```

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 14
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 14

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Phe Tyr Gly Ile Thr Pro Leu His Leu Ala Ala Ala Tyr Gly
        35                  40                  45

His Leu Glu Ile Val Glu Val Leu Leu Lys His Gly Ala Asp Val Asn
    50                  55                  60

Ala His Asp Trp Asn Gly Trp Thr Pro Leu His Leu Ala Ala Lys Tyr
65                  70                  75                  80

Gly His Leu Glu Ile Val Glu Val Leu Leu Lys His Gly Ala Asp Val
                85                  90                  95

Asn Ala Ile Asp Asn Ala Gly Lys Thr Pro Leu His Leu Ala Ala Ala
            100                 105                 110

His Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 15
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 15

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Phe Tyr Gly Ile Thr Pro Leu His Leu Ala Ala Ala Tyr Gly
        35                  40                  45

His Leu Glu Ile Val Glu Val Leu Leu Lys His Gly Ala Asp Val Asn
    50                  55                  60

Ala His Asp Trp Asn Gly Trp Thr Pro Leu His Leu Ala Ala Lys Tyr
65                  70                  75                  80

Gly His Leu Glu Ile Val Glu Val Leu Leu Lys His Gly Ala Asp Val
                85                  90                  95

Asn Ala Ile Asp Asn Ala Gly Lys Thr Pro Leu His Leu Ala Ala Ala
            100                 105                 110

```
His Gly His Leu Glu Ile Val Glu Val Leu Leu Lys Tyr Gly Ala Asp
        115                 120                 125

Val Asn Ala Gln Asp Lys Phe Gly Lys Thr Pro Phe Asp Leu Ala Ile
    130                 135                 140

Asp Asn Gly Asn Glu Asp Ile Ala Glu Val Leu Gln Lys Ala Ala
145                 150                 155


<210> SEQ ID NO 16
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 16

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Phe Tyr Gly Ile Thr Pro Leu His Leu Ala Ala Ala Tyr Gly
        35                  40                  45

His Leu Glu Ile Val Glu Val Leu Leu Lys His Gly Ala Asp Val Asn
    50                  55                  60

Ala His Asp Trp Asn Gly Trp Thr Pro Leu His Leu Ala Ala Lys Tyr
65                  70                  75                  80

Gly His Leu Glu Ile Val Glu Val Leu Leu Lys His Gly Ala Asp Val
                85                  90                  95

Asn Ala Ile Asp Asn Ala Gly Lys Thr Pro Leu His Leu Ala Ala Ala
            100                 105                 110

His Gly His Leu Glu Ile Val Glu Val Leu Leu Lys Tyr Gly Ala Asp
        115                 120                 125

Val Asn Ala Gln Asp Lys Phe Gly Lys Thr Ala Glu Asp Leu Ala Lys
    130                 135                 140

Asp Asn Gly Asn Gln Asp Ile Ala Asp Leu Leu Glu Lys Ala Leu
145                 150                 155


<210> SEQ ID NO 17
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 17

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Phe Tyr Gly Ile Thr Pro Leu His Leu Ala Ala Ala Tyr Gly
        35                  40                  45

His Leu Glu Ile Val Glu Val Leu Leu Lys His Gly Ala Asp Val Asn
    50                  55                  60

Ala His Asp Trp Asn Gly Trp Thr Pro Leu His Leu Ala Ala Lys Tyr
65                  70                  75                  80

Gly His Leu Glu Ile Val Glu Val Leu Leu Lys His Gly Ala Asp Val
                85                  90                  95
```

Asn Ala Ile Asp Asn Ala Gly Lys Thr Pro Leu His Leu Ala Ala Ala
100 105 110

His Gly His Leu Glu Ile Val Glu Val Leu Leu Lys Tyr Gly Ala Asp
115 120 125

Val Asn Ala Gln Asp Lys Phe Gly Lys Thr Ala Met Asp Leu Ala Arg
130 135 140

Asp Asn Gly Asn Glu Asp Ile Tyr Lys Leu Leu Ala Lys Ala Leu
145 150 155

<210> SEQ ID NO 18
<211> LENGTH: 158
<212> TYPE: PRT
<213> ORGANISM: Artificial Sequence
<220> FEATURE:
<223> OTHER INFORMATION: designed akyrin repeat protein ligand binding the extracellular domain 1 of the HER2

<400> SEQUENCE: 18

Gly Ser Asp Leu Gly Lys Lys Leu Leu Glu Ala Ala Arg Ala Gly Gln
1 5 10 15

Asp Asp Glu Val Arg Ile Leu Met Ala Asn Gly Ala Asp Val Asn Ala
20 25 30

His Asp Phe Tyr Gly Ile Thr Pro Leu His Leu Ala Ala Asn Phe Gly
35 40 45

His Leu Glu Ile Val Glu Val Leu Leu Lys His Gly Ala Asp Val Asn
50 55 60

Ala Phe Asp Tyr Asp Asn Thr Pro Leu His Leu Ala Ala Asp Ala Gly
65 70 75 80

His Leu Glu Ile Val Glu Val Leu Leu Lys Tyr Gly Ala Asp Val Asn
85 90 95

Ala Ser Asp Arg Asp Gly His Thr Pro Leu His Leu Ala Ala Arg Glu
100 105 110

Gly His Leu Glu Ile Val Glu Val Leu Leu Lys Asn Gly Ala Asp Val
115 120 125

Asn Ala Gln Asp Lys Phe Gly Lys Thr Ala Phe Asp Ile Ser Ile Asp
130 135 140

Asn Gly Asn Glu Asp Leu Ala Glu Ile Leu Gln Lys Leu Asn
145 150 155

<210> SEQ ID NO 19
<211> LENGTH: 158
<212> TYPE: PRT
<213> ORGANISM: Artificial Sequence
<220> FEATURE:
<223> OTHER INFORMATION: designed akyrin repeat protein ligand binding the extracellular domain 1 of the HER2

<400> SEQUENCE: 19

Gly Ser Asp Leu Gly Lys Lys Leu Leu Glu Ala Ala Arg Ala Gly Gln
1 5 10 15

Asp Asp Glu Val Arg Ile Leu Met Ala Asn Gly Ala Asp Val Asn Ala
20 25 30

His Asp Phe Tyr Gly Ile Thr Pro Leu His Leu Ala Ala Asn Phe Gly
35 40 45

His Leu Glu Ile Val Glu Val Leu Leu Lys His Gly Ala Asp Val Asn
50 55 60

Ala Phe Asp Tyr Asp Asn Thr Pro Leu His Leu Ala Ala Asp Ala Gly
65 70 75 80

-continued

```
His Leu Glu Ile Val Glu Val Leu Leu Lys Tyr Gly Ala Asp Val Asn
                85                  90                  95

Ala Ser Asp Arg Asp Gly His Thr Pro Leu His Leu Ala Ala Arg Glu
            100                 105                 110

Gly His Leu Glu Ile Val Glu Val Leu Leu Lys Asn Gly Ala Asp Val
        115                 120                 125

Asn Ala Gln Asp Lys Phe Gly Lys Thr Pro Phe Asp Leu Ala Ile Asp
    130                 135                 140

Asn Gly Asn Glu Asp Ile Ala Glu Val Leu Gln Lys Ala Ala
145                 150                 155
```

<210> SEQ ID NO 20
<211> LENGTH: 158
<212> TYPE: PRT
<213> ORGANISM: Artificial Sequence
<220> FEATURE:
<223> OTHER INFORMATION: designed akyrin repeat protein ligand binding the extracellular domain 1 of the HER2

<400> SEQUENCE: 20

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Phe Tyr Gly Ile Thr Pro Leu His Leu Ala Ala Asn Phe Gly
        35                  40                  45

His Leu Glu Ile Val Glu Val Leu Leu Lys His Gly Ala Asp Val Asn
    50                  55                  60

Ala Phe Asp Tyr Asp Asn Thr Pro Leu His Leu Ala Ala Asp Ala Gly
65                  70                  75                  80

His Leu Glu Ile Val Glu Val Leu Leu Lys Tyr Gly Ala Asp Val Asn
                85                  90                  95

Ala Ser Asp Arg Asp Gly His Thr Pro Leu His Leu Ala Ala Arg Glu
            100                 105                 110

Gly His Leu Glu Ile Val Glu Val Leu Leu Lys Asn Gly Ala Asp Val
        115                 120                 125

Asn Ala Gln Asp Lys Phe Gly Lys Thr Ala Glu Asp Leu Ala Lys Asp
    130                 135                 140

Asn Gly Asn Gln Asp Ile Ala Asp Leu Leu Glu Lys Ala Leu
145                 150                 155
```

<210> SEQ ID NO 21
<211> LENGTH: 158
<212> TYPE: PRT
<213> ORGANISM: Artificial Sequence
<220> FEATURE:
<223> OTHER INFORMATION: designed akyrin repeat protein ligand binding the extracellular domain 1 of the HER2

<400> SEQUENCE: 21

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Phe Tyr Gly Ile Thr Pro Leu His Leu Ala Ala Asn Phe Gly
        35                  40                  45

His Leu Glu Ile Val Glu Val Leu Leu Lys His Gly Ala Asp Val Asn
    50                  55                  60
```

```
Ala Phe Asp Tyr Asp Asn Thr Pro Leu His Leu Ala Ala Asp Ala Gly
65                  70                  75                  80

His Leu Glu Ile Val Glu Val Leu Leu Lys Tyr Gly Ala Asp Val Asn
                85                  90                  95

Ala Ser Asp Arg Asp Gly His Thr Pro Leu His Leu Ala Ala Arg Glu
            100                 105                 110

Gly His Leu Glu Ile Val Glu Val Leu Leu Lys Asn Gly Ala Asp Val
        115                 120                 125

Asn Ala Gln Asp Lys Phe Gly Lys Thr Ala Met Asp Leu Ala Arg Asp
    130                 135                 140

Asn Gly Asn Glu Asp Ile Tyr Lys Leu Leu Ala Lys Ala Leu
145                 150                 155
```

<210> SEQ ID NO 22
<211> LENGTH: 159
<212> TYPE: PRT
<213> ORGANISM: Artificial Sequence
<220> FEATURE:
<223> OTHER INFORMATION: designed akyrin repeat protein ligand binding the extracellular domain 1 of the HER2

<400> SEQUENCE: 22

```
Gly Ser Asp Leu Gly Lys Lys Leu Leu Glu Thr Ala Arg Ala Gly Gln
1               5                   10                  15

Asp Asp Glu Val Arg Ile Leu Met Ala Asn Gly Ala Asp Val Asn Ala
            20                  25                  30

Thr Asp Phe Tyr Gly Leu Thr Pro Leu His Leu Ala Ala Tyr Tyr Gly
        35                  40                  45

His Leu Glu Ile Val Glu Val Leu Leu Lys Asn Gly Ala Asp Val Asn
    50                  55                  60

Ala Ser Asp Trp Asn Gly Tyr Thr Pro Leu Arg Leu Ala Ala Asp Ala
65                  70                  75                  80

Gly His Leu Glu Ile Val Glu Val Leu Leu Lys Asn Gly Ala Asp Val
                85                  90                  95

Asn Ala Phe Asp Gln Phe Gly Ser Thr Pro Leu His Leu Ala Ala Ala
            100                 105                 110

Thr Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155
```

<210> SEQ ID NO 23
<211> LENGTH: 158
<212> TYPE: PRT
<213> ORGANISM: Artificial Sequence
<220> FEATURE:
<223> OTHER INFORMATION: designed akyrin repeat protein ligand binding the extracellular domain 1 of the HER2

<400> SEQUENCE: 23

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Phe Tyr Gly Lys Thr Pro Leu His Leu Ala Ala Ala Ile Gly
        35                  40                  45
```

```
His Leu Glu Ile Val Glu Val Leu Leu Lys Asn Gly Ala Asp Val Asn
    50                  55                  60

Ala Thr Asp Tyr Gly Leu Thr Pro Leu His Leu Ala Ala Asp Asn Gly
65                  70                  75                  80

His Leu Glu Ile Val Glu Val Leu Leu Lys Asn Gly Ala Asp Val Asn
                85                  90                  95

Ala Phe Asp Phe Thr Gly Arg Thr Pro Leu His Leu Ala Ala Ser Gln
            100                 105                 110

Gly His Leu Glu Ile Val Glu Val Leu Leu Lys Asn Gly Ala Asp Val
        115                 120                 125

Asn Ala Gln Asp Lys Phe Gly Lys Thr Ala Phe Asp Ile Ser Ile Asp
    130                 135                 140

Asn Gly Asn Glu Asp Leu Ala Glu Ile Leu Gln Lys Leu Asn
145                 150                 155


<210> SEQ ID NO 24
<211> LENGTH: 160
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 24

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Trp His Gly Ile Thr Pro Leu His Leu Ala Ala Phe Tyr Gly
        35                  40                  45

His Leu Glu Ile Val Glu Val Leu Leu Lys Asn Gly Ala Asp Val Asn
    50                  55                  60

Ala Phe Asp Asp Tyr Asp Gly Ser Thr Pro Leu His Leu Ala Ala Trp
65                  70                  75                  80

Met Gly His Leu Glu Ile Val Glu Val Leu Leu Lys His Gly Ala Asp
                85                  90                  95

Val Asn Ala Thr Asp His Phe Gly Asn Thr Pro Leu His Leu Ala Ala
            100                 105                 110

Ala Met Gly His Leu Glu Ile Val Glu Val Leu Leu Lys His Gly Ala
        115                 120                 125

Asp Val Asn Ala Gln Asp Lys Phe Gly Lys Thr Ala Phe Asp Ile Ser
    130                 135                 140

Ile Asp Asn Gly Asn Glu Asp Leu Ala Glu Ile Leu Gln Lys Leu Asn
145                 150                 155                 160


<210> SEQ ID NO 25
<211> LENGTH: 126
<212> TYPE: PRT
<213> ORGANISM: Artificial Sequence
<220> FEATURE:
<223> OTHER INFORMATION: designed akyrin repeat protein ligand binding
      the extracellular domain 4 of the HER2

<400> SEQUENCE: 25

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30
```

Lys Asp Glu Tyr Gly Leu Thr Pro Leu Tyr Leu Ala Thr Ala His Gly
35 40 45

His Leu Glu Ile Val Glu Val Leu Leu Lys Asn Gly Ala Asp Val Asn
50 55 60

Ala Val Asp Ala Ile Gly Phe Thr Pro Leu His Leu Ala Ala Phe Ile
65 70 75 80

Gly His Leu Glu Ile Ala Glu Val Leu Leu Lys His Gly Ala Asp Val
85 90 95

Asn Ala Gln Asp Lys Phe Gly Lys Thr Ala Phe Asp Ile Ser Ile Gly
100 105 110

Asn Gly Asn Glu Asp Leu Ala Glu Ile Leu Gln Lys Leu Asn
115 120 125

<210> SEQ ID NO 26
<211> LENGTH: 159
<212> TYPE: PRT
<213> ORGANISM: Artificial Sequence
<220> FEATURE:
<223> OTHER INFORMATION: designed akyrin repeat protein ligand binding the extracellular domain 4 of the HER2

<400> SEQUENCE: 26

Gly Ser Asp Leu Gly Lys Lys Leu Leu Glu Ala Ala Arg Ala Gly Gln
1 5 10 15

Asp Asp Glu Val Arg Ile Leu Met Ala Asn Gly Ala Asp Val Asn Ala
20 25 30

Thr Asp Ile His Gly His Thr Pro Leu His Leu Ala Ala Ala Met Gly
35 40 45

His Leu Glu Ile Val Glu Val Leu Leu Lys Asn Gly Ala Asp Val Asn
50 55 60

Ala Asn Asp Trp Arg Gly Phe Thr Pro Leu His Leu Ala Ala Leu Asn
65 70 75 80

Gly His Leu Glu Ile Val Glu Val Leu Leu Lys Asn Gly Ala Asp Val
85 90 95

Asn Ala Thr Asp Thr Ala Gly Asn Thr Pro Leu His Leu Ala Ala Trp
100 105 110

Phe Gly His Leu Glu Ile Val Glu Val Leu Leu Lys Asn Gly Ala Asp
115 120 125

Val Asn Ala Gln Asp Lys Phe Gly Lys Thr Ala Phe Asp Ile Ser Ile
130 135 140

Asp Asn Gly Asn Glu Asp Leu Ala Glu Ile Leu Gln Lys Leu Asn
145 150 155

<210> SEQ ID NO 27
<211> LENGTH: 159
<212> TYPE: PRT
<213> ORGANISM: Artificial Sequence
<220> FEATURE:
<223> OTHER INFORMATION: designed akyrin repeat protein ligand binding the extracellular domain 4 of the HER2

<400> SEQUENCE: 27

Gly Ser Asp Leu Gly Lys Lys Leu Leu Glu Ala Ala Arg Ala Gly Gln
1 5 10 15

Asp Asp Glu Val Arg Ile Leu Met Ala Asn Gly Ala Asp Val Asn Ala
20 25 30

Thr Asp Ile His Gly His Thr Pro Leu His Leu Ala Ala Ala Met Gly
35 40 45

His Leu Glu Ile Val Glu Val Leu Leu Lys Asn Gly Ala Asp Val Asn
            50                  55                  60

Ala Asn Asp Trp Arg Gly Phe Thr Pro Leu His Leu Ala Ala Leu Asn
 65                  70                  75                  80

Gly His Leu Glu Ile Val Glu Val Leu Leu Lys Asn Gly Ala Asp Val
                 85                  90                  95

Asn Ala Thr Asp Thr Ala Gly Asn Thr Pro Leu His Leu Ala Ala Trp
            100                 105                 110

Phe Gly His Leu Glu Ile Val Glu Val Leu Leu Lys Asn Gly Ala Asp
            115                 120                 125

Val Asn Ala Gln Asp Lys Phe Gly Lys Thr Pro Phe Asp Leu Ala Ile
        130                 135                 140

Asp Asn Gly Asn Glu Asp Ile Ala Glu Val Leu Gln Lys Ala Ala
145                 150                 155

<210> SEQ ID NO 28
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 4 of the HER2

<400> SEQUENCE: 28

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
             20                  25                  30

Thr Asp Ile His Gly His Thr Pro Leu His Leu Ala Ala Ala Met Gly
         35                  40                  45

His Leu Glu Ile Val Glu Val Leu Leu Lys Asn Gly Ala Asp Val Asn
     50                  55                  60

Ala Asn Asp Trp Arg Gly Phe Thr Pro Leu His Leu Ala Ala Leu Asn
 65                  70                  75                  80

Gly His Leu Glu Ile Val Glu Val Leu Leu Lys Asn Gly Ala Asp Val
                 85                  90                  95

Asn Ala Thr Asp Thr Ala Gly Asn Thr Pro Leu His Leu Ala Ala Trp
            100                 105                 110

Phe Gly His Leu Glu Ile Val Glu Val Leu Leu Lys Asn Gly Ala Asp
            115                 120                 125

Val Asn Ala Gln Asp Lys Phe Gly Lys Thr Ala Glu Asp Leu Ala Lys
        130                 135                 140

Asp Asn Gly Asn Gln Asp Ile Ala Asp Leu Leu Glu Lys Ala Leu
145                 150                 155

<210> SEQ ID NO 29
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 4 of the HER2

<400> SEQUENCE: 29

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
             20                  25                  30

```
Thr Asp Ile His Gly His Thr Pro Leu His Leu Ala Ala Ala Met Gly
        35                  40                  45

His Leu Glu Ile Val Glu Val Leu Leu Lys Asn Gly Ala Asp Val Asn
    50                  55                  60

Ala Asn Asp Trp Arg Gly Phe Thr Pro Leu His Leu Ala Ala Leu Asn
65                  70                  75                  80

Gly His Leu Glu Ile Val Glu Val Leu Leu Lys Asn Gly Ala Asp Val
                85                  90                  95

Asn Ala Thr Asp Thr Ala Gly Asn Thr Pro Leu His Leu Ala Ala Trp
            100                 105                 110

Phe Gly His Leu Glu Ile Val Glu Val Leu Leu Lys Asn Gly Ala Asp
        115                 120                 125

Val Asn Ala Gln Asp Lys Phe Gly Lys Thr Ala Met Asp Leu Ala Arg
    130                 135                 140

Asp Asn Gly Asn Glu Asp Ile Tyr Lys Leu Leu Ala Lys Ala Leu
145                 150                 155


<210> SEQ ID NO 30
<211> LENGTH: 158
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 30

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ser Asp Tyr Tyr Gly Ile Thr Pro Leu His Leu Ala Ala His Thr Gly
        35                  40                  45

His Leu Glu Ile Val Glu Val Leu Leu Lys His Gly Ala Asp Val Asn
    50                  55                  60

Ala Arg Asn Trp Gly Trp Thr Pro Leu His Leu Ala Ala Met Thr Gly
65                  70                  75                  80

His Leu Glu Ile Val Glu Val Leu Leu Lys Tyr Gly Ala Asp Val Asn
                85                  90                  95

Ala Val Asp Glu Asp Gly Asp Thr Pro Leu His Leu Ala Ala Thr His
            100                 105                 110

Gly His Leu Glu Ile Val Glu Val Leu Leu Lys Tyr Gly Ala Asp Val
        115                 120                 125

Asn Ala Gln Asp Lys Phe Gly Lys Thr Pro Phe Asp Leu Ala Ile Asp
    130                 135                 140

Asn Gly Asn Glu Asp Ile Ala Glu Val Leu Gln Lys Ala Ala
145                 150                 155


<210> SEQ ID NO 31
<211> LENGTH: 158
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 31

Gly Ser Asp Leu Gly Lys Lys Leu Leu Glu Ala Ala Arg Ala Gly Gln
1               5                   10                  15
```

```
Asp Asp Glu Val Arg Ile Leu Met Ala Asn Gly Ala Asp Val Asn Ala
            20                  25                  30

Ser Asp Tyr Tyr Gly Ile Thr Pro Leu His Leu Ala Ala His Thr Gly
        35                  40                  45

His Leu Glu Ile Val Glu Val Leu Leu Lys His Gly Ala Asp Val Asn
    50                  55                  60

Ala Arg Asn Trp Gly Trp Thr Pro Leu His Leu Ala Ala Met Thr Gly
65                  70                  75                  80

His Leu Glu Ile Val Glu Val Leu Leu Lys Tyr Gly Ala Asp Val Asn
                85                  90                  95

Ala Val Asp Glu Asp Gly Asp Thr Pro Leu His Leu Ala Ala Thr His
            100                 105                 110

Gly His Leu Glu Ile Val Glu Val Leu Leu Lys Tyr Gly Ala Asp Val
        115                 120                 125

Asn Ala Gln Asp Lys Phe Gly Lys Thr Ala Glu Asp Leu Ala Lys Asp
    130                 135                 140

Asn Gly Asn Gln Asp Ile Ala Asp Leu Leu Glu Lys Ala Leu
145                 150                 155


<210> SEQ ID NO 32
<211> LENGTH: 158
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 32

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ser Asp Tyr Tyr Gly Ile Thr Pro Leu His Leu Ala Ala His Thr Gly
        35                  40                  45

His Leu Glu Ile Val Glu Val Leu Leu Lys His Gly Ala Asp Val Asn
    50                  55                  60

Ala Arg Asn Trp Gly Trp Thr Pro Leu His Leu Ala Ala Met Thr Gly
65                  70                  75                  80

His Leu Glu Ile Val Glu Val Leu Leu Lys Tyr Gly Ala Asp Val Asn
                85                  90                  95

Ala Val Asp Glu Asp Gly Asp Thr Pro Leu His Leu Ala Ala Thr His
            100                 105                 110

Gly His Leu Glu Ile Val Glu Val Leu Leu Lys Tyr Gly Ala Asp Val
        115                 120                 125

Asn Ala Gln Asp Lys Phe Gly Lys Thr Ala Met Asp Leu Ala Arg Asp
    130                 135                 140

Asn Gly Asn Glu Asp Ile Tyr Lys Leu Leu Ala Lys Ala Leu
145                 150                 155


<210> SEQ ID NO 33
<211> LENGTH: 160
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 33
```

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Trp Tyr Gly Ile Thr Pro Leu His Leu Ala Ala Asp Thr Gly
        35                  40                  45

His Leu Glu Ile Val Glu Val Leu Leu Lys His Gly Ala Asp Val Asn
    50                  55                  60

Ala Phe Asp Ser Tyr Thr Gly His Thr Pro Leu His Leu Ala Ala Gln
65                  70                  75                  80

Lys Gly Gln Leu Glu Ile Val Glu Val Leu Leu Lys Tyr Gly Ala Asp
                85                  90                  95

Val Asn Ala Ile Asp Arg His Gly Lys Thr Pro Leu His Leu Ala Ala
            100                 105                 110

Leu Met Gly His Leu Glu Ile Val Glu Val Leu Leu Lys Tyr Gly Ala
        115                 120                 125

Asp Val Asn Ala Gln Asp Lys Phe Gly Lys Thr Pro Phe Asp Leu Ala
    130                 135                 140

Ile Asp Asn Gly Asn Glu Asp Ile Ala Glu Val Leu Gln Lys Ala Ala
145                 150                 155                 160


<210> SEQ ID NO 34
<211> LENGTH: 160
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 34

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Trp Tyr Gly Ile Thr Pro Leu His Leu Ala Ala Asp Thr Gly
        35                  40                  45

His Leu Glu Ile Val Glu Val Leu Leu Lys His Gly Ala Asp Val Asn
    50                  55                  60

Ala Phe Asp Ser Tyr Thr Gly His Thr Pro Leu His Leu Ala Ala Gln
65                  70                  75                  80

Lys Gly Gln Leu Glu Ile Val Glu Val Leu Leu Lys Tyr Gly Ala Asp
                85                  90                  95

Val Asn Ala Ile Asp Arg His Gly Lys Thr Pro Leu His Leu Ala Ala
            100                 105                 110

Leu Met Gly His Leu Glu Ile Val Glu Val Leu Leu Lys Tyr Gly Ala
        115                 120                 125

Asp Val Asn Ala Gln Asp Lys Phe Gly Lys Thr Ala Glu Asp Leu Ala
    130                 135                 140

Lys Asp Asn Gly Asn Gln Asp Ile Ala Asp Leu Leu Glu Lys Ala Leu
145                 150                 155                 160


<210> SEQ ID NO 35
<211> LENGTH: 160
<212> TYPE: PRT
<213> ORGANISM: Artificial Sequence
<220> FEATURE:
<223> OTHER INFORMATION: designed akyrin repeat protein ligand binding
```

the extracellular domain 1 of the HER2

<400> SEQUENCE: 35

Gly Ser Asp Leu Gly Lys Lys Leu Leu Glu Ala Ala Arg Ala Gly Gln
1 5 10 15

Asp Asp Glu Val Arg Ile Leu Met Ala Asn Gly Ala Asp Val Asn Ala
20 25 30

Lys Asp Trp Tyr Gly Ile Thr Pro Leu His Leu Ala Ala Asp Thr Gly
35 40 45

His Leu Glu Ile Val Glu Val Leu Leu Lys His Gly Ala Asp Val Asn
50 55 60

Ala Phe Asp Ser Tyr Thr Gly His Thr Pro Leu His Leu Ala Ala Gln
65 70 75 80

Lys Gly Gln Leu Glu Ile Val Glu Val Leu Leu Lys Tyr Gly Ala Asp
85 90 95

Val Asn Ala Ile Asp Arg His Gly Lys Thr Pro Leu His Leu Ala Ala
100 105 110

Leu Met Gly His Leu Glu Ile Val Glu Val Leu Leu Lys Tyr Gly Ala
115 120 125

Asp Val Asn Ala Gln Asp Lys Phe Gly Lys Thr Ala Met Asp Leu Ala
130 135 140

Arg Asp Asn Gly Asn Glu Asp Ile Tyr Lys Leu Leu Ala Lys Ala Leu
145 150 155 160

<210> SEQ ID NO 36
<211> LENGTH: 125
<212> TYPE: PRT
<213> ORGANISM: Artificial Sequence
<220> FEATURE:
<223> OTHER INFORMATION: designed akyrin repeat protein ligand binding
the extracellular domain 1 of the HER2

<400> SEQUENCE: 36

Gly Ser Asp Leu Gly Lys Lys Leu Leu Glu Ala Ala Arg Ala Gly Gln
1 5 10 15

Asp Asp Glu Val Arg Ile Leu Met Ala Asn Gly Ala Asp Val Asn Ala
20 25 30

Ser Asp Phe Tyr Gly Lys Thr Pro Leu His Leu Ala Ala Thr Ile Gly
35 40 45

His Leu Lys Ile Val Glu Val Leu Leu Lys Tyr Gly Ala Asp Val Asn
50 55 60

Ala Thr Asp Trp Gly Asn Thr Pro Leu His Leu Ala Ala Ile Asn Gly
65 70 75 80

His Leu Glu Ile Val Glu Val Leu Leu Lys His Gly Ala Asp Val Asn
85 90 95

Ala Gln Asp Lys Phe Gly Lys Thr Pro Phe Asp Leu Ala Ile Asp Asn
100 105 110

Gly Asn Glu Asp Ile Ala Glu Val Leu Gln Lys Ala Ala
115 120 125

<210> SEQ ID NO 37
<211> LENGTH: 125
<212> TYPE: PRT
<213> ORGANISM: Artificial Sequence
<220> FEATURE:
<223> OTHER INFORMATION: designed akyrin repeat protein ligand binding
the extracellular domain 1 of the HER2

<400> SEQUENCE: 37

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ser Asp Phe Tyr Gly Lys Thr Pro Leu His Leu Ala Ala Thr Ile Gly
        35                  40                  45

His Leu Lys Ile Val Glu Val Leu Leu Lys Tyr Gly Ala Asp Val Asn
    50                  55                  60

Ala Thr Asp Trp Gly Asn Thr Pro Leu His Leu Ala Ala Ile Asn Gly
65                  70                  75                  80

His Leu Glu Ile Val Glu Val Leu Leu Lys His Gly Ala Asp Val Asn
                85                  90                  95

Ala Gln Asp Lys Phe Gly Lys Thr Ala Glu Asp Leu Ala Lys Asp Asn
            100                 105                 110

Gly Asn Gln Asp Ile Ala Asp Leu Leu Glu Lys Ala Leu
        115                 120                 125


<210> SEQ ID NO 38
<211> LENGTH: 125
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 38

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ser Asp Phe Tyr Gly Lys Thr Pro Leu His Leu Ala Ala Thr Ile Gly
        35                  40                  45

His Leu Lys Ile Val Glu Val Leu Leu Lys Tyr Gly Ala Asp Val Asn
    50                  55                  60

Ala Thr Asp Trp Gly Asn Thr Pro Leu His Leu Ala Ala Ile Asn Gly
65                  70                  75                  80

His Leu Glu Ile Val Glu Val Leu Leu Lys His Gly Ala Asp Val Asn
                85                  90                  95

Ala Gln Asp Lys Phe Gly Lys Thr Ala Met Asp Leu Ala Arg Asp Asn
            100                 105                 110

Gly Asn Glu Asp Ile Tyr Lys Leu Leu Ala Lys Ala Leu
        115                 120                 125


<210> SEQ ID NO 39
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 39

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Phe His Gly Leu Thr Pro Leu His Leu Ala Ala Gly Met Gly
        35                  40                  45
```

-continued

```
His Leu Glu Ile Val Glu Val Leu Leu Lys Asn Gly Ala Asp Val Asn
    50                  55                  60

Ala Val Asp Thr Asp Gly Ile Thr Leu Leu His Leu Ala Ala Tyr Tyr
65                  70                  75                  80

Gly His Leu Glu Ile Val Glu Val Leu Leu Lys His Gly Ala Asp Val
                85                  90                  95

Asn Ala His Asp Tyr Ala Gly Ser Thr Pro Leu His Leu Ala Ala Asn
            100                 105                 110

Thr Gly His Leu Glu Ile Val Glu Val Leu Leu Lys Asn Gly Ala Asp
        115                 120                 125

Val Asn Ala Gln Asp Lys Phe Gly Lys Thr Pro Phe Asp Leu Ala Ile
    130                 135                 140

Asp Asn Gly Asn Glu Asp Ile Ala Glu Val Leu Gln Lys Ala Ala
145                 150                 155


<210> SEQ ID NO 40
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 40

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Phe His Gly Leu Thr Pro Leu His Leu Ala Ala Gly Met Gly
        35                  40                  45

His Leu Glu Ile Val Glu Val Leu Leu Lys Asn Gly Ala Asp Val Asn
    50                  55                  60

Ala Val Asp Thr Asp Gly Ile Thr Leu Leu His Leu Ala Ala Tyr Tyr
65                  70                  75                  80

Gly His Leu Glu Ile Val Glu Val Leu Leu Lys His Gly Ala Asp Val
                85                  90                  95

Asn Ala His Asp Tyr Ala Gly Ser Thr Pro Leu His Leu Ala Ala Asn
            100                 105                 110

Thr Gly His Leu Glu Ile Val Glu Val Leu Leu Lys Asn Gly Ala Asp
        115                 120                 125

Val Asn Ala Gln Asp Lys Phe Gly Lys Thr Ala Glu Asp Leu Ala Lys
    130                 135                 140

Asp Asn Gly Asn Gln Asp Ile Ala Asp Leu Leu Glu Lys Ala Leu
145                 150                 155


<210> SEQ ID NO 41
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 41

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30
```

-continued

His Asp Phe His Gly Leu Thr Pro Leu His Leu Ala Ala Gly Met Gly
35 40 45

His Leu Glu Ile Val Glu Val Leu Leu Lys Asn Gly Ala Asp Val Asn
50 55 60

Ala Val Asp Thr Asp Gly Ile Thr Leu Leu His Leu Ala Ala Tyr Tyr
65 70 75 80

Gly His Leu Glu Ile Val Glu Val Leu Leu Lys His Gly Ala Asp Val
85 90 95

Asn Ala His Asp Tyr Ala Gly Ser Thr Pro Leu His Leu Ala Ala Asn
100 105 110

Thr Gly His Leu Glu Ile Val Glu Val Leu Leu Lys Asn Gly Ala Asp
115 120 125

Val Asn Ala Gln Asp Lys Phe Gly Lys Thr Ala Met Asp Leu Ala Arg
130 135 140

Asp Asn Gly Asn Glu Asp Ile Tyr Lys Leu Leu Ala Lys Ala Leu
145 150 155

<210> SEQ ID NO 42
<211> LENGTH: 159
<212> TYPE: PRT
<213> ORGANISM: Artificial Sequence
<220> FEATURE:
<223> OTHER INFORMATION: designed akyrin repeat protein ligand binding the extracellular domain 1 of the HER2

<400> SEQUENCE: 42

Gly Ser Asp Leu Gly Lys Lys Leu Leu Glu Thr Ala Arg Ala Gly Gln
1 5 10 15

Asp Asp Glu Val Arg Ile Leu Met Ala Asn Gly Ala Asp Val Asn Ala
20 25 30

Thr Asp Phe Tyr Gly Leu Thr Pro Leu His Leu Ala Ala Tyr Tyr Gly
35 40 45

His Leu Glu Ile Val Glu Val Leu Leu Lys Asn Gly Ala Asp Val Asn
50 55 60

Ala Ser Asp Trp Asn Gly Tyr Thr Pro Leu Arg Leu Ala Ala Asp Ala
65 70 75 80

Gly His Leu Glu Ile Val Glu Val Leu Leu Lys Asn Gly Ala Asp Val
85 90 95

Asn Ala Phe Asp Gln Phe Gly Ser Thr Pro Leu His Leu Ala Ala Ala
100 105 110

Thr Gly His Leu Glu Ile Val Glu Val Leu Leu Lys Tyr Gly Ala Asp
115 120 125

Val Asn Ala Gln Asp Lys Phe Gly Lys Thr Pro Phe Asp Leu Ala Ile
130 135 140

Asp Asn Gly Asn Glu Asp Ile Ala Glu Val Leu Gln Lys Ala Ala
145 150 155

<210> SEQ ID NO 43
<211> LENGTH: 159
<212> TYPE: PRT
<213> ORGANISM: Artificial Sequence
<220> FEATURE:
<223> OTHER INFORMATION: designed akyrin repeat protein ligand binding the extracellular domain 1 of the HER2

<400> SEQUENCE: 43

Gly Ser Asp Leu Gly Lys Lys Leu Leu Glu Thr Ala Arg Ala Gly Gln
1 5 10 15

```
Asp Asp Glu Val Arg Ile Leu Met Ala Asn Gly Ala Asp Val Asn Ala
            20                  25                  30

Thr Asp Phe Tyr Gly Leu Thr Pro Leu His Leu Ala Ala Tyr Tyr Gly
        35                  40                  45

His Leu Glu Ile Val Glu Val Leu Leu Lys Asn Gly Ala Asp Val Asn
    50                  55                  60

Ala Ser Asp Trp Asn Gly Tyr Thr Pro Leu Arg Leu Ala Ala Asp Ala
65                  70                  75                  80

Gly His Leu Glu Ile Val Glu Val Leu Leu Lys Asn Gly Ala Asp Val
                85                  90                  95

Asn Ala Phe Asp Gln Phe Gly Ser Thr Pro Leu His Leu Ala Ala Ala
            100                 105                 110

Thr Gly His Leu Glu Ile Val Glu Val Leu Leu Lys Tyr Gly Ala Asp
        115                 120                 125

Val Asn Ala Gln Asp Lys Phe Gly Lys Thr Ala Glu Asp Leu Ala Lys
    130                 135                 140

Asp Asn Gly Asn Gln Asp Ile Ala Asp Leu Leu Glu Lys Ala Leu
145                 150                 155


<210> SEQ ID NO 44
<211> LENGTH: 159
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 44

Gly Ser Asp Leu Gly Lys Lys Leu Leu Glu Thr Ala Arg Ala Gly Gln
1               5                   10                  15

Asp Asp Glu Val Arg Ile Leu Met Ala Asn Gly Ala Asp Val Asn Ala
            20                  25                  30

Thr Asp Phe Tyr Gly Leu Thr Pro Leu His Leu Ala Ala Tyr Tyr Gly
        35                  40                  45

His Leu Glu Ile Val Glu Val Leu Leu Lys Asn Gly Ala Asp Val Asn
    50                  55                  60

Ala Ser Asp Trp Asn Gly Tyr Thr Pro Leu Arg Leu Ala Ala Asp Ala
65                  70                  75                  80

Gly His Leu Glu Ile Val Glu Val Leu Leu Lys Asn Gly Ala Asp Val
                85                  90                  95

Asn Ala Phe Asp Gln Phe Gly Ser Thr Pro Leu His Leu Ala Ala Ala
            100                 105                 110

Thr Gly His Leu Glu Ile Val Glu Val Leu Leu Lys Tyr Gly Ala Asp
        115                 120                 125

Val Asn Ala Gln Asp Lys Phe Gly Lys Thr Ala Met Asp Leu Ala Arg
    130                 135                 140

Asp Asn Gly Asn Glu Asp Ile Tyr Lys Leu Leu Ala Lys Ala Leu
145                 150                 155


<210> SEQ ID NO 45
<211> LENGTH: 158
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 45
```

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Phe Tyr Gly Lys Thr Pro Leu His Leu Ala Ala Ala Ile Gly
        35                  40                  45

His Leu Glu Ile Val Glu Val Leu Leu Lys Asn Gly Ala Asp Val Asn
    50                  55                  60

Ala Thr Asp Tyr Gly Leu Thr Pro Leu His Leu Ala Ala Asp Asn Gly
65                  70                  75                  80

His Leu Glu Ile Val Glu Val Leu Leu Lys Asn Gly Ala Asp Val Asn
                85                  90                  95

Ala Phe Asp Phe Thr Gly Arg Thr Pro Leu His Leu Ala Ala Ser Gln
            100                 105                 110

Gly His Leu Glu Ile Val Glu Val Leu Leu Lys Asn Gly Ala Asp Val
        115                 120                 125

Asn Ala Gln Asp Lys Phe Gly Lys Thr Pro Phe Asp Leu Ala Ile Asp
    130                 135                 140

Asn Gly Asn Glu Asp Ile Ala Glu Val Leu Gln Lys Ala Ala
145                 150                 155


<210> SEQ ID NO 46
<211> LENGTH: 158
<212> TYPE: PRT
<213> ORGANISM: Artificial Sequence
<220> FEATURE:
<223> OTHER INFORMATION: designed akyrin repeat protein ligand binding
      the extracellular domain 1 of the HER2

<400> SEQUENCE: 46

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Phe Tyr Gly Lys Thr Pro Leu His Leu Ala Ala Ala Ile Gly
        35                  40                  45

His Leu Glu Ile Val Glu Val Leu Leu Lys Asn Gly Ala Asp Val Asn
    50                  55                  60

Ala Thr Asp Tyr Gly Leu Thr Pro Leu His Leu Ala Ala Asp Asn Gly
65                  70                  75                  80

His Leu Glu Ile Val Glu Val Leu Leu Lys Asn Gly Ala Asp Val Asn
                85                  90                  95

Ala Phe Asp Phe Thr Gly Arg Thr Pro Leu His Leu Ala Ala Ser Gln
            100                 105                 110

Gly His Leu Glu Ile Val Glu Val Leu Leu Lys Asn Gly Ala Asp Val
        115                 120                 125

Asn Ala Gln Asp Lys Phe Gly Glu Thr Lys Glu Asp Leu Ala Lys Asp
    130                 135                 140

Asn Gly Asn Gln Asp Ile Ala Asp Leu Leu Glu Lys Ala Leu
145                 150                 155


<210> SEQ ID NO 47
<211> LENGTH: 158
<212> TYPE: PRT
<213> ORGANISM: Artificial Sequence
<220> FEATURE:
<223> OTHER INFORMATION: designed akyrin repeat protein ligand binding
```

the extracellular domain 1 of the HER2

<400> SEQUENCE: 47

Gly Ser Asp Leu Gly Lys Lys Leu Leu Glu Ala Ala Arg Ala Gly Gln
1 5 10 15

Asp Asp Glu Val Arg Ile Leu Met Ala Asn Gly Ala Asp Val Asn Ala
20 25 30

His Asp Phe Tyr Gly Lys Thr Pro Leu His Leu Ala Ala Ala Ile Gly
35 40 45

His Leu Glu Ile Val Glu Val Leu Leu Lys Asn Gly Ala Asp Val Asn
50 55 60

Ala Thr Asp Tyr Gly Leu Thr Pro Leu His Leu Ala Ala Asp Asn Gly
65 70 75 80

His Leu Glu Ile Val Glu Val Leu Leu Lys Asn Gly Ala Asp Val Asn
85 90 95

Ala Phe Asp Phe Thr Gly Arg Thr Pro Leu His Leu Ala Ala Ser Gln
100 105 110

Gly His Leu Glu Ile Val Glu Val Leu Leu Lys Asn Gly Ala Asp Val
115 120 125

Asn Ala Gln Asp Lys Phe Gly Glu Thr Lys Met Asp Leu Ala Arg Asp
130 135 140

Asn Gly Asn Glu Asp Ile Tyr Lys Leu Leu Ala Lys Ala Leu
145 150 155

<210> SEQ ID NO 48
<211> LENGTH: 160
<212> TYPE: PRT
<213> ORGANISM: Artificial Sequence
<220> FEATURE:
<223> OTHER INFORMATION: designed akyrin repeat protein ligand binding
the extracellular domain 1 of the HER2

<400> SEQUENCE: 48

Gly Ser Asp Leu Gly Lys Lys Leu Leu Glu Ala Ala Arg Ala Gly Gln
1 5 10 15

Asp Asp Glu Val Arg Ile Leu Met Ala Asn Gly Ala Asp Val Asn Ala
20 25 30

His Asp Trp His Gly Ile Thr Pro Leu His Leu Ala Ala Phe Tyr Gly
35 40 45

His Leu Glu Ile Val Glu Val Leu Leu Lys Asn Gly Ala Asp Val Asn
50 55 60

Ala Phe Asp Asp Tyr Asp Gly Ser Thr Pro Leu His Leu Ala Ala Trp
65 70 75 80

Met Gly His Leu Glu Ile Val Glu Val Leu Leu Lys His Gly Ala Asp
85 90 95

Val Asn Ala Thr Asp His Phe Gly Asn Thr Pro Leu His Leu Ala Ala
100 105 110

Ala Met Gly His Leu Glu Ile Val Glu Val Leu Leu Lys His Gly Ala
115 120 125

Asp Val Asn Ala Gln Asp Lys Phe Gly Lys Thr Pro Phe Asp Leu Ala
130 135 140

Ile Asp Asn Gly Asn Glu Asp Ile Ala Glu Val Leu Gln Lys Ala Ala
145 150 155 160

<210> SEQ ID NO 49
<211> LENGTH: 160
<212> TYPE: PRT

<213> ORGANISM: Artificial Sequence
<220> FEATURE:
<223> OTHER INFORMATION: designed akyrin repeat protein ligand binding the extracellular domain 1 of the HER2

<400> SEQUENCE: 49

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Trp His Gly Ile Thr Pro Leu His Leu Ala Ala Phe Tyr Gly
        35                  40                  45

His Leu Glu Ile Val Glu Val Leu Leu Lys Asn Gly Ala Asp Val Asn
    50                  55                  60

Ala Phe Asp Asp Tyr Asp Gly Ser Thr Pro Leu His Leu Ala Ala Trp
65                  70                  75                  80

Met Gly His Leu Glu Ile Val Glu Val Leu Leu Lys His Gly Ala Asp
                85                  90                  95

Val Asn Ala Thr Asp His Phe Gly Asn Thr Pro Leu His Leu Ala Ala
            100                 105                 110

Ala Met Gly His Leu Glu Ile Val Glu Val Leu Leu Lys His Gly Ala
        115                 120                 125

Asp Val Asn Ala Gln Asp Lys Phe Gly Lys Thr Ala Glu Asp Leu Ala
    130                 135                 140

Lys Asp Asn Gly Asn Gln Asp Ile Ala Asp Leu Leu Glu Lys Ala Leu
145                 150                 155                 160
```

<210> SEQ ID NO 50
<211> LENGTH: 160
<212> TYPE: PRT
<213> ORGANISM: Artificial Sequence
<220> FEATURE:
<223> OTHER INFORMATION: designed akyrin repeat protein ligand binding the extracellular domain 1 of the HER2

<400> SEQUENCE: 50

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Trp His Gly Ile Thr Pro Leu His Leu Ala Ala Phe Tyr Gly
        35                  40                  45

His Leu Glu Ile Val Glu Val Leu Leu Lys Asn Gly Ala Asp Val Asn
    50                  55                  60

Ala Phe Asp Asp Tyr Asp Gly Ser Thr Pro Leu His Leu Ala Ala Trp
65                  70                  75                  80

Met Gly His Leu Glu Ile Val Glu Val Leu Leu Lys His Gly Ala Asp
                85                  90                  95

Val Asn Ala Thr Asp His Phe Gly Asn Thr Pro Leu His Leu Ala Ala
            100                 105                 110

Ala Met Gly His Leu Glu Ile Val Glu Val Leu Leu Lys His Gly Ala
        115                 120                 125

Asp Val Asn Ala Gln Asp Lys Phe Gly Lys Thr Ala Met Asp Leu Ala
    130                 135                 140

Arg Asp Asn Gly Asn Glu Asp Ile Tyr Lys Leu Leu Ala Lys Ala Leu
145                 150                 155                 160
```

<210> SEQ ID NO 51
<211> LENGTH: 5
<212> TYPE: PRT
<213> ORGANISM: Artificial Sequence
<220> FEATURE:
<223> OTHER INFORMATION: designed peptide linker

<400> SEQUENCE: 51

Gly Gly Gly Gly Ser
1               5

<210> SEQ ID NO 52
<211> LENGTH: 10
<212> TYPE: PRT
<213> ORGANISM: Artificial Sequence
<220> FEATURE:
<223> OTHER INFORMATION: designed peptide linker

<400> SEQUENCE: 52

Gly Gly Gly Gly Ser Gly Gly Gly Gly Ser
1               5                   10

<210> SEQ ID NO 53
<211> LENGTH: 15
<212> TYPE: PRT
<213> ORGANISM: Artificial Sequence
<220> FEATURE:
<223> OTHER INFORMATION: designed peptide linker

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 20
<212> TYPE: PRT
<213> ORGANISM: Artificial Sequence
<220> FEATURE:
<223> OTHER INFORMATION: designed peptide linker

<400> SEQUENCE: 54

Gly Gly Gly Gly Ser Gly Gly Gly Gly Ser Gly Gly Gly Gly Ser Gly
1               5                   10                  15

Gly Gly Gly Ser
            20

<210> SEQ ID NO 55
<211> LENGTH: 77
<212> TYPE: PRT
<213> ORGANISM: Homo sapiens

<400> SEQUENCE: 55

Glu Asp Asn Tyr Ala Leu Ala Val Leu Asp Asn Gly Asp Pro Leu Asn
1               5                   10                  15

Asn Thr Thr Pro Val Thr Gly Ala Ser Pro Gly Gly Leu Arg Glu Leu
            20                  25                  30

Gln Leu Arg Ser Leu Thr Glu Ile Leu Lys Gly Gly Val Leu Ile Gln
        35                  40                  45

Arg Asn Pro Gln Leu Cys Tyr Gln Asp Thr Ile Leu Trp Lys Asp Ile
    50                  55                  60

Phe His Lys Asn Asn Gln Leu Ala Leu Thr Leu Ile Asp
65                  70                  75

<210> SEQ ID NO 56

<211> LENGTH: 27
<212> TYPE: PRT
<213> ORGANISM: Homo sapiens

<400> SEQUENCE: 56

Phe Leu Arg Gly Gln Glu Cys Val Glu Glu Cys Arg Val Leu Gln Gly
1 5 10 15

Leu Pro Arg Glu Tyr Val Asn Ala Arg His Cys
20 25

<210> SEQ ID NO 57
<211> LENGTH: 65
<212> TYPE: PRT
<213> ORGANISM: Homo sapiens

<400> SEQUENCE: 57

Leu Pro Cys His Pro Glu Cys Gln Pro Gln Asn Gly Ser Val Thr Cys
1 5 10 15

Phe Gly Pro Glu Ala Asp Gln Cys Val Ala Cys Ala His Tyr Lys Asp
20 25 30

Pro Pro Phe Cys Val Ala Arg Cys Pro Ser Gly Val Lys Pro Asp Leu
35 40 45

Ser Tyr Met Pro Ile Trp Lys Phe Pro Asp Glu Glu Gly Ala Cys Gln
50 55 60

Pro
65

<210> SEQ ID NO 58
<211> LENGTH: 313
<212> TYPE: PRT
<213> ORGANISM: Artificial Sequence
<220> FEATURE:
<223> OTHER INFORMATION: 9_20_G, a designed akyrin repeat protein domain binding the extracellular domain 1 of HER2 and a designed akyrin repeat protein domain binding the extracellular domain 4 of HER2 connected by a glycine/serine peptide linker and with a

<400> SEQUENCE: 58

Met Arg Gly Ser His His His His His His Gly Ser Asp Leu Gly Lys
1 5 10 15

Lys Leu Leu Glu Ala Ala Arg Ala Gly Gln Asp Asp Glu Val Arg Ile
20 25 30

Leu Met Ala Asn Gly Ala Asp Val Asn Ala His Asp Phe Tyr Gly Ile
35 40 45

Thr Pro Leu His Leu Ala Ala Asn Phe Gly His Leu Glu Ile Val Glu
50 55 60

Val Leu Leu Lys His Gly Ala Asp Val Asn Ala Phe Asp Tyr Asp Asn
65 70 75 80

Thr Pro Leu His Leu Ala Ala Asp Ala Gly His Leu Glu Ile Val Glu
85 90 95

Val Leu Leu Lys Tyr Gly Ala Asp Val Asn Ala Ser Asp Arg Asp Gly
100 105 110

His Thr Pro Leu His Leu Ala Ala Arg Glu Gly His Leu Glu Ile Val
115 120 125

Glu Val Leu Leu Lys Asn Gly Ala Asp Val Asn Ala Gln Asp Lys Phe
130 135 140

Gly Lys Thr Ala Phe Asp Ile Ser Ile Asp Asn Gly Asn Glu Asp Leu
145 150 155 160

Ala Glu Ile Leu Gln Lys Leu Gly Gly Gly Gly Ser Gly Gly Gly Gly

-continued

```
                165                 170                 175

Ser Gly Gly Gly Gly Ser Gly Gly Gly Gly Ser Arg Ser Asp Leu Gly
            180                 185                 190

Lys Lys Leu Leu Glu Ala Ala Arg Ala Gly Gln Asp Asp Glu Val Arg
        195                 200                 205

Ile Leu Met Ala Asn Gly Ala Asp Val Asn Ala Lys Asp Glu Tyr Gly
    210                 215                 220

Leu Thr Pro Leu Tyr Leu Ala Thr Ala His Gly His Leu Glu Ile Val
225                 230                 235                 240

Glu Val Leu Leu Lys Asn Gly Ala Asp Val Asn Ala Val Asp Ala Ile
                245                 250                 255

Gly Phe Thr Pro Leu His Leu Ala Ala Phe Ile Gly His Leu Glu Ile
            260                 265                 270

Ala Glu Val Leu Leu Lys His Gly Ala Asp Val Asn Ala Gln Asp Lys
        275                 280                 285

Phe Gly Lys Thr Ala Phe Asp Ile Ser Ile Gly Asn Gly Asn Glu Asp
    290                 295                 300

Leu Ala Glu Ile Leu Gln Lys Leu Asn
305                 310


<210> SEQ ID NO 59
<211> LENGTH: 303
<212> TYPE: PRT
<213> ORGANISM: Artificial Sequence
<220> FEATURE:
<223> OTHER INFORMATION: 9_10_G, a designed akyrin repeat protein domain
      binding the extracellular domain 1 of HER2 and a designed akyrin
      repeat protein domain binding the extracellular domain 4 of HER2
      connected by a glycine/serine peptide linker and with a

<400> SEQUENCE: 59

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Asn Ala Ser Asp Arg Asp Gly
            100                 105                 110

His Thr Pro Leu His Leu Ala Ala Arg Glu Gly His Leu Glu Ile Val
        115                 120                 125

Glu Val Leu Leu Lys Asn Gly Ala Asp Val Asn Ala Gln Asp Lys Phe
    130                 135                 140

Gly Lys Thr Ala Phe Asp Ile Ser Ile Asp Asn Gly Asn Glu Asp Leu
145                 150                 155                 160

Ala Glu Ile Leu Gln Lys Leu Gly Gly Gly Gly Ser Gly Gly Gly Gly
                165                 170                 175

Ser Arg Ser Asp Leu Gly Lys Lys Leu Leu Glu Ala Ala Arg Ala Gly
            180                 185                 190

Gln Asp Asp Glu Val Arg Ile Leu Met Ala Asn Gly Ala Asp Val Asn
```

```
        195                 200                 205

Ala Lys Asp Glu Tyr Gly Leu Thr Pro Leu Tyr Leu Ala Thr Ala His
    210                 215                 220

Gly His Leu Glu Ile Val Glu Val Leu Leu Lys Asn Gly Ala Asp Val
225                 230                 235                 240

Asn Ala Val Asp Ala Ile Gly Phe Thr Pro Leu His Leu Ala Ala Phe
                245                 250                 255

Ile Gly His Leu Glu Ile Ala Glu Val Leu Leu Lys His Gly Ala Asp
            260                 265                 270

Val Asn Ala Gln Asp Lys Phe Gly Lys Thr Ala Phe Asp Ile Ser Ile
        275                 280                 285

Gly Asn Gly Asn Glu Asp Leu Ala Glu Ile Leu Gln Lys Leu Asn
    290                 295                 300


<210> SEQ ID NO 60
<211> LENGTH: 314
<212> TYPE: PRT
<213> ORGANISM: Artificial Sequence
<220> FEATURE:
<223> OTHER INFORMATION: 6_20_G, a designed akyrin repeat protein domain
      binding the extracellular domain 1 of HER2 and a designed akyrin
      repeat protein domain binding the extracellular domain 4 of HER2
      connected by a glycine/serine peptide linker and with a

<400> SEQUENCE: 60

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Phe Tyr Gly Ile
        35                  40                  45

Thr Pro Leu His Leu Ala Ala Ala Tyr Gly His Leu Glu Ile Val Glu
    50                  55                  60

Val Leu Leu Lys His Gly Ala Asp Val Asn Ala His Asp Trp Asn Gly
65                  70                  75                  80

Trp Thr Pro Leu His Leu Ala Ala Lys Tyr Gly His Leu Glu Ile Val
                85                  90                  95

Glu Val Leu Leu Lys His Gly Ala Asp Val Asn Ala Ile Asp Asn Ala
            100                 105                 110

Gly Lys Thr Pro Leu His Leu Ala Ala Ala His Gly His Leu Glu Ile
        115                 120                 125

Val Glu Val Leu Leu Lys Tyr Gly Ala Asp Val Asn Ala Gln Asp Lys
    130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Gly Gly Gly Gly Ser Gly Gly Gly
                165                 170                 175

Gly Ser Gly Gly Gly Gly Ser Gly Gly Gly Gly Ser Arg Ser Asp Leu
            180                 185                 190

Gly Lys Lys Leu Leu Glu Ala Ala Arg Ala Gly Gln Asp Asp Glu Val
        195                 200                 205

Arg Ile Leu Met Ala Asn Gly Ala Asp Val Asn Ala Lys Asp Glu Tyr
    210                 215                 220

Gly Leu Thr Pro Leu Tyr Leu Ala Thr Ala His Gly His Leu Glu Ile
225                 230                 235                 240

Val Glu Val Leu Leu Lys Asn Gly Ala Asp Val Asn Ala Val Asp Ala
```

```
                245                 250                 255

Ile Gly Phe Thr Pro Leu His Leu Ala Ala Phe Ile Gly His Leu Glu
            260                 265                 270

Ile Ala Glu Val Leu Leu Lys His Gly Ala Asp Val Asn Ala Gln Asp
        275                 280                 285

Lys Phe Gly Lys Thr Ala Phe Asp Ile Ser Ile Gly Asn Gly Asn Glu
    290                 295                 300

Asp Leu Ala Glu Ile Leu Gln Lys Leu Asn
305                 310


<210> SEQ ID NO 61
<211> LENGTH: 168
<212> TYPE: PRT
<213> ORGANISM: Artificial Sequence
<220> FEATURE:
<223> OTHER INFORMATION: 9_29, designed akyrin repeat protein ligand
      binding the extracellular domain 1 of the HER2 with N-terminal
      His-tag

<400> SEQUENCE: 61

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Asn Ala Ser Asp Arg Asp Gly
            100                 105                 110

His Thr Pro Leu His Leu Ala Ala Arg Glu Gly His Leu Glu Ile Val
        115                 120                 125

Glu Val Leu Leu Lys Asn Gly Ala Asp Val Asn Ala Gln Asp Lys Phe
    130                 135                 140

Gly Lys Thr Ala Phe Asp Ile Ser Ile Asp Asn Gly Asn Glu Asp Leu
145                 150                 155                 160

Ala Glu Ile Leu Gln Lys Leu Asn
                165


<210> SEQ ID NO 62
<211> LENGTH: 168
<212> TYPE: PRT
<213> ORGANISM: Artificial Sequence
<220> FEATURE:
<223> OTHER INFORMATION: 9_29_newCcap, designed akyrin repeat protein
      ligand binding the extracellular domain 1 of the HER2 with
      N-terminal His-tag

<400> SEQUENCE: 62

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45
```

```
Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Asn Ala Ser Asp Arg Asp Gly
            100                 105                 110

His Thr Pro Leu His Leu Ala Ala Arg Glu Gly His Leu Glu Ile Val
        115                 120                 125

Glu Val Leu Leu Lys Asn Gly Ala Asp Val Asn Ala Gln Asp Lys Phe
    130                 135                 140

Gly Lys Thr Pro Phe Asp Leu Ala Ile Asp Asn Gly Asn Glu Asp Ile
145                 150                 155                 160

Ala Glu Val Leu Gln Lys Ala Ala
                165
```

<210> SEQ ID NO 63
<211> LENGTH: 169
<212> TYPE: PRT
<213> ORGANISM: Artificial Sequence
<220> FEATURE:
<223> OTHER INFORMATION: 9_26, designed akyrin repeat protein ligand binding the extracellular domain 1 of the HER2 with N-terminal His-tag

<400> SEQUENCE: 63

```
Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Phe Tyr Gly Ile
        35                  40                  45

Thr Pro Leu His Leu Ala Ala Ala Tyr Gly His Leu Glu Ile Val Glu
    50                  55                  60

Val Leu Leu Lys His Gly Ala Asp Val Asn Ala His Asp Trp Asn Gly
65                  70                  75                  80

Trp Thr Pro Leu His Leu Ala Ala Lys Tyr Gly His Leu Glu Ile Val
                85                  90                  95

Glu Val Leu Leu Lys His Gly Ala Asp Val Asn Ala Ile Asp Asn Ala
            100                 105                 110

Gly Lys Thr Pro Leu His Leu Ala Ala Ala His Gly His Leu Glu Ile
        115                 120                 125

Val Glu Val Leu Leu Lys Tyr Gly Ala Asp Val Asn Ala Gln Asp Lys
    130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Asn
                165
```

<210> SEQ ID NO 64
<211> LENGTH: 169
<212> TYPE: PRT
<213> ORGANISM: Artificial Sequence
<220> FEATURE:
<223> OTHER INFORMATION: 9_26_new_Ccap, designed akyrin repeat protein ligand binding the extracellular domain 1 of the HER2 with N-terminal His-tag

<400> SEQUENCE: 64

```
Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Phe Tyr Gly Ile
        35                  40                  45

Thr Pro Leu His Leu Ala Ala Ala Tyr Gly His Leu Glu Ile Val Glu
    50                  55                  60

Val Leu Leu Lys His Gly Ala Asp Val Asn Ala His Asp Trp Asn Gly
65                  70                  75                  80

Trp Thr Pro Leu His Leu Ala Ala Lys Tyr Gly His Leu Glu Ile Val
                85                  90                  95

Glu Val Leu Leu Lys His Gly Ala Asp Val Asn Ala Ile Asp Asn Ala
            100                 105                 110

Gly Lys Thr Pro Leu His Leu Ala Ala Ala His Gly His Leu Glu Ile
        115                 120                 125

Val Glu Val Leu Leu Lys Tyr Gly Ala Asp Val Asn Ala Gln Asp Lys
    130                 135                 140

Phe Gly Lys Thr Pro Phe Asp Leu Ala Ile Asp Asn Gly Asn Glu Asp
145                 150                 155                 160

Ile Ala Glu Val Leu Gln Lys Ala Ala
                165
```

<210> SEQ ID NO 65
<211> LENGTH: 254
<212> TYPE: PRT
<213> ORGANISM: Artificial Sequence
<220> FEATURE:
<223> OTHER INFORMATION: scFV-A21HL, a scFV binding the extracellular domain 1 of HER2 with a glycine serine linker connecting heavy and light chain

<400> SEQUENCE: 65

```
Glu Val Gln Leu Gln Gln Ser Gly Pro Glu Val Val Lys Thr Gly Ala
1               5                   10                  15

Ser Val Lys Ile Ser Cys Lys Ala Ser Gly Tyr Ser Phe Thr Gly Tyr
            20                  25                  30

Phe Ile Asn Trp Val Lys Lys Asn Ser Gly Lys Ser Pro Glu Trp Ile
        35                  40                  45

Gly His Ile Ser Ser Ser Tyr Ala Thr Ser Thr Tyr Asn Gln Lys Phe
    50                  55                  60

Lys Asn Lys Ala Ala Phe Thr Val Asp Thr Ser Ser Ser Thr Ala Phe
65                  70                  75                  80

Met Gln Leu Asn Ser Leu Thr Ser Glu Asp Ser Ala Asp Tyr Tyr Cys
                85                  90                  95

Val Arg Ser Gly Asn Tyr Glu Glu Tyr Ala Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Val Leu
    130                 135                 140

Thr Gln Thr Pro Ser Ser Leu Pro Val Ser Val Gly Glu Lys Val Thr
145                 150                 155                 160

Met Thr Cys Lys Ser Ser Gln Thr Leu Leu Tyr Ser Asn Asn Gln Lys
```

-continued

```
                165                 170                 175

Asn Tyr Leu Ala Trp Tyr Gln Gln Lys Pro Gly Gln Ser Pro Lys Leu
            180                 185                 190

Leu Ile Ser Trp Ala Phe Thr Arg Lys Ser Gly Val Pro Asp Arg Phe
        195                 200                 205

Thr Gly Ser Gly Ser Gly Thr Asp Phe Thr Leu Thr Ile Gly Ser Val
    210                 215                 220

Lys Ala Glu Asp Leu Ala Val Tyr Tyr Cys Gln Gln Tyr Ser Asn Tyr
225                 230                 235                 240

Pro Trp Thr Phe Gly Gly Gly Thr Arg Leu Glu Ile Lys Arg
                245                 250


<210> SEQ ID NO 66
<211> LENGTH: 254
<212> TYPE: PRT
<213> ORGANISM: Artificial Sequence
<220> FEATURE:
<223> OTHER INFORMATION: scFV A21LH, a scFV binding the extracellular
      domain 1 of HER2 with a glycine serine linker connecting heavy and
      light chain

<400> SEQUENCE: 66

Asp Ile Val Leu Thr Gln Thr Pro Ser Ser Leu Pro Val Ser Val Gly
1               5                   10                  15

Glu Lys Val Thr Met Thr Cys Lys Ser Ser Gln Thr Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Ser Trp Ala Phe Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Gly Ser Val Lys Ala Glu Asp Leu Ala Val Tyr Tyr Cys Gln Gln
                85                  90                  95

Tyr Ser Asn Tyr Pro Trp Thr Phe Gly Gly Gly Thr Arg Leu Glu Ile
            100                 105                 110

Lys Arg Gly Gly Gly Gly Ser Gly Gly Gly Gly Ser Gly Gly Gly Gly
        115                 120                 125

Ser Gly Gly Gly Gly Ser Glu Val Gln Leu Gln Gln Ser Gly Pro Glu
    130                 135                 140

Val Val Lys Thr Gly Ala Ser Val Lys Ile Ser Cys Lys Ala Ser Gly
145                 150                 155                 160

Tyr Ser Phe Thr Gly Tyr Phe Ile Asn Trp Val Lys Lys Asn Ser Gly
                165                 170                 175

Lys Ser Pro Glu Trp Ile Gly His Ile Ser Ser Ser Tyr Ala Thr Ser
            180                 185                 190

Thr Tyr Asn Gln Lys Phe Lys Asn Lys Ala Ala Phe Thr Val Asp Thr
        195                 200                 205

Ser Ser Ser Thr Ala Phe Met Gln Leu Asn Ser Leu Thr Ser Glu Asp
    210                 215                 220

Ser Ala Asp Tyr Tyr Cys Val Arg Ser Gly Asn Tyr Glu Glu Tyr Ala
225                 230                 235                 240

Met Asp Tyr Trp Gly Gln Gly Thr Ser Val Thr Val Ser Ser
                245                 250


<210> SEQ ID NO 67
```

<211> LENGTH: 248
<212> TYPE: PRT
<213> ORGANISM: Artificial Sequence
<220> FEATURE:
<223> OTHER INFORMATION: scFV 4D5HL, a scFV binding the extracellular domain 4 of HER2 with a glycine serine linker connecting heavy and light chain

<400> SEQUENCE: 67

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Val Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Asn Thr Ala Val Ala Trp Tyr
                165                 170                 175

Gln Gln Lys Pro Gly Lys Ala Pro Lys Leu Leu Ile Tyr Ser Ala Ser
            180                 185                 190

Phe Leu Tyr Ser Gly Val Pro Ser Arg Phe Ser Gly Ser Arg Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln His Tyr Thr Thr Pro Pro Thr Phe Gly Gln
225                 230                 235                 240

Gly Thr Lys Val Glu Leu Lys Arg
                245
```

<210> SEQ ID NO 68
<211> LENGTH: 248
<212> TYPE: PRT
<213> ORGANISM: Artificial Sequence
<220> FEATURE:
<223> OTHER INFORMATION: scFV 4D5LH, a scFV binding the extracellular domain 4 of HER2 with a glycine serine linker connecting heavy and light chain

<400> SEQUENCE: 68

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Leu Lys Arg Gly Gly Gly Gly
            100                 105                 110

Ser Gly Gly Gly Gly Ser Gly Gly Gly Gly Ser Gly Gly Gly Gly Ser
        115                 120                 125

Glu Val Lys Leu Val Glu Ser Gly Gly Gly Leu Val Gln Pro Gly Gly
    130                 135                 140

Ser Leu Arg Leu Ser Cys Ala Thr Ser Gly Phe Asn Ile Lys Asp Thr
145                 150                 155                 160

Tyr Ile His Trp Val Arg Gln Ala Pro Gly Lys Gly Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Thr Val Thr Val Ser Ser
                245


<210> SEQ ID NO 69
<211> LENGTH: 249
<212> TYPE: PRT
<213> ORGANISM: Artificial Sequence
<220> FEATURE:
<223> OTHER INFORMATION: scFV 4D5LH alternative, a scFV binding the
      extracellular domain 4 of HER2 with an alternative linker
      connecting heavy and light chain

<400> SEQUENCE: 69

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Leu Lys Arg Ala Thr Pro Ser
            100                 105                 110

His Asn Ser His Gln Val Pro Ser Ala Gly Gly Pro Thr Ala Asn Ser
        115                 120                 125

Gly Glu Val Lys Leu Val Glu Ser Gly Gly Gly Leu Val Gln Pro Gly
    130                 135                 140

Gly Ser Leu Arg Leu Ser Cys Ala Thr Ser Gly Phe Asn Ile Lys Asp
```

```
145                 150                 155                 160

Thr Tyr Ile His Trp Val Arg Gln Ala Pro Gly Lys Gly Leu Glu Trp
                165                 170                 175

Val Ala Arg Ile Tyr Pro Thr Asn Gly Tyr Thr Arg Tyr Ala Asp Ser
            180                 185                 190

Val Lys Gly Arg Phe Thr Ile Ser Ala Asp Thr Ser Lys Asn Thr Ala
        195                 200                 205

Tyr Leu Gln Met Asn Ser Leu Arg Ala Glu Asp Thr Ala Val Tyr Tyr
    210                 215                 220

Cys Ser Arg Trp Gly Gly Asp Gly Phe Tyr Ala Met Asp Tyr Trp Gly
225                 230                 235                 240

Gln Gly Thr Thr Val Thr Val Ser Ser
                245


<210> SEQ ID NO 70
<211> LENGTH: 412
<212> TYPE: PRT
<213> ORGANISM: Artificial Sequence
<220> FEATURE:
<223> OTHER INFORMATION: A21HL_L4_G3, a bispecific HER2 binding agent
      comprising a scFV antibody fragment binding domain 1 of HER2 and
      a DARPin binding domain 4 of HER2 connected by a glycine serine
      linker

<400> SEQUENCE: 70

Ala Gly Ser Glu Val Gln Leu Gln Gln Ser Gly Pro Glu Val Val Lys
1               5                   10                  15

Thr Gly Ala Ser Val Lys Ile Ser Cys Lys Ala Ser Gly Tyr Ser Phe
            20                  25                  30

Thr Gly Tyr Phe Ile Asn Trp Val Lys Lys Asn Ser Gly Lys Ser Pro
        35                  40                  45

Glu Trp Ile Gly His Ile Ser Ser Ser Tyr Ala Thr Ser Thr Tyr Asn
    50                  55                  60

Gln Lys Phe Lys Asn Lys Ala Ala Phe Thr Val Asp Thr Ser Ser Ser
65                  70                  75                  80

Thr Ala Phe Met Gln Leu Asn Ser Leu Thr Ser Glu Asp Ser Ala Asp
                85                  90                  95

Tyr Tyr Cys Val Arg Ser Gly Asn Tyr Glu Glu Tyr Ala Met Asp Tyr
            100                 105                 110

Trp Gly Gln Gly Thr Ser Val Thr Val Ser Ser Gly Gly Gly Gly Ser
        115                 120                 125

Gly Gly Gly Gly Ser Gly Gly Gly Gly Ser Gly Gly Gly Gly Ser Asp
    130                 135                 140

Ile Val Leu Thr Gln Thr Pro Ser Ser Leu Pro Val Ser Val Gly Glu
145                 150                 155                 160

Lys Val Thr Met Thr Cys Lys Ser Ser Gln Thr Leu Leu Tyr Ser Asn
                165                 170                 175

Asn Gln Lys Asn Tyr Leu Ala Trp Tyr Gln Gln Lys Pro Gly Gln Ser
            180                 185                 190

Pro Lys Leu Leu Ile Ser Trp Ala Phe Thr Arg Lys Ser Gly Val Pro
        195                 200                 205

Asp Arg Phe Thr Gly Ser Gly Ser Gly Thr Asp Phe Thr Leu Thr Ile
    210                 215                 220

Gly Ser Val Lys Ala Glu Asp Leu Ala Val Tyr Tyr Cys Gln Gln Tyr
225                 230                 235                 240

Ser Asn Tyr Pro Trp Thr Phe Gly Gly Gly Thr Arg Leu Glu Ile Lys
```

-continued

```
                245                 250                 255

Arg Lys Leu Gly Gly Gly Gly Ser Gly Gly Gly Gly Ser Gly Gly Gly
            260                 265                 270

Gly Ser Gly Gly Gly Gly Ser Arg Ser Asp Leu Gly Lys Lys Leu Leu
        275                 280                 285

Glu Ala Ala Arg Ala Gly Gln Asp Asp Glu Val Arg Ile Leu Met Ala
    290                 295                 300

Asn Gly Ala Asp Val Asn Ala Lys Asp Glu Tyr Gly Leu Thr Pro Leu
305                 310                 315                 320

Tyr Leu Ala Thr Ala His Gly His Leu Glu Ile Val Glu Val Leu Leu
                325                 330                 335

Lys Asn Gly Ala Asp Val Asn Ala Val Asp Ala Ile Gly Phe Thr Pro
            340                 345                 350

Leu His Leu Ala Ala Phe Ile Gly His Leu Glu Ile Ala Glu Val Leu
        355                 360                 365

Leu Lys His Gly Ala Asp Val Asn Ala Gln Asp Lys Phe Gly Lys Thr
    370                 375                 380

Ala Phe Asp Ile Ser Ile Gly Asn Gly Asn Glu Asp Leu Ala Glu Ile
385                 390                 395                 400

Leu Gln Lys Leu Gly Ser His His His His His His
                405                 410


<210> SEQ ID NO 71
<211> LENGTH: 412
<212> TYPE: PRT
<213> ORGANISM: Artificial Sequence
<220> FEATURE:
<223> OTHER INFORMATION: A21LH_L4_G3, a bispecific HER2 binding agent
      comprising a scFV antibody fragment binding domain 1 of HER2 and
      a DARPin binding domain 4 of HER2 connected by a glycine serine
      linker

<400> SEQUENCE: 71

Ala Gly Ser Asp Ile Val Leu Thr Gln Thr Pro Ser Ser Leu Pro Val
1               5                   10                  15

Ser Val Gly Glu Lys Val Thr Met Thr Cys Lys Ser Ser Gln Thr Leu
            20                  25                  30

Leu Tyr Ser Asn Asn Gln Lys Asn Tyr Leu Ala Trp Tyr Gln Gln Lys
        35                  40                  45

Pro Gly Gln Ser Pro Lys Leu Leu Ile Ser Trp Ala Phe Thr Arg Lys
    50                  55                  60

Ser Gly Val Pro Asp Arg Phe Thr Gly Ser Gly Ser Gly Thr Asp Phe
65                  70                  75                  80

Thr Leu Thr Ile Gly Ser Val Lys Ala Glu Asp Leu Ala Val Tyr Tyr
                85                  90                  95

Cys Gln Gln Tyr Ser Asn Tyr Pro Trp Thr Phe Gly Gly Gly Thr Arg
            100                 105                 110

Leu Glu Ile Lys Arg Gly Gly Gly Gly Ser Gly Gly Gly Gly Ser Gly
        115                 120                 125

Gly Gly Gly Ser Gly Gly Gly Gly Ser Glu Val Gln Leu Gln Gln Ser
    130                 135                 140

Gly Pro Glu Val Val Lys Thr Gly Ala Ser Val Lys Ile Ser Cys Lys
145                 150                 155                 160

Ala Ser Gly Tyr Ser Phe Thr Gly Tyr Phe Ile Asn Trp Val Lys Lys
                165                 170                 175

Asn Ser Gly Lys Ser Pro Glu Trp Ile Gly His Ile Ser Ser Ser Tyr
```

```
            180                 185                 190

Ala Thr Ser Thr Tyr Asn Gln Lys Phe Lys Asn Lys Ala Ala Phe Thr
        195                 200                 205

Val Asp Thr Ser Ser Ser Thr Ala Phe Met Gln Leu Asn Ser Leu Thr
    210                 215                 220

Ser Glu Asp Ser Ala Asp Tyr Tyr Cys Val Arg Ser Gly Asn Tyr Glu
225                 230                 235                 240

Glu Tyr Ala Met Asp Tyr Trp Gly Gln Gly Thr Ser Val Thr Val Ser
                245                 250                 255

Ser Lys Leu Gly Gly Gly Gly Ser Gly Gly Gly Gly Ser Gly Gly Gly
            260                 265                 270

Gly Ser Gly Gly Gly Gly Ser Arg Ser Asp Leu Gly Lys Lys Leu Leu
        275                 280                 285

Glu Ala Ala Arg Ala Gly Gln Asp Asp Glu Val Arg Ile Leu Met Ala
    290                 295                 300

Asn Gly Ala Asp Val Asn Ala Lys Asp Glu Tyr Gly Leu Thr Pro Leu
305                 310                 315                 320

Tyr Leu Ala Thr Ala His Gly His Leu Glu Ile Val Glu Val Leu Leu
                325                 330                 335

Lys Asn Gly Ala Asp Val Asn Ala Val Asp Ala Ile Gly Phe Thr Pro
            340                 345                 350

Leu His Leu Ala Ala Phe Ile Gly His Leu Glu Ile Ala Glu Val Leu
        355                 360                 365

Leu Lys His Gly Ala Asp Val Asn Ala Gln Asp Lys Phe Gly Lys Thr
    370                 375                 380

Ala Phe Asp Ile Ser Ile Gly Asn Gly Asn Glu Asp Leu Ala Glu Ile
385                 390                 395                 400

Leu Gln Lys Leu Gly Ser His His His His His His
                405                 410


<210> SEQ ID NO 72
<211> LENGTH: 445
<212> TYPE: PRT
<213> ORGANISM: Artificial Sequence
<220> FEATURE:
<223> OTHER INFORMATION: A21HL_L4_H14, a bispecific HER2 binding agent
      comprising a scFV antibody fragment binding domain 1 of HER2 and
      a DARPin binding domain 4 of HER2 connected by a glycine serine
      linker

<400> SEQUENCE: 72

Ala Gly Ser Glu Val Gln Leu Gln Gln Ser Gly Pro Glu Val Val Lys
1               5                   10                  15

Thr Gly Ala Ser Val Lys Ile Ser Cys Lys Ala Ser Gly Tyr Ser Phe
            20                  25                  30

Thr Gly Tyr Phe Ile Asn Trp Val Lys Lys Asn Ser Gly Lys Ser Pro
        35                  40                  45

Glu Trp Ile Gly His Ile Ser Ser Ser Tyr Ala Thr Ser Thr Tyr Asn
    50                  55                  60

Gln Lys Phe Lys Asn Lys Ala Ala Phe Thr Val Asp Thr Ser Ser Ser
65                  70                  75                  80

Thr Ala Phe Met Gln Leu Asn Ser Leu Thr Ser Glu Asp Ser Ala Asp
                85                  90                  95

Tyr Tyr Cys Val Arg Ser Gly Asn Tyr Glu Glu Tyr Ala Met Asp Tyr
            100                 105                 110

Trp Gly Gln Gly Thr Ser Val Thr Val Ser Ser Gly Gly Gly Gly Ser
```

```
        115                 120                 125

Gly Gly Gly Gly Ser Gly Gly Gly Gly Ser Gly Gly Gly Gly Ser Asp
    130                 135                 140

Ile Val Leu Thr Gln Thr Pro Ser Ser Leu Pro Val Ser Val Gly Glu
145                 150                 155                 160

Lys Val Thr Met Thr Cys Lys Ser Ser Gln Thr Leu Leu Tyr Ser Asn
                165                 170                 175

Asn Gln Lys Asn Tyr Leu Ala Trp Tyr Gln Gln Lys Pro Gly Gln Ser
            180                 185                 190

Pro Lys Leu Leu Ile Ser Trp Ala Phe Thr Arg Lys Ser Gly Val Pro
        195                 200                 205

Asp Arg Phe Thr Gly Ser Gly Ser Gly Thr Asp Phe Thr Leu Thr Ile
    210                 215                 220

Gly Ser Val Lys Ala Glu Asp Leu Ala Val Tyr Tyr Cys Gln Gln Tyr
225                 230                 235                 240

Ser Asn Tyr Pro Trp Thr Phe Gly Gly Gly Thr Arg Leu Glu Ile Lys
                245                 250                 255

Arg Lys Leu Gly Gly Gly Gly Ser Gly Gly Gly Gly Ser Gly Gly Gly
            260                 265                 270

Gly Ser Gly Gly Gly Gly Ser Arg Ser Asp Leu Gly Lys Lys Leu Leu
        275                 280                 285

Glu Ala Ala Arg Ala Gly Gln Asp Asp Glu Val Arg Ile Leu Met Ala
    290                 295                 300

Asn Gly Ala Asp Val Asn Ala Thr Asp Ile His Gly His Thr Pro Leu
305                 310                 315                 320

His Leu Ala Ala Ala Met Gly His Leu Glu Ile Val Glu Val Leu Leu
                325                 330                 335

Lys Asn Gly Ala Asp Val Asn Ala Asn Asp Trp Arg Gly Phe Thr Pro
            340                 345                 350

Leu His Leu Ala Ala Leu Asn Gly His Leu Glu Ile Val Glu Val Leu
        355                 360                 365

Leu Lys Asn Gly Ala Asp Val Asn Ala Thr Asp Thr Ala Gly Asn Thr
    370                 375                 380

Pro Leu His Leu Ala Ala Trp Phe Gly His Leu Glu Ile Val Glu Val
385                 390                 395                 400

Leu Leu Lys Asn Gly Ala Asp Val Asn Ala Gln Asp Lys Phe Gly Lys
                405                 410                 415

Thr Ala Phe Asp Ile Ser Ile Asp Asn Gly Asn Glu Asp Leu Ala Glu
            420                 425                 430

Ile Leu Gln Lys Leu Gly Ser His His His His His His
        435                 440                 445


<210> SEQ ID NO 73
<211> LENGTH: 438
<212> TYPE: PRT
<213> ORGANISM: Artificial Sequence
<220> FEATURE:
<223> OTHER INFORMATION: H14_L4_A21LH, a bispecific HER2 binding agent
      comprising a DARPin binding domain 4 of HER2 and a scFV antibody
      fragment binding domain 1 of HER2connected by a glycine serine
      linker

<400> SEQUENCE: 73

Ala Gly Ser Asp Leu Gly Lys Lys Leu Leu Glu Ala Ala Arg Ala Gly
1               5                   10                  15

Gln Asp Asp Glu Val Arg Ile Leu Met Ala Asn Gly Ala Asp Val Asn
```

```
            20                  25                  30

Ala Thr Asp Ile His Gly His Thr Pro Leu His Leu Ala Ala Ala Met
        35                  40                  45

Gly His Leu Glu Ile Val Glu Val Leu Leu Lys Asn Gly Ala Asp Val
    50                  55                  60

Asn Ala Asn Asp Trp Arg Gly Phe Thr Pro Leu His Leu Ala Ala Leu
65                  70                  75                  80

Asn Gly His Leu Glu Ile Val Glu Val Leu Leu Lys Asn Gly Ala Asp
                85                  90                  95

Val Asn Ala Thr Asp Thr Ala Gly Asn Thr Pro Leu His Leu Ala Ala
            100                 105                 110

Trp Phe Gly His Leu Glu Ile Val Glu Val Leu Leu Lys Asn Gly Ala
        115                 120                 125

Asp Val Asn Ala Gln Asp Lys Phe Gly Lys Thr Ala Phe Asp Ile Ser
    130                 135                 140

Ile Asp Asn Gly Asn Glu Asp Leu Ala Glu Ile Leu Gln Lys Leu Gly
145                 150                 155                 160

Gly Gly Gly Ser Gly Gly Gly Gly Ser Gly Gly Gly Gly Ser Gly Gly
                165                 170                 175

Gly Gly Ser Arg Ser Asp Ile Val Leu Thr Gln Thr Pro Ser Ser Leu
            180                 185                 190

Pro Val Ser Val Gly Glu Lys Val Thr Met Thr Cys Lys Ser Ser Gln
        195                 200                 205

Thr Leu Leu Tyr Ser Asn Asn Gln Lys Asn Tyr Leu Ala Trp Tyr Gln
    210                 215                 220

Gln Lys Pro Gly Gln Ser Pro Lys Leu Leu Ile Ser Trp Ala Phe Thr
225                 230                 235                 240

Arg Lys Ser Gly Val Pro Asp Arg Phe Thr Gly Ser Gly Ser Gly Thr
                245                 250                 255

Asp Phe Thr Leu Thr Ile Gly Ser Val Lys Ala Glu Asp Leu Ala Val
            260                 265                 270

Tyr Tyr Cys Gln Gln Tyr Ser Asn Tyr Pro Trp Thr Phe Gly Gly Gly
        275                 280                 285

Thr Arg Leu Glu Ile Lys Arg Gly Gly Gly Gly Ser Gly Gly Gly Gly
    290                 295                 300

Ser Gly Gly Gly Gly Ser Gly Gly Gly Gly Ser Glu Val Gln Leu Gln
305                 310                 315                 320

Gln Ser Gly Pro Glu Val Val Lys Thr Gly Ala Ser Val Lys Ile Ser
                325                 330                 335

Cys Lys Ala Ser Gly Tyr Ser Phe Thr Gly Tyr Phe Ile Asn Trp Val
            340                 345                 350

Lys Lys Asn Ser Gly Lys Ser Pro Glu Trp Ile Gly His Ile Ser Ser
        355                 360                 365

Ser Tyr Ala Thr Ser Thr Tyr Asn Gln Lys Phe Lys Asn Lys Ala Ala
    370                 375                 380

Phe Thr Val Asp Thr Ser Ser Ser Thr Ala Phe Met Gln Leu Asn Ser
385                 390                 395                 400

Leu Thr Ser Glu Asp Ser Ala Asp Tyr Tyr Cys Val Arg Ser Gly Asn
                405                 410                 415

Tyr Glu Glu Tyr Ala Met Asp Tyr Trp Gly Gln Gly Thr Ser Val Thr
            420                 425                 430

Val Ser Ser Lys Leu Asn
        435
```

<210> SEQ ID NO 74
<211> LENGTH: 438
<212> TYPE: PRT
<213> ORGANISM: Artificial Sequence
<220> FEATURE:
<223> OTHER INFORMATION: H14_L4_A21HL, a bispecific HER2 binding agent comprising a DARPin binding domain 4 of HER2 and a scFV antibody fragment binding domain 1 of HER2connected by a glycine serine linker

<400> SEQUENCE: 74

```
Ala Gly Ser Asp Leu Gly Lys Lys Leu Leu Glu Ala Ala Arg Ala Gly
1               5                   10                  15

Gln Asp Asp Glu Val Arg Ile Leu Met Ala Asn Gly Ala Asp Val Asn
            20                  25                  30

Ala Thr Asp Ile His Gly His Thr Pro Leu His Leu Ala Ala Ala Met
        35                  40                  45

Gly His Leu Glu Ile Val Glu Val Leu Leu Lys Asn Gly Ala Asp Val
    50                  55                  60

Asn Ala Asn Asp Trp Arg Gly Phe Thr Pro Leu His Leu Ala Ala Leu
65                  70                  75                  80

Asn Gly His Leu Glu Ile Val Glu Val Leu Leu Lys Asn Gly Ala Asp
                85                  90                  95

Val Asn Ala Thr Asp Thr Ala Gly Asn Thr Pro Leu His Leu Ala Ala
            100                 105                 110

Trp Phe Gly His Leu Glu Ile Val Glu Val Leu Leu Lys Asn Gly Ala
        115                 120                 125

Asp Val Asn Ala Gln Asp Lys Phe Gly Lys Thr Ala Phe Asp Ile Ser
    130                 135                 140

Ile Asp Asn Gly Asn Glu Asp Leu Ala Glu Ile Leu Gln Lys Leu Gly
145                 150                 155                 160

Gly Gly Gly Ser Gly Gly Gly Gly Ser Gly Gly Gly Gly Ser Gly Gly
                165                 170                 175

Gly Gly Ser Arg Ser Glu Val Gln Leu Gln Gln Ser Gly Pro Glu Val
            180                 185                 190

Val Lys Thr Gly Ala Ser Val Lys Ile Ser Cys Lys Ala Ser Gly Tyr
        195                 200                 205

Ser Phe Thr Gly Tyr Phe Ile Asn Trp Val Lys Lys Asn Ser Gly Lys
    210                 215                 220

Ser Pro Glu Trp Ile Gly His Ile Ser Ser Ser Tyr Ala Thr Ser Thr
225                 230                 235                 240

Tyr Asn Gln Lys Phe Lys Asn Lys Ala Ala Phe Thr Val Asp Thr Ser
                245                 250                 255

Ser Ser Thr Ala Phe Met Gln Leu Asn Ser Leu Thr Ser Glu Asp Ser
            260                 265                 270

Ala Asp Tyr Tyr Cys Val Arg Ser Gly Asn Tyr Glu Glu Tyr Ala Met
        275                 280                 285

Asp Tyr Trp Gly Gln Gly Thr Ser Val Thr Val Ser Ser Gly Gly Gly
    290                 295                 300

Gly Ser Gly Gly Gly Gly Ser Gly Gly Gly Gly Ser Gly Gly Gly Gly
305                 310                 315                 320

Ser Asp Ile Val Leu Thr Gln Thr Pro Ser Ser Leu Pro Val Ser Val
                325                 330                 335

Gly Glu Lys Val Thr Met Thr Cys Lys Ser Ser Gln Thr Leu Leu Tyr
            340                 345                 350
```

```
Ser Asn Asn Gln Lys Asn Tyr Leu Ala Trp Tyr Gln Gln Lys Pro Gly
        355                 360                 365

Gln Ser Pro Lys Leu Leu Ile Ser Trp Ala Phe Thr Arg Lys Ser Gly
    370                 375                 380

Val Pro Asp Arg Phe Thr Gly Ser Gly Ser Gly Thr Asp Phe Thr Leu
385                 390                 395                 400

Thr Ile Gly Ser Val Lys Ala Glu Asp Leu Ala Val Tyr Tyr Cys Gln
                405                 410                 415

Gln Tyr Ser Asn Tyr Pro Trp Thr Phe Gly Gly Gly Thr Arg Leu Glu
            420                 425                 430

Ile Lys Arg Lys Leu Asn
        435


<210> SEQ ID NO 75
<211> LENGTH: 405
<212> TYPE: PRT
<213> ORGANISM: Artificial Sequence
<220> FEATURE:
<223> OTHER INFORMATION: G3_L4_A21LH, a bispecific HER2 binding agent
      comprising a DARPin binding domain 4 of HER2 and a scFV antibody
      fragment binding domain 1 of HER2connected by a glycine serine
      linker

<400> SEQUENCE: 75

Ala Gly Ser Asp Leu Gly Lys Lys Leu Leu Glu Ala Ala Arg Ala Gly
1               5                   10                  15

Gln Asp Asp Glu Val Arg Ile Leu Met Ala Asn Gly Ala Asp Val Asn
            20                  25                  30

Ala Lys Asp Glu Tyr Gly Leu Thr Pro Leu Tyr Leu Ala Thr Ala His
        35                  40                  45

Gly His Leu Glu Ile Val Glu Val Leu Leu Lys Asn Gly Ala Asp Val
    50                  55                  60

Asn Ala Val Asp Ala Ile Gly Phe Thr Pro Leu His Leu Ala Ala Phe
65                  70                  75                  80

Ile Gly His Leu Glu Ile Ala Glu Val Leu Leu Lys His Gly Ala Asp
                85                  90                  95

Val Asn Ala Gln Asp Lys Phe Gly Lys Thr Ala Phe Asp Ile Ser Ile
            100                 105                 110

Gly Asn Gly Asn Glu Asp Leu Ala Glu Ile Leu Gln Lys Leu Gly Gly
        115                 120                 125

Gly Gly Ser Gly Gly Gly Gly Ser Gly Gly Gly Gly Ser Gly Gly Gly
    130                 135                 140

Gly Ser Arg Ser Asp Ile Val Leu Thr Gln Thr Pro Ser Ser Leu Pro
145                 150                 155                 160

Val Ser Val Gly Glu Lys Val Thr Met Thr Cys Lys Ser Ser Gln Thr
                165                 170                 175

Leu Leu Tyr Ser Asn Asn Gln Lys Asn Tyr Leu Ala Trp Tyr Gln Gln
            180                 185                 190

Lys Pro Gly Gln Ser Pro Lys Leu Leu Ile Ser Trp Ala Phe Thr Arg
        195                 200                 205

Lys Ser Gly Val Pro Asp Arg Phe Thr Gly Ser Gly Ser Gly Thr Asp
    210                 215                 220

Phe Thr Leu Thr Ile Gly Ser Val Lys Ala Glu Asp Leu Ala Val Tyr
225                 230                 235                 240

Tyr Cys Gln Gln Tyr Ser Asn Tyr Pro Trp Thr Phe Gly Gly Gly Thr
                245                 250                 255
```

```
Arg Leu Glu Ile Lys Arg Gly Gly Gly Gly Ser Gly Gly Gly Gly Ser
            260                 265                 270

Gly Gly Gly Gly Ser Gly Gly Gly Gly Ser Glu Val Gln Leu Gln Gln
        275                 280                 285

Ser Gly Pro Glu Val Val Lys Thr Gly Ala Ser Val Lys Ile Ser Cys
    290                 295                 300

Lys Ala Ser Gly Tyr Ser Phe Thr Gly Tyr Phe Ile Asn Trp Val Lys
305                 310                 315                 320

Lys Asn Ser Gly Lys Ser Pro Glu Trp Ile Gly His Ile Ser Ser Ser
                325                 330                 335

Tyr Ala Thr Ser Thr Tyr Asn Gln Lys Phe Lys Asn Lys Ala Ala Phe
            340                 345                 350

Thr Val Asp Thr Ser Ser Ser Thr Ala Phe Met Gln Leu Asn Ser Leu
        355                 360                 365

Thr Ser Glu Asp Ser Ala Asp Tyr Tyr Cys Val Arg Ser Gly Asn Tyr
    370                 375                 380

Glu Glu Tyr Ala Met Asp Tyr Trp Gly Gln Gly Thr Ser Val Thr Val
385                 390                 395                 400

Ser Ser Lys Leu Asn
                405


<210> SEQ ID NO 76
<211> LENGTH: 405
<212> TYPE: PRT
<213> ORGANISM: Artificial Sequence
<220> FEATURE:
<223> OTHER INFORMATION: G3_L4_A21HL, a bispecific HER2 binding agent
      comprising a DARPin binding domain 4 of HER2 and a scFV antibody
      fragment binding domain 1 of HER2connected by a glycine serine
      linker

<400> SEQUENCE: 76

Ala Gly Ser Asp Leu Gly Lys Lys Leu Leu Glu Ala Ala Arg Ala Gly
1               5                   10                  15

Gln Asp Asp Glu Val Arg Ile Leu Met Ala Asn Gly Ala Asp Val Asn
            20                  25                  30

Ala Lys Asp Glu Tyr Gly Leu Thr Pro Leu Tyr Leu Ala Thr Ala His
        35                  40                  45

Gly His Leu Glu Ile Val Glu Val Leu Leu Lys Asn Gly Ala Asp Val
    50                  55                  60

Asn Ala Val Asp Ala Ile Gly Phe Thr Pro Leu His Leu Ala Ala Phe
65                  70                  75                  80

Ile Gly His Leu Glu Ile Ala Glu Val Leu Leu Lys His Gly Ala Asp
                85                  90                  95

Val Asn Ala Gln Asp Lys Phe Gly Lys Thr Ala Phe Asp Ile Ser Ile
            100                 105                 110

Gly Asn Gly Asn Glu Asp Leu Ala Glu Ile Leu Gln Lys Leu Gly Gly
        115                 120                 125

Gly Gly Ser Gly Gly Gly Gly Ser Gly Gly Gly Gly Ser Gly Gly Gly
    130                 135                 140

Gly Ser Arg Ser Glu Val Gln Leu Gln Gln Ser Gly Pro Glu Val Val
145                 150                 155                 160

Lys Thr Gly Ala Ser Val Lys Ile Ser Cys Lys Ala Ser Gly Tyr Ser
                165                 170                 175

Phe Thr Gly Tyr Phe Ile Asn Trp Val Lys Lys Asn Ser Gly Lys Ser
            180                 185                 190
```

```
Pro Glu Trp Ile Gly His Ile Ser Ser Ser Tyr Ala Thr Ser Thr Tyr
        195                 200                 205

Asn Gln Lys Phe Lys Asn Lys Ala Ala Phe Thr Val Asp Thr Ser Ser
    210                 215                 220

Ser Thr Ala Phe Met Gln Leu Asn Ser Leu Thr Ser Glu Asp Ser Ala
225                 230                 235                 240

Asp Tyr Tyr Cys Val Arg Ser Gly Asn Tyr Glu Glu Tyr Ala Met Asp
                245                 250                 255

Tyr Trp Gly Gln Gly Thr Ser Val Thr Val Ser Ser Gly Gly Gly Gly
            260                 265                 270

Ser Gly Gly Gly Gly Ser Gly Gly Gly Gly Ser Gly Gly Gly Gly Ser
        275                 280                 285

Asp Ile Val Leu Thr Gln Thr Pro Ser Ser Leu Pro Val Ser Val Gly
    290                 295                 300

Glu Lys Val Thr Met Thr Cys Lys Ser Ser Gln Thr Leu Leu Tyr Ser
305                 310                 315                 320

Asn Asn Gln Lys Asn Tyr Leu Ala Trp Tyr Gln Gln Lys Pro Gly Gln
                325                 330                 335

Ser Pro Lys Leu Leu Ile Ser Trp Ala Phe Thr Arg Lys Ser Gly Val
            340                 345                 350

Pro Asp Arg Phe Thr Gly Ser Gly Ser Gly Thr Asp Phe Thr Leu Thr
        355                 360                 365

Ile Gly Ser Val Lys Ala Glu Asp Leu Ala Val Tyr Tyr Cys Gln Gln
    370                 375                 380

Tyr Ser Asn Tyr Pro Trp Thr Phe Gly Gly Gly Thr Arg Leu Glu Ile
385                 390                 395                 400

Lys Arg Lys Leu Asn
                405
```

<210> SEQ ID NO 77
<211> LENGTH: 397
<212> TYPE: PRT
<213> ORGANISM: Artificial Sequence
<220> FEATURE:
<223> OTHER INFORMATION: A21HL_L1_G3, a bispecific HER2 binding agent comprising a DARPin binding domain 4 of HER2 and a scFV antibody fragment binding domain 1 of HER2connected by a glycine serine linker

<400> SEQUENCE: 77

```
Ala Gly Ser Glu Val Gln Leu Gln Gln Ser Gly Pro Glu Val Val Lys
1               5                   10                  15

Thr Gly Ala Ser Val Lys Ile Ser Cys Lys Ala Ser Gly Tyr Ser Phe
            20                  25                  30

Thr Gly Tyr Phe Ile Asn Trp Val Lys Lys Asn Ser Gly Lys Ser Pro
        35                  40                  45

Glu Trp Ile Gly His Ile Ser Ser Ser Tyr Ala Thr Ser Thr Tyr Asn
    50                  55                  60

Gln Lys Phe Lys Asn Lys Ala Ala Phe Thr Val Asp Thr Ser Ser Ser
65                  70                  75                  80

Thr Ala Phe Met Gln Leu Asn Ser Leu Thr Ser Glu Asp Ser Ala Asp
                85                  90                  95

Tyr Tyr Cys Val Arg Ser Gly Asn Tyr Glu Glu Tyr Ala Met Asp Tyr
            100                 105                 110

Trp Gly Gln Gly Thr Ser Val Thr Val Ser Ser Gly Gly Gly Gly Ser
        115                 120                 125
```

```
Gly Gly Gly Gly Ser Gly Gly Gly Gly Ser Gly Gly Gly Gly Ser Asp
    130                 135                 140

Ile Val Leu Thr Gln Thr Pro Ser Ser Leu Pro Val Ser Val Gly Glu
145                 150                 155                 160

Lys Val Thr Met Thr Cys Lys Ser Ser Gln Thr Leu Leu Tyr Ser Asn
                165                 170                 175

Asn Gln Lys Asn Tyr Leu Ala Trp Tyr Gln Gln Lys Pro Gly Gln Ser
            180                 185                 190

Pro Lys Leu Leu Ile Ser Trp Ala Phe Thr Arg Lys Ser Gly Val Pro
        195                 200                 205

Asp Arg Phe Thr Gly Ser Gly Ser Gly Thr Asp Phe Thr Leu Thr Ile
    210                 215                 220

Gly Ser Val Lys Ala Glu Asp Leu Ala Val Tyr Tyr Cys Gln Gln Tyr
225                 230                 235                 240

Ser Asn Tyr Pro Trp Thr Phe Gly Gly Gly Thr Arg Leu Glu Ile Lys
                245                 250                 255

Arg Lys Leu Gly Gly Gly Gly Ser Arg Ser Asp Leu Gly Lys Lys Leu
            260                 265                 270

Leu Glu Ala Ala Arg Ala Gly Gln Asp Asp Glu Val Arg Ile Leu Met
        275                 280                 285

Ala Asn Gly Ala Asp Val Asn Ala Lys Asp Glu Tyr Gly Leu Thr Pro
    290                 295                 300

Leu Tyr Leu Ala Thr Ala His Gly His Leu Glu Ile Val Glu Val Leu
305                 310                 315                 320

Leu Lys Asn Gly Ala Asp Val Asn Ala Val Asp Ala Ile Gly Phe Thr
                325                 330                 335

Pro Leu His Leu Ala Ala Phe Ile Gly His Leu Glu Ile Ala Glu Val
            340                 345                 350

Leu Leu Lys His Gly Ala Asp Val Asn Ala Gln Asp Lys Phe Gly Lys
        355                 360                 365

Thr Ala Phe Asp Ile Ser Ile Gly Asn Gly Asn Glu Asp Leu Ala Glu
    370                 375                 380

Ile Leu Gln Lys Leu Gly Ser His His His His His His
385                 390                 395
```

```
<210> SEQ ID NO 78
<211> LENGTH: 414
<212> TYPE: PRT
<213> ORGANISM: Artificial Sequence
<220> FEATURE:
<223> OTHER INFORMATION: 9.29_L1_4D5LH, a bispecific HER2 binding agent
      comprising a DARPin binding domain 1 of HER2 and a scFV antibody
      fragment binding domain 4 of HER2connected by a glycine serine
      linker

<400> SEQUENCE: 78

Ala Gly Ser Asp Leu Gly Lys Lys Leu Leu Glu Ala Ala Arg Ala Gly
1               5                   10                  15

Gln Asp Asp Glu Val Arg Ile Leu Met Ala Asn Gly Ala Asp Val Asn
            20                  25                  30

Ala His Asp Phe Tyr Gly Ile Thr Pro Leu His Leu Ala Ala Asn Phe
        35                  40                  45

Gly His Leu Glu Ile Val Glu Val Leu Leu Lys His Gly Ala Asp Val
    50                  55                  60

Asn Ala Phe Asp Tyr Asp Asn Thr Pro Leu His Leu Ala Ala Asp Ala
65                  70                  75                  80
```

Gly His Leu Glu Ile Val Glu Val Leu Leu Lys Tyr Gly Ala Asp Val
85 90 95

Asn Ala Ser Asp Arg Asp Gly His Thr Pro Leu His Leu Ala Ala Arg
100 105 110

Glu Gly His Leu Glu Ile Val Glu Val Leu Leu Lys Asn Gly Ala Asp
115 120 125

Val Asn Ala Gln Asp Lys Phe Gly Lys Thr Ala Phe Asp Ile Ser Ile
130 135 140

Asp Asn Gly Asn Glu Asp Leu Ala Glu Ile Leu Gln Lys Leu Gly Gly
145 150 155 160

Gly Gly Ser Arg Ser Asp Ile Val Met Thr Gln Ser Pro Ser Ser Leu
165 170 175

Ser Ala Ser Val Gly Asp Arg Val Thr Ile Thr Cys Arg Ala Ser Gln
180 185 190

Asp Val Asn Thr Ala Val Ala Trp Tyr Gln Gln Lys Pro Gly Lys Ala
195 200 205

Pro Lys Leu Leu Ile Tyr Ser Ala Ser Phe Leu Tyr Ser Gly Val Pro
210 215 220

Ser Arg Phe Ser Gly Ser Arg Ser Gly Thr Asp Phe Thr Leu Thr Ile
225 230 235 240

Ser Ser Leu Gln Pro Glu Asp Phe Ala Thr Tyr Tyr Cys Gln Gln His
245 250 255

Tyr Thr Thr Pro Pro Thr Phe Gly Gln Gly Thr Lys Val Glu Leu Lys
260 265 270

Arg Ala Thr Pro Ser His Asn Ser His Gln Val Pro Ser Ala Gly Gly
275 280 285

Pro Thr Ala Asn Ser Gly Glu Val Lys Leu Val Glu Ser Gly Gly Gly
290 295 300

Leu Val Gln Pro Gly Gly Ser Leu Arg Leu Ser Cys Ala Thr Ser Gly
305 310 315 320

Phe Asn Ile Lys Asp Thr Tyr Ile His Trp Val Arg Gln Ala Pro Gly
325 330 335

Lys Gly Leu Glu Trp Val Ala Arg Ile Tyr Pro Thr Asn Gly Tyr Thr
340 345 350

Arg Tyr Ala Asp Ser Val Lys Gly Arg Phe Thr Ile Ser Ala Asp Thr
355 360 365

Ser Lys Asn Thr Ala Tyr Leu Gln Met Asn Ser Leu Arg Ala Glu Asp
370 375 380

Thr Ala Val Tyr Tyr Cys Ser Arg Trp Gly Gly Asp Gly Phe Tyr Ala
385 390 395 400

Met Asp Tyr Trp Gly Gln Gly Thr Thr Val Thr Val Ser Ser
405 410

<210> SEQ ID NO 79
<211> LENGTH: 521
<212> TYPE: PRT
<213> ORGANISM: Artificial Sequence
<220> FEATURE:
<223> OTHER INFORMATION: diabody A21H_4D5LH_A21L, comprising scFV A21 binding to domain 1 of HER2 and scFV 4D5 binding to domain 4 of HER2

<400> SEQUENCE: 79

Met Glu Thr Asp Thr Leu Leu Leu Trp Val Leu Leu Leu Trp Val Pro
1 5 10 15

```
Gly Ser Thr Gly Ser Glu Val Gln Leu Gln Gln Ser Gly Pro Glu Val
            20                  25                  30

Val Lys Thr Gly Ala Ser Val Lys Ile Ser Cys Lys Ala Ser Gly Tyr
        35                  40                  45

Ser Phe Thr Gly Tyr Phe Ile Asn Trp Val Lys Lys Asn Ser Gly Lys
    50                  55                  60

Ser Pro Glu Trp Ile Gly His Ile Ser Ser Ser Tyr Ala Thr Ser Thr
65                  70                  75                  80

Tyr Asn Gln Lys Phe Lys Asn Lys Ala Ala Phe Thr Val Asp Thr Ser
                85                  90                  95

Ser Ser Thr Ala Phe Met Gln Leu Asn Ser Leu Thr Ser Glu Asp Ser
            100                 105                 110

Ala Asp Tyr Tyr Cys Val Arg Ser Gly Asn Tyr Glu Glu Tyr Ala Met
        115                 120                 125

Asp Tyr Trp Gly Gln Gly Thr Ser Val Thr Val Ser Ser Gly Gly Gly
    130                 135                 140

Gly Ser Asp Ile Val Met Thr Gln Ser Pro Ser Ser Leu Ser Ala Ser
145                 150                 155                 160

Val Gly Asp Arg Val Thr Ile Thr Cys Arg Ala Ser Gln Asp Val Asn
                165                 170                 175

Thr Ala Val Ala Trp Tyr Gln Gln Lys Pro Gly Lys Ala Pro Lys Leu
            180                 185                 190

Leu Ile Tyr Ser Ala Ser Phe Leu Tyr Ser Gly Val Pro Ser Arg Phe
        195                 200                 205

Ser Gly Ser Arg Ser Gly Thr Asp Phe Thr Leu Thr Ile Ser Ser Leu
    210                 215                 220

Gln Pro Glu Asp Phe Ala Thr Tyr Tyr Cys Gln Gln His Tyr Thr Thr
225                 230                 235                 240

Pro Pro Thr Phe Gly Gln Gly Thr Lys Val Glu Leu Lys Arg Gly Gly
                245                 250                 255

Gly Gly Ser Gly Gly Gly Gly Ser Gly Gly Gly Gly Ser Gly Gly Gly
            260                 265                 270

Gly Ser Glu Val Lys Leu Val Glu Ser Gly Gly Gly Leu Val Gln Pro
        275                 280                 285

Gly Gly Ser Leu Arg Leu Ser Cys Ala Thr Ser Gly Phe Asn Ile Lys
    290                 295                 300

Asp Thr Tyr Ile His Trp Val Arg Gln Ala Pro Gly Lys Gly Leu Glu
305                 310                 315                 320

Trp Val Ala Arg Ile Tyr Pro Thr Asn Gly Tyr Thr Arg Tyr Ala Asp
                325                 330                 335

Ser Val Lys Gly Arg Phe Thr Ile Ser Ala Asp Thr Ser Lys Asn Thr
            340                 345                 350

Ala Tyr Leu Gln Met Asn Ser Leu Arg Ala Glu Asp Thr Ala Val Tyr
        355                 360                 365

Tyr Cys Ser Arg Trp Gly Gly Asp Gly Phe Tyr Ala Met Asp Tyr Trp
    370                 375                 380

Gly Gln Gly Thr Thr Val Thr Val Ser Ser Gly Gly Gly Gly Ser Asp
385                 390                 395                 400

Ile Val Leu Thr Gln Thr Pro Ser Ser Leu Pro Val Ser Val Gly Glu
                405                 410                 415

Lys Val Thr Met Thr Cys Lys Ser Ser Gln Thr Leu Leu Tyr Ser Asn
            420                 425                 430

Asn Gln Lys Asn Tyr Leu Ala Trp Tyr Gln Gln Lys Pro Gly Gln Ser
```

```
        435                 440                 445

Pro Lys Leu Leu Ile Ser Trp Ala Phe Thr Arg Lys Ser Gly Val Pro
    450                 455                 460

Asp Arg Phe Thr Gly Ser Gly Ser Gly Thr Asp Phe Thr Leu Thr Ile
465                 470                 475                 480

Gly Ser Val Lys Ala Glu Asp Leu Ala Val Tyr Tyr Cys Gln Gln Tyr
                485                 490                 495

Ser Asn Tyr Pro Trp Thr Phe Gly Gly Gly Thr Arg Leu Glu Ile Lys
            500                 505                 510

Arg Lys Leu His His His His His His
        515                 520


<210> SEQ ID NO 80
<211> LENGTH: 548
<212> TYPE: PRT
<213> ORGANISM: Artificial Sequence
<220> FEATURE:
<223> OTHER INFORMATION: 4D5HL-L1-A21HL, a bispecific HER2 binding agent
      comprising a scFV antibody fragment binding domain I of HER2 and a
      a scFV antibody fragment binding domain 4 of HER2 connected by a
      glycine serine linker

<400> SEQUENCE: 80

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser Glu Val Lys Leu Val
            20                  25                  30

Glu Ser Gly Gly Gly Leu Val Gln Pro Gly Gly Ser Leu Arg Leu Ser
        35                  40                  45

Cys Ala Thr Ser Gly Phe Asn Ile Lys Asp Thr Tyr Ile His Trp Val
    50                  55                  60

Arg Gln Ala Pro Gly Lys Gly Leu Glu Trp Val Ala Arg Ile Tyr Pro
65                  70                  75                  80

Thr Asn Gly Tyr Thr Arg Tyr Ala Asp Ser Val Lys Gly Arg Phe Thr
                85                  90                  95

Ile Ser Ala Asp Thr Ser Lys Asn Thr Ala Tyr Leu Gln Met Asn Ser
            100                 105                 110

Leu Arg Ala Glu Asp Thr Ala Val Tyr Tyr Cys Ser Arg Trp Gly Gly
        115                 120                 125

Asp Gly Phe Tyr Ala Met Asp Tyr Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Val Met Thr Gln Ser Pro Ser
                165                 170                 175

Ser Leu Ser Ala Ser Val Gly Asp Arg Val Thr Ile Thr Cys Arg Ala
            180                 185                 190

Ser Gln Asp Val Asn Thr Ala Val Ala Trp Tyr Gln Gln Lys Pro Gly
        195                 200                 205

Lys Ala Pro Lys Leu Leu Ile Tyr Ser Ala Ser Phe Leu Tyr Ser Gly
    210                 215                 220

Val Pro Ser Arg Phe Ser Gly Ser Arg Ser Gly Thr Asp Phe Thr Leu
225                 230                 235                 240

Thr Ile Ser Ser Leu Gln Pro Glu Asp Phe Ala Thr Tyr Tyr Cys Gln
                245                 250                 255

Gln His Tyr Thr Thr Pro Pro Thr Phe Gly Gln Gly Thr Lys Val Glu
```

```
            260                 265                 270

Leu Lys Arg Lys Leu Gly Gly Gly Gly Ser Arg Ser Glu Val Gln Leu
        275                 280                 285

Gln Gln Ser Gly Pro Glu Val Val Lys Thr Gly Ala Ser Val Lys Ile
    290                 295                 300

Ser Cys Lys Ala Ser Gly Tyr Ser Phe Thr Gly Tyr Phe Ile Asn Trp
305                 310                 315                 320

Val Lys Lys Asn Ser Gly Lys Ser Pro Glu Trp Ile Gly His Ile Ser
                325                 330                 335

Ser Ser Tyr Ala Thr Ser Thr Tyr Asn Gln Lys Phe Lys Asn Lys Ala
            340                 345                 350

Ala Phe Thr Val Asp Thr Ser Ser Ser Thr Ala Phe Met Gln Leu Asn
        355                 360                 365

Ser Leu Thr Ser Glu Asp Ser Ala Asp Tyr Tyr Cys Val Arg Ser Gly
    370                 375                 380

Asn Tyr Glu Glu Tyr Ala Met Asp Tyr Trp Gly Gln Gly Thr Ser Val
385                 390                 395                 400

Thr Val Ser Ser Gly Gly Gly Gly Ser Gly Gly Gly Gly Ser Gly Gly
                405                 410                 415

Gly Gly Ser Gly Gly Gly Gly Ser Asp Ile Val Leu Thr Gln Thr Pro
            420                 425                 430

Ser Ser Leu Pro Val Ser Val Gly Glu Lys Val Thr Met Thr Cys Lys
        435                 440                 445

Ser Ser Gln Thr Leu Leu Tyr Ser Asn Asn Gln Lys Asn Tyr Leu Ala
    450                 455                 460

Trp Tyr Gln Gln Lys Pro Gly Gln Ser Pro Lys Leu Leu Ile Ser Trp
465                 470                 475                 480

Ala Phe Thr Arg Lys Ser Gly Val Pro Asp Arg Phe Thr Gly Ser Gly
                485                 490                 495

Ser Gly Thr Asp Phe Thr Leu Thr Ile Gly Ser Val Lys Ala Glu Asp
            500                 505                 510

Leu Ala Val Tyr Tyr Cys Gln Gln Tyr Ser Asn Tyr Pro Trp Thr Phe
        515                 520                 525

Gly Gly Gly Thr Arg Leu Glu Ile Lys Arg Lys Leu Gly Ser His His
    530                 535                 540

His His His His
545


<210> SEQ ID NO 81
<211> LENGTH: 548
<212> TYPE: PRT
<213> ORGANISM: Artificial Sequence
<220> FEATURE:
<223> OTHER INFORMATION: 4D5HL-L4-A21LH, a bispecific HER2 binding agent
      comprising a scFV antibody fragment binding domain 1 of HER2 and a
      a scFV antibody fragment binding domain 4 of HER2 connected by a
      glycine serine linker

<400> SEQUENCE: 81

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser Glu Val Lys Leu Val
            20                  25                  30

Glu Ser Gly Gly Gly Leu Val Gln Pro Gly Gly Ser Leu Arg Leu Ser
        35                  40                  45

Cys Ala Thr Ser Gly Phe Asn Ile Lys Asp Thr Tyr Ile His Trp Val
```

-continued

```
    50                  55                  60

Arg Gln Ala Pro Gly Lys Gly Leu Glu Trp Val Ala Arg Ile Tyr Pro
65                  70                  75                  80

Thr Asn Gly Tyr Thr Arg Tyr Ala Asp Ser Val Lys Gly Arg Phe Thr
                85                  90                  95

Ile Ser Ala Asp Thr Ser Lys Asn Thr Ala Tyr Leu Gln Met Asn Ser
            100                 105                 110

Leu Arg Ala Glu Asp Thr Ala Val Tyr Tyr Cys Ser Arg Trp Gly Gly
        115                 120                 125

Asp Gly Phe Tyr Ala Met Asp Tyr Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Val Met Thr Gln Ser Pro Ser
                165                 170                 175

Ser Leu Ser Ala Ser Val Gly Asp Arg Val Thr Ile Thr Cys Arg Ala
            180                 185                 190

Ser Gln Asp Val Asn Thr Ala Val Ala Trp Tyr Gln Gln Lys Pro Gly
        195                 200                 205

Lys Ala Pro Lys Leu Leu Ile Tyr Ser Ala Ser Phe Leu Tyr Ser Gly
    210                 215                 220

Val Pro Ser Arg Phe Ser Gly Ser Arg Ser Gly Thr Asp Phe Thr Leu
225                 230                 235                 240

Thr Ile Ser Ser Leu Gln Pro Glu Asp Phe Ala Thr Tyr Tyr Cys Gln
                245                 250                 255

Gln His Tyr Thr Thr Pro Pro Thr Phe Gly Gln Gly Thr Lys Val Glu
            260                 265                 270

Leu Lys Arg Lys Leu Gly Gly Gly Gly Ser Arg Ser Asp Ile Val Leu
        275                 280                 285

Thr Gln Thr Pro Ser Ser Leu Pro Val Ser Val Gly Glu Lys Val Thr
    290                 295                 300

Met Thr Cys Lys Ser Ser Gln Thr Leu Leu Tyr Ser Asn Asn Gln Lys
305                 310                 315                 320

Asn Tyr Leu Ala Trp Tyr Gln Gln Lys Pro Gly Gln Ser Pro Lys Leu
                325                 330                 335

Leu Ile Ser Trp Ala Phe Thr Arg Lys Ser Gly Val Pro Asp Arg Phe
            340                 345                 350

Thr Gly Ser Gly Ser Gly Thr Asp Phe Thr Leu Thr Ile Gly Ser Val
        355                 360                 365

Lys Ala Glu Asp Leu Ala Val Tyr Tyr Cys Gln Gln Tyr Ser Asn Tyr
    370                 375                 380

Pro Trp Thr Phe Gly Gly Gly Thr Arg Leu Glu Ile Lys Arg Gly Gly
385                 390                 395                 400

Gly Gly Ser Gly Gly Gly Gly Ser Gly Gly Gly Gly Ser Gly Gly Gly
                405                 410                 415

Gly Ser Glu Val Gln Leu Gln Gln Ser Gly Pro Glu Val Val Lys Thr
            420                 425                 430

Gly Ala Ser Val Lys Ile Ser Cys Lys Ala Ser Gly Tyr Ser Phe Thr
        435                 440                 445

Gly Tyr Phe Ile Asn Trp Val Lys Lys Asn Ser Gly Lys Ser Pro Glu
    450                 455                 460

Trp Ile Gly His Ile Ser Ser Ser Tyr Ala Thr Ser Thr Tyr Asn Gln
465                 470                 475                 480
```

```
Lys Phe Lys Asn Lys Ala Ala Phe Thr Val Asp Thr Ser Ser Ser Thr
                485                 490                 495

Ala Phe Met Gln Leu Asn Ser Leu Thr Ser Glu Asp Ser Ala Asp Tyr
            500                 505                 510

Tyr Cys Val Arg Ser Gly Asn Tyr Glu Glu Tyr Ala Met Asp Tyr Trp
        515                 520                 525

Gly Gln Gly Thr Ser Val Thr Val Ser Ser Lys Leu Gly Ser His His
    530                 535                 540

His His His His
545


<210> SEQ ID NO 82
<211> LENGTH: 548
<212> TYPE: PRT
<213> ORGANISM: Artificial Sequence
<220> FEATURE:
<223> OTHER INFORMATION: 4D5LH-L1-A21HL, a bispecific HER2 binding agent
      comprising a scFV antibody fragment binding domain 1 of HER2 and a
      a scFV antibody fragment binding domain 4 of HER2 connected by a
      glycine serine linker

<400> SEQUENCE: 82

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser Asp Ile Val Met Thr
            20                  25                  30

Gln Ser Pro Ser Ser Leu Ser Ala Ser Val Gly Asp Arg Val Thr Ile
        35                  40                  45

Thr Cys Arg Ala Ser Gln Asp Val Asn Thr Ala Val Ala Trp Tyr Gln
    50                  55                  60

Gln Lys Pro Gly Lys Ala Pro Lys Leu Leu Ile Tyr Ser Ala Ser Phe
65                  70                  75                  80

Leu Tyr Ser Gly Val Pro Ser Arg Phe Ser Gly Ser Arg Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln His Tyr Thr Thr Pro Pro Thr Phe Gly Gln Gly
        115                 120                 125

Thr Lys Val Glu Leu Lys Arg Gly Gly Gly Gly Ser Gly Gly Gly Gly
    130                 135                 140

Ser Gly Gly Gly Gly Ser Gly Gly Gly Gly Ser Glu Val Lys Leu Val
145                 150                 155                 160

Glu Ser Gly Gly Gly Leu Val Gln Pro Gly Gly Ser Leu Arg Leu Ser
                165                 170                 175

Cys Ala Thr Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
                245                 250                 255

Asp Gly Phe Tyr Ala Met Asp Tyr Trp Gly Gln Gly Thr Thr Val Thr
            260                 265                 270
```

```
Val Ser Ser Lys Leu Gly Gly Gly Gly Ser Arg Ser Glu Val Gln Leu
        275                 280                 285

Gln Gln Ser Gly Pro Glu Val Val Lys Thr Gly Ala Ser Val Lys Ile
    290                 295                 300

Ser Cys Lys Ala Ser Gly Tyr Ser Phe Thr Gly Tyr Phe Ile Asn Trp
305                 310                 315                 320

Val Lys Lys Asn Ser Gly Lys Ser Pro Glu Trp Ile Gly His Ile Ser
                325                 330                 335

Ser Ser Tyr Ala Thr Ser Thr Tyr Asn Gln Lys Phe Lys Asn Lys Ala
            340                 345                 350

Ala Phe Thr Val Asp Thr Ser Ser Ser Thr Ala Phe Met Gln Leu Asn
        355                 360                 365

Ser Leu Thr Ser Glu Asp Ser Ala Asp Tyr Tyr Cys Val Arg Ser Gly
    370                 375                 380

Asn Tyr Glu Glu Tyr Ala Met Asp Tyr Trp Gly Gln Gly Thr Ser Val
385                 390                 395                 400

Thr Val Ser Ser Gly Gly Gly Gly Ser Gly Gly Gly Gly Ser Gly Gly
                405                 410                 415

Gly Gly Ser Gly Gly Gly Gly Ser Asp Ile Val Leu Thr Gln Thr Pro
            420                 425                 430

Ser Ser Leu Pro Val Ser Val Gly Glu Lys Val Thr Met Thr Cys Lys
        435                 440                 445

Ser Ser Gln Thr Leu Leu Tyr Ser Asn Asn Gln Lys Asn Tyr Leu Ala
    450                 455                 460

Trp Tyr Gln Gln Lys Pro Gly Gln Ser Pro Lys Leu Leu Ile Ser Trp
465                 470                 475                 480

Ala Phe Thr Arg Lys Ser Gly Val Pro Asp Arg Phe Thr Gly Ser Gly
                485                 490                 495

Ser Gly Thr Asp Phe Thr Leu Thr Ile Gly Ser Val Lys Ala Glu Asp
            500                 505                 510

Leu Ala Val Tyr Tyr Cys Gln Gln Tyr Ser Asn Tyr Pro Trp Thr Phe
        515                 520                 525

Gly Gly Gly Thr Arg Leu Glu Ile Lys Arg Lys Leu Gly Ser His His
    530                 535                 540

His His His His
545


<210> SEQ ID NO 83
<211> LENGTH: 563
<212> TYPE: PRT
<213> ORGANISM: Artificial Sequence
<220> FEATURE:
<223> OTHER INFORMATION: 4D5LH-L4-A21HL, a bispecific HER2 binding agent
      comprising a scFV antibody fragment binding domain 1 of HER2 and a
      a scFV antibody fragment binding domain 4 of HER2 connected by a
      glycine serine linker

<400> SEQUENCE: 83

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser Asp Ile Val Met Thr
            20                  25                  30

Gln Ser Pro Ser Ser Leu Ser Ala Ser Val Gly Asp Arg Val Thr Ile
        35                  40                  45

Thr Cys Arg Ala Ser Gln Asp Val Asn Thr Ala Val Ala Trp Tyr Gln
    50                  55                  60
```

```
Gln Lys Pro Gly Lys Ala Pro Lys Leu Leu Ile Tyr Ser Ala Ser Phe
65                  70                  75                  80

Leu Tyr Ser Gly Val Pro Ser Arg Phe Ser Gly Ser Arg Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln His Tyr Thr Thr Pro Pro Thr Phe Gly Gln Gly
        115                 120                 125

Thr Lys Val Glu Leu Lys Arg Gly Gly Gly Gly Ser Gly Gly Gly Gly
    130                 135                 140

Ser Gly Gly Gly Gly Ser Gly Gly Gly Gly Ser Glu Val Lys Leu Val
145                 150                 155                 160

Glu Ser Gly Gly Gly Leu Val Gln Pro Gly Gly Ser Leu Arg Leu Ser
                165                 170                 175

Cys Ala Thr Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
                245                 250                 255

Asp Gly Phe Tyr Ala Met Asp Tyr Trp Gly Gln Gly Thr Thr Val Thr
            260                 265                 270

Val Ser Ser Lys Leu Gly Gly Gly Gly Ser Gly Gly Gly Gly Ser Gly
        275                 280                 285

Gly Gly Gly Ser Gly Gly Gly Gly Ser Arg Ser Glu Val Gln Leu Gln
    290                 295                 300

Gln Ser Gly Pro Glu Val Val Lys Thr Gly Ala Ser Val Lys Ile Ser
305                 310                 315                 320

Cys Lys Ala Ser Gly Tyr Ser Phe Thr Gly Tyr Phe Ile Asn Trp Val
                325                 330                 335

Lys Lys Asn Ser Gly Lys Ser Pro Glu Trp Ile Gly His Ile Ser Ser
            340                 345                 350

Ser Tyr Ala Thr Ser Thr Tyr Asn Gln Lys Phe Lys Asn Lys Ala Ala
        355                 360                 365

Phe Thr Val Asp Thr Ser Ser Ser Thr Ala Phe Met Gln Leu Asn Ser
    370                 375                 380

Leu Thr Ser Glu Asp Ser Ala Asp Tyr Tyr Cys Val Arg Ser Gly Asn
385                 390                 395                 400

Tyr Glu Glu Tyr Ala Met Asp Tyr Trp Gly Gln Gly Thr Ser Val Thr
                405                 410                 415

Val Ser Ser Gly Gly Gly Gly Ser Gly Gly Gly Gly Ser Gly Gly Gly
            420                 425                 430

Gly Ser Gly Gly Gly Gly Ser Asp Ile Val Leu Thr Gln Thr Pro Ser
        435                 440                 445

Ser Leu Pro Val Ser Val Gly Glu Lys Val Thr Met Thr Cys Lys Ser
    450                 455                 460

Ser Gln Thr Leu Leu Tyr Ser Asn Asn Gln Lys Asn Tyr Leu Ala Trp
465                 470                 475                 480
```

-continued

```
Tyr Gln Gln Lys Pro Gly Gln Ser Pro Lys Leu Leu Ile Ser Trp Ala
                485                 490                 495

Phe Thr Arg Lys Ser Gly Val Pro Asp Arg Phe Thr Gly Ser Gly Ser
            500                 505                 510

Gly Thr Asp Phe Thr Leu Thr Ile Gly Ser Val Lys Ala Glu Asp Leu
        515                 520                 525

Ala Val Tyr Tyr Cys Gln Gln Tyr Ser Asn Tyr Pro Trp Thr Phe Gly
    530                 535                 540

Gly Gly Thr Arg Leu Glu Ile Lys Arg Lys Leu Gly Ser His His His
545                 550                 555                 560

His His His


<210> SEQ ID NO 84
<211> LENGTH: 563
<212> TYPE: PRT
<213> ORGANISM: Artificial Sequence
<220> FEATURE:
<223> OTHER INFORMATION: 4D5LH-L4-A21LH, a bispecific HER2 binding agent
      comprising a scFV antibody fragment binding domain 1 of HER2 and a
      a scFV antibody fragment binding domain 4 of HER2 connected by a
      glycine serine linker

<400> SEQUENCE: 84

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser Asp Ile Val Met Thr
            20                  25                  30

Gln Ser Pro Ser Ser Leu Ser Ala Ser Val Gly Asp Arg Val Thr Ile
        35                  40                  45

Thr Cys Arg Ala Ser Gln Asp Val Asn Thr Ala Val Ala Trp Tyr Gln
    50                  55                  60

Gln Lys Pro Gly Lys Ala Pro Lys Leu Leu Ile Tyr Ser Ala Ser Phe
65                  70                  75                  80

Leu Tyr Ser Gly Val Pro Ser Arg Phe Ser Gly Ser Arg Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln His Tyr Thr Thr Pro Pro Thr Phe Gly Gln Gly
        115                 120                 125

Thr Lys Val Glu Leu Lys Arg Gly Gly Gly Gly Ser Gly Gly Gly Gly
    130                 135                 140

Ser Gly Gly Gly Gly Ser Gly Gly Gly Gly Ser Glu Val Lys Leu Val
145                 150                 155                 160

Glu Ser Gly Gly Gly Leu Val Gln Pro Gly Gly Ser Leu Arg Leu Ser
                165                 170                 175

Cys Ala Thr Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
                245                 250                 255

Asp Gly Phe Tyr Ala Met Asp Tyr Trp Gly Gln Gly Thr Thr Val Thr
```

```
            260                 265                 270

Val Ser Ser Lys Leu Gly Gly Gly Gly Ser Gly Gly Gly Gly Ser Gly
        275                 280                 285

Gly Gly Gly Ser Gly Gly Gly Gly Ser Arg Ser Asp Ile Val Leu Thr
    290                 295                 300

Gln Thr Pro Ser Ser Leu Pro Val Ser Val Gly Glu Lys Val Thr Met
305                 310                 315                 320

Thr Cys Lys Ser Ser Gln Thr Leu Leu Tyr Ser Asn Asn Gln Lys Asn
                325                 330                 335

Tyr Leu Ala Trp Tyr Gln Gln Lys Pro Gly Gln Ser Pro Lys Leu Leu
            340                 345                 350

Ile Ser Trp Ala Phe Thr Arg Lys Ser Gly Val Pro Asp Arg Phe Thr
        355                 360                 365

Gly Ser Gly Ser Gly Thr Asp Phe Thr Leu Thr Ile Gly Ser Val Lys
    370                 375                 380

Ala Glu Asp Leu Ala Val Tyr Tyr Cys Gln Gln Tyr Ser Asn Tyr Pro
385                 390                 395                 400

Trp Thr Phe Gly Gly Gly Thr Arg Leu Glu Ile Lys Arg Gly Gly Gly
                405                 410                 415

Gly Ser Gly Gly Gly Gly Ser Gly Gly Gly Gly Ser Gly Gly Gly Gly
            420                 425                 430

Ser Glu Val Gln Leu Gln Gln Ser Gly Pro Glu Val Val Lys Thr Gly
        435                 440                 445

Ala Ser Val Lys Ile Ser Cys Lys Ala Ser Gly Tyr Ser Phe Thr Gly
    450                 455                 460

Tyr Phe Ile Asn Trp Val Lys Lys Asn Ser Gly Lys Ser Pro Glu Trp
465                 470                 475                 480

Ile Gly His Ile Ser Ser Ser Tyr Ala Thr Ser Thr Tyr Asn Gln Lys
                485                 490                 495

Phe Lys Asn Lys Ala Ala Phe Thr Val Asp Thr Ser Ser Ser Thr Ala
            500                 505                 510

Phe Met Gln Leu Asn Ser Leu Thr Ser Glu Asp Ser Ala Asp Tyr Tyr
        515                 520                 525

Cys Val Arg Ser Gly Asn Tyr Glu Glu Tyr Ala Met Asp Tyr Trp Gly
    530                 535                 540

Gln Gly Thr Ser Val Thr Val Ser Ser Lys Leu Gly Ser His His His
545                 550                 555                 560

His His His
```

```
<210> SEQ ID NO 85
<211> LENGTH: 563
<212> TYPE: PRT
<213> ORGANISM: Artificial Sequence
<220> FEATURE:
<223> OTHER INFORMATION: A21HL_L4_4D5LH, a bispecific HER2 binding agent
      comprising a scFV antibody fragment binding domain 1 of HER2 and a
      a scFV antibody fragment binding domain 4 of HER2 connected by a
      glycine serine linker

<400> SEQUENCE: 85

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser Glu Val Gln Leu Gln
            20                  25                  30

Gln Ser Gly Pro Glu Val Val Lys Thr Gly Ala Ser Val Lys Ile Ser
        35                  40                  45
```

```
Cys Lys Ala Ser Gly Tyr Ser Phe Thr Gly Tyr Phe Ile Asn Trp Val
    50                  55                  60

Lys Lys Asn Ser Gly Lys Ser Pro Glu Trp Ile Gly His Ile Ser Ser
65                  70                  75                  80

Ser Tyr Ala Thr Ser Thr Tyr Asn Gln Lys Phe Lys Asn Lys Ala Ala
                85                  90                  95

Phe Thr Val Asp Thr Ser Ser Ser Thr Ala Phe Met Gln Leu Asn Ser
            100                 105                 110

Leu Thr Ser Glu Asp Ser Ala Asp Tyr Tyr Cys Val Arg Ser Gly Asn
        115                 120                 125

Tyr Glu Glu Tyr Ala Met Asp Tyr Trp Gly Gln Gly Thr Ser Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Val Leu Thr Gln Thr Pro Ser
                165                 170                 175

Ser Leu Pro Val Ser Val Gly Glu Lys Val Thr Met Thr Cys Lys Ser
            180                 185                 190

Ser Gln Thr Leu Leu Tyr Ser Asn Asn Gln Lys Asn Tyr Leu Ala Trp
        195                 200                 205

Tyr Gln Gln Lys Pro Gly Gln Ser Pro Lys Leu Leu Ile Ser Trp Ala
    210                 215                 220

Phe Thr Arg Lys Ser Gly Val Pro Asp Arg Phe Thr Gly Ser Gly Ser
225                 230                 235                 240

Gly Thr Asp Phe Thr Leu Thr Ile Gly Ser Val Lys Ala Glu Asp Leu
                245                 250                 255

Ala Val Tyr Tyr Cys Gln Gln Tyr Ser Asn Tyr Pro Trp Thr Phe Gly
            260                 265                 270

Gly Gly Thr Arg Leu Glu Ile Lys Arg Lys Leu Gly Gly Gly Gly Ser
        275                 280                 285

Gly Gly Gly Gly Ser Gly Gly Gly Gly Ser Gly Gly Gly Gly Ser Arg
    290                 295                 300

Ser Asp Ile Val Met Thr Gln Ser Pro Ser Ser Leu Ser Ala Ser Val
305                 310                 315                 320

Gly Asp Arg Val Thr Ile Thr Cys Arg Ala Ser Gln Asp Val Asn Thr
                325                 330                 335

Ala Val Ala Trp Tyr Gln Gln Lys Pro Gly Lys Ala Pro Lys Leu Leu
            340                 345                 350

Ile Tyr Ser Ala Ser Phe Leu Tyr Ser Gly Val Pro Ser Arg Phe Ser
        355                 360                 365

Gly Ser Arg Ser Gly Thr Asp Phe Thr Leu Thr Ile Ser Ser Leu Gln
    370                 375                 380

Pro Glu Asp Phe Ala Thr Tyr Tyr Cys Gln Gln His Tyr Thr Thr Pro
385                 390                 395                 400

Pro Thr Phe Gly Gln Gly Thr Lys Val Glu Leu Lys Arg Gly Gly Gly
                405                 410                 415

Gly Ser Gly Gly Gly Gly Ser Gly Gly Gly Gly Ser Gly Gly Gly Gly
            420                 425                 430

Ser Glu Val Lys Leu Val Glu Ser Gly Gly Gly Leu Val Gln Pro Gly
        435                 440                 445

Gly Ser Leu Arg Leu Ser Cys Ala Thr Ser Gly Phe Asn Ile Lys Asp
    450                 455                 460
```

```
Thr Tyr Ile His Trp Val Arg Gln Ala Pro Gly Lys Gly Leu Glu Trp
465                 470                 475                 480

Val Ala Arg Ile Tyr Pro Thr Asn Gly Tyr Thr Arg Tyr Ala Asp Ser
                485                 490                 495

Val Lys Gly Arg Phe Thr Ile Ser Ala Asp Thr Ser Lys Asn Thr Ala
            500                 505                 510

Tyr Leu Gln Met Asn Ser Leu Arg Ala Glu Asp Thr Ala Val Tyr Tyr
        515                 520                 525

Cys Ser Arg Trp Gly Gly Asp Gly Phe Tyr Ala Met Asp Tyr Trp Gly
    530                 535                 540

Gln Gly Thr Thr Val Thr Val Ser Ser Lys Leu Gly Ser His His His
545                 550                 555                 560

His His His


<210> SEQ ID NO 86
<211> LENGTH: 548
<212> TYPE: PRT
<213> ORGANISM: Artificial Sequence
<220> FEATURE:
<223> OTHER INFORMATION: A21LH-L1-4D5LH,  a bispecific HER2 binding
      agent comprising a scFV antibody fragment binding domain 1 of HER2
      and a a scFV antibody fragment binding domain 4 of HER2 connected
      by a glycine serine linker

<400> SEQUENCE: 86

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser Asp Ile Val Leu Thr
            20                  25                  30

Gln Thr Pro Ser Ser Leu Pro Val Ser Val Gly Glu Lys Val Thr Met
        35                  40                  45

Thr Cys Lys Ser Ser Gln Thr Leu Leu Tyr Ser Asn Asn Gln Lys Asn
    50                  55                  60

Tyr Leu Ala Trp Tyr Gln Gln Lys Pro Gly Gln Ser Pro Lys Leu Leu
65                  70                  75                  80

Ile Ser Trp Ala Phe Thr Arg Lys Ser Gly Val Pro Asp Arg Phe Thr
                85                  90                  95

Gly Ser Gly Ser Gly Thr Asp Phe Thr Leu Thr Ile Gly Ser Val Lys
            100                 105                 110

Ala Glu Asp Leu Ala Val Tyr Tyr Cys Gln Gln Tyr Ser Asn Tyr Pro
        115                 120                 125

Trp Thr Phe Gly Gly Gly Thr Arg Leu Glu Ile Lys Arg Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Gln Gln Ser Gly Pro Glu Val Val Lys Thr Gly
                165                 170                 175

Ala Ser Val Lys Ile Ser Cys Lys Ala Ser Gly Tyr Ser Phe Thr Gly
            180                 185                 190

Tyr Phe Ile Asn Trp Val Lys Lys Asn Ser Gly Lys Ser Pro Glu Trp
        195                 200                 205

Ile Gly His Ile Ser Ser Ser Tyr Ala Thr Ser Thr Tyr Asn Gln Lys
    210                 215                 220

Phe Lys Asn Lys Ala Ala Phe Thr Val Asp Thr Ser Ser Ser Thr Ala
225                 230                 235                 240

Phe Met Gln Leu Asn Ser Leu Thr Ser Glu Asp Ser Ala Asp Tyr Tyr
```

```
                245                 250                 255

Cys Val Arg Ser Gly Asn Tyr Glu Glu Tyr Ala Met Asp Tyr Trp Gly
            260                 265                 270

Gln Gly Thr Ser Val Thr Val Ser Ser Lys Leu Gly Gly Gly Gly Ser
        275                 280                 285

Arg Ser Asp Ile Val Met Thr Gln Ser Pro Ser Ser Leu Ser Ala Ser
    290                 295                 300

Val Gly Asp Arg Val Thr Ile Thr Cys Arg Ala Ser Gln Asp Val Asn
305                 310                 315                 320

Thr Ala Val Ala Trp Tyr Gln Gln Lys Pro Gly Lys Ala Pro Lys Leu
                325                 330                 335

Leu Ile Tyr Ser Ala Ser Phe Leu Tyr Ser Gly Val Pro Ser Arg Phe
            340                 345                 350

Ser Gly Ser Arg Ser Gly Thr Asp Phe Thr Leu Thr Ile Ser Ser Leu
        355                 360                 365

Gln Pro Glu Asp Phe Ala Thr Tyr Tyr Cys Gln Gln His Tyr Thr Thr
    370                 375                 380

Pro Pro Thr Phe Gly Gln Gly Thr Lys Val Glu Leu Lys Arg Gly Gly
385                 390                 395                 400

Gly Gly Ser Gly Gly Gly Gly Ser Gly Gly Gly Gly Ser Gly Gly Gly
                405                 410                 415

Gly Ser Glu Val Lys Leu Val Glu Ser Gly Gly Gly Leu Val Gln Pro
            420                 425                 430

Gly Gly Ser Leu Arg Leu Ser Cys Ala Thr Ser Gly Phe Asn Ile Lys
        435                 440                 445

Asp Thr Tyr Ile His Trp Val Arg Gln Ala Pro Gly Lys Gly Leu Glu
    450                 455                 460

Trp Val Ala Arg Ile Tyr Pro Thr Asn Gly Tyr Thr Arg Tyr Ala Asp
465                 470                 475                 480

Ser Val Lys Gly Arg Phe Thr Ile Ser Ala Asp Thr Ser Lys Asn Thr
                485                 490                 495

Ala Tyr Leu Gln Met Asn Ser Leu Arg Ala Glu Asp Thr Ala Val Tyr
            500                 505                 510

Tyr Cys Ser Arg Trp Gly Gly Asp Gly Phe Tyr Ala Met Asp Tyr Trp
        515                 520                 525

Gly Gln Gly Thr Thr Val Thr Val Ser Ser Lys Leu Gly Ser His His
    530                 535                 540

His His His His
545
```

<210> SEQ ID NO 87
<211> LENGTH: 563
<212> TYPE: PRT
<213> ORGANISM: Artificial Sequence
<220> FEATURE:
<223> OTHER INFORMATION: A21LH-L4-4D5LH, a bispecific HER2 binding agent comprising a scFV antibody fragment binding domain 1 of HER2 and a a scFV antibody fragment binding domain 4 of HER2 connected by a glycine serine linker

<400> SEQUENCE: 87

```
Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser Asp Ile Val Leu Thr
            20                  25                  30

Gln Thr Pro Ser Ser Leu Pro Val Ser Val Gly Glu Lys Val Thr Met
```

```
        35                  40                  45

Thr Cys Lys Ser Ser Gln Thr Leu Leu Tyr Ser Asn Asn Gln Lys Asn
    50                  55                  60

Tyr Leu Ala Trp Tyr Gln Gln Lys Pro Gly Gln Ser Pro Lys Leu Leu
65                  70                  75                  80

Ile Ser Trp Ala Phe Thr Arg Lys Ser Gly Val Pro Asp Arg Phe Thr
                85                  90                  95

Gly Ser Gly Ser Gly Thr Asp Phe Thr Leu Thr Ile Gly Ser Val Lys
            100                 105                 110

Ala Glu Asp Leu Ala Val Tyr Tyr Cys Gln Gln Tyr Ser Asn Tyr Pro
        115                 120                 125

Trp Thr Phe Gly Gly Gly Thr Arg Leu Glu Ile Lys Arg Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Gln Gln Ser Gly Pro Glu Val Val Lys Thr Gly
                165                 170                 175

Ala Ser Val Lys Ile Ser Cys Lys Ala Ser Gly Tyr Ser Phe Thr Gly
            180                 185                 190

Tyr Phe Ile Asn Trp Val Lys Lys Asn Ser Gly Lys Ser Pro Glu Trp
        195                 200                 205

Ile Gly His Ile Ser Ser Ser Tyr Ala Thr Ser Thr Tyr Asn Gln Lys
    210                 215                 220

Phe Lys Asn Lys Ala Ala Phe Thr Val Asp Thr Ser Ser Ser Thr Ala
225                 230                 235                 240

Phe Met Gln Leu Asn Ser Leu Thr Ser Glu Asp Ser Ala Asp Tyr Tyr
                245                 250                 255

Cys Val Arg Ser Gly Asn Tyr Glu Glu Tyr Ala Met Asp Tyr Trp Gly
            260                 265                 270

Gln Gly Thr Ser Val Thr Val Ser Ser Lys Leu Gly Gly Gly Gly Ser
        275                 280                 285

Gly Gly Gly Gly Ser Gly Gly Gly Gly Ser Gly Gly Gly Gly Ser Arg
    290                 295                 300

Ser Asp Ile Val Met Thr Gln Ser Pro Ser Ser Leu Ser Ala Ser Val
305                 310                 315                 320

Gly Asp Arg Val Thr Ile Thr Cys Arg Ala Ser Gln Asp Val Asn Thr
                325                 330                 335

Ala Val Ala Trp Tyr Gln Gln Lys Pro Gly Lys Ala Pro Lys Leu Leu
            340                 345                 350

Ile Tyr Ser Ala Ser Phe Leu Tyr Ser Gly Val Pro Ser Arg Phe Ser
        355                 360                 365

Gly Ser Arg Ser Gly Thr Asp Phe Thr Leu Thr Ile Ser Ser Leu Gln
    370                 375                 380

Pro Glu Asp Phe Ala Thr Tyr Tyr Cys Gln Gln His Tyr Thr Thr Pro
385                 390                 395                 400

Pro Thr Phe Gly Gln Gly Thr Lys Val Glu Leu Lys Arg Gly Gly Gly
                405                 410                 415

Gly Ser Gly Gly Gly Gly Ser Gly Gly Gly Gly Ser Gly Gly Gly Gly
            420                 425                 430

Ser Glu Val Lys Leu Val Glu Ser Gly Gly Gly Leu Val Gln Pro Gly
        435                 440                 445

Gly Ser Leu Arg Leu Ser Cys Ala Thr Ser Gly Phe Asn Ile Lys Asp
    450                 455                 460
```

Thr Tyr Ile His Trp Val Arg Gln Ala Pro Gly Lys Gly Leu Glu Trp
465 470 475 480

Val Ala Arg Ile Tyr Pro Thr Asn Gly Tyr Thr Arg Tyr Ala Asp Ser
485 490 495

Val Lys Gly Arg Phe Thr Ile Ser Ala Asp Thr Ser Lys Asn Thr Ala
500 505 510

Tyr Leu Gln Met Asn Ser Leu Arg Ala Glu Asp Thr Ala Val Tyr Tyr
515 520 525

Cys Ser Arg Trp Gly Gly Asp Gly Phe Tyr Ala Met Asp Tyr Trp Gly
530 535 540

Gln Gly Thr Thr Val Thr Val Ser Ser Lys Leu Gly Ser His His His
545 550 555 560

His His His

<210> SEQ ID NO 88
<211> LENGTH: 467
<212> TYPE: PRT
<213> ORGANISM: Artificial Sequence
<220> FEATURE:
<223> OTHER INFORMATION: 926E-L4-4D5HL, a bispecific HER2 binding agent comprising a DARPin binding domain 1 of HER2 and a scFV antibody fragment binding domain 4 of HER2connected by a glycine serine linker

<400> SEQUENCE: 88

Met Lys Lys Ile Trp Leu Ala Leu Ala Gly Leu Val Leu Ala Phe Ser
1 5 10 15

Ala Ser Ala Asp Tyr Lys Asp Asp Ile Gly Ser His His His His His
20 25 30

His Gly Ser Asp Leu Gly Lys Lys Leu Leu Glu Ala Ala Arg Ala Gly
35 40 45

Gln Asp Asp Glu Val Arg Ile Leu Met Ala Asn Gly Ala Asp Val Asn
50 55 60

Ala Lys Asp Phe Tyr Gly Ile Thr Pro Leu His Leu Ala Ala Ala Tyr
65 70 75 80

Gly His Leu Glu Ile Val Glu Val Leu Leu Lys His Gly Ala Asp Val
85 90 95

Asn Ala His Asp Trp Asn Gly Trp Thr Pro Leu His Leu Ala Ala Lys
100 105 110

Tyr Gly His Leu Glu Ile Val Glu Val Leu Leu Lys His Gly Ala Asp
115 120 125

Val Asn Ala Ile Asp Asn Ala Gly Lys Thr Pro Leu His Leu Ala Ala
130 135 140

Ala His Gly His Leu Glu Ile Val Glu Val Leu Leu Lys Tyr Gly Ala
145 150 155 160

Asp Val Asn Ala Gln Asp Lys Phe Gly Glu Thr Ala Glu Asp Leu Ala
165 170 175

Lys Asp Asn Gly Asn Gln Asp Ile Ala Asp Leu Leu Glu Lys Ala Leu
180 185 190

Lys Leu Gly Gly Gly Gly Ser Gly Gly Gly Gly Ser Gly Gly Gly Gly
195 200 205

Ser Gly Gly Gly Gly Ser Arg Ser Glu Val Lys Leu Val Glu Ser Gly
210 215 220

Gly Gly Leu Val Gln Pro Gly Gly Ser Leu Arg Leu Ser Cys Ala Thr
225 230 235 240

```
Ser Gly Phe Asn Ile Lys Asp Thr Tyr Ile His Trp Val Arg Gln Ala
                245                 250                 255

Pro Gly Lys Gly Leu Glu Trp Val Ala Arg Ile Tyr Pro Thr Asn Gly
            260                 265                 270

Tyr Thr Arg Tyr Ala Asp Ser Val Lys Gly Arg Phe Thr Ile Ser Ala
        275                 280                 285

Asp Thr Ser Lys Asn Thr Ala Tyr Leu Gln Met Asn Ser Leu Arg Ala
    290                 295                 300

Glu Asp Thr Ala Val Tyr Tyr Cys Ser Arg Trp Gly Gly Asp Gly Phe
305                 310                 315                 320

Tyr Ala Met Asp Tyr Trp Gly Gln Gly Thr Thr Val Thr Val Ser Ser
                325                 330                 335

Gly Gly Gly Gly Ser Gly Gly Gly Gly Ser Gly Gly Gly Gly Ser Gly
            340                 345                 350

Gly Gly Gly Ser Asp Ile Val Met Thr Gln Ser Pro Ser Ser Leu Ser
        355                 360                 365

Ala Ser Val Gly Asp Arg Val Thr Ile Thr Cys Arg Ala Ser Gln Asp
    370                 375                 380

Val Asn Thr Ala Val Ala Trp Tyr Gln Gln Lys Pro Gly Lys Ala Pro
385                 390                 395                 400

Lys Leu Leu Ile Tyr Ser Ala Ser Phe Leu Tyr Ser Gly Val Pro Ser
                405                 410                 415

Arg Phe Ser Gly Ser Arg Ser Gly Thr Asp Phe Thr Leu Thr Ile Ser
            420                 425                 430

Ser Leu Gln Pro Glu Asp Phe Ala Thr Tyr Tyr Cys Gln Gln His Tyr
        435                 440                 445

Thr Thr Pro Pro Thr Phe Gly Gln Gly Thr Lys Val Glu Leu Lys Arg
    450                 455                 460

Lys Leu Asn
465
```

<210> SEQ ID NO 89
<211> LENGTH: 467
<212> TYPE: PRT
<213> ORGANISM: Artificial Sequence
<220> FEATURE:
<223> OTHER INFORMATION: 926E-L4-4D5LH, a bispecific HER2 binding agent comprising a DARPin binding domain 1 of HER2 and a scFV antibody fragment binding domain 4 of HER2connected by a glycine serine linker

<400> SEQUENCE: 89

```
Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser His His His His His
            20                  25                  30

His Gly Ser Asp Leu Gly Lys Lys Leu Leu Glu Ala Ala Arg Ala Gly
        35                  40                  45

Gln Asp Asp Glu Val Arg Ile Leu Met Ala Asn Gly Ala Asp Val Asn
    50                  55                  60

Ala Lys Asp Phe Tyr Gly Ile Thr Pro Leu His Leu Ala Ala Ala Tyr
65                  70                  75                  80

Gly His Leu Glu Ile Val Glu Val Leu Leu Lys His Gly Ala Asp Val
                85                  90                  95

Asn Ala His Asp Trp Asn Gly Trp Thr Pro Leu His Leu Ala Ala Lys
            100                 105                 110
```

-continued

```
Tyr Gly His Leu Glu Ile Val Glu Val Leu Leu Lys His Gly Ala Asp
        115                 120                 125

Val Asn Ala Ile Asp Asn Ala Gly Lys Thr Pro Leu His Leu Ala Ala
    130                 135                 140

Ala His Gly His Leu Glu Ile Val Glu Val Leu Leu Lys Tyr Gly Ala
145                 150                 155                 160

Asp Val Asn Ala Gln Asp Lys Phe Gly Glu Thr Ala Glu Asp Leu Ala
                165                 170                 175

Lys Asp Asn Gly Asn Gln Asp Ile Ala Asp Leu Leu Glu Lys Ala Leu
            180                 185                 190

Lys Leu Gly Gly Gly Gly Ser Gly Gly Gly Gly Ser Gly Gly Gly Gly
        195                 200                 205

Ser Gly Gly Gly Gly Ser Arg Ser Asp Ile Val Met Thr Gln Ser Pro
    210                 215                 220

Ser Ser Leu Ser Ala Ser Val Gly Asp Arg Val Thr Ile Thr Cys Arg
225                 230                 235                 240

Ala Ser Gln Asp Val Asn Thr Ala Val Ala Trp Tyr Gln Gln Lys Pro
                245                 250                 255

Gly Lys Ala Pro Lys Leu Leu Ile Tyr Ser Ala Ser Phe Leu Tyr Ser
            260                 265                 270

Gly Val Pro Ser Arg Phe Ser Gly Ser Arg Ser Gly Thr Asp Phe Thr
        275                 280                 285

Leu Thr Ile Ser Ser Leu Gln Pro Glu Asp Phe Ala Thr Tyr Tyr Cys
    290                 295                 300

Gln Gln His Tyr Thr Thr Pro Pro Thr Phe Gly Gln Gly Thr Lys Val
305                 310                 315                 320

Glu Leu Lys Arg Gly Gly Gly Gly Ser Gly Gly Gly Gly Ser Gly Gly
                325                 330                 335

Gly Gly Ser Gly Gly Gly Gly Ser Glu Val Lys Leu Val Glu Ser Gly
            340                 345                 350

Gly Gly Leu Val Gln Pro Gly Gly Ser Leu Arg Leu Ser Cys Ala Thr
        355                 360                 365

Ser Gly Phe Asn Ile Lys Asp Thr Tyr Ile His Trp Val Arg Gln Ala
    370                 375                 380

Pro Gly Lys Gly Leu Glu Trp Val Ala Arg Ile Tyr Pro Thr Asn Gly
385                 390                 395                 400

Tyr Thr Arg Tyr Ala Asp Ser Val Lys Gly Arg Phe Thr Ile Ser Ala
                405                 410                 415

Asp Thr Ser Lys Asn Thr Ala Tyr Leu Gln Met Asn Ser Leu Arg Ala
            420                 425                 430

Glu Asp Thr Ala Val Tyr Tyr Cys Ser Arg Trp Gly Gly Asp Gly Phe
        435                 440                 445

Tyr Ala Met Asp Tyr Trp Gly Gln Gly Thr Thr Val Thr Val Ser Ser
    450                 455                 460

Lys Leu Asn
465
```

<210> SEQ ID NO 90
<211> LENGTH: 463
<212> TYPE: PRT
<213> ORGANISM: Artificial Sequence
<220> FEATURE:
<223> OTHER INFORMATION: 929-L4-4D5HL, a bispecific HER2 binding agent comprising a DARPin binding domain 1 of HER2 and a scFV antibody fragment binding domain 4 of HER2connected by a glycine serine linker

<400> SEQUENCE: 90

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser His His His His His
            20                  25                  30

His Gly Ser Asp Leu Gly Lys Lys Leu Leu Glu Ala Ala Arg Ala Gly
        35                  40                  45

Gln Asp Asp Glu Val Arg Ile Leu Met Ala Asn Gly Ala Asp Val Asn
    50                  55                  60

Ala His Asp Phe Tyr Gly Ile Thr Pro Leu His Leu Ala Ala Asn Phe
65                  70                  75                  80

Gly His Leu Glu Ile Val Glu Val Leu Leu Lys His Gly Ala Asp Val
                85                  90                  95

Asn Ala Phe Asp Tyr Asp Asn Thr Pro Leu His Leu Ala Ala Asp Ala
            100                 105                 110

Gly His Leu Glu Ile Val Glu Val Leu Leu Lys Tyr Gly Ala Asp Val
        115                 120                 125

Asn Ala Ser Asp Arg Asp Gly His Thr Pro Leu His Leu Ala Ala Arg
    130                 135                 140

Glu Gly His Leu Glu Ile Val Glu Val Leu Leu Lys Asn Gly Ala Asp
145                 150                 155                 160

Val Asn Ala Gln Asp Lys Phe Gly Lys Thr Ala Phe Asp Ile Ser Ile
                165                 170                 175

Asp Asn Gly Asn Glu Asp Leu Ala Glu Ile Leu Gln Lys Leu Gly Gly
            180                 185                 190

Gly Gly Ser Gly Gly Gly Gly Ser Gly Gly Gly Gly Ser Gly Gly Gly
        195                 200                 205

Gly Ser Arg Ser Glu Val Lys Leu Val Glu Ser Gly Gly Gly Leu Val
    210                 215                 220

Gln Pro Gly Gly Ser Leu Arg Leu Ser Cys Ala Thr Ser Gly Phe Asn
225                 230                 235                 240

Ile Lys Asp Thr Tyr Ile His Trp Val Arg Gln Ala Pro Gly Lys Gly
                245                 250                 255

Leu Glu Trp Val Ala Arg Ile Tyr Pro Thr Asn Gly Tyr Thr Arg Tyr
            260                 265                 270

Ala Asp Ser Val Lys Gly Arg Phe Thr Ile Ser Ala Asp Thr Ser Lys
        275                 280                 285

Asn Thr Ala Tyr Leu Gln Met Asn Ser Leu Arg Ala Glu Asp Thr Ala
    290                 295                 300

Val Tyr Tyr Cys Ser Arg Trp Gly Gly Asp Gly Phe Tyr Ala Met Asp
305                 310                 315                 320

Tyr Trp Gly Gln Gly Thr Thr Val Thr Val Ser Ser Gly Gly Gly Gly
                325                 330                 335

Ser Gly Gly Gly Gly Ser Gly Gly Gly Gly Ser Gly Gly Gly Gly Ser
            340                 345                 350

Asp Ile Val Met Thr Gln Ser Pro Ser Ser Leu Ser Ala Ser Val Gly
        355                 360                 365

Asp Arg Val Thr Ile Thr Cys Arg Ala Ser Gln Asp Val Asn Thr Ala
    370                 375                 380

Val Ala Trp Tyr Gln Gln Lys Pro Gly Lys Ala Pro Lys Leu Leu Ile
385                 390                 395                 400

Tyr Ser Ala Ser Phe Leu Tyr Ser Gly Val Pro Ser Arg Phe Ser Gly

```
                405                 410                 415

Ser Arg Ser Gly Thr Asp Phe Thr Leu Thr Ile Ser Ser Leu Gln Pro
            420                 425                 430

Glu Asp Phe Ala Thr Tyr Tyr Cys Gln Gln His Tyr Thr Thr Pro Pro
        435                 440                 445

Thr Phe Gly Gln Gly Thr Lys Val Glu Leu Lys Arg Lys Leu Asn
    450                 455                 460


<210> SEQ ID NO 91
<211> LENGTH: 463
<212> TYPE: PRT
<213> ORGANISM: Artificial Sequence
<220> FEATURE:
<223> OTHER INFORMATION: 929-L4-4D5LH,  a bispecific HER2 binding agent
      comprising a DARPin binding domain 1 of HER2 and a scFV antibody
      fragment binding domain 4 of HER2connected by a glycine serine
      linker

<400> SEQUENCE: 91

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser His His His His His
            20                  25                  30

His Gly Ser Asp Leu Gly Lys Lys Leu Leu Glu Ala Ala Arg Ala Gly
        35                  40                  45

Gln Asp Asp Glu Val Arg Ile Leu Met Ala Asn Gly Ala Asp Val Asn
    50                  55                  60

Ala His Asp Phe Tyr Gly Ile Thr Pro Leu His Leu Ala Ala Asn Phe
65                  70                  75                  80

Gly His Leu Glu Ile Val Glu Val Leu Leu Lys His Gly Ala Asp Val
                85                  90                  95

Asn Ala Phe Asp Tyr Asp Asn Thr Pro Leu His Leu Ala Ala Asp Ala
            100                 105                 110

Gly His Leu Glu Ile Val Glu Val Leu Leu Lys Tyr Gly Ala Asp Val
        115                 120                 125

Asn Ala Ser Asp Arg Asp Gly His Thr Pro Leu His Leu Ala Ala Arg
    130                 135                 140

Glu Gly His Leu Glu Ile Val Glu Val Leu Leu Lys Asn Gly Ala Asp
145                 150                 155                 160

Val Asn Ala Gln Asp Lys Phe Gly Lys Thr Ala Phe Asp Ile Ser Ile
                165                 170                 175

Asp Asn Gly Asn Glu Asp Leu Ala Glu Ile Leu Gln Lys Leu Gly Gly
            180                 185                 190

Gly Gly Ser Gly Gly Gly Gly Ser Gly Gly Gly Gly Ser Gly Gly Gly
        195                 200                 205

Gly Ser Arg Ser Asp Ile Val Met Thr Gln Ser Pro Ser Ser Leu Ser
    210                 215                 220

Ala Ser Val Gly Asp Arg Val Thr Ile Thr Cys Arg Ala Ser Gln Asp
225                 230                 235                 240

Val Asn Thr Ala Val Ala Trp Tyr Gln Gln Lys Pro Gly Lys Ala Pro
                245                 250                 255

Lys Leu Leu Ile Tyr Ser Ala Ser Phe Leu Tyr Ser Gly Val Pro Ser
            260                 265                 270

Arg Phe Ser Gly Ser Arg Ser Gly Thr Asp Phe Thr Leu Thr Ile Ser
        275                 280                 285

Ser Leu Gln Pro Glu Asp Phe Ala Thr Tyr Tyr Cys Gln Gln His Tyr
```

```
    290                 295                 300

Thr Thr Pro Pro Thr Phe Gly Gln Gly Thr Lys Val Glu Leu Lys Arg
305                 310                 315                 320

Gly Gly Gly Gly Ser Gly Gly Gly Gly Ser Gly Gly Gly Gly Ser Gly
                325                 330                 335

Gly Gly Gly Ser Glu Val Lys Leu Val Glu Ser Gly Gly Gly Leu Val
            340                 345                 350

Gln Pro Gly Gly Ser Leu Arg Leu Ser Cys Ala Thr Ser Gly Phe Asn
        355                 360                 365

Ile Lys Asp Thr Tyr Ile His Trp Val Arg Gln Ala Pro Gly Lys Gly
    370                 375                 380

Leu Glu Trp Val Ala Arg Ile Tyr Pro Thr Asn Gly Tyr Thr Arg Tyr
385                 390                 395                 400

Ala Asp Ser Val Lys Gly Arg Phe Thr Ile Ser Ala Asp Thr Ser Lys
                405                 410                 415

Asn Thr Ala Tyr Leu Gln Met Asn Ser Leu Arg Ala Glu Asp Thr Ala
            420                 425                 430

Val Tyr Tyr Cys Ser Arg Trp Gly Gly Asp Gly Phe Tyr Ala Met Asp
        435                 440                 445

Tyr Trp Gly Gln Gly Thr Thr Val Thr Val Ser Ser Lys Leu Asn
    450                 455                 460


<210> SEQ ID NO 92
<211> LENGTH: 281
<212> TYPE: PRT
<213> ORGANISM: Artificial Sequence
<220> FEATURE:
<223> OTHER INFORMATION: scFV 4D5LH alternative, a scFV binding the
      extracellular domain 4 of HER2 with a glycine serine linker
      connecting heavy and light chain with C-term His-tag and
      additional N-term peptide

<400> SEQUENCE: 92

Met Lys Lys Thr Ala Ile Ala Ile Ala Val Ala Leu Ala Gly Phe Ala
1               5                   10                  15

Thr Val Ala Gln Ala Asp Ile Gly Ser Asp Ile Val Met Thr Gln Ser
            20                  25                  30

Pro Ser Ser Leu Ser Ala Ser Val Gly Asp Arg Val Thr Ile Thr Cys
        35                  40                  45

Arg Ala Ser Gln Asp Val Asn Thr Ala Val Ala Trp Tyr Gln Gln Lys
    50                  55                  60

Pro Gly Lys Ala Pro Lys Leu Leu Ile Tyr Ser Ala Ser Phe Leu Tyr
65                  70                  75                  80

Ser Gly Val Pro Ser Arg Phe Ser Gly Ser Arg Ser Gly Thr Asp Phe
                85                  90                  95

Thr Leu Thr Ile Ser Ser Leu Gln Pro Glu Asp Phe Ala Thr Tyr Tyr
            100                 105                 110

Cys Gln Gln His Tyr Thr Thr Pro Pro Thr Phe Gly Gln Gly Thr Lys
        115                 120                 125

Val Glu Leu Lys Arg Gly Gly Gly Gly Ser Gly Gly Gly Gly Ser Gly
    130                 135                 140

Gly Gly Gly Ser Gly Gly Gly Gly Ser Glu Val Lys Leu Val Glu Ser
145                 150                 155                 160

Gly Gly Gly Leu Val Gln Pro Gly Gly Ser Leu Arg Leu Ser Cys Ala
                165                 170                 175

Thr Ser Gly Phe Asn Ile Lys Asp Thr Tyr Ile His Trp Val Arg Gln
```

```
            180                 185                 190

Ala Pro Gly Lys Gly Leu Glu Trp Val Ala Arg Ile Tyr Pro Thr Asn
        195                 200                 205

Gly Tyr Thr Arg Tyr Ala Asp Ser Val Lys Gly Arg Phe Thr Ile Ser
    210                 215                 220

Ala Asp Thr Ser Lys Asn Thr Ala Tyr Leu Gln Met Asn Ser Leu Arg
225                 230                 235                 240

Ala Glu Asp Thr Ala Val Tyr Tyr Cys Ser Arg Trp Gly Gly Asp Gly
                245                 250                 255

Phe Tyr Ala Met Asp Tyr Trp Gly Gln Gly Thr Thr Val Thr Val Ser
            260                 265                 270

Ser Lys Leu His His His His His His
        275                 280


<210> SEQ ID NO 93
<211> LENGTH: 287
<212> TYPE: PRT
<213> ORGANISM: Artificial Sequence
<220> FEATURE:
<223> OTHER INFORMATION: scFV A21LH alternative, scFV 4D5 alternative,
      a scFV binding the extracellular domain 1 of HER2 with a glycine
      serine linker connecting heavy and light chain with C-term His-tag
      and additional N-term peptide

<400> SEQUENCE: 93

Met Lys Lys Thr Ala Ile Ala Ile Ala Val Ala Leu Ala Gly Phe Ala
1               5                   10                  15

Thr Val Ala Gln Ala Asp Ile Gly Ser Asp Ile Val Leu Thr Gln Thr
            20                  25                  30

Pro Ser Ser Leu Pro Val Ser Val Gly Glu Lys Val Thr Met Thr Cys
        35                  40                  45

Lys Ser Ser Gln Thr Leu Leu Tyr Ser Asn Asn Gln Lys Asn Tyr Leu
    50                  55                  60

Ala Trp Tyr Gln Gln Lys Pro Gly Gln Ser Pro Lys Leu Leu Ile Ser
65                  70                  75                  80

Trp Ala Phe Thr Arg Lys Ser Gly Val Pro Asp Arg Phe Thr Gly Ser
                85                  90                  95

Gly Ser Gly Thr Asp Phe Thr Leu Thr Ile Gly Ser Val Lys Ala Glu
            100                 105                 110

Asp Leu Ala Val Tyr Tyr Cys Gln Gln Tyr Ser Asn Tyr Pro Trp Thr
        115                 120                 125

Phe Gly Gly Gly Thr Arg Leu Glu Ile Lys Arg Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Gln Gln Ser Gly Pro Glu Val Val Lys Thr Gly Ala Ser
                165                 170                 175

Val Lys Ile Ser Cys Lys Ala Ser Gly Tyr Ser Phe Thr Gly Tyr Phe
            180                 185                 190

Ile Asn Trp Val Lys Lys Asn Ser Gly Lys Ser Pro Glu Trp Ile Gly
        195                 200                 205

His Ile Ser Ser Ser Tyr Ala Thr Ser Thr Tyr Asn Gln Lys Phe Lys
    210                 215                 220

Asn Lys Ala Ala Phe Thr Val Asp Thr Ser Ser Ser Thr Ala Phe Met
225                 230                 235                 240

Gln Leu Asn Ser Leu Thr Ser Glu Asp Ser Ala Asp Tyr Tyr Cys Val
```

```
            245                 250                 255

Arg Ser Gly Asn Tyr Glu Glu Tyr Ala Met Asp Tyr Trp Gly Gln Gly
        260                 265                 270

Thr Ser Val Thr Val Ser Ser Lys Leu His His His His His His
    275                 280                 285


<210> SEQ ID NO 94
<211> LENGTH: 27
<212> TYPE: PRT
<213> ORGANISM: Artificial Sequence
<220> FEATURE:
<223> OTHER INFORMATION: N-terminal peptide for periplasmic expression
<220> FEATURE:
<221> NAME/KEY: SITE
<222> LOCATION: (1)..(19)
<223> OTHER INFORMATION: DsbA-signal sequence
<220> FEATURE:
<221> NAME/KEY: SITE
<222> LOCATION: (20)..(25)
<223> OTHER INFORMATION: FLAG-Tag M1
<220> FEATURE:
<221> NAME/KEY: SITE
<222> LOCATION: (26)..(27)
<223> OTHER INFORMATION: BamHI cloning site

<400> SEQUENCE: 94

Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser
            20                  25


<210> SEQ ID NO 95
<211> LENGTH: 24
<212> TYPE: PRT
<213> ORGANISM: Artificial Sequence
<220> FEATURE:
<223> OTHER INFORMATION: a glycine/serine linker comprising a N-terminal
      HindIII cloning site and a C-terminal BgIII cloning site
<220> FEATURE:
<221> NAME/KEY: SITE
<222> LOCATION: (1)..(2)
<223> OTHER INFORMATION: HindIII cloning site
<220> FEATURE:
<221> NAME/KEY: SITE
<222> LOCATION: (3)..(22)
<223> OTHER INFORMATION: flexible glycine/serine linker
<220> FEATURE:
<221> NAME/KEY: SITE
<222> LOCATION: (23)..(24)
<223> OTHER INFORMATION: BglII cloning site

<400> SEQUENCE: 95

Lys Leu Gly Gly Gly Gly Ser Gly Gly Gly Gly Ser Gly Gly Gly Gly
1               5                   10                  15

Ser Gly Gly Gly Gly Ser Arg Ser
            20


<210> SEQ ID NO 96
<211> LENGTH: 10
<212> TYPE: PRT
<213> ORGANISM: Artificial Sequence
<220> FEATURE:
<223> OTHER INFORMATION: His-Tag with flexible linker and Bsa1 cloning
      site
<220> FEATURE:
<221> NAME/KEY: SITE
<222> LOCATION: (1)..(2)
<223> OTHER INFORMATION: Bsa1 cloning site
<220> FEATURE:
<221> NAME/KEY: SITE
```

<222> LOCATION: (3)..(4)
<223> OTHER INFORMATION: flexible glycine serine linker
<220> FEATURE:
<221> NAME/KEY: SITE
<222> LOCATION: (5)..(10)
<223> OTHER INFORMATION: His-tag

<400> SEQUENCE: 96

Lys Leu Gly Ser His His His His His His
1 5 10

<210> SEQ ID NO 97
<211> LENGTH: 21
<212> TYPE: PRT
<213> ORGANISM: Artificial Sequence
<220> FEATURE:
<223> OTHER INFORMATION: N-terminal peptide for expression in CHO cells
<220> FEATURE:
<221> NAME/KEY: SITE
<222> LOCATION: (1)..(19)
<223> OTHER INFORMATION: mouse Ig Kappa light chain signal sequence
<220> FEATURE:
<221> NAME/KEY: SITE
<222> LOCATION: (20)..(21)
<223> OTHER INFORMATION: BamHI cloning site

<400> SEQUENCE: 97

Met Glu Thr Asp Thr Leu Leu Leu Trp Val Leu Leu Leu Trp Val Pro
1 5 10 15

Gly Ser Thr Gly Ser
20

<210> SEQ ID NO 98
<211> LENGTH: 8
<212> TYPE: PRT
<213> ORGANISM: Artificial Sequence
<220> FEATURE:
<223> OTHER INFORMATION: His-tag with HindIII cloning site
<220> FEATURE:
<221> NAME/KEY: SITE
<222> LOCATION: (1)..(2)
<223> OTHER INFORMATION: HindIII cloning site
<220> FEATURE:
<221> NAME/KEY: SITE
<222> LOCATION: (3)..(8)
<223> OTHER INFORMATION: His-tag

<400> SEQUENCE: 98

Lys Leu His His His His His His
1 5

<210> SEQ ID NO 99
<211> LENGTH: 9
<212> TYPE: PRT
<213> ORGANISM: Apis mellifera

<400> SEQUENCE: 99

Met Val Val Tyr Ile Ser Tyr Ile Tyr
1 5

<210> SEQ ID NO 100
<211> LENGTH: 548
<212> TYPE: PRT
<213> ORGANISM: Artificial Sequence
<220> FEATURE:
<223> OTHER INFORMATION: 4D5LH-L1-A21LH, bispecific HER2 binding agent
comprising a scFV antibody fragment binding domain 1 of HER2 and
a a scFV antibody fragment binding domain 4 of HER2 connected by a
glycine serine linker -continued

<400> SEQUENCE: 100

```
Met Lys Lys Ile Trp Leu Ala Leu Ala Gly Leu Val Leu Ala Phe Ser
1               5                   10                  15

Ala Ser Ala Asp Tyr Lys Asp Asp Ile Gly Ser Asp Ile Val Met Thr
            20                  25                  30

Gln Ser Pro Ser Ser Leu Ser Ala Ser Val Gly Asp Arg Val Thr Ile
        35                  40                  45

Thr Cys Arg Ala Ser Gln Asp Val Asn Thr Ala Val Ala Trp Tyr Gln
    50                  55                  60

Gln Lys Pro Gly Lys Ala Pro Lys Leu Leu Ile Tyr Ser Ala Ser Phe
65                  70                  75                  80

Leu Tyr Ser Gly Val Pro Ser Arg Phe Ser Gly Ser Arg Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln His Tyr Thr Thr Pro Pro Thr Phe Gly Gln Gly
        115                 120                 125

Thr Lys Val Glu Leu Lys Arg Gly Gly Gly Gly Ser Gly Gly Gly Gly
    130                 135                 140

Ser Gly Gly Gly Gly Ser Gly Gly Gly Gly Ser Glu Val Lys Leu Val
145                 150                 155                 160

Glu Ser Gly Gly Gly Leu Val Gln Pro Gly Gly Ser Leu Arg Leu Ser
                165                 170                 175

Cys Ala Thr Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
                245                 250                 255

Asp Gly Phe Tyr Ala Met Asp Tyr Trp Gly Gln Gly Thr Thr Val Thr
            260                 265                 270

Val Ser Ser Lys Leu Gly Gly Gly Gly Ser Arg Ser Asp Ile Val Leu
        275                 280                 285

Thr Gln Thr Pro Ser Ser Leu Pro Val Ser Val Gly Glu Lys Val Thr
    290                 295                 300

Met Thr Cys Lys Ser Ser Gln Thr Leu Leu Tyr Ser Asn Asn Gln Lys
305                 310                 315                 320

Asn Tyr Leu Ala Trp Tyr Gln Gln Lys Pro Gly Gln Ser Pro Lys Leu
                325                 330                 335

Leu Ile Ser Trp Ala Phe Thr Arg Lys Ser Gly Val Pro Asp Arg Phe
            340                 345                 350

Thr Gly Ser Gly Ser Gly Thr Asp Phe Thr Leu Thr Ile Gly Ser Val
        355                 360                 365

Lys Ala Glu Asp Leu Ala Val Tyr Tyr Cys Gln Gln Tyr Ser Asn Tyr
    370                 375                 380

Pro Trp Thr Phe Gly Gly Gly Thr Arg Leu Glu Ile Lys Arg Gly Gly
385                 390                 395                 400

Gly Gly Ser Gly Gly Gly Gly Ser Gly Gly Gly Gly Ser Gly Gly Gly
                405                 410                 415
```

```
Gly Ser Glu Val Gln Leu Gln Gln Ser Gly Pro Glu Val Val Lys Thr
            420                 425                 430

Gly Ala Ser Val Lys Ile Ser Cys Lys Ala Ser Gly Tyr Ser Phe Thr
        435                 440                 445

Gly Tyr Phe Ile Asn Trp Val Lys Lys Asn Ser Gly Lys Ser Pro Glu
    450                 455                 460

Trp Ile Gly His Ile Ser Ser Ser Tyr Ala Thr Ser Thr Tyr Asn Gln
465                 470                 475                 480

Lys Phe Lys Asn Lys Ala Ala Phe Thr Val Asp Thr Ser Ser Ser Thr
                485                 490                 495

Ala Phe Met Gln Leu Asn Ser Leu Thr Ser Glu Asp Ser Ala Asp Tyr
            500                 505                 510

Tyr Cys Val Arg Ser Gly Asn Tyr Glu Glu Tyr Ala Met Asp Tyr Trp
        515                 520                 525

Gly Gln Gly Thr Ser Val Thr Val Ser Ser Lys Leu Gly Ser His His
    530                 535                 540

His His His His
545


<210> SEQ ID NO 101
<211> LENGTH: 21
<212> TYPE: PRT
<213> ORGANISM: Apis mellifera

<400> SEQUENCE: 101

Met Lys Phe Leu Val Asn Val Ala Leu Val Phe Met Val Val Tyr Ile
1               5                   10                  15

Ser Tyr Ile Tyr Ala
            20


<210> SEQ ID NO 102
<211> LENGTH: 250
<212> TYPE: PRT
<213> ORGANISM: Artificial Sequence
<220> FEATURE:
<223> OTHER INFORMATION: 9.29_SH_G3 #2, a bispecific HER2 binding agent
      comprising a DARPin binding domain 1 of HER2 and a a DARPin
      binding domain 4 of HER2 connected by a shared alpha helix

<400> SEQUENCE: 102

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Ser Ala Gln Asp Lys Phe Gly
            100                 105                 110

Lys Thr Pro Gly Asp Leu Ala Gly Asp Asn Gly Asn Glu Trp Ile Ala
        115                 120                 125

Lys Lys Leu Leu Leu Ala Ala Ala Arg Glu Gly His Arg Glu Ala Val
```

```
    130                 135                 140

Glu Arg Ala Ile Lys Ala Gly Ala Asp Val Asn Ala Lys Asp Glu Tyr
145                 150                 155                 160

Gly Leu Thr Pro Leu Tyr Leu Ala Thr Ala His Gly His Leu Glu Ile
                165                 170                 175

Val Glu Val Leu Leu Lys Asn Gly Ala Asp Val Asn Ala Val Asp Ala
            180                 185                 190

Ile Gly Phe Thr Pro Leu His Leu Ala Ala Phe Ile Gly His Leu Glu
        195                 200                 205

Ile Ala Glu Val Leu Leu Lys His Gly Ala Asp Val Asn Ala Gln Asp
    210                 215                 220

Lys Phe Gly Lys Thr Ala Phe Asp Ile Ser Ile Gly Asn Gly Asn Glu
225                 230                 235                 240

Asp Leu Ala Glu Ile Leu Gln Lys Leu Asn
                245                 250


<210> SEQ ID NO 103
<211> LENGTH: 254
<212> TYPE: PRT
<213> ORGANISM: Artificial Sequence
<220> FEATURE:
<223> OTHER INFORMATION: 9.29_SH_G3 #6, a bispecific HER2 binding agent
      comprising a DARPin binding domain 1 of HER2 and a a DARPin
      binding domain 4 of HER2 connected by a shared alpha helix

<400> SEQUENCE: 103

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Phe Ala Gln Asp Lys Phe Gly
            100                 105                 110

Lys Thr Pro Phe Asp Leu Ala Arg Asp Asn Gly Asn Glu Trp Ile Ala
        115                 120                 125

Lys Leu Leu Leu Ala Ala Ala Leu Leu Glu Ala Ala Arg Gln Gly Gln
    130                 135                 140

Arg Asp Arg Val Glu Lys Leu Met Ala Asn Gly Ala Asp Val Asn Ala
145                 150                 155                 160

Lys Asp Glu Tyr Gly Leu Thr Pro Leu Tyr Leu Ala Thr Ala His Gly
                165                 170                 175

His Leu Glu Ile Val Glu Val Leu Leu Lys Asn Gly Ala Asp Val Asn
            180                 185                 190

Ala Val Asp Ala Ile Gly Phe Thr Pro Leu His Leu Ala Ala Phe Ile
        195                 200                 205

Gly His Leu Glu Ile Ala Glu Val Leu Leu Lys His Gly Ala Asp Val
    210                 215                 220

Asn Ala Gln Asp Lys Phe Gly Lys Thr Ala Phe Asp Ile Ser Ile Gly
225                 230                 235                 240
```

Asn Gly Asn Glu Asp Leu Ala Glu Ile Leu Gln Lys Leu Asn
245 250

<210> SEQ ID NO 104
<211> LENGTH: 257
<212> TYPE: PRT
<213> ORGANISM: Artificial Sequence
<220> FEATURE:
<223> OTHER INFORMATION: 9.29_SH_G3 #9, a bispecific HER2 binding agent comprising a DARPin binding domain 1 of HER2 and a a DARPin binding domain 4 of HER2 connected by a shared alpha helix

<400> SEQUENCE: 104

Met Arg Gly Ser His His His His His His Gly Ser Asp Leu Gly Lys
1 5 10 15

Lys Leu Leu Glu Ala Ala Arg Ala Gly Gln Asp Asp Glu Val Arg Ile
20 25 30

Leu Met Ala Asn Gly Ala Asp Val Asn Ala His Asp Phe Tyr Gly Ile
35 40 45

Thr Pro Leu His Leu Ala Ala Asn Phe Gly His Leu Glu Ile Val Glu
50 55 60

Val Leu Leu Lys His Gly Ala Asp Val Asn Ala Phe Asp Tyr Asp Asn
65 70 75 80

Thr Pro Leu His Leu Ala Ala Asp Ala Gly His Leu Glu Ile Val Glu
85 90 95

Val Leu Leu Lys Tyr Gly Ala Asp Val Ser Ala Gln Asp Lys Phe Gly
100 105 110

Lys Thr Pro Arg Asp Leu Ala Arg Asp Asn Gly Asn Glu Trp Ile Trp
115 120 125

Lys Leu Leu Leu Asp Ala Leu Lys Tyr Leu Leu Leu Glu Ala Ala Arg
130 135 140

Glu Gly His Arg Asp Arg Val Glu Lys Leu Ile Lys Ala Gly Ala Asp
145 150 155 160

Val Asn Ala Lys Asp Glu Tyr Gly Leu Thr Pro Leu Tyr Leu Ala Thr
165 170 175

Ala His Gly His Leu Glu Ile Val Glu Val Leu Leu Lys Asn Gly Ala
180 185 190

Asp Val Asn Ala Val Asp Ala Ile Gly Phe Thr Pro Leu His Leu Ala
195 200 205

Ala Phe Ile Gly His Leu Glu Ile Ala Glu Val Leu Leu Lys His Gly
210 215 220

Ala Asp Val Asn Ala Gln Asp Lys Phe Gly Lys Thr Ala Phe Asp Ile
225 230 235 240

Ser Ile Gly Asn Gly Asn Glu Asp Leu Ala Glu Ile Leu Gln Lys Leu
245 250 255

Asn

<210> SEQ ID NO 105
<211> LENGTH: 258
<212> TYPE: PRT
<213> ORGANISM: Artificial Sequence
<220> FEATURE:
<223> OTHER INFORMATION: 9.29_SH_G3 #10, a bispecific HER2 binding agent comprising a DARPin binding domain 1 of HER2 and a a DARPin binding domain 4 of HER2 connected by a shared alpha helix

<400> SEQUENCE: 105

Met Arg Gly Ser His His His His His His Gly Ser Asp Leu Gly Lys

```
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Asn Ala Gln Asp Lys Phe Gly
            100                 105                 110

Lys Thr Pro Tyr Asp Leu Ala Thr Asp Asn Gly Asn Gln Trp Ile Ala
        115                 120                 125

Glu Leu Leu Lys Arg Ala Ala Leu Arg Arg Lys Leu Leu Glu Ala Ala
    130                 135                 140

Arg Ala Gly His Arg Asp Glu Val Glu Asp Leu Ile Lys Asn Gly Ala
145                 150                 155                 160

Asp Val Asn Ala Lys Asp Glu Tyr Gly Leu Thr Pro Leu Tyr Leu Ala
                165                 170                 175

Thr Ala His Gly His Leu Glu Ile Val Glu Val Leu Leu Lys Asn Gly
            180                 185                 190

Ala Asp Val Asn Ala Val Asp Ala Ile Gly Phe Thr Pro Leu His Leu
        195                 200                 205

Ala Ala Phe Ile Gly His Leu Glu Ile Ala Glu Val Leu Leu Lys His
    210                 215                 220

Gly Ala Asp Val Asn Ala Gln Asp Lys Phe Gly Lys Thr Ala Phe Asp
225                 230                 235                 240

Ile Ser Ile Gly Asn Gly Asn Glu Asp Leu Ala Glu Ile Leu Gln Lys
                245                 250                 255

Leu Asn


<210> SEQ ID NO 106
<211> LENGTH: 259
<212> TYPE: PRT
<213> ORGANISM: Artificial Sequence
<220> FEATURE:
<223> OTHER INFORMATION: 9.29_SH_G3 #11, a bispecific HER2 binding agent
      comprising a DARPin binding domain 1 of HER2 and a a DARPin
      binding domain 4 of HER2 connected by a shared alpha helix

<400> SEQUENCE: 106

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95
```

```
Val Leu Leu Lys Tyr Gly Ala Leu Val Lys Ala Lys Asp Lys Phe Gly
            100                 105                 110

Lys Thr Pro Lys Asp Leu Ala Arg Asp Asn Gly Asn Gln Phe Ile Tyr
        115                 120                 125

Glu Leu Leu Glu Lys Ala Glu Leu Leu Glu Lys Leu Leu Leu Glu Ala
    130                 135                 140

Ala Arg Glu Gly His Arg Asp Arg Val Glu Glu Phe Ile Lys Arg Gly
145                 150                 155                 160

Ala Asp Val Asn Ala Lys Asp Glu Tyr Gly Leu Thr Pro Leu Tyr Leu
                165                 170                 175

Ala Thr Ala His Gly His Leu Glu Ile Val Glu Val Leu Leu Lys Asn
            180                 185                 190

Gly Ala Asp Val Asn Ala Val Asp Ala Ile Gly Phe Thr Pro Leu His
        195                 200                 205

Leu Ala Ala Phe Ile Gly His Leu Glu Ile Ala Glu Val Leu Leu Lys
    210                 215                 220

His Gly Ala Asp Val Asn Ala Gln Asp Lys Phe Gly Lys Thr Ala Phe
225                 230                 235                 240

Asp Ile Ser Ile Gly Asn Gly Asn Glu Asp Leu Ala Glu Ile Leu Gln
                245                 250                 255

Lys Leu Asn


<210> SEQ ID NO 107
<211> LENGTH: 260
<212> TYPE: PRT
<213> ORGANISM: Artificial Sequence
<220> FEATURE:
<223> OTHER INFORMATION: 9.29_SH_G3 #12, a bispecific HER2 binding agent
      comprising a DARPin binding domain 1 of HER2 and a a DARPin
      binding domain 4 of HER2 connected by a shared alpha helix

<400> SEQUENCE: 107

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Ala Val Gly Ala Gln Asp Lys Phe Gly
            100                 105                 110

Lys Thr Pro Lys Asp Leu Ala Arg Asp Asn Gly Asn Gln Trp Ile Tyr
        115                 120                 125

Glu Leu Leu Glu Lys Ala Glu Lys Asp Leu Arg Arg Lys Leu Leu Glu
    130                 135                 140

Ala Ala Arg Ala Gly His Arg Glu Glu Val Glu Lys Leu Ile Lys Leu
145                 150                 155                 160

Gly Ala Asp Val Asn Ala Lys Asp Glu Tyr Gly Leu Thr Pro Leu Tyr
                165                 170                 175

Leu Ala Thr Ala His Gly His Leu Glu Ile Val Glu Val Leu Leu Lys
            180                 185                 190
```

```
Asn Gly Ala Asp Val Asn Ala Val Asp Ala Ile Gly Phe Thr Pro Leu
        195                 200                 205

His Leu Ala Ala Phe Ile Gly His Leu Glu Ile Ala Glu Val Leu Leu
    210                 215                 220

Lys His Gly Ala Asp Val Asn Ala Gln Asp Lys Phe Gly Lys Thr Ala
225                 230                 235                 240

Phe Asp Ile Ser Ile Gly Asn Gly Asn Glu Asp Leu Ala Glu Ile Leu
                245                 250                 255

Gln Lys Leu Asn
            260


<210> SEQ ID NO 108
<211> LENGTH: 261
<212> TYPE: PRT
<213> ORGANISM: Artificial Sequence
<220> FEATURE:
<223> OTHER INFORMATION: 9.29_SH_G3 #13, a bispecific HER2 binding agent
      comprising a DARPin binding domain 1 of HER2 and a a DARPin
      binding domain 4 of HER2 connected by a shared alpha helix

<400> SEQUENCE: 108

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Asn Ala Gln Asp Lys Phe Gly
            100                 105                 110

Lys Thr Pro Glu Asp Leu Ala Lys Asp Asn Gly Asn Gln Trp Ile Ala
        115                 120                 125

Gln Lys Leu Glu Glu Ala Lys Lys Glu Asp Leu Asp Arg Lys Leu Leu
    130                 135                 140

Glu Ala Ala Arg Ala Gly His Arg Asp Glu Val Glu Asp Leu Ile Lys
145                 150                 155                 160

Asn Gly Ala Asp Val Asn Ala Lys Asp Glu Tyr Gly Leu Thr Pro Leu
                165                 170                 175

Tyr Leu Ala Thr Ala His Gly His Leu Glu Ile Val Glu Val Leu Leu
            180                 185                 190

Lys Asn Gly Ala Asp Val Asn Ala Val Asp Ala Ile Gly Phe Thr Pro
        195                 200                 205

Leu His Leu Ala Ala Phe Ile Gly His Leu Glu Ile Ala Glu Val Leu
    210                 215                 220

Leu Lys His Gly Ala Asp Val Asn Ala Gln Asp Lys Phe Gly Lys Thr
225                 230                 235                 240

Ala Phe Asp Ile Ser Ile Gly Asn Gly Asn Glu Asp Leu Ala Glu Ile
                245                 250                 255

Leu Gln Lys Leu Asn
            260
```

<210> SEQ ID NO 109
<211> LENGTH: 262
<212> TYPE: PRT
<213> ORGANISM: Artificial Sequence
<220> FEATURE:
<223> OTHER INFORMATION: 9.29_SH_G3 #14, a bispecific HER2 binding agent comprising a DARPin binding domain 1 of HER2 and a a DARPin binding domain 4 of HER2 connected by a shared alpha helix

<400> SEQUENCE: 109

```
Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Glu Ala Gln Asp Lys Phe Gly
            100                 105                 110

Lys Thr Pro Glu Asp Leu Ala Lys Asp Asn Gly Asn Gln Trp Ile Ala
        115                 120                 125

Gln Lys Leu Glu Glu Ala Lys Lys Lys Lys Asp Leu Asp Glu Lys Leu
    130                 135                 140

Leu Glu Ala Ala Arg Ala Gly His Arg Asp Glu Val Glu Asp Leu Ile
145                 150                 155                 160

Lys Asn Gly Ala Asp Val Asn Ala Lys Asp Glu Tyr Gly Leu Thr Pro
                165                 170                 175

Leu Tyr Leu Ala Thr Ala His Gly His Leu Glu Ile Val Glu Val Leu
            180                 185                 190

Leu Lys Asn Gly Ala Asp Val Asn Ala Val Asp Ala Ile Gly Phe Thr
        195                 200                 205

Pro Leu His Leu Ala Ala Phe Ile Gly His Leu Glu Ile Ala Glu Val
    210                 215                 220

Leu Leu Lys His Gly Ala Asp Val Asn Ala Gln Asp Lys Phe Gly Lys
225                 230                 235                 240

Thr Ala Phe Asp Ile Ser Ile Gly Asn Gly Asn Glu Asp Leu Ala Glu
                245                 250                 255

Ile Leu Gln Lys Leu Asn
            260
```

<210> SEQ ID NO 110
<211> LENGTH: 263
<212> TYPE: PRT
<213> ORGANISM: Artificial Sequence
<220> FEATURE:
<223> OTHER INFORMATION: 9.29_SH_G3 #15, a bispecific HER2 binding agent comprising a DARPin binding domain 1 of HER2 and a a DARPin binding domain 4 of HER2 connected by a shared alpha helix

<400> SEQUENCE: 110

```
Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
```

```
            20                  25                  30

Leu Met Ala Asn Gly Ala Asp Val Asn Ala His Asp Phe Tyr Gly Ile
        35                  40                  45

Thr Pro Leu His Leu Ala Ala Asn Phe Gly His Leu Glu Ile Val Glu
    50                  55                  60

Val Leu Leu Lys His Gly Ala Asp Val Asn Ala Phe Asp Tyr Asp Asn
65                  70                  75                  80

Thr Pro Leu His Leu Ala Ala Asp Ala Gly His Leu Glu Ile Val Glu
                85                  90                  95

Val Leu Leu Lys Tyr Gly Ala Asp Val Arg Ala Gln Asp Lys Phe Gly
            100                 105                 110

Lys Thr Pro Lys Asp Leu Ala Arg Asp Asn Gly Asn Glu Trp Ile Arg
        115                 120                 125

Glu Leu Leu Glu Lys Ala Glu Arg Lys Leu Lys Asp Leu Asp Arg Lys
    130                 135                 140

Leu Leu Glu Ala Ala Arg Ala Gly His Arg Asp Glu Val Glu Asp Leu
145                 150                 155                 160

Ile Lys Asn Gly Ala Asp Val Asn Ala Lys Asp Glu Tyr Gly Leu Thr
                165                 170                 175

Pro Leu Tyr Leu Ala Thr Ala His Gly His Leu Glu Ile Val Glu Val
            180                 185                 190

Leu Leu Lys Asn Gly Ala Asp Val Asn Ala Val Asp Ala Ile Gly Phe
        195                 200                 205

Thr Pro Leu His Leu Ala Ala Phe Ile Gly His Leu Glu Ile Ala Glu
    210                 215                 220

Val Leu Leu Lys His Gly Ala Asp Val Asn Ala Gln Asp Lys Phe Gly
225                 230                 235                 240

Lys Thr Ala Phe Asp Ile Ser Ile Gly Asn Gly Asn Glu Asp Leu Ala
                245                 250                 255

Glu Ile Leu Gln Lys Leu Asn
            260


<210> SEQ ID NO 111
<211> LENGTH: 25
<212> TYPE: PRT
<213> ORGANISM: Artificial Sequence
<220> FEATURE:
<223> OTHER INFORMATION: artificial GGGGS linker with 5 repeats

<400> SEQUENCE: 111

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 112
<211> LENGTH: 19
<212> TYPE: PRT
<213> ORGANISM: Escherichia coli

<400> SEQUENCE: 112

Met Lys Lys Ile Trp Leu Ala Leu Ala Gly Leu Val Leu Ala Phe Ser
1               5                   10                  15

Ala Ser Ala


<210> SEQ ID NO 113
<211> LENGTH: 6
```

-continued

```
<212> TYPE: PRT
<213> ORGANISM: Artificial Sequence
<220> FEATURE:
<223> OTHER INFORMATION: FLAG-Tag M1

<400> SEQUENCE: 113

Asp Tyr Lys Asp Asp Ile
1               5


<210> SEQ ID NO 114
<211> LENGTH: 6
<212> TYPE: PRT
<213> ORGANISM: Artificial Sequence
<220> FEATURE:
<223> OTHER INFORMATION: 6xHis-Tag

<400> SEQUENCE: 114

His His His His His His
1               5


<210> SEQ ID NO 115
<211> LENGTH: 19
<212> TYPE: PRT
<213> ORGANISM: Mus musculus

<400> SEQUENCE: 115

Met Glu Thr Asp Thr Leu Leu Leu Trp Val Leu Leu Leu Trp Val Pro
1               5                   10                  15

Gly Ser Thr
```

BISPECIFIC HER2 LIGANDS FOR CANCER THERAPY

CROSS-REFERENCE TO RELATED APPLICATIONS

This is the U.S. National Stage of International Application No. PCT/EP2013/071443, filed Oct. 14, 2013, which was published in English under PCT Article 21(2), and which in turn claims the benefit of European Patent Application Nos. 12188598.2 filed on Oct. 15, 2012, 12191673.8 filed on Nov. 7, 2012, 12192465.8 filed on Nov. 13, 2012, and 13185724.5 filed on Sep. 24, 2013.

DESCRIPTION

The present invention relates to bispecific targeting agents, particularly to antibodies, antibody fragments or other polypeptide ligands targeting HER2, and their use in cancer therapy.

BACKGROUND

The members of the HER family of receptor tyrosine kinases are important mediators of cell growth, differentiation, migration and survival. The receptor family includes four distinct members including epidermal growth factor receptor (EGFR, ErbB1, or HER1), HER2 (ErbB2 or p185<neu>), HER3 (ErbB3) and HER4 (ErbB4). The members of the EGFR family are closely related single-chain modular glycoproteins with an extracellular ligand binding region, a single transmembrane domain and an intracellular tyrosine kinase, followed by specific phosphorylation sites which are important for the docking of downstream signaling proteins.

The extracellular regions of the HER receptor family contain two homologous ligand binding domains (domains 1 and 3) and two cysteine-rich domains (domains 2 and 4), which are important for receptor dimerization. In the absence of a ligand, HER receptors normally exist as inactive monomers, known as the "tethered" structure, which is characterized by close interaction of domain 2 and 4. Ligand binding to the extracellular domain initiates a conformational rearrangement, exposing the dimerization domains 2 and 4. Therefore, binding of growth factors to HER receptors induces conformational changes that allow receptor dimerization. After extracellular receptor dimerization, transmembrane helices switch to an active conformation that enables the intracellular kinase domains to trans-auto-phosphorylate each other. This phosphorylation event allows the recruitment of specific downstream signaling proteins.

Epidermal Growth factor receptor 1, (EGFR), has been causally implicated in human malignancy. In particular, increased expression of EGFR has been observed in breast, bladder, lung, head, neck and stomach cancer as well as glioblastomas.

Human epidermal growth factor receptor 2 (HER2, also known as ErbB2 or Neu; UniProtKB/Swiss-Prot No. P04626) consists of 1233 amino acids and is structurally similar to EGFR, with an extracellular domain consisting of four subdomains 1-4, a transmembrane domain, a juxtamembrane domain, an intracellular cytoplasmic tyrosine kinase and a regulatory C-terminal region. The structure of HER2's extracellular region is different in important aspects from the other EGF receptors, however. In the other EGF receptors, in a non-activated state, domain 2 binds to domain 4. Upon binding to domains 1 and 3, the activating growth factor (ligand) selects and stabilizes a conformation that allows a dimerization arm to extend from domain 2 to interact with an ErbB dimer partner. HER2, on the other hand, has a fixed conformation that resembles the ligand-activated state of the other receptor members: the domain 2-4 interaction is absent and the dimerization loop in domain 2 is continuously exposed. HER2 is activated via formation of heterodimeric complexes with other ErbB family members and thereby indirectly regulated by EGFR and HER3 ligands. HER2 is the preferred heterodimerization partner of the three other ErbB receptors, enhancing the affinity of the other ErbB receptors for their ligands by slowing down the rate of ligand-receptor complex dissociation, whereby HER2 enhances and prolongs signaling.

An excess of HER2 on the cell surface causes transformation of epithelial cells from multiple tissues. Amplification of the human homolog of the neu gene (also known as HER2) is observed in breast and ovarian cancers and correlates with a poor prognosis (U.S. Pat. No. 4,968,603). Overexpression of HER2 has also been observed in other carcinomas including carcinomas of the stomach, endometrium, salivary gland, lung, kidney, colon, thyroid, pancreas and bladder.

Antibodies Targeting HER2

Drebin and colleagues have raised antibodies against the rat neu gene product, p185<neu>disclosed in U.S. Pat. No. 6,733,752 (B1).

Hudziak et al., Mol. Cell. Biol. 9(3):1165-1172 (1989) describe the generation of a panel of HER2 antibodies which were characterized using the human breast tumor cell line SkBr-3. Using a cell proliferation assay, maximum inhibition was obtained with an antibody called 4D5. The antibody 4D5 was further found to sensitize HER2-overexpressing breast tumor cell lines to the cytotoxic effects of TNF-[alpha]; see also U.S. Pat. No. 5,677,171. A recombinant humanized version of the murine HER2 antibody 4D5 (huMAb4D5-8, rhuMAb HER2, trastuzumab or HERCEPTIN; U.S. Pat. No. 5,821,337) is clinically active in patients with HER2-overexpressing metastatic breast cancers that have received extensive prior anti-cancer therapy. Herceptin is approved in combination with chemotherapy for use in patients with HER2-positive metastatic stomach (gastric) cancer.

Herceptin is widely used for the treatment of patients with early as well as metastatic breast cancer whose tumors overexpress HER2 protein and/or have HER2 gene amplification. The treatment of breast cancer patients with Herceptin/trastuzumab is, for example, recommended and now routine for patients having HER2-positive disease; see US 2002/0064785, US 2003/0170234A1, US2003/0134344 and US 2003/0147884. The prior art thus focuses on the eligibility of breast cancer patients for trastuzumab/Herceptin therapy based on a high HER2 protein expression level (e.g. defined as HER2(3+) by immunohistochemistry (IHC)). HER2-positive disease in breast cancer is defined to be present if a high HER2 (protein) expression level is detected by immunohistochemical methods (e.g. HER2 (+++) or as HER2 gene amplification (e.g. a HER2 gene copy number higher than 4 copies of the HER2 gene per tumor cell) or both, found in samples obtained from the patients such as breast tissue biopsies or breast tissue resections or in tissue derived from metastatic sites. One frequently applied method for detecting HER2 overexpression and amplification at the gene level is fluorescence in situ hybridization (FISH), which is also described in US2003/0152987, Cohen et al.

Pertuzumab, a humanized antibody, is the first of a new class of agents known as HER dimerization inhibitors (HD's). Pertuzumab binds to HER2 at its dimerization domain, thereby inhibiting its ability to form active heterodimer receptor complexes, thus blocking the downstream signal cascade that ultimately results in cell growth and division. Pertuzumab is directed against the extracellular domain 2 of HER2. In contrast to trastuzumab, which acts by binding to domain 4 of HER2, pertuzumab is a HER dimerization inhibitor which inhibits dimerization of HER2 with HER3 and the other members of the EGFR receptor family in the presence of the respective activating ligands. By blocking complex formation, pertuzumab prevents the growth-stimulatory effects and cell survival signals activated by ligands of HER1, HER3 and HER4. Pertuzumab has been approved by the FDA under the name Perjeta for treatment in combination with trastuzumab and docetaxel for patients with HER2-positive metastatic breast cancer, who have not received prior anti-HER2 therapy or chemotherapy for metastatic disease. Pertuzumab is a fully humanized recombinant monoclonal antibody based on the human IgG1([kappa]) framework sequences. Patent publications concerning pertuzumab and selection of patients for therapy therewith include: US20060073143 (A1); US2003/0086924; US2004/0013667A1, and US2004/0106161.

For trastuzumab, while known to show clinical benefits in terms of e.g. prolonged survival in combination with chemotherapy compared to chemotherapy alone, a majority of HER2 positive breast cancer patients were nevertheless found to be non-responders (45% overall response rate for Herceptin+chemotherapy vs. 29% for chemotherapy alone).

Thus, while monoclonal antibody therapy directed against HER2 has been shown to provide improved treatment in e.g. metastatic breast cancers that overexpress HER2, there is still considerable room for improvement.

Non-Antibody Scaffolds Targeting HER2

Alternative targeting proteins have been proposed recently, which are more diverse in molecular structure than human immunoglobulin-derived antibody fragments and antibody-derived constructs and formats, and thus allow additional molecular formats by creating heterodimeric and multimeric assemblies, leading to new biological functions. A number of such targeting proteins have been described (reviewed in (Binz et al., Nat. Biotech 2005, Vol 23:1257-1268)). Non-limiting examples of such targeting proteins are camelid antibodies, protein scaffolds derived from protein A domains (termed "Affibodies", Affibody AB), tendamistat (an alpha-amylase inhibitor, a 74 amino acid beta-sheet protein from *Streptomyces tendae*), fibronectin, lipocalin ("Anticalins", *Pieris*), T-cell receptors, ankyrins (designed ankyrin repeat proteins termed "DARPins", Univ. Zurich and Molecular Partners; see US20120142611 (A1)), A-domains of several receptors ("Avimers", Avidia) and PDZ domains, fibronectin domains (FN3) ("Adnectins", Adnexus), consensus fibronectin domains ("Centyrins", Centyrex/Johnson&Johnson) and Ubiquitin ("Affilins", SCIL Proteins) and knottins (Moore and Cochrane, Methods in Enzymology 503 (2012), 223-251 and references cited therein).

From these proteins, multimeric and multispecific assemblies can be constructed (Caravella and Lugovskoy, Current Opinions in Chemical Biology 2010, 14:520-528; Vanlandschoot et al. Antiviral Research 2011 92:389-407; Lofblom et al. 2011 Current Opinion in Biotechnology 2011 22:843-848, Boersma et al. 2011 Curr. Opin. Biotechnol. 22:849-857). It is also possible to fuse these and other peptidic domains to antibodies to create so-called Zybodies (Zyngenia Inc., Gaithersburg, Md.).

All of these scaffolds, with different inherent properties, have in common that they can be directed to bind specific epitopes, by using selection technologies well known to practitioners in the field (Binz et al., Nat. Biotech 2005, 23:1257-1268).

For example, the different individual domains of HER2 can be individually expressed in insect cells, using a baculovirus expression system, as demonstrated for domain 1 and domain 4 (Frei et al., Nat Biotechnol. 2012 30:997-1001). Thereby, it is guaranteed that binders selected will be directed towards the domain of interest. The HER2 domains can then be biotinylated as previously described (Zahnd et al., (2006). Selection and characterization of HER2 binding-designed ankyrin repeat proteins. J. Biol. Chem. 281), and thus be immobilized on streptavidin-coated magnetic beads or on microtiter plates coated with streptavidin or neutravidin (Steiner et al. (2008) J. Mol. Biol. 382, 1211-1227); (Zahnd et al. (2007) J. Mol. Biol. 369, 1015-1028.)). The HER2 domains so immobilized can then serve as targets for diverse protein libraries in either phage display or ribosome display format. A large variety of different antibody libraries has been published (Mondon P. et al., Human antibody libraries: a race to engineer and explore a larger diversity. Frontiers in Bioscience. 13:1117-1129, 2008.) and the technology of selecting binding antibodies is well known to the practitioners of the field. Phage display is a suitable format for antibody fragments (Fab fragments, scFv fragments or single domain antibodies s) (Hoogenboom H R. Nature Biotechnology. 23(9):1105-1116, 2005 September) and any other scaffold that contain disulfide bonds, but it can also be used for scaffolds not containing disulfide bonds (e.g., Steiner et al. (2008) J. Mol. Biol. 382, 1211-1227)(Rentero et al. Chimia. 65(11):843-5, 2011., Skerra A. Current Opinion in Biotechnology. 18(4):295-304, 2007 August). Similarly, ribosome display can be used for antibody fragments (Hanes et al. (2000), Picomolar affinity antibodies from a fully synthetic naive library selected and evolved by ribosome display. Nat. Biotechnol. 18, 1287-1292) and for other scaffolds (Zahnd et al. (2007). Ribosome display: selecting and evolving proteins in vitro that specifically bind to a target. Nat. Methods 4, 269-279; Zahnd et al. (2007) J. Mol. Biol. 369, 1015-28.). A third powerful technology is yeast display (Pepper et al., Combinatorial Chemistry & High Throughput Screening. 11(2):127-134, 2008 February). In this case a library of the binding protein of interest is displayed on the surface of yeast, and the respective domain of HER2 is either directly labeled with a fluorescent dye or its his tag is detected with an anti-histag antibody, which is in turn detected with a secondary antibody. Such methods are well known to the practitioners in the field (Boder et al., Yeast surface display for directed evolution of protein expression, affinity, and stability, Methods in Enzymology. 328:430-44, 2000.).

Another possibility of engineering represents the connection of those binders to create bispecific or higher multivalent binding molecules. Such connection can be achieved genetically by fusions of two or more of these binding molecules or chemically by crosslinking separately expressed molecules, or by adding a dimerization domain include separate dependent claims for each or any combination thereof (see, e.g. Stefan et al. (2011) J. Mol. Biol. 413:826-843; Boersma et al. (2011) J. Biol. Chem. 286: 41273-41285)).

A bispecific anti-HER2 camelidae antibody construct (Bispecific Nanobody) is shown in US20110059090 (A1). The document relates to a bispecific molecule that simultaneously targets HER2 at the extracellular domain 2, defined by competition with pertuzumab, and domain 4, defined by competition with trastuzumab. This molecule has been described to exhibit stronger anti-proliferative activity than trastuzumab (Herceptin) in a direct comparison in an in vitro cell culture model using the cell line SkBr3.

Due to the absence of any known HER2-specific ligand, current HER2 targeting strategies aim to block the dimerization of the receptor by binding to the interaction interface. Today's knowledge of HER2 receptor dimerization is mostly based on the crystal structure of the ligand-bound form of the EGFR homodimer, which is broadly accepted as the active mode of all EGF receptor family members (Garret et al. (2002) Cell 110, 763-773). The two EGFR molecules show a back-to-back interaction. Extending these findings to HER2 and its possible interaction with other members of the EGFR family, one interaction interface is present on domain 2 of the extracellular part of HER2. Pertuzumab binds to domain 2 and is indeed known to block receptor interaction at this interface. Another known interaction is present on domain 4 of the extracellular part of HER2. This interaction interface is presumably blocked by trastuzumab. Yet both antibodies, trastuzumab and pertuzumab, even when simultaneously applied, are not able to block all HER2 interactions to completeness. The interaction of the extracellular part and the kinase domain of HER2 are thought to be linked in such a way as to allow some residual interactions even in the trastuzumab- and pertuzumab-blocked state, which is in accordance with crystal structure data (Lu et al. (2010) Mol. Cell. Biol. (22):5432-5443). The bispecific ligand mentioned above that binds both epitopes (pertuzumab and trastuzumab) simultaneously (US20110059090 A1) reduces the cell growth in a cell culture model by approx. 50%, in comparison to a reduction of about 40% effected by trastuzumab. This same effect, however, can also be achieved by treating with the mixture of trastuzumab and pertuzumab.

In view of the above mentioned state of the art, the objective of the present invention is to provide improved means and methods for targeting the HER2 protein for use in therapy of cancer. This objective is attained by the subject-matter of the independent claims.

SUMMARY OF THE INVENTION

According to one aspect of the invention, a bispecific agent is provided, comprising a. a first ligand that binds HER2 extracellular domain 1,
b. a second ligand that binds HER2 extracellular domain 4, and
c. a linker that connects said first ligand to said second ligand.

In some embodiments, the bispecific agent is a polypeptide. While the person skilled in the art can conceive of non-polypeptide targeting agents that can be rationally designed simply on the basis of the present specification, such as, by way of non-limiting example, RNA aptamers or L-RNA aptamers (see U.S. Pat. No. 6,605,713 and documents citing this publication), the majority of contemplated embodiments of the present invention relate to polypeptide ligands. For reasons of structural definition, the majority of these embodiments again are linked by a polypeptide linker as part of one single amino acid chain. While non-polypeptide bispecific agents are explicitly encompassed in the present invention, all embodiments mentioned herein below are to be read to explicitly include a polypeptide agent, particularly a single amino acid chain polypeptide agent.

In some embodiments, the bispecific agent is composed of a single sequence of amino acids. In some embodiments, the first ligand is connected to the second ligand covalently through a bridging moiety attached to amino acid side chains on the first and second ligands. In some embodiments, the first ligand is connected to the second ligand through a dimerization domain binding both the first ligand and the second ligand by non-covalent interactions.

According to an alternative to this aspect of the invention, a polypeptide is provided, comprising a. a first binding site that binds HER2 extracellular domain 1,
b. a second binding site that binds HER2 extracellular domain 4, and
c. a linker that covalently links the first binding site and the second binding site.

The term "binding site" in the context of the present specification refers to the constituent parts, in particular the amino acid residues, of the first or second polypeptide ligand that in binding interact with particular constituent parts, for example a particular epitope, of the extracellular domain 1 or 4 of HER2.

According to another alternative of this aspect of the invention, a bispecific HER2-targeting agent is provided, comprising a. a first polypeptide ligand that binds to HER2 extracellular domain 1 (Seq. ID 01),
b. a second polypeptide ligand that binds to HER2 extracellular domain 4 (Seq. ID 02) and
c. a linker covalently attaching the first polypeptide ligand to the second polypeptide ligand.

The term "bispecific" in the context of the present specification refers to the ability of the agent to specifically bind to two different epitopes of HER2.

"Binding" or "specifically binding" in the context of the present specification refers to the ability of the first (and respectively, second) polypeptide ligand to specifically and noncovalently attach to domain 1 (or, respectively, domain 4) of HER2 with a dissociation constant of equal or less than $10^{-7}$ M, $10^{-8}$ M or $10^{-9}$ M.

Domain 1 (SEQ ID 01) of HER2 (ErbB-2; Accession no. NP 004439.2) is the amino acid sequence

```
QVCT GTDMKLRLPA SPETHLDMLR HLYQGCQVVQ GNLELTYLPT
NASLSFLQDI QEVQGYVLIA HNQVRQVPLQ RLRIVRGTQL
FEDNYALAVL DNGDPLNNTT PVTGASPGGL RELQLRSLTE
ILKGGVLIQR NPQLCYQDTI LWKDIFHKNN QLALTLIDTN
RSRACHPCSP MCKGSRCWGE SSEDCQSLTR TVA.
```

Domain 4 (SEQ ID02) of HER2 (ErbB-2; Accession no. NP 004439.2) is the amino acid sequence

```
VNCS QFLRGQECVE ECRVLQGLPR EYVNARHCLP CHPECQPQNG
SVTCFGPEADQCVACAHYKD PPFCVARCPS GVKPDLSYMP
IWKFPDEEGA CQP
```

Accession numbers and Gene ID numbers refer to entries in the National Center for Biotechnology Information, Bethesda, Md., MD.

UniProt. No refer to entries in the UniProt Knowledgebase.

ATCC numbers refer to entries in the American Type Culture Collection.

PDB IDs refer to entries in the protein data bank.

In some embodiments, the first polypeptide ligand or the second polypeptide ligand is an antibody, antibody fragment, an antibody-like molecule or a protein A domains derived polypeptide.

In some embodiments, the antibody is an immunoglobulin consisting of two heavy chains and two light chains. In some embodiments, the antibody is a single domain antibody, consisting of an isolated variable domain from a heavy or light chain. In some embodiments, the antibody is a heavy-chain antibody consisting of only heavy chains such as antibodies found in camelids.

In some embodiments, the antibody fragment is a Fab fragment, i.e. the antigen-binding fragment of an antibody, or a single-chain variable fragment, i.e. a fusion protein of the variable region of heavy and the light chain of an antibody connected by a peptide linker.

An antibody-like molecule in the context of the present specification refers to a molecule showing a specific binding to another molecule or target similar to the specific binding of an antibody. In some embodiments, the antibody-like molecule is a repeat protein, such as a designed ankyrin repeat protein (Molecular Partners, Zurich), a polypeptide derived from armadillo repeat proteins, a polypeptide derived from leucine-rich repeat proteins or a polypeptide derived from tetratricopeptide repeat proteins.

In some embodiments, the antibody-like molecule may also be a polypeptide derived from protein A domains, a polypeptide derived from fibronectin domain FN3, a polypeptide derived from consensus fibronectin domains, a polypeptide derived from lipocalins, a polypeptide derived from Zinc fingers, a polypeptide derived from Src homology domain 2 (SH2), a polypeptide derived from Src homology domain 3 (SH3), a polypeptide derived from PDZ domains, a polypeptide derived from gamma-crystallin, a polypeptide derived from ubiquitin, a polypeptide derived from a cysteine knot polypeptide or a polypeptide derived from a knottin.

A protein A domains derived polypeptide refers to a molecule that is a derivative of protein A and is capable of specifically binding the Fc region and the Fab region of immunoglobulins.

An armadillo repeat protein refers to a polypeptide comprising at least one armadillo repeat, wherein a armadillo repeat is characterized by a pair of alpha helices that form a hairpin structure.

A humanized camelid antibody in the context of the present specification refers to an antibody consisting of only the heavy chain or the variable domain of the heavy chain (VHH domain) and whose amino acid sequence has been modified to increase their similarity to antibodies naturally produced in humans and, thus show a reduced immunogenicity when administered to a human being.

A general strategy to humanize camelid antibodies is shown in Vincke et al. "General strategy to humanize a camelid single-domain antibody and identification of a universal humanized nanobody scaffold", J Biol Chem. 2009 Jan. 30; 284(5):3273-3284, and US2011165621A1.

In some embodiments, the first polypeptide ligand and/or the second polypeptide ligand is selected from a. an immunoglobulin Fab fragment,
b. an immunoglobulin scFv fragment,
c. an immunoglobulin variable domain (domain antibody),
d. a humanized camelid antibody,
e. a polypeptide derived from protein A domains,
f. a polypeptide derived from fibronectin domain FN3,
g. a polypeptide derived from consensus fibronectin domains,
h. a polypeptide derived from lipocalins,
i. a polypeptide derived from armadillo repeat proteins,
j. a polypeptide derived from tetratricopeptide repeat proteins,
k. a polypeptide derived from leucine-rich repeat proteins,
l. a polypeptide derived from Zinc fingers,
m. a polypeptide derived from Src homology domain 2 (SH2),
n. a polypeptide derived from Src homology domain 3 (SH3),
o. a polypeptide derived from PDZ domains,
p. a polypeptide derived from gamma-crystallin,
q. a polypeptide derived from ubiquitin,
r. a polypeptide derived from a cysteine knot polypeptide,
s. a polypeptide derived from a knottin and
t. a peptide selected from a random peptide library to bind to domain 1 or domain 4 of HER2.

According to another aspect of the invention, a bispecific antibody is provided, which is selected from a. a bispecific IgG comprising a first Fab fragment binding to domain 1 of HER2 and a second Fab fragment binding to domain 4 of HER2,
b. an IgG comprising a VH domain binding to domain 1 of HER2 and a VL domain binding to domain 4 of HER2,
c. an IgG comprising a VH domain binding to domain 4 of HER2 and a VL domain binding to domain 1 of HER2,
d. a construct comprising a first scFv fragment binding to domain 1 of HER2, a second scFv fragment binding to domain 4 of HER2 and a linker connecting said first scFv fragment and said second scFv fragment,
e. a diabody comprising a first binding site binding to domain 1 of HER2 and a second binding site binding to domain 4 of HER2,
f. an IgG targeting HER2 domain 4 connected to a polypeptide ligand selected from the list recited in the above embodiment of the invention targeting domain 1 of HER2, or to a peptide ligand of 5 to 35 amino acids selected from a peptide library to bind to domain 1 of HER2, wherein the polypeptide ligand or the peptide ligand is connected to
   i. the N-terminus of a heavy chain of the IgG,
   ii. the C-terminus of a heavy chain of the IgG,
   iii. the N-terminus of a light chain of the IgG or
   iv. the C-terminus of a light chain of the IgG,
g. an IgG targeting HER2 domain 1 connected a polypeptide ligand selected from the list recited in the above embodiment of the invention targeting domain 4 of HER2 or to a peptide ligand of 5 to 35 amino acids selected from a peptide library to bind to domain 1 of HER2, wherein the polypeptide ligand or the peptide ligand is connected to
   i. the N-terminus of a heavy chain of the IgG,
   ii. the C-terminus of a heavy chain of the IgG,
   iii. the N-terminus of a light chain of the IgG or
   iv. the C-terminus of a light chain of the IgG.

The term "diabody" in the context of the present specification refers to a bispecific antibody comprising the VH (variable heavy) domain of a first antibody linked to the VL (variable light) domain of a second antibody and the VL domain of the first antibody fused to the VH domain of the second antibody.

The term “VL domain” in the context of the present specification refers to the variable domain of the light chain of an antibody.

Likewise, the term “VH domain” in the context of the present specification refers to the variable domain of the heavy chain of an antibody.

In some embodiments, a bispecific IgG is provided, consisting exclusively of a VH domain binding to domain 1 of HER2 and a VL domain binding to domain 4 of HER2 or exclusively of a VH domain binding to domain 1 of HER2, a VL domain binding to domain 4 of HER2 and a linker.

In some embodiments, the bispecific HER2-targeting agent of the invention is a bispecific IgG, consisting exclusively of a VH domain binding to domain 4 of HER2 and a VL domain binding to domain 1 of HER2 and a linker connecting the two domains, or of a VH domain binding to domain 4 of HER2, a VL domain binding to domain 1 of HER2 and a linker connecting the two domains.

In some embodiments, the bispecific HER2-targeting agent of the invention is a bispecific IgG, consisting exclusively of an IgG targeting HER2 domain 4, where one or more of the structural loops of the Fc chain have been modified to bind to an epitope in HER2 domain 1 (see Wozniak-Knopp et al. (2010), Protein Engineering, Design and Selection 23, 289-297).

In some embodiments, the bispecific HER2-targeting agent of the invention is a bispecific IgG, consisting exclusively of an IgG targeting HER2 domain 1, where one or more of the structural loops of the Fc chain have been modified binding to an epitope in HER2 domain 4.

In some embodiments, the first polypeptide ligand and/or the second polypeptide ligand is an ankyrin repeat based polypeptide.

An ankyrin repeat based polypeptide in the context of the present specification refers to a polypeptide that comprises repetitive amino acid sequences, each repetitive sequence comprising two α-helices separated by loops.

In one embodiment, the antibody-like molecules are the Designed Ankyrin Repeat Proteins (DARPins) disclosed in US2012142611 (A1).

In some embodiments, the first polypeptide ligand comprises or is a sequence selected from the group composed of SEQ ID 10, SEQ ID 11, SEQ ID 12, SEQ ID 13, SEQ ID 14, SEQ ID 15, SEQ ID 16, SEQ ID 17, SEQ ID 18, SEQ ID 19, SEQ ID 20, SEQ ID 21, SEQ ID 22, SEQ ID 23, SEQ ID 24, SEQ ID 30, SEQ ID 31, SEQ ID 32, SEQ ID 33, SEQ ID 34, SEQ ID 35, SEQ ID 36, SEQ ID 37, SEQ ID 38, SEQ ID 39, SEQ ID 40, SEQ ID 41, SEQ ID 42, SEQ ID 43, SEQ ID 44, SEQ ID 45, SEQ ID 46, SEQ ID 47, SEQ ID 48, SEQ ID 49, SEQ ID 50, SEQ ID 61, SEQ ID 62, SEQ ID 63, SEQ ID 64, SEQ ID 65, SEQ ID 66 and SEQ ID 93.

Such polypeptide, which comprises or is a sequence described in the preceding paragraph, is an ankyrin repeat based polypeptide that binds the extracellular domain 1 of HER2.

In some embodiments, the second polypeptide ligand comprises or is a sequence from the group composed of SEQ ID 25, SEQ ID 26, SEQ ID 27, SEQ ID 28, SEQ ID 29, SEQ ID 67, SEQ ID 68, SEQ ID 69 and SEQ ID 92.

Such polypeptide, which comprises or is a sequence described in the preceding paragraph, is an ankyrin repeat based polypeptide that binds the extracellular domain 4 of HER2.

Where reference is made herein to a polypeptide characterized by a particular sequence, such reference is meant to also encompass polypeptides having an identical function to the particular sequence, and showing a sequence identity of at least 70%, 80%, 90% or 95% to the certain sequence.

Identity in the context of the present invention is a single quantitative parameter representing the result of a sequence comparison position by position. Methods of sequence comparison are known in the art; the BLAST algorithm available publicly is an example.

In some embodiments, the first polypeptide ligand and the second polypeptide ligand are attached to each other by an oligopeptide linker, the first polypeptide, the second polypeptide ligand and the linker forming a continuous polypeptide chain.

One advantage of a bispecific HER2-targeting agent consisting of a continuous polypeptide chain is that such agent easily can be manufactured by recombinant biotechnology in a suitable host such as *E. coli*, yeast or mammal cells by expression of a single nucleotide sequence coding the continuous polypeptide chain.

In some embodiments, the first polypeptide ligand is located at the N-terminus of the continuous polypeptide chain, the second polypeptide ligand is located at the C-terminus of the continuous polypeptide chain, and the linker is located between the first and the second polypeptide ligand. Embodiments wherein the agent of the invention is constituted by one continuous polypeptide chain offers advantages of production of the agent in a single step by methods of recombinant biotechnology, facilitating reproducibility of composition of the agent.

In some embodiments, the first polypeptide ligand and the second polypeptide ligand are attached covalently to each other by a bridging moiety or a crosslinker.

In some embodiments, the crosslinker connects a functionality such as an amino function on the side chain of lysine or a thiol function on a side chain of cysteine or the N-terminal amino group in the first polypeptide ligand to an amino acid side chain functional group in the second polypeptide ligand.

In some embodiments, the crosslinker is selected from glutaraldehyde, succinimide, tris[2-maleimidoethyl]amine, 1,4-bismaleimidobutane, and 1,4 bismaleimidyl-2,3-dihydroxybutane.

In some embodiments, a bispecific HER2-targeting agent according to the above aspects or embodiments of the invention is provided, wherein a) the first polypeptide ligand partially or fully interacts non-covalently with
   i. a first D1 (domain 1) epitope, wherein the first D1 epitope comprises the amino acid residues E87, N89, Y90, L132, R135, D143, I145, W147, K148, L157, A158, L159, T160, L161 and I162 comprised within the amino acid sequence of HER2,
   ii. a second D1 epitope, wherein the second D1 epitope comprises the amino acid residues D88, A93, V94, I133, Q134, Q142, T144, L146, F151, H152, K153, N154, Q156 and D163 comprised within the amino acid sequence of HER2,
   iii. a third D1 epitope characterized by Seq. ID 55,
   iv. a fourth D1 epitope, wherein the fourth D1 epitope comprises the amino acid residues P100, L101, N102, N103, T104, R135, N136, P137, Y141, D143, T144, or
   v. a D1 epitope of domain 1 of HER2 (SEQ ID 01), wherein binding to the D1 epitope is competed by a polypeptide selected from SEQ ID 10, SEQ ID 11, SEQ ID 12, SEQ ID 13, SEQ ID 14, SEQ ID 15, SEQ ID 16, SEQ ID 17, SEQ ID 18, SEQ ID 19, SEQ ID 20, SEQ ID 21, SEQ ID 22, SEQ ID 23, SEQ ID 24, SEQ ID 30, SEQ ID 31, SEQ ID 32, SEQ ID 33, SEQ ID 34, SEQ ID 35, SEQ ID 36, SEQ ID 37, SEQ ID 38, SEQ ID 39, SEQ ID 40, SEQ ID 41, SEQ ID 42, SEQ ID 43, SEQ ID 44, SEQ ID 45, SEQ ID 46, SEQ ID 47, SEQ ID 48, SEQ ID 49, SEQ ID 50, SEQ ID 61, SEQ ID 62, SEQ ID 63, SEQ ID 64, SEQ ID 65, SEQ ID 66 and SEQ ID 93, and/or, b) the second polypeptide ligand partially or fully interacts non-covalently with
   i. a first D4 (domain 4) epitope, wherein the first D4 epitope comprises the amino acid residues F512, E521, V524, L525, Q526, Y532, V533, N534, A535, R536, D549, G550, S551, V552, C554, F555 and V563 comprised within the amino acid sequence of HER2,
   ii. a second D4 epitope, wherein the second D4 epitope comprises the amino acid residues C522, R523, T553, C562 and A564 comprised within the amino acid sequence of HER2,
   iii. a third D4 epitope characterized by Seq. ID 56,
   iv. a fourth D4 epitope characterized by Seq. ID 57,
   v. a fifth D4 epitope, wherein the fifth epitope comprises the amino acid residues P557, E558, A559, D560, 0561, D570, P571, P572, F573, P595, D596, E597, E598, G599, A600, C601, Q602 and P603 comprised within the amino acid sequence of HER2, or
   vi. a D4 epitope of domain 4 of HER2 (SEQ ID 02), wherein binding to the D4 epitope is competed by a polypeptide having a sequence selected from SEQ ID 25, SEQ ID 26, SEQ ID 27, SEQ ID 28, SEQ ID 29, SEQ ID 67, SEQ ID 68, SEQ ID 69 and SEQ ID 92.

Non-covalent interactions in the context of the present specification include, without being restricted to, electrostatic interaction, hydrophobic interactions and van-der-Waals-interactions.

In some embodiments, the non-covalently interaction mediates the binding of the polypeptide ligand with a dissociation constant of equal or less than $10^{-7}$ M, $10^{-8}$ M or $10^{-9}$ M.

The term "epitope" in the context of the present specification refers to the part of the extracellular domain 1 or 4 of HER2 that is bound by the first or second polypeptide.

A polypeptide ligand is deemed to interact partially with an epitope in the context of the above definition if about 20%, 30%, 40%, 50%, 60%, 70%, 80%, or 90% of the indicated amino acid residues of the epitope, as laid out above, show interaction (e.g. hydrogen bond, van-der-Waals and similar non-covalent interaction) with the polypeptide ligand.

Likewise, a polypeptide ligand interacts fully with an epitope, when all or at least about 95% of the indicated amino acid residues of the epitope show interaction with the polypeptide ligand.

In some embodiments, a bispecific HER2-targeting agent according to the invention is provided, wherein a) the first polypeptide ligand is an ankyrin repeat based polypeptide, and the second polypeptide ligand is an antibody, an antibody fragment, an antibody variable domain or a polypeptide ligand selected from the list under point a, b, c, d, e, f, g, h, i, j, k, l, m, n, o, p, q, r, s or t recited in the above embodiment, or b) the first polypeptide ligand is an antibody, an antibody fragment, an antibody variable domain or a polypeptide ligand selected from the list under point a, b, c, d, e, f, g, h, j, k, l, m, n, o, p, q, r, s or t recited in the above embodiment, and the second polypeptide ligand is an ankyrin repeat based polypeptide.

In some embodiments, a bispecific HER2-targeting agent according to the invention is provided, wherein a) the first polypeptide ligand is a polypeptide ligand selected from the list under point a, b, c, d, e, f, g, h, i, j, k, l, m, n, o, p, q, r, s or t recited in the above embodiment, and the second polypeptide ligand is an antibody, an antibody fragment or an antibody variable domain, or b) the first polypeptide ligand is an antibody, an antibody fragment or an antibody variable domain, and the second polypeptide ligand is polypeptide ligand selected from the list under point a, b, c, d, e, f, g, h, i, j, k, l, m, n, o, p, q, r, s or t recited in the above embodiment.

In some embodiments, the linker has a length of equal or less than 65 Å, 60 Å, 55 Å, 50 Å, 45 Å, 40 Å, 35 Å, 30 Å, 25 Å, 20 Å, 15 Å, 10 Å or 5 Å.

In some embodiments, a bispecific HER2-targeting agent according to the above aspects or embodiments is provided, wherein a) the first polypeptide ligand contacts the HER2 extracellular domain 1 through a D1 binding site, b) the second polypeptide ligand contacts the HER2 extracellular domain 4 through a D4 binding site, and c) the linker is selected to allow a direct spatial separation, or in other words a maximal distance between the D1 binding site and the D4 binding site of less than 80 Å, 75 Å. 70 Å, 65 Å, 60 Å, 55 Å, 50 Å, 45 Å, 40 Å, 35 Å, 30 Å, 25 Å, 20 Å, 15 Å, 10 Å or 5 Å.

In some embodiments, the linker consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids. In some embodiments, the linker consists of 1-10, 1-15, 1-20, 5-15, 5-10, 5-20, or 5-25 amino acids.

In some embodiments, the linker is a polyglycine/serine linker.

The term "polyglycine/serine linker" refers to a polypeptide linker that is composed of at least 50%, 60%, 70%, 80%, 90% or 100% of glycine and/or serine residues.

In some embodiments, the linker is characterized by an amino acid sequence (GGGGS), with n being 1 (SEQ ID 51), 2 (SEQ ID 52), 3 (SEQ ID 53), 4 (SEQ ID 54) or 5 (SEQ ID 111).

In some embodiments, the linker has the sequence SEQ ID 51, SEQ ID 52, SEQ ID 53 or SEQ ID 54.

In an alternative aspect of the present invention, a bispecific HER2-targeting agent is provided that comprises a. a first polypeptide ligand that binds to HER2 extracellular domain 1, b. a second polypeptide ligand that binds to HER2 extracellular domain 4 and c. wherein said first polypeptide ligand and said second polypeptide ligand are covalently linked by a structural element common to said first polypeptide ligand and said second polypeptide ligand.

In other words, instead of having a flexible linker, the first and second ligands are rigidly connected by a sequence tract defined by structural motif of peptide secondary structure, wherein said connecting sequence tract is common to, or shared by, both of the ligands, such as, by way of non-limiting example, an alpha helix.

In some embodiments, the linker is formed by the C-terminus of the first polypeptide ligand and the N-terminus of the second polypeptide ligand, or the linker is formed by the C-terminus of the second polypeptide ligand and the N-terminus of the first polypeptide ligand.

In some embodiments, the linker is or comprises a secondary structure element, which is shared by the first polypeptide ligand and the second polypeptide ligand. In some embodiments, the shared structural element connecting the first polypeptide ligand and the second polypeptide ligand is an α-helix, in other words, the same alpha helix secondary structure motif is shared by the first polypeptide ligand and the second polypeptide ligand.

In some embodiments, the first polypeptide ligand is an ankyrin repeat based polypeptide, for example a "DARPin" as set forth in US20120142611 (A1), and the second polypeptide is also an ankyrin repeat based polypeptide or DARPin, and the C-terminal α-helix of the first polypeptide ligand and the N-terminal α-helix of the second polypeptide ligand together form a shared α-helix connecting the first polypeptide ligand and the second polypeptide ligand, or the C-terminal α-helix of the second polypeptide ligand and the N-terminal α-helix of the first polypeptide ligand form together a shared α-helix connecting the first polypeptide ligand and the second polypeptide ligand.

In some embodiments, a bispecific HER2-targeting agent according to the invention is provided, which leads to a higher reduction of the viability of a cell culture cancer cell line selected from the group comprised of AU565 (also AU-565, ATCC number CRL-2351), BT474 (also BT-474, ATCC number HTB-20), HCC1149 (ATCC number CRL-2326), HCC2218 (ATCC number CRL-2343), SkBr3 (ATCC number HTB-30) and/or ZR7530 (ATCC number CRL-1504). A higher reduction of viability in the sense of the above comparison relates to the comparison with similar treatment by the agent trastuzumab.

Viability in the context of the present specification refers to the ability of a cell to maintain its homeostasis. The viability of a cell may be determined, inter alia, by spectroscopy measuring the concentration of a formazan dye, wherein the formazan dye is formed during reduction of tetrazolium salts such as MTT (3-(4, 5-dimethyl-2-thiazolyl)-2, 5-diphenyl-2H-tetrazolium bromide) or XTT (2,3-bis-(2-methoxy-4-nitro-5-sulfophenyl)-2H-tetrazolium-5-carboxanilide) catalyzed by dehydrogenases or reductases of viable cells.

The ability of a bispecific agent of the invention to reduce the viability of the cancer cells described in the preceding paragraphs is useful in a method for treating cancer.

A reduction of cell viability may be accompanied by an inhibition of proliferation, a reduction of cell count, a reduced protein content of the cells, a reduced metabolic activity of the cells or an induction of apoptosis of the cells.

In some embodiments, a bispecific HER2-targeting agent according to the invention is provided, which leads to a signal reduction of HER2-Y1248, HER3-Y1289, AKT-S473, ERK1/2-T202/Y204 and/or PARP in a Western blot when incubated with the AU565 cell line.

In some embodiments, a bispecific HER2-targeting agent according to the invention is provided, which leads a signal reduction of HER2-Y1248, HER3-Y1289, AKT-S473 and/or ERK1/2-T202/Y204 in a Western blot when incubated with the HCC1419 cell line.

In some embodiments, a bispecific HER2-targeting agent according to the invention is provided, which leads to a signal reduction of HER2-Y1248, HER3-Y1289, AKT-S473 and/or ERK1/2-T202/Y204 in a Western blot when incubated with the HCC2218 cell line.

In some embodiments, a bispecific HER2-targeting agent according to the invention is provided, which leads to a signal reduction of HER2-Y1248, HER3-Y1289, AKT-S473, ERK1/2-T202/Y204 and/or PARP in a Western blot when incubated with the ZR7530 cell line.

The term "HER2-Y1248" in the context of the present specification refers to the human epidermal growth factor receptor 2 (NP_004439.2), wherein the residue Tyr1248 is phosphorylated.

The term "HER3-Y1289" in the context of the present specification refers to the human epidermal growth factor receptor 3 (NP_001005915.1), wherein the residue TYR1289 is phosphorylated.

The term "AKT-S473" in the context of the present specification refers to the protein kinase B (UniProt. No P31749), wherein the serine residue 473 is phosphorylated.

The term "ERK1/2-T202/Y204" in the context of the present specification refers to the mitogen-activated protein kinase 3 (NP_001035145.1), wherein the residue threonine 202 is phosphorylated, and the mitogen-activated kinase 1 (NP_002736.3), wherein the residue tyrosine 204 is phosphorylated.

The term "PARR" in the context of the present specification refers to the Poly ADP ribose polymerase 1 (UniProt. No. P09874).

A signal reduction in a Western blot refers to the decrease of the amount of the indicated protein that is immobilized and stained on the blotting membrane.

An example of signal reduction of the above described signals caused by the use of agents of the invention is shown in example 1.

In some embodiments, a bispecific HER2-targeting agent according to the invention is provided, which leads to an induction of apoptosis in at least 40% of BT474 cells, 8% of AU565 cells, 20% of HCC1419 cells an/or 20% of HCC2218 cells when incubated with the indicated cell line.

According to another aspect of the invention, a bispecific HER2-targeting agent is provided, wherein the bispecific HER2-targeting agent is characterized by a sequence selected from SEQ ID 03, SEQ ID 04, SEQ ID 05, SEQ ID 06, SEQ ID 07, SEQ ID 08, SEQ ID 09, SEQ ID 58, SEQ ID 59, SEQ ID 60, SEQ ID 70, SEQ ID 71, SEQ ID 72, SEQ ID 73, SEQ ID 74, SEQ ID 75, SEQ ID 76, SEQ ID 77, SEQ ID 78, SEQ ID 79, SEQ ID 80, SEQ ID 81, SEQ ID 82, SEQ ID 83, SEQ ID 84, SEQ ID 85, SEQ ID 86, SEQ ID 87, SEQ ID 88, SEQ ID 89, SEQ ID 90, SEQ ID 91, SEQ ID 102, SEQ ID 103, SEQ ID 104, SEQ ID 105, SEQ ID 106, SEQ ID 107, SEQ ID 108, SEQ ID 109 and SEQ ID 110.

According to another aspect of the invention, a bispecific HER2-targeting agent according to any of the above aspect or embodiments of the invention is provided for use in a method for preventing or treating malignant neoplastic diseases.

According to another aspect of the invention, a bispecific HER2-targeting agent according to any of the above aspect or embodiments of the invention is provided for use in a method for preventing or treating malignant neoplastic diseases, wherein the disease is characterized by cells overexpressing HER2.

A disease characterized by cells overexpressing HER2 or a HER2-positive disease is defined in the context of the present specification to be present if a high HER2 (protein) expression level is detected by immunohistochemical methods, by flow-cytometric methods such as FACS, or as HER2 gene amplification, for example a HER2 gene copy number higher than 4 copies of the HER2 gene per tumor cell, or by a combination of these methods, in samples obtained from the patient. One example of such disease is often breast cancer, where cells overexpressing HER2 can be cells obtained from breast tissue biopsies or breast tissue resections or in tissue derived from metastatic sites. One frequently applied method for detecting HER2 overexpression and amplification at the gene level is fluorescence in situ hybridization (FISH), which is also described in US2003/0152987 to Cohen et al.

In some embodiments, a cell overexpressing HER2 is characterized by at least 2, 4, 6, 8, 10, 15, 20 or 25 copies of the HER2 gene (ERBB2 gene, Gene ID: 2064) in the nucleus in a FISH (fluorescence in-situ hybridization) assay.

In one embodiment, the copy number of the HER2 gene is measured by fluorescence in situ hybridization.

In one embodiment, a cell overexpressing HER2 is characterized by at least 2, 4, 6, 8, 10, 15, 20 or 25 signals per nucleus in a fluorescence in situ hybridization assay.

According to yet another aspect of the invention, a method is provided for treating a patient suffering from malignant neoplastic disease, comprising the administration of a bispecific agent according to any of the above specified aspects or embodiments of the invention to said patient.

In some embodiments, the malignant neoplasitic disease is a carcinoma of the stomach, endometrium, salivary gland, lung, kidney, colon, thyroid, pancreas or bladder.

DETAILED DESCRIPTION OF CERTAIN EMBODIMENTS

The Principle of Anti-Tumor Activity of Bispecific Targeting Agents

The minimal setup of a bispecific targeting agent of the invention is composed of 3 units. Firstly, the bispecific binding agent comprises a binding unit targeting domain 1 of the extracellular domain (ECD) of HER2. Secondly, the bispecific binding agent comprises a binding unit targeting domain 4 of the ECD of HER2. Thirdly, the bispecific binding agent comprises a linker unit or linker in-between the binding unit targeting domain 1 of HER2 and the binding unit targeting domain 4 of HER2, whose optimal length depends on the nature of both binding units.

In some embodiments, the linker or linker unit is a polypeptide linker.

In some embodiment, the linker is a polyglycine/serine linker. Such linker has the advantage that it is highly soluble in water, has a flexible fold, is resistant against proteolysis and adopts either a random coil or an extended structure.

In some embodiments, the linker is a short linker composed of the amino acids: GGGGS ($G_4S$). Bispecific constructs comprising 1 to 4 (SEQ IDs 51 to 54) repeats of $G_4S$ show superior anti-tumor activity. Bispecific constructs comprising 5 (SEQ ID 111) or more repeats of $G_4S$ show decreasing anti-tumor activity with longer linker length. Other amino acid compositions might be used to connect the binding units.

In some embodiments, the linker or linker unit comprises flexible regions of binding scaffolds described above or is a chemical cross-linker, wherein both binding units are covalently connected by the linker. A chemical cross-linker in the context of the present specification refers to a compound capable of covalently connecting the first and the second polypeptide ligand of the invention. Examples for such chemical crosslinkers include, without being restricted to, glutaraldehyde, bissulfosuccinimidyl suberate, carbodiimide, bis(succinimidyl)penta(ethylene glycol), bis(succinimidyl) nona(ethylene glycol), bis(sulfosuccinimidyl) suberate, dimethyl suberimidate, an ethylene glycol characterized by formula $(\text{—CH2OH—CH2OH—})_n$, wherein n is 2, 3, 4, 5, 6, 7, 8, 9, 10, 11, 12, 13, 14, 15, 16, 17, 18, 19, 20, 21, 22, 23, 24 or 25 and one or both termini of the ethylene glycol are substituted by a succinimide or maleimide group, N-(κ-Maleimidoundecanoyloxy) sulfosuccinimide ester, sulfosuccinimidyl (4-iodoacetyl) aminobenzoate, 1,8-bismaleimidodiethyleneglycol and 1,11-bismaleimidotriethyleneglycol.

In some embodiments, the linker or linker unit is a dimerization domain or additional functional units inducing the dimerization of both binding units to connect both epitopes on HER2 or, in other words, dimerization domains.

A dimerization domain in the context of the present specification refers to a functional unit consisting of two polypeptides that are capable of specific binding to each other or dimerizing. The two polypetides may be part of the same polypeptide chain. Non-limiting examples for such dimerization domains are leucine zipper domains such as in GCN4 (UniProt. No. P03069), helix-helix domains, dimerization domains composed of beta-sheets, coiled coil helices such as in c-Jun (Uniprot. No. P05412) or c-Fos (Uniprot. No P01100), helix bundles like in the dimerization domain of the mip protein (Uniprot. No Q70YI1), helix-turn-helix motifs such as in the repressor protein cl (Uniprot. No. P03034) and antibody Fc regions.

Such linker unit may determine the anti-tumor activity of the bispecific targeting agent. The single binding units used in the examples disclosed here have no or only weak anti-tumor activity as single agents.

In some embodiments, linkers of other composition can be used, provided they bring said binding domains into a disposition leading to apoptosis in the targeted cell, as can be assayed by the methods provided herein.

In certain embodiments, DARPin fusions of the composition BinderA-FL-BinderB (FL standing for "flexible linker", for example a linker characterized by formula $(G_4S)_n$, wherein n is 1 to 5) are provided, which have strong anti-tumor activity (reduce cancer cell growth by 80-90%).

Here "BinderA" can be a DARPin binding to the described epitope in subdomain 1 of HER2, or any other protein binding to an overlapping epitope, while "BinderB" can be a DARPin binding to HER2 subdomain 4, or any other protein binding to an overlapping epitope. "FL" refers to a flexible linker. The examples have been demonstrated with "BinderA" being either DARPin 9.29 (also referred to as "9_29", SEQ ID 18, SEQ ID 19, SEQ ID 20, SEQ ID 21, SEQ ID 61 or SEQ ID 62) or DARPin 9.26 (also referred to as "9_26", SEQ ID 14, SEQ ID 15, SEQ ID 16, SEQ ID 17, SEQ ID 63 or SEQ ID 64) binding to subdomain 1 (SEQ ID 01), while "BinderB" being either DARPin G3 (SEQ ID 25) or H14 (SEQ ID 26, SEQ ID 27, SEQ ID 28 or Seq ID 29) binding to subdomain 4 (SEQ ID 02). In the examples, "FL" was a linker of the composition $(\text{Gly-Gly-Gly-Gly-Ser})_n$ with n being 1, 2, 3 or 4 (SEQ IDs 51 to 54).

The term "flexible linker" in the context of the present specification refers to a polypeptide connecting the first polypeptide ligand and the second ligand that is characterized by a random coil conformation or extended structure. A flexible linker may further be characterized by the absence of secondary structures such as helices or β-sheets or a maximal secondary structure content of 10%, 20% 30% or 40%.

The term "overlapping epitope" in the context of the present specification refers to an epitope that is partially identical to a certain epitope.

In some embodiments, binders to the most preferred epitopes are generated in using the display methods described above (phage display, ribosome display or yeast display). The DARPins 926, 929 or G3, whose sequences are disclosed in SEQ ID 14, SEQ ID 15, SEQ ID 16, SEQ ID 17, SEQ ID 18 SEQ ID 19, SEQ ID 20, SEQ ID 21, SEQ ID 25, SEQ ID 61, SEQ ID 62, SEQ ID 63 and SEQ ID 64 can be used as competitors. Their genes can be synthesized and they can be expressed and purified as detailed in Zahnd et al. (2007) J. Mol. Biol. 369, 1015-1028. When the pool of binders selected in ribosome display or in phage display to the HER2 domains immobilized on magnetic beads or in microtiter plates are exposed to the competing DARPins, the binders will be preferentially eluted which show the same epitope.

In one embodiment, the mode of binding for one bispecific molecule, constructed according to the invention, is intermolecular. The linker unit in the bispecific agents determines the mode of binding. To be more precise, the length of the linker, and the orientation imparted on the binding domains by the attachment points of the linker influence whether the bispecific molecule binds in an intermolecular way, i.e. connecting two HER2 molecules. Hence, upon binding on a cell, the bispecific agents connect domain 1 of one HER2 receptor molecule with the domain 4 of another HER2 receptor molecule.

In some embodiments, the connection between both epitopes bound by the binding units of particularly active bispecific constructs is bridged by a short linker (5 amino acids or approx. 15 Å).

In the structure of the whole extracellular domain of HER2 (PDB ID: 1N8Z) (Cho H S, et al. (2003), Nature 421:756-760), the distance between the epitope on domain 1 and the epitope on domain 4 is at least 80 Å long, and it is thus impossible that the bispecific molecule binds in an intramolecular way to this structure of HER2 (i.e., the domain 1 binding moiety and the domain 4 binding moiety cannot bind to domains 1 and 4 of one and the same HER2 molecule).

Domain 4 of the HER2 receptor is close to the transmembrane helix of the HER2 receptor and therefore restricted in its motional freedom. Domains 1, 2 and 3 are connected to domain 4 by flexible hinges. As it is known for other EGFR receptors, domains 1, 2 and 4 can change their relative orientation upon ligand binding. The conformational change in other EGFR receptors occurs from a state where domain 2 and 4 are in direct contact and domain 1 and 3 are separated (tethered conformation) to a state where domain 2 and 4 separate and domain 1 and 3 are connected via the respective ligand (Mark A. Lemmon, Ligand-induced ErbB receptor dimerization, Experimental Cell Research, 315(4), 2009, Pages 638-664). However, even in the tethered conformation, the distance between domain 1 and domain 4 remains too large to be compatible with a 15 Å linker. Furthermore, the "tethered" conformation is thought to be absent in HER2, due several findings like e.g. the absence of stabilizing amino acids in the domain 4 contact region (e.g. G563 and H565 of HER3 are replaced with P and F) found in the crystal structure of HER2 (Cho et al., 2003 Nature 421: 756-760).

Hence, without wishing to be bound by theory, a conformation is postulated which is induced or stabilized by the bispecific targeting agents of the invention. This conformation is referred in the following as the stabilized inactive HER2 homodimer conformation. These stabilized inactive homodimers of HER2 may also exist in the context of larger HER2-HER2 interaction units like e.g. trimers, tetramers or up to HER2 clusters. The examples shown herein demonstrate that, in certain embodiments of the present invention, key tyrosine residues on the intracellular part of HER2 at the "phosphorylation tail" and in the kinase domain become dephosphorylated upon treatment with the bispecific targeting agents, while total HER2 levels remain quite constant in cancer cells that have not yet undergone apoptosis.

In certain embodiments, the stabilization of inactive HER2 homodimers by the bispecific targeting agents disclosed in the present invention consequently inhibits other HER2 interactions, e.g. with HER3. HER2 and HER3 receptor form a heterodimer with strong oncogenic, anti-apoptotic signaling. As a consequence of both inhibition of HER2 phosphorylation and HER3 phosphorylation, both downstream pathways PI3K-AKT and MAPK-ERK, and possibly other signaling pathways, become persistently inactivated and or down-regulated. Both pathways are down-regulated to such an extent that the pro-apoptotic protein BIM becomes increasingly expressed in the cancer cells, leading to caspase activation and finally apoptosis.

Delineation of the Invention: Design Criteria of Active Bispecific Molecules.

While the examples provided relate to the DARPins 9.26 or 9.29 linked to the DARPins G3 or H14 by a short flexible linker, a person skilled in the art can replace, in light of the information provided herein, any or both of said DARPins by other scaffolds or antibody Fab fragments or antibody scFv fragments or antibody domains, binding to an overlapping epitope on domain 1 or domain 4, respectively. If the orientation of the binding protein is not known from structural modeling or experimental structure determination, both linkages (BinderA-FL-BinderB and BinderA-FL-BinderB) can be readily constructed and tested in light of the information provided herein. The modular principle of the bispecific targeting agent makes it thus facile for the person skilled in the art to replace single parts in the construct by other binding or linking units.

Bispecific HER2 Targeting

The present invention is based on a binding molecule that functions as a HER2-specific molecular crosslinker, which leads to the formation of inactive HER2 homodimers, instead of inhibiting HER2 dimerization. The mechanism of action of the targeting molecule of the invention is thus radically different from the HER2-directed therapies so far described. The agents of the invention lead to HER2 homodimers being linked in such way that they become signalling-inactivated. The examples shown herein demonstrate the dephosphorylation of key tyrosine residues of the intracellular part of HER2. Hence, the so induced HER2 homodimers show a strongly reduced downstream signalling via the MAPK pathway, which is directly shown by the dephosphorylation of the MAP-kinase extracellular-signal regulated kinase 1 and 2 (Erk1/2).

In addition, these inactive HER2 homodimers fail to interact, in some embodiments, with other members of the EGF receptor family, most importantly with HER3. HER2-HER3 interactions and the corresponding phosphatidylinositol 3-kinase protein kinase B (PI3K-PKB, alternatively called PI3K-AKT) signalling pathway are known to drive cell proliferation and inhibit apoptosis in HER2-overexpressing cancer cells.

In still other embodiments, by preventing HER2-HER3 interactions by the stabilization of inactive HER2 homodimers, the downstream pathway PI3K-AKT becomes also inhibited. Hence, dephosphorylation of AKT was shown to result from application of the molecules of this invention. The simultaneous inhibition of both pathways, to a higher extent than achieved by the application of trastuzumab or pertuzumab or their combined action, stimulates, in yet other embodiments, the expression of Bcl-2-like protein 11 (BIM).

The expression of BIM, mainly the short isoform $BIM_S$, finally leads, in certain embodiments, to the induction of the cell's intrinsic apoptotic program. As shown, the mode of action of the bispecific targeting agents is not the sum of actions of known molecular formats, because the building blocks, the single binding units, do not necessarily need to have anti-tumor activity by themselves. However, the connection of both disclosed epitopes in a preferentially intermolecular manner of preferred geometric disposition generates the potent anti-tumor agent.

Disclosed herein are two epitopes that may be bound by the HER2 targeting molecule, at the level of single amino acids of the HER2 extracellular domain, which are derived from multiple crystal structures of HER2 in complex with the respective binding proteins. Furthermore disclosed is the construction plan of such a bispecific molecule, which enables a person having ordinary skill in the art to readily construct such molecules.

In certain embodiments, the molecular structure is thus a bispecific binding molecule, which exhibits superior anti-tumor activity in comparison to trastuzumab and pertuzumab and induces apoptosis in HER2-dependent cancer cells. This bispecific binding molecule can, in certain embodiments, be further modified by fusing moieties like e.g. toxins, half life extending groups and other functionalities.

The invention is exemplarily shown with bispecific binding molecules that are built of designed ankyrin repeat proteins (Binz et al. (2004) Nat. Bio. Tech. 22 575-582; US20120142611 (A1)-2012-06-07). However, there are no DARPin-specific functions in the molecules according to this disclosure, and thus the DARPins can be substituted by other binding proteins that serve to juxtapose the same epitopes such that they bring two HER2 molecules into a similar inactive orientation on the cell surface.

The agents and methods of the present invention are distinct from any method or reagent combination known in the art that binds to the same epitopes as the bispecific agent of the present invention. When converting IgGs into monovalent binding agents (by producing e.g. Fab fragments, or scFv fragments) the anti-tumor activity can vanish mostly or even completely. The results presented herein show that the scFv of 4D5 has only approx. 20% anti-tumor activity of the full length antibody in cell culture (measured in the absence of secondary functions like ADCC, FIG. 8).

Importantly, therefore, a bispecific agent comprising binding units that bind to the domain 1 of the ECD of HER2 and to domain 4 of the ECD of HER2 is not the sum of both modes of action that the respective antibody possesses, but is a new molecular entity according to the present invention.

Wherever alternatives for single separable features such as, for example, a first ligand, a second ligand, a bound epitope, a binding scaffold, a linker length or linker chemical constitution are laid out herein as "embodiments", it is to be understood that such alternatives may be combined freely to form discrete embodiments of the invention disclosed herein. Thus, any of the alternative embodiments for a domain 1 epitope may be combined with any of the alternative embodiments of domain 4 epitope, and these combinations may be combined with any linker mentioned herein.

The invention is further illustrated by the following examples and figures, from which further embodiments and advantages can be drawn. These examples are meant to illustrate the invention but not to limit its scope.

Any US patent or US patent application cited in the present specification shall be incorporated herein by reference.

SHORT DESCRIPTION OF THE FIGURES

FIG. 1 shows the increased anti-tumor activity of bispecific targeting agents in cell proliferation assays. The Y axis shows cell viability in different indicated cell lines expressing HER2 after treatment with any of the agents identified in the X axis; A: AU565 (upper panel), BT474 (lower panel); B: HCC2218 (upper panel), HCC1419 (lower panel), C: SkBr3 (upper panel), ZR7530 (lower panel).

FIG. 2 shows the quantification of cellular DNA content by flow cytometry in absence and presence of different anti-tumor agents.

FIG. 3 shows the induction of apoptosis by bispecific targeting agents quantified by terminal transferase dUTP nick end labeling (TUNEL) assays and flow cytometry wherein the Y-axis shows fraction of positive cells after treatment with any of the agent identified in the X axis; A: AU565 cells (upper panel), BT474 cells (lower panel); B: HCC2218 cells (upper panel), HCC1419 cells (lower panel).

FIG. 4 shows the Western blot analysis of HER2/HER3 signaling pathway, PI3K/AKT and MAPK pathway and downstream targets of cell cycle and apoptosis.

FIG. 5 shows quantitative western blot analyses of the treatment time course measuring HER2/HER3 receptor expression and phosphorylation after treatment with anti-HER2 binding agents, wherein the Y axis shows normalized signal intensity of the western blot band, and the X axis the time after treatment of the respective anti-HER2 binding agent indicated in the respective legends; A: phosphoHER2 band in BT474 cells; B phospho-HER3 in BT474 cells.

FIG. 12 shows the effect of different anti-tumor agents on the viability of trastuzumab-resistant cell lines in cell proliferation assays, the Y-axis showing the viability of the cell lines determined by absorbance of reduced XTT after treatment with any of the agents identified in the figure. Tested cell lines were A: MDA-MB-361; B: MDA-MB-453; C: Sk-Ov-3; D: JIMT-1; and E: several XTT resistant cells lines as indicated.

Figure 13A:
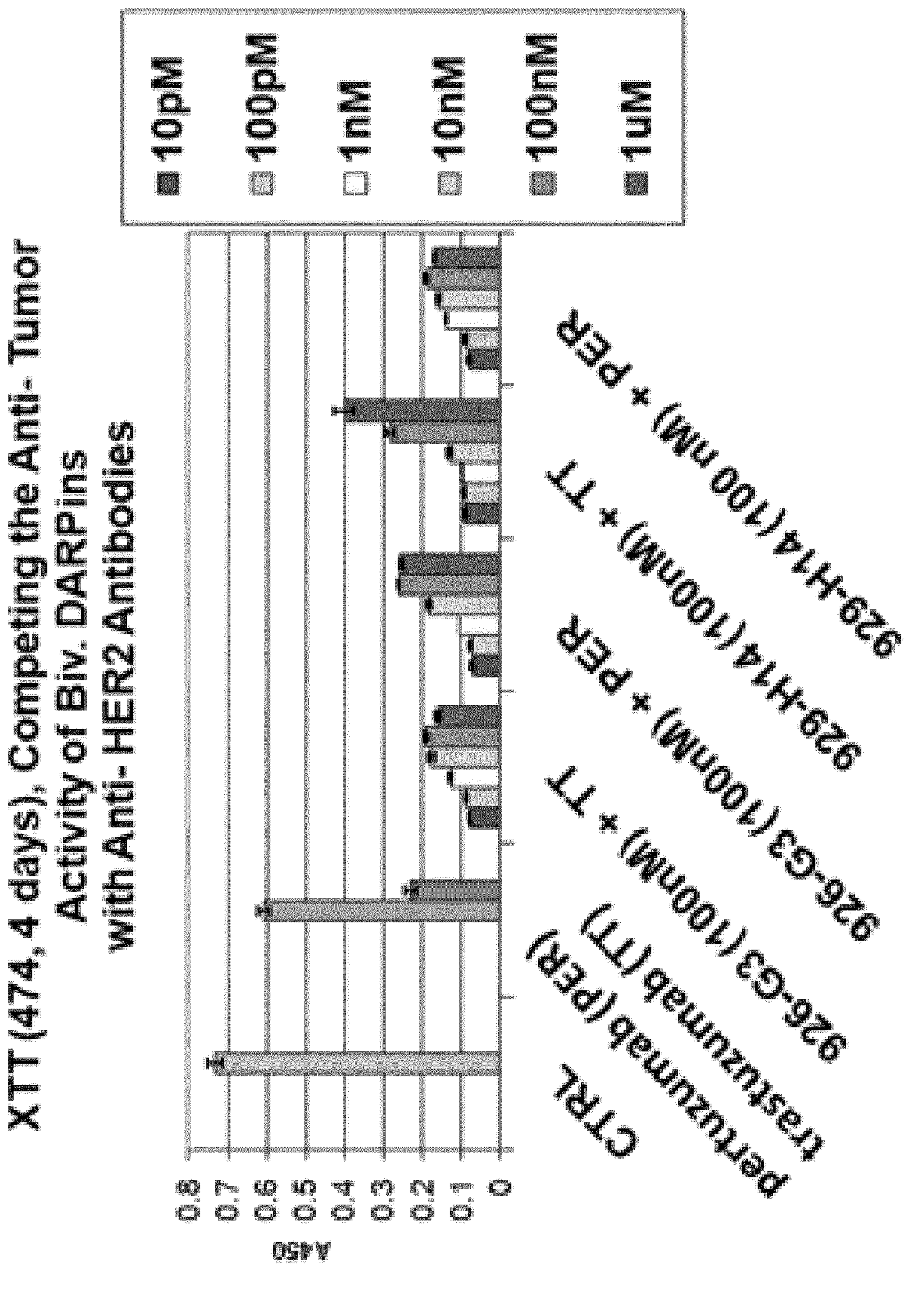
Figure 13B:
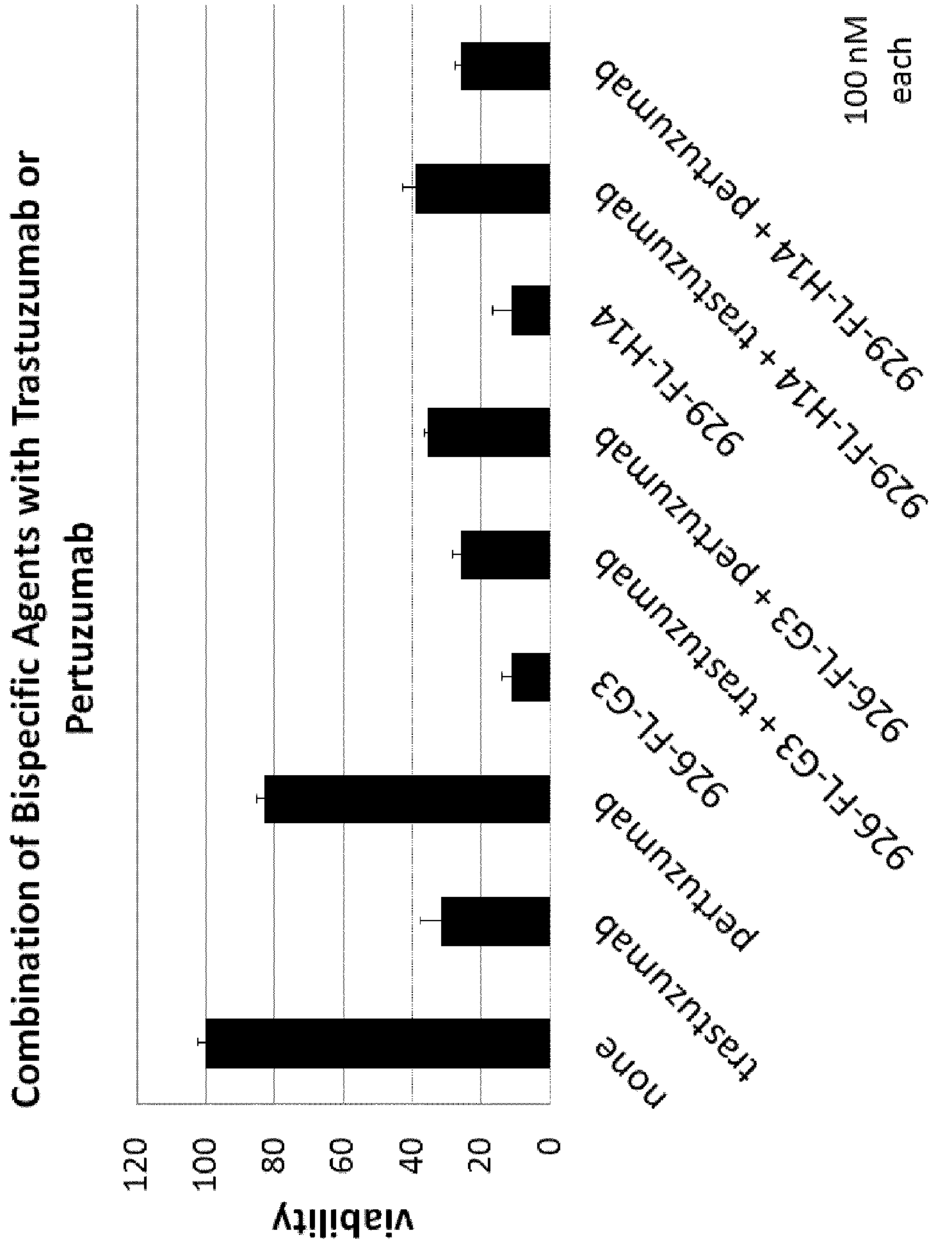

FIG. 13 shows the effect of trastuzumab and pertuzumab on the anti-tumor activity of the bispecific targeting agents in cell proliferation assays. Data presentation as in FIG. 11, wherein the Y axis shows the viability of cells treated with the anti-tumor agents as indicated in the X axis. A: XTT competing with the activity of the indicated bivalent ligands; B: combination of the indicated agents with trastuzumab or pertuzumab.

Figure 14:
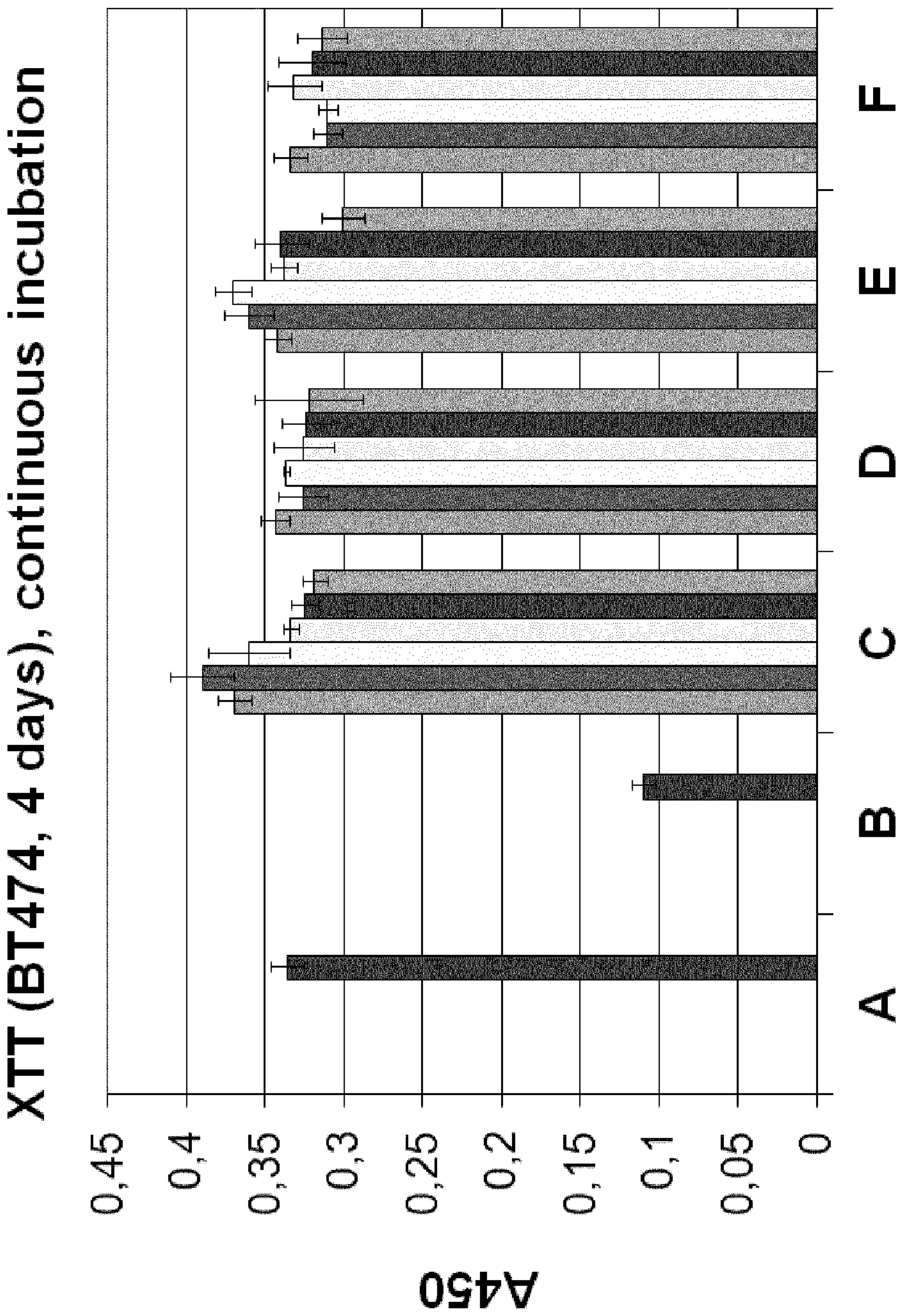

FIG. 14 shows the anti-tumor activity of different anti-tumor agents in cell proliferation assays. Data presentation as in FIG. 11.

Figure 15:
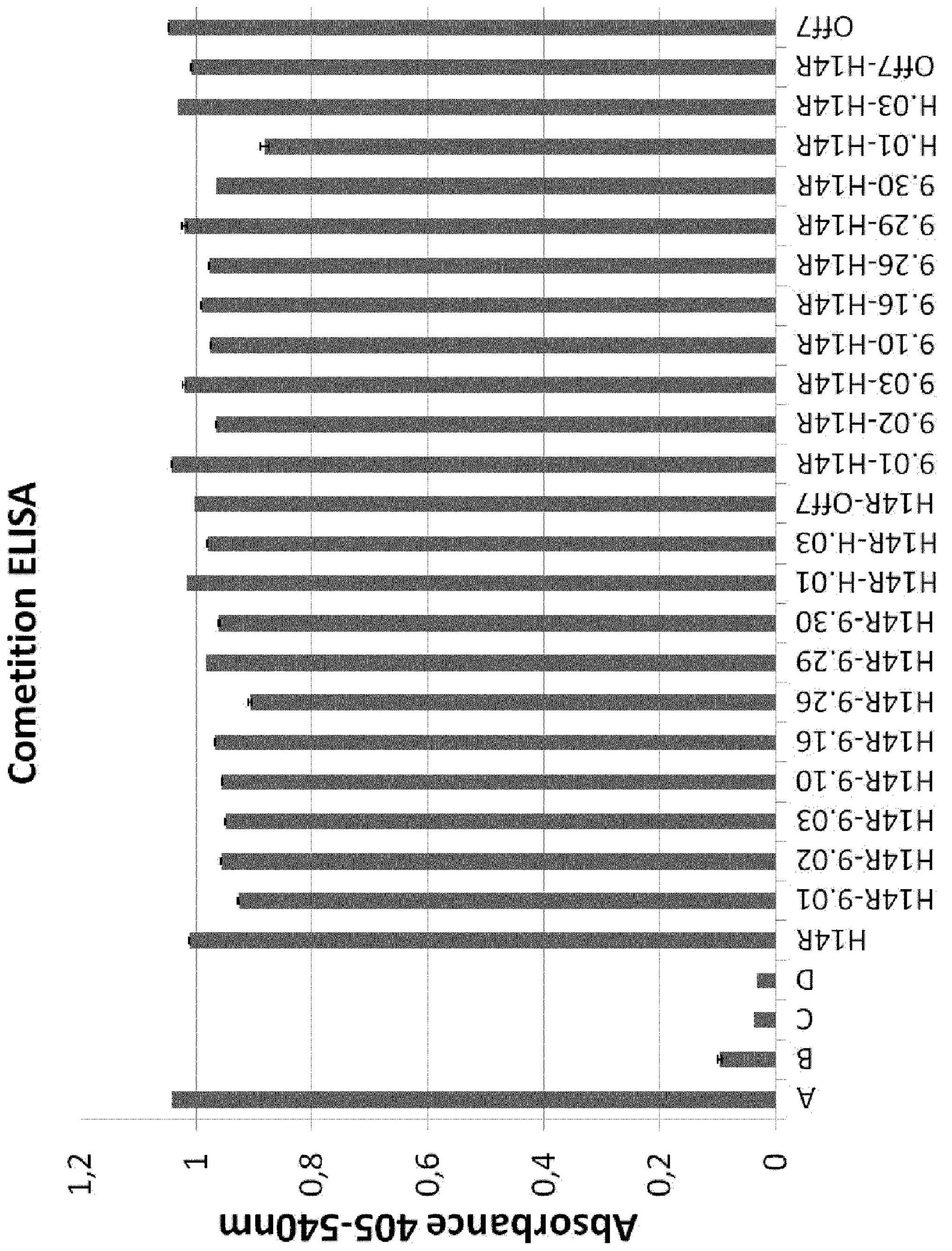

FIG. 15 shows the results of an ELISA with bispecific targeting agents and pertuzumab. The Y-axis shows the concentration of the agents identified in the legend bound to HER2 in presence of pertuzumab.

Figure 16:
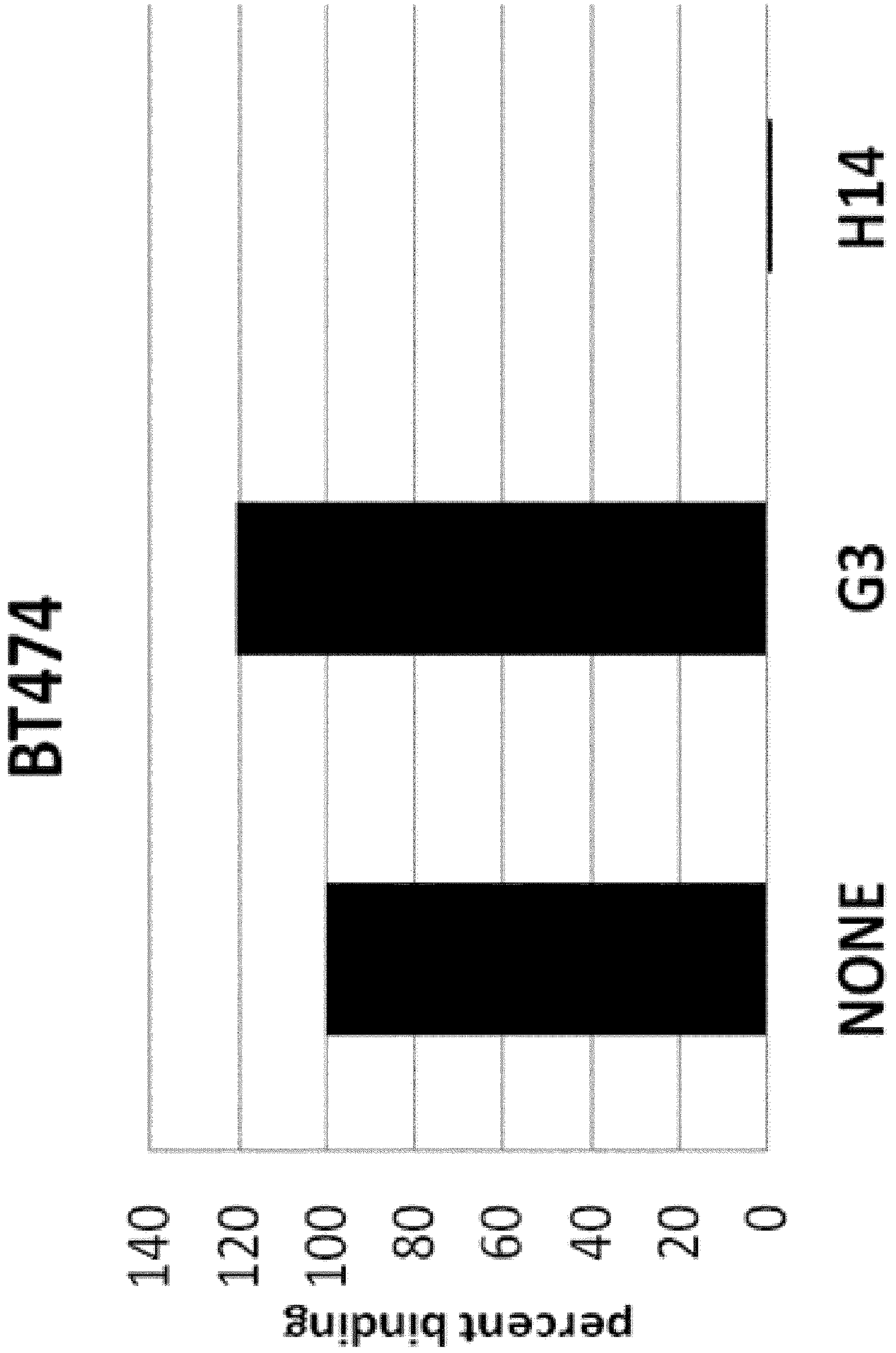

FIG. 16 shows the competitive binding of G3 and H14 with trastuzumab. The Y-axis shows the percent binding of the agents identified in the legend to domain 4 of HER2 in presence of trastuzumab.

Figure 17:
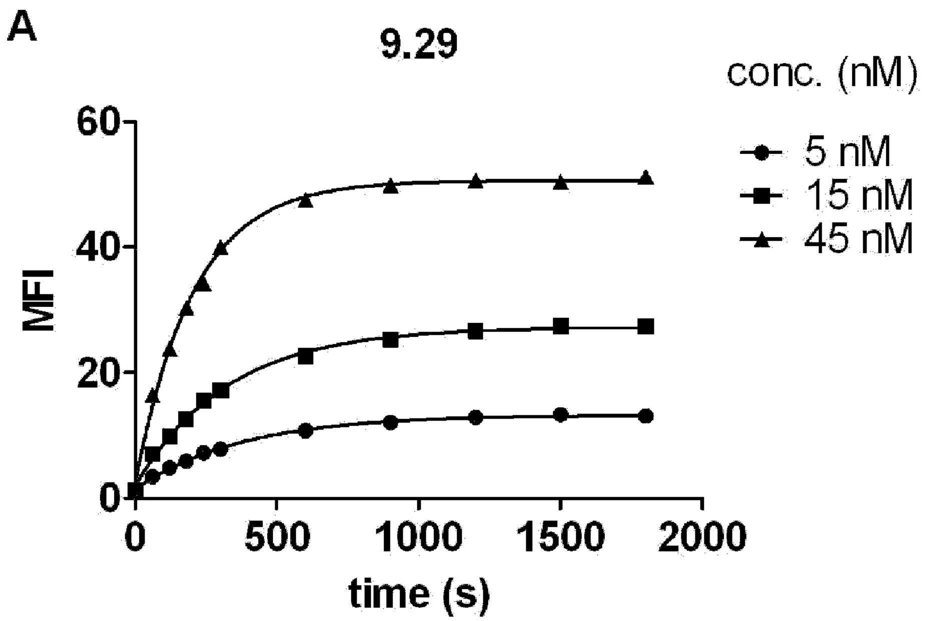
Figure 17:
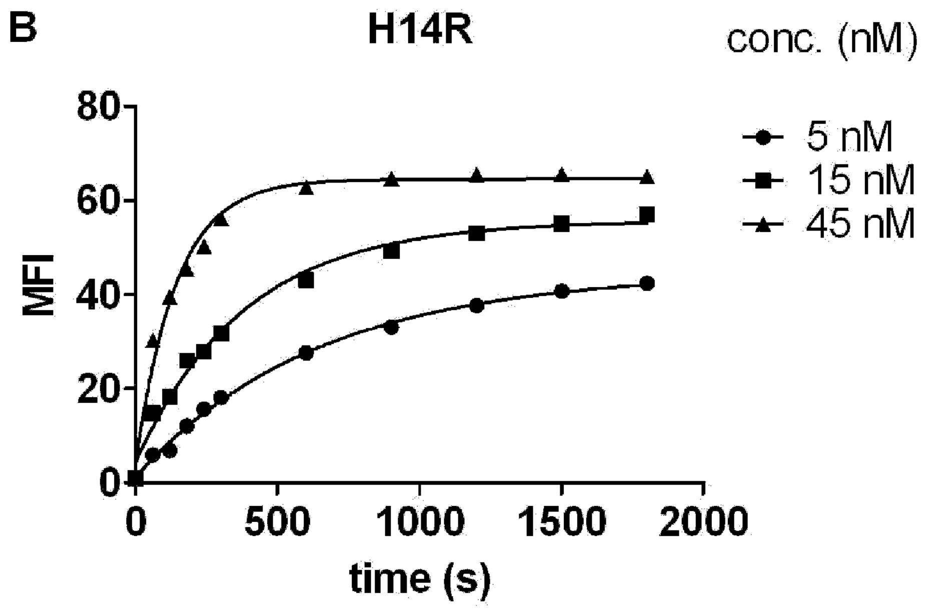
Figure 17:
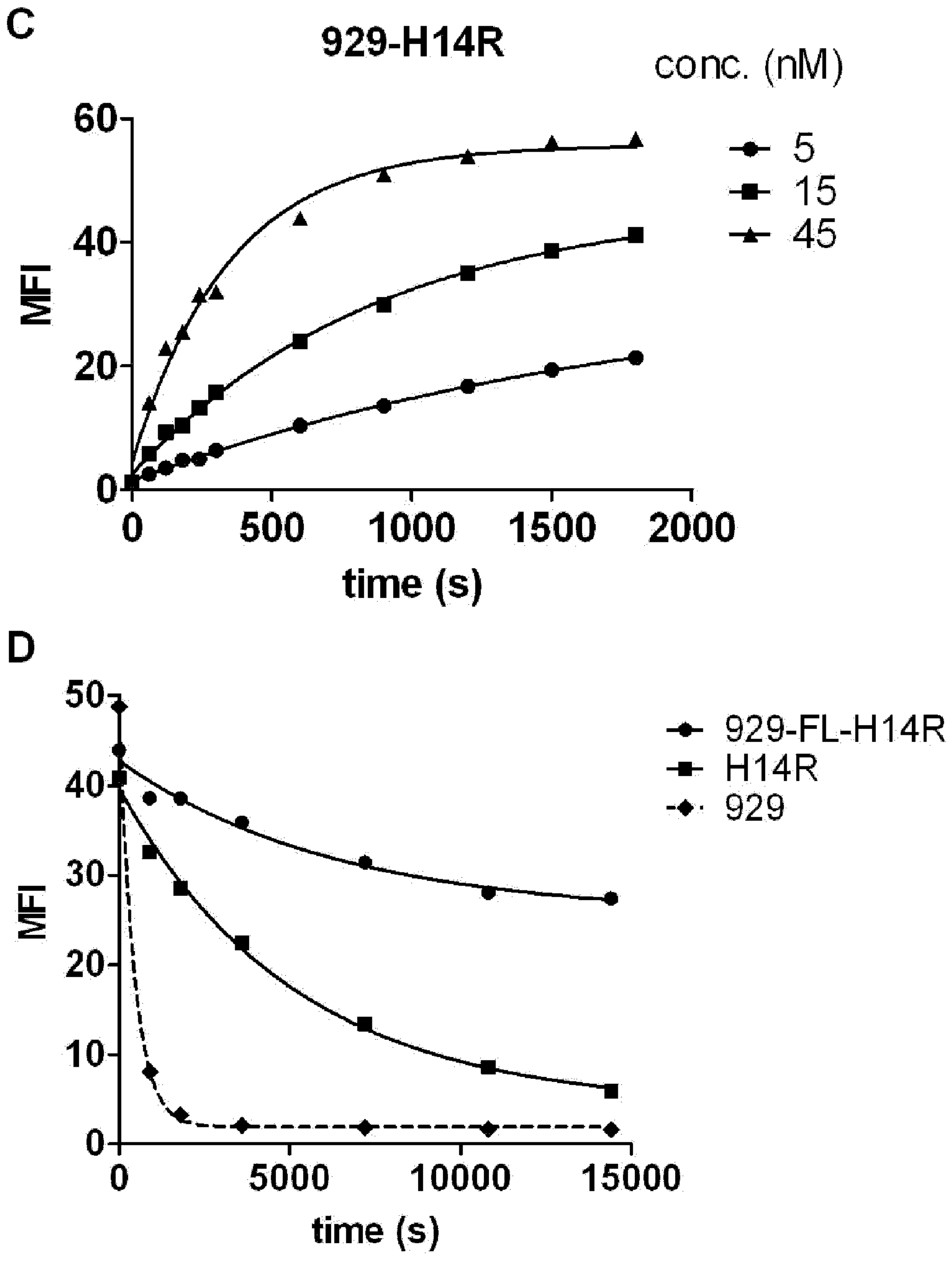

FIG. 17 shows the binding affinity, binding stoichiometry and binding mode of single binding units and bispecific binding agent to HER2 on the surface of cancer cells; A and B, on-rate determination of single binding agents; C, on-rate determination of bispecific binding agents; D, off-rate determination of single and bispecific binding agents; MFI mean fluorescence intensity.

Figure 18:
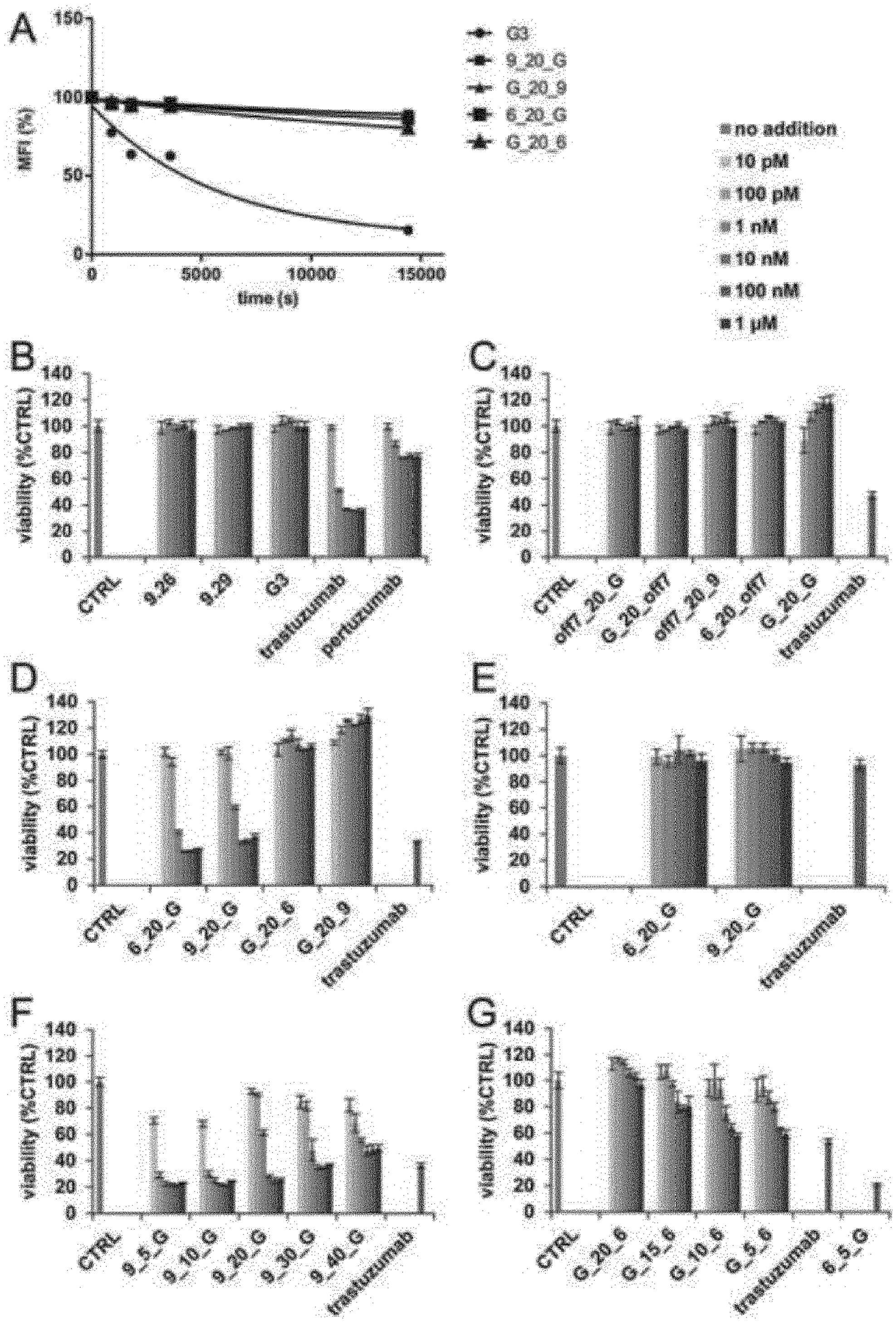

FIG. 18 shows the dissociation from the surface of BT474 cells (A) and the anti-tumor activity (B-G) of single binding agents and bispecific binding agents. A: median fluorescence intensities of fluorescently labeled agents bound to the BT474 surface are plotted as function of dissociation time; B-G: The Y-axes show the viability of BT474 (B-D, F,G) or MCF7 (E) cells after treatment with any of the agents identified in the legend.

Figure 19:
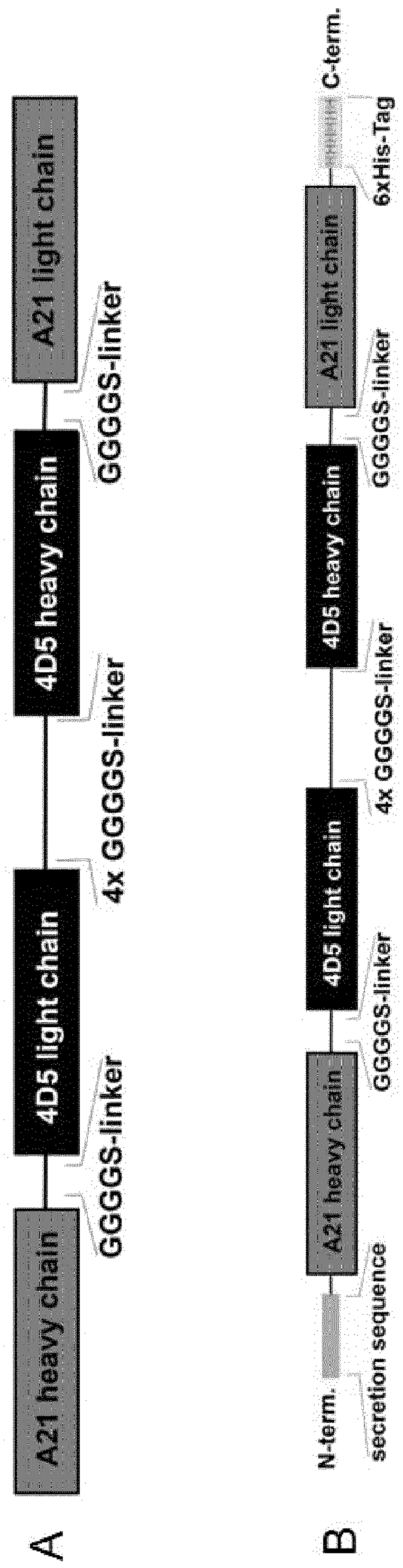

FIG. 19 shows the construction principle of the A21H_4D5LH_A21L anti-tumor agent (A) and a cartoon of the complete diabody construct (B) as expressed in CHO cells. Here "heavy chain" refers to the VH domain, "light chain" to the VL domain, "GGGGS-linker" to peptide linker with 4 glycine and 1 serine (eg. as set forth at positions 172-176 of SEQ ID NO. 3), "4×GGGGS-linker" to a linker peptide consisting of 4 repeats of 4 glycine and 1 serine (eg. as set forth at positions 168-187 of SEQ ID NO. 9).

Figure 20:
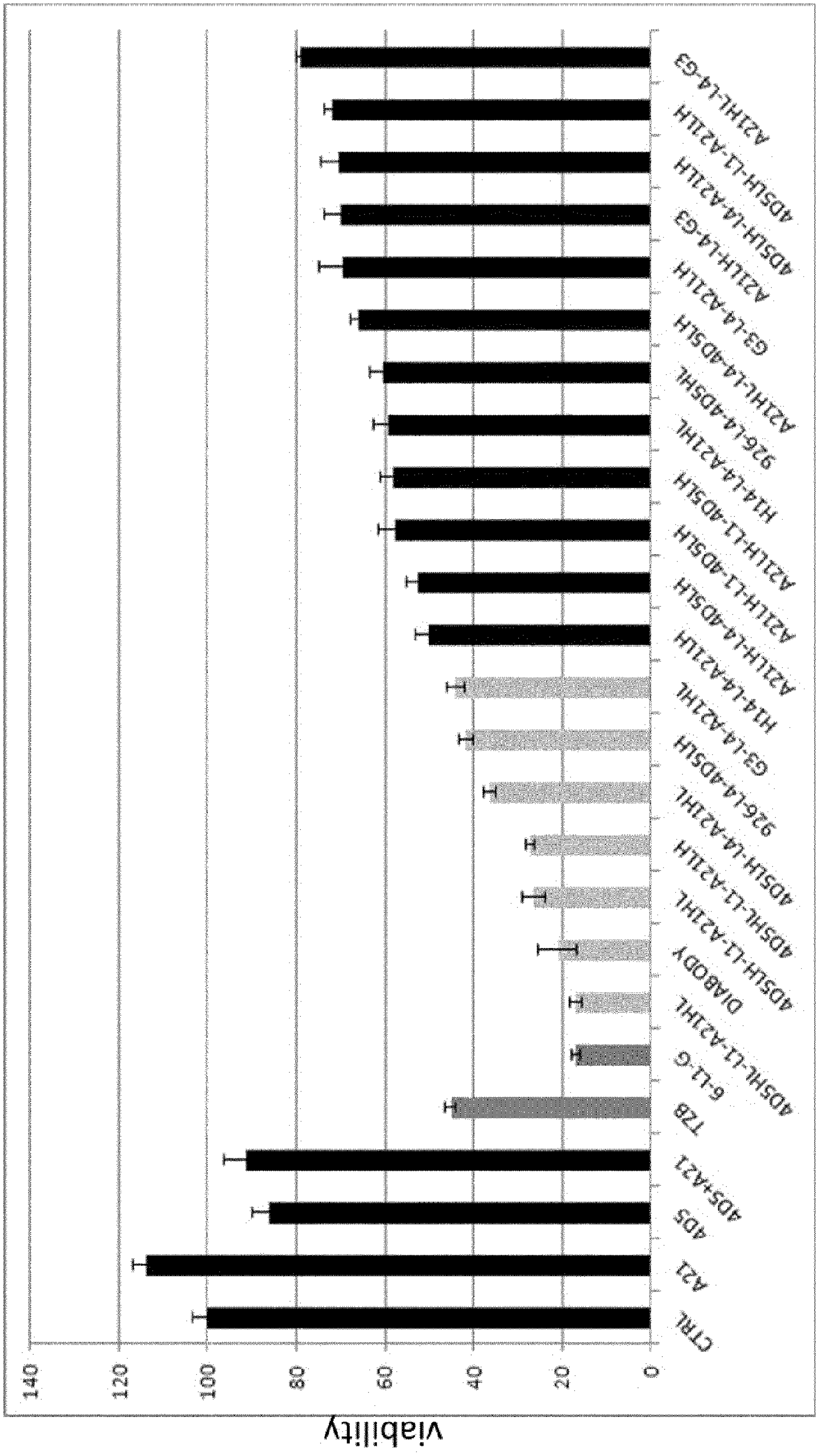

FIG. 20 shows the effect of different anti-tumor agents on the viability of BT474 cells in cell proliferation assays, the Y-axis showing the viability of the cell lines determined by absorbance of reduced XTT after treatment with any of the agents (100 nM) identified in the legend. Data were normalized to the control, which was set to 100%.

Figure 21:
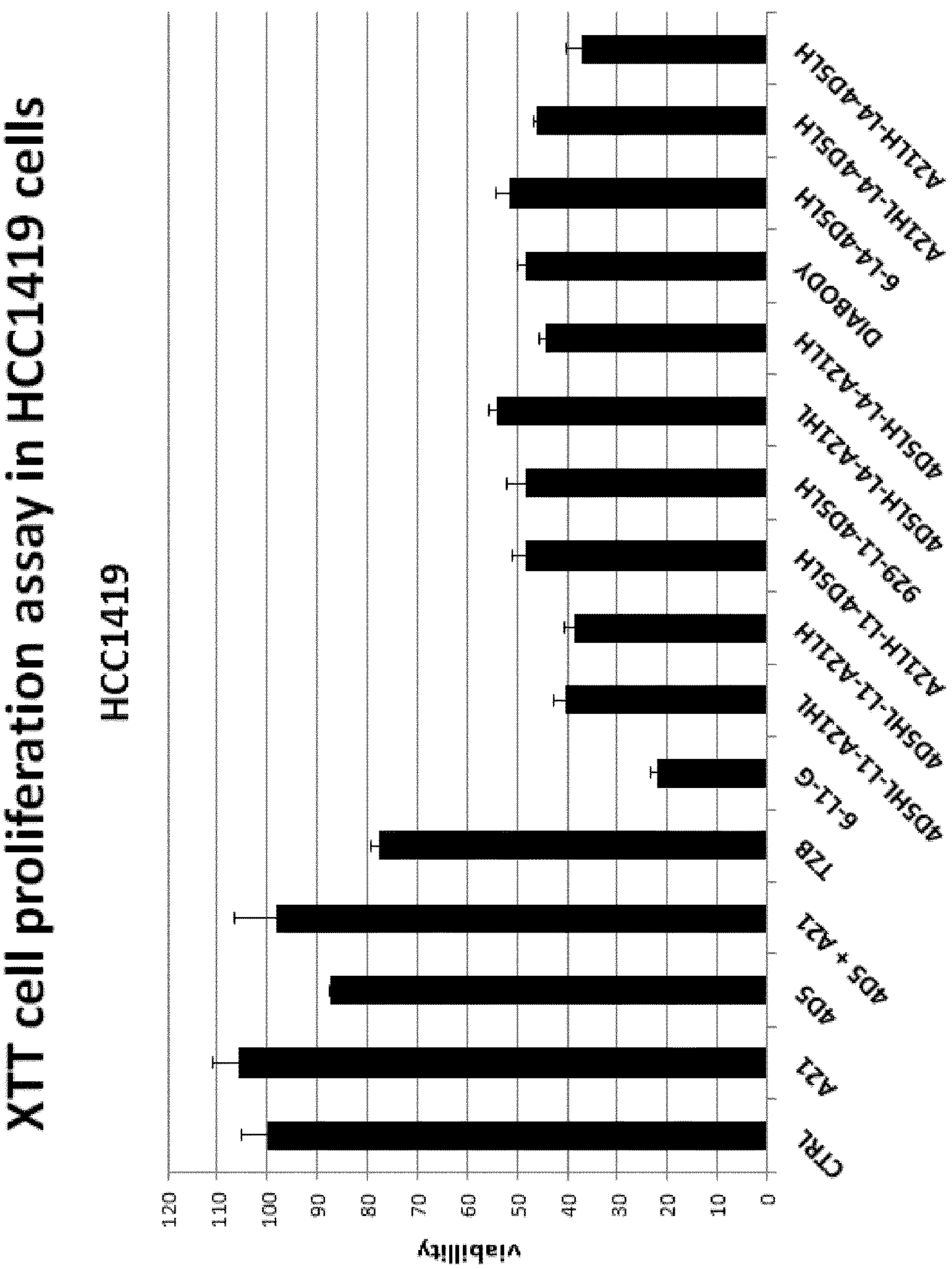

FIG. 21 shows the effect of different anti-tumor agents on the viability of HCC1419 cells in cell proliferation assays, the Y-axis showing the viability of the cell lines determined by absorbance of reduced XTT after treatment with any of the agents (100 nM) identified in the legend. Data were normalized to the control, which was set to 100%.

Figure 22:
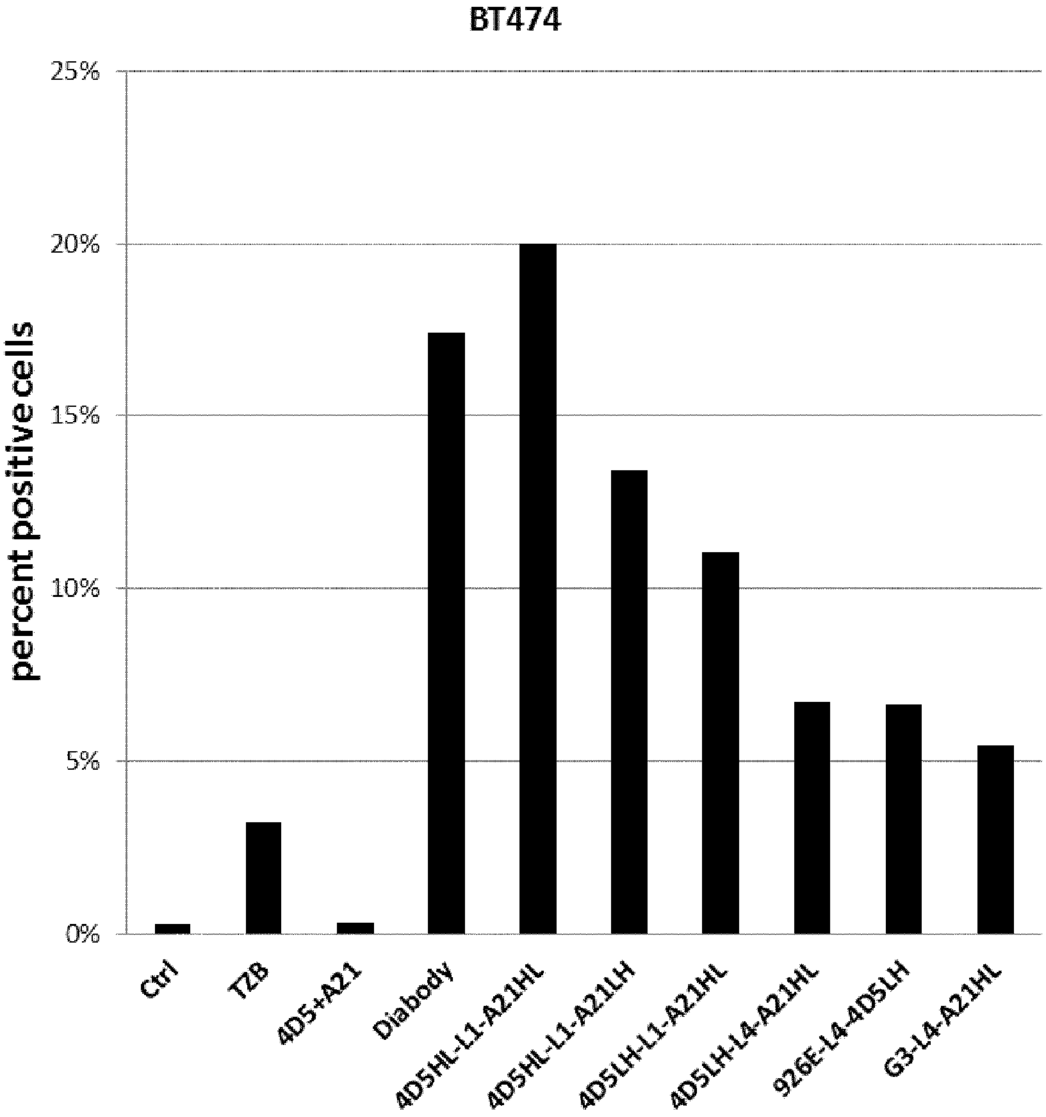

FIG. 22 shows the induction of apoptosis in BT474 cells by bispecific targeting agents quantified by terminal transferase dUTP nick end labeling (TUNEL) assays and flow cytometry.

Figure 23:
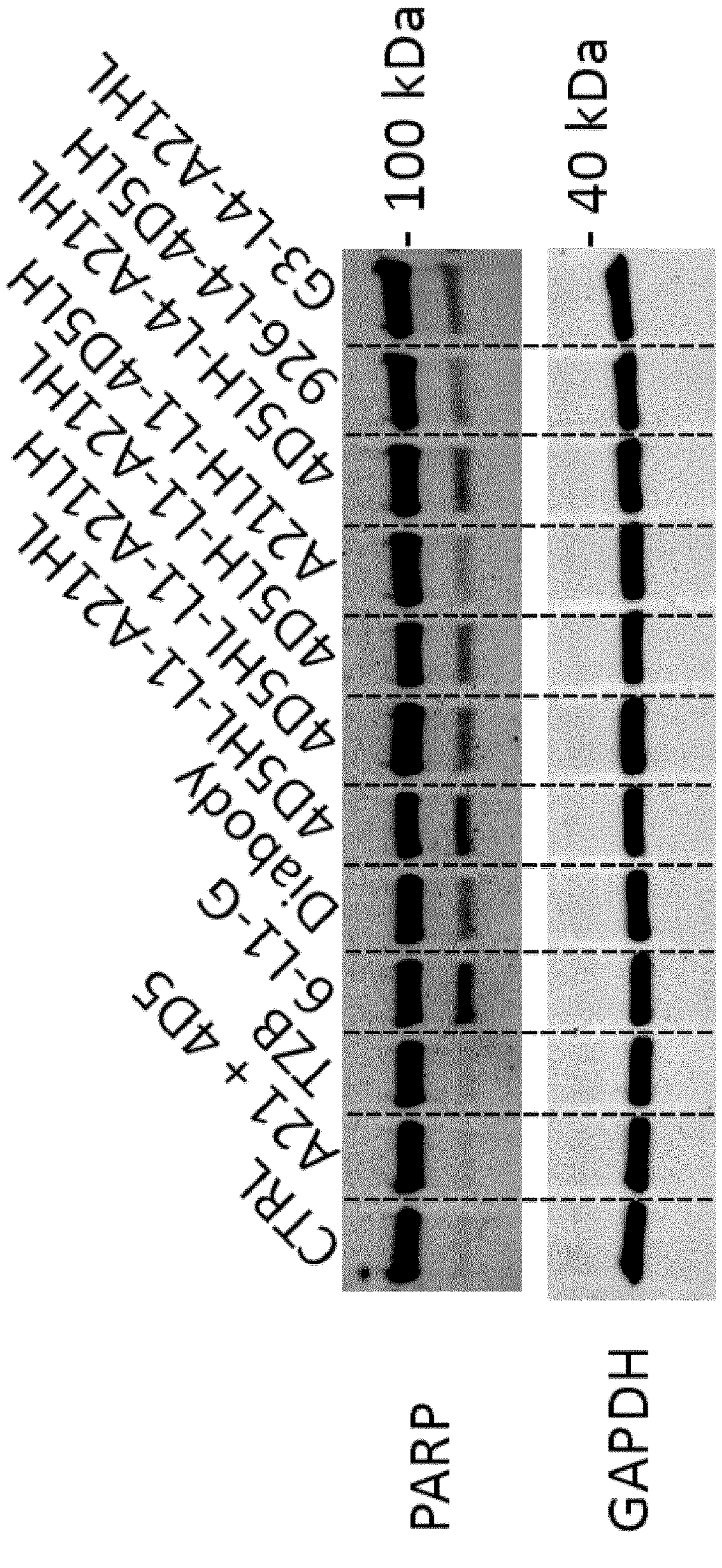

FIG. 23 shows the Western blot analysis of apoptosis as detected by the cleavage of Poly ADP Ribose Polymerase (PARP). GAPDH is a loading control.

Figure 24:
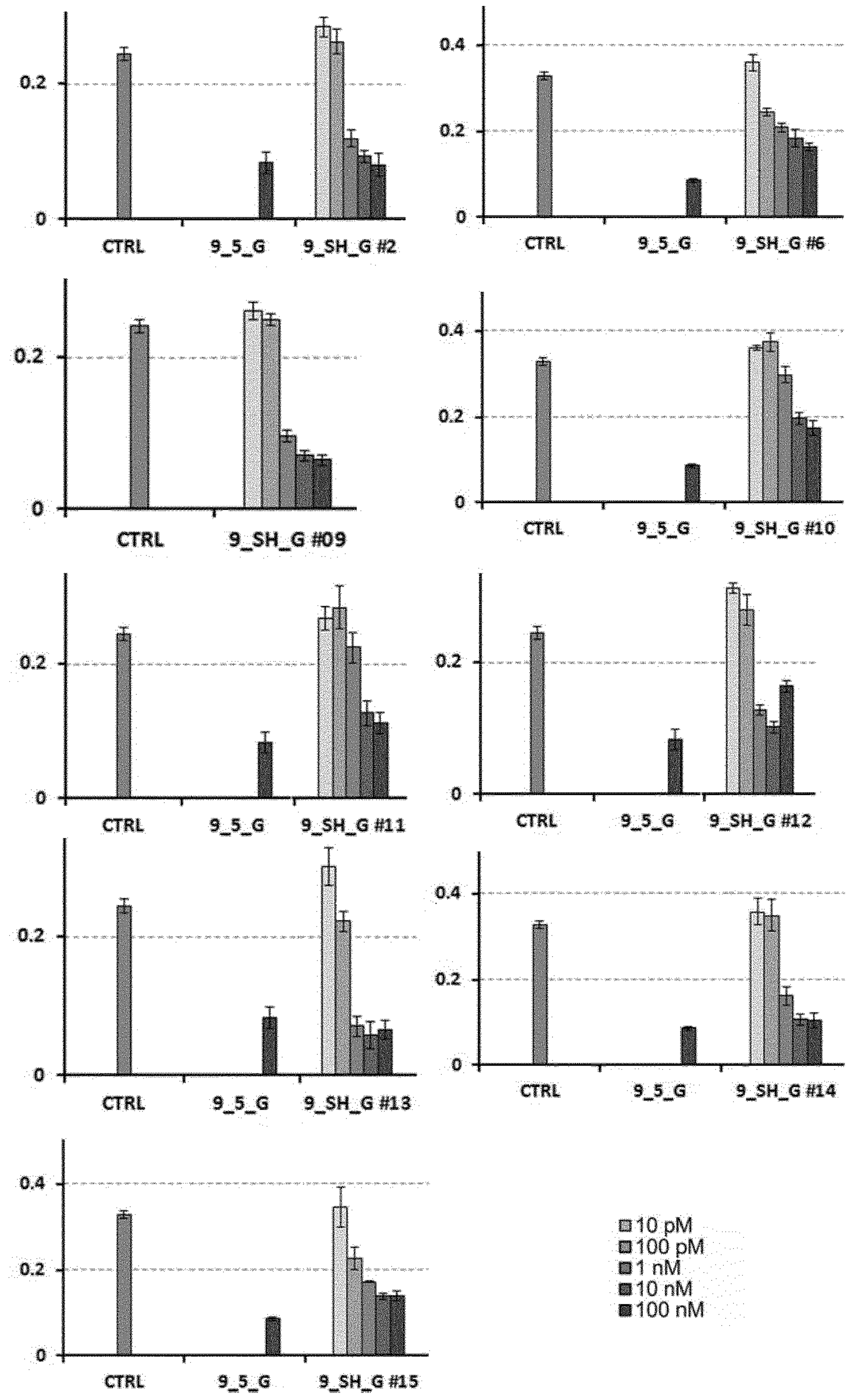

FIG. 24 shows the effect of different anti-tumor agents on the viability of BT474 cells in cell proliferation assays, the Y-axis showing the viability of the cell lines determined by absorbance of reduced XTT after treatment with any of the agents identified in the legend.

EXAMPLES

Example 1: Anti-Tumor Activity of the Bispecific Anti-HER2 Binding Agents in Comparison to Trastuzumab and Pertuzumab A XTT cell proliferation assay was performed with a panel of HER2 overexpressing cancer cell lines in 96-well tissue culture plates (FIG. 1). A defined number of cells were seeded in RPMI1640 medium containing 10% fetal calf serum (FCS). Cancer cells were treated for 4 days with 100 nM of anti-HER2 agents and controls. Measuring points were recorded in triplicates. XTT cell viability assays were developed according to the manufacturer's protocol. At a concentration of 100 nM, all anti-HER2 agents show maximal anti-tumor activity (titration not shown). The average of three data points is plotted with standard error. Data were normalized against the negative control on each plate, which corresponds to untreated cells (maximal growth). Bispecific targeting agents reduce cell growth of HER2-dependent cancer cells by 60-80%, while trastuzumab (hu4D5) reduces cell growth by only 20-60%. Bispecific targeting agents (926-FL-G3, 929-FL-H14) show consistently strong anti-tumor activity in all cell lines, while some cell lines show resistance against trastuzumab treatment. Sensitive cell lines can be roughly defined as HER2 dependent (e.g. HER2 overexpressing) and lacking any PI3K activating mutation.

Figure 1A:
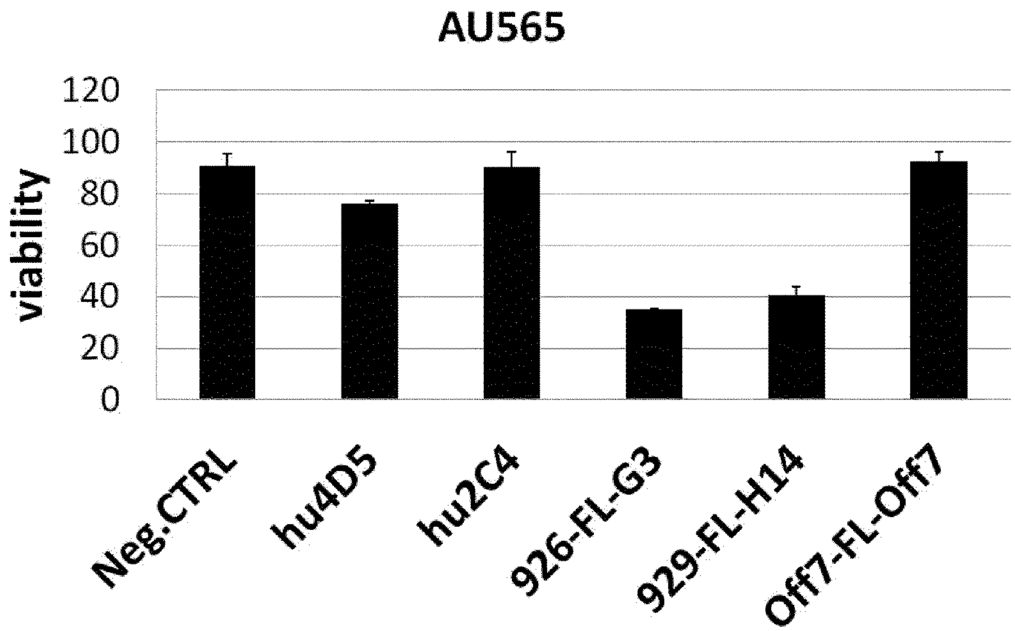
Figure 1A:
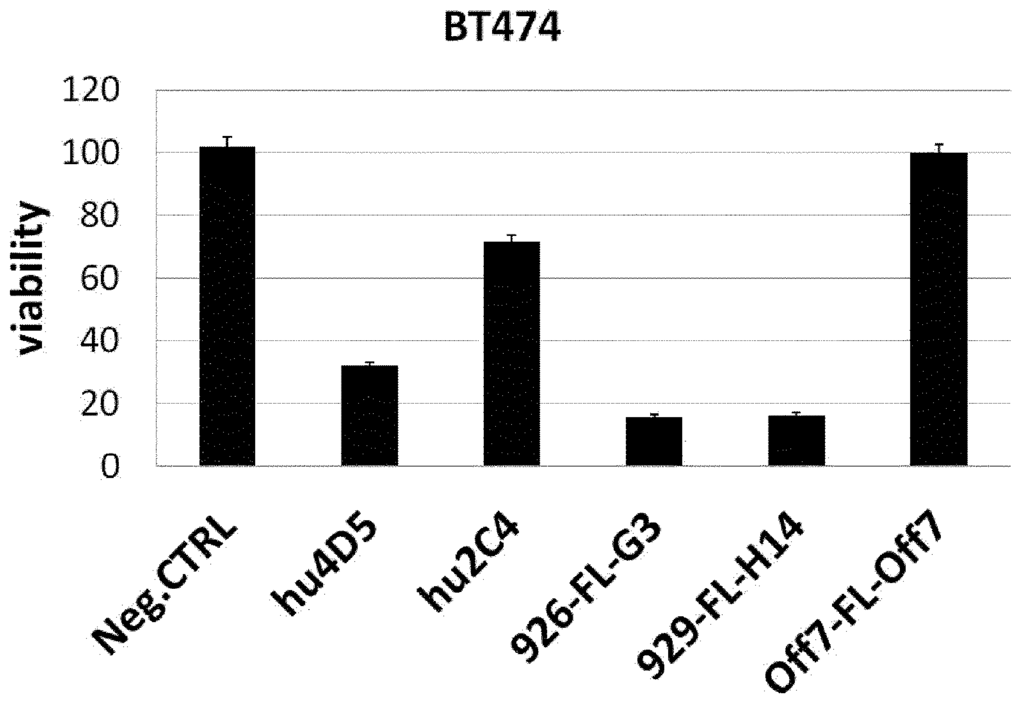
Figure 1B:
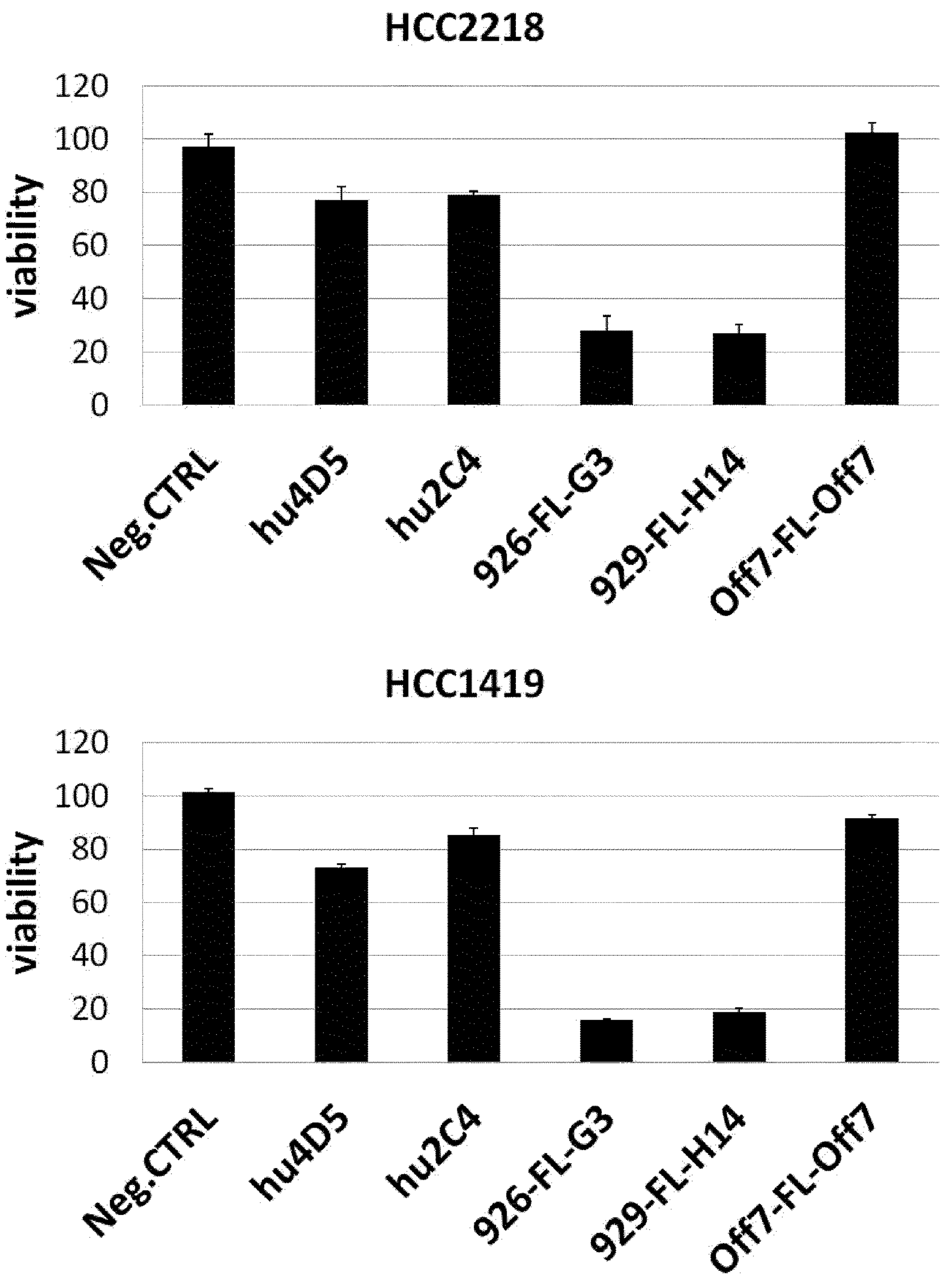
Figure 1C:
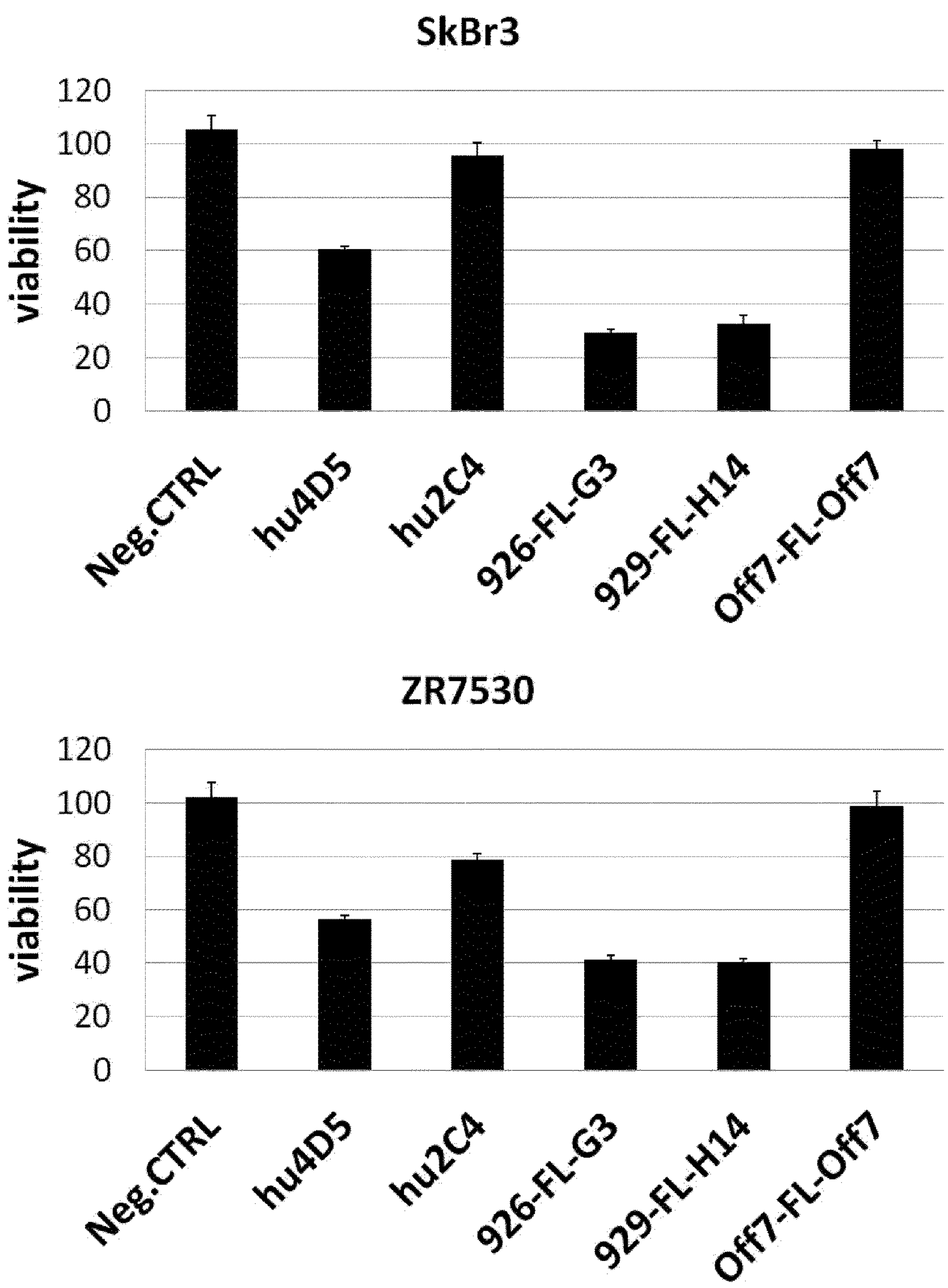
Figure 2:
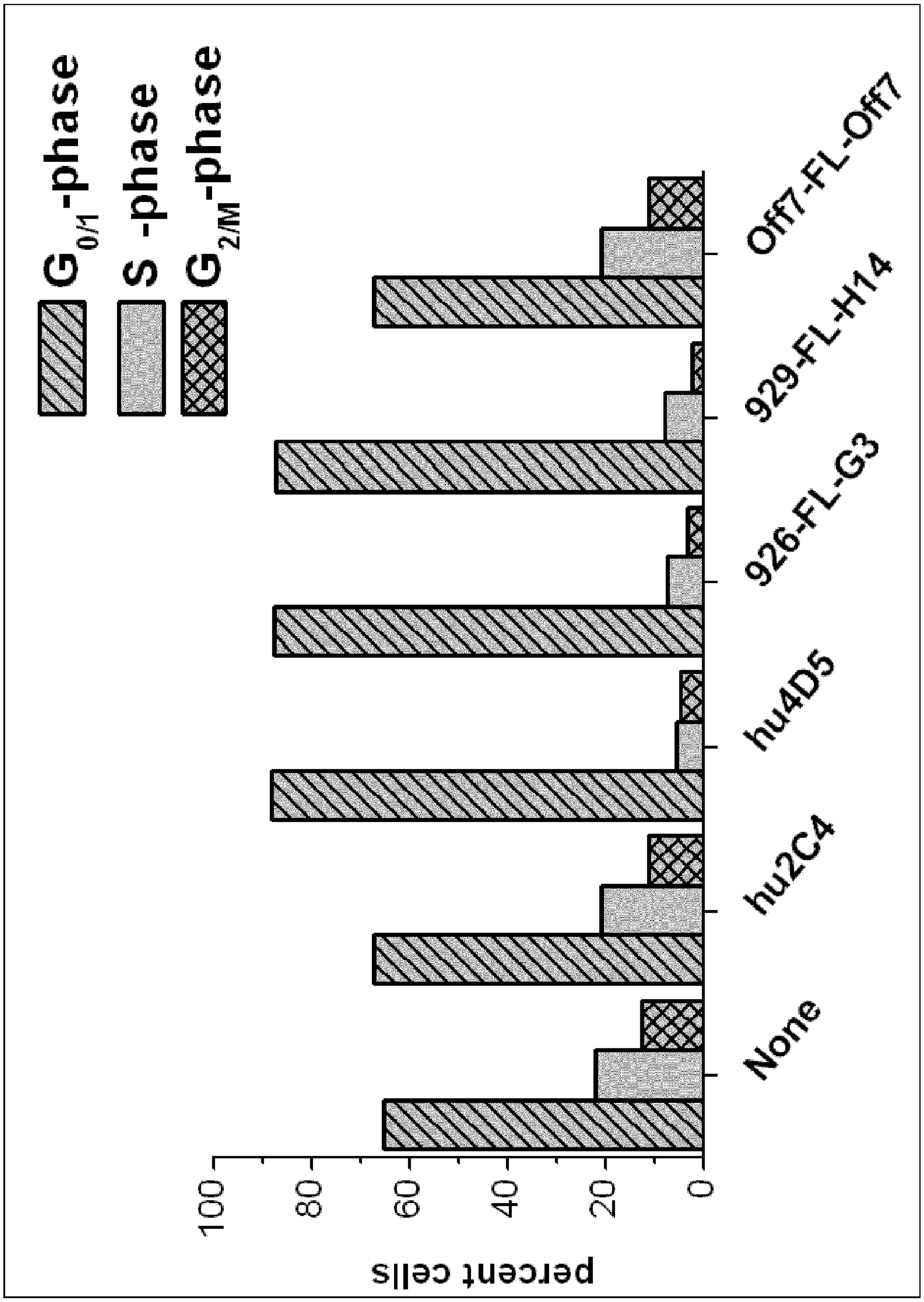

FIG. 2 shows that bispecific targeting agents block entrance into S-phase and induce accumulation in $G_{0/1}$-Phase. BT474 cells were seeded 16 h before treatment in RPMI1640 containing 10% FCS. Anti-HER2 agents were added to a final concentration of 100 nM and cells were treated for 3 days. Afterwards, cells were fixed in 70% EtOH and stained with propidium iodide (PI). FACS measurements were gated to exclude cell debris in a forward vs. side scatter plot and $10^4$ events were recorded. PI fluorescence histograms were analyzed by FlowJo 7.2.5 software, and cell cycle distribution was fitted using the Dean-Jett-Fox algorithm, which excludes the apoptotic SubG1-population of cells. Treatment with bispecific targeting agents (926-FL-G3, 929-FL-H14) reduces S-phase and $G_{2/M}$-phase content in HER2-dependent cancer cells. It was shown that trastuzumab (hu4D5) treatment induces cell cycle arrest by blocking entrance into S-phase of sensitive HER2 dependent cancer cell lines. Here it is shown that bispecific targeting agents also induce cell cycle arrest in trastuzumab sensitive cell lines.

Figure 3A:
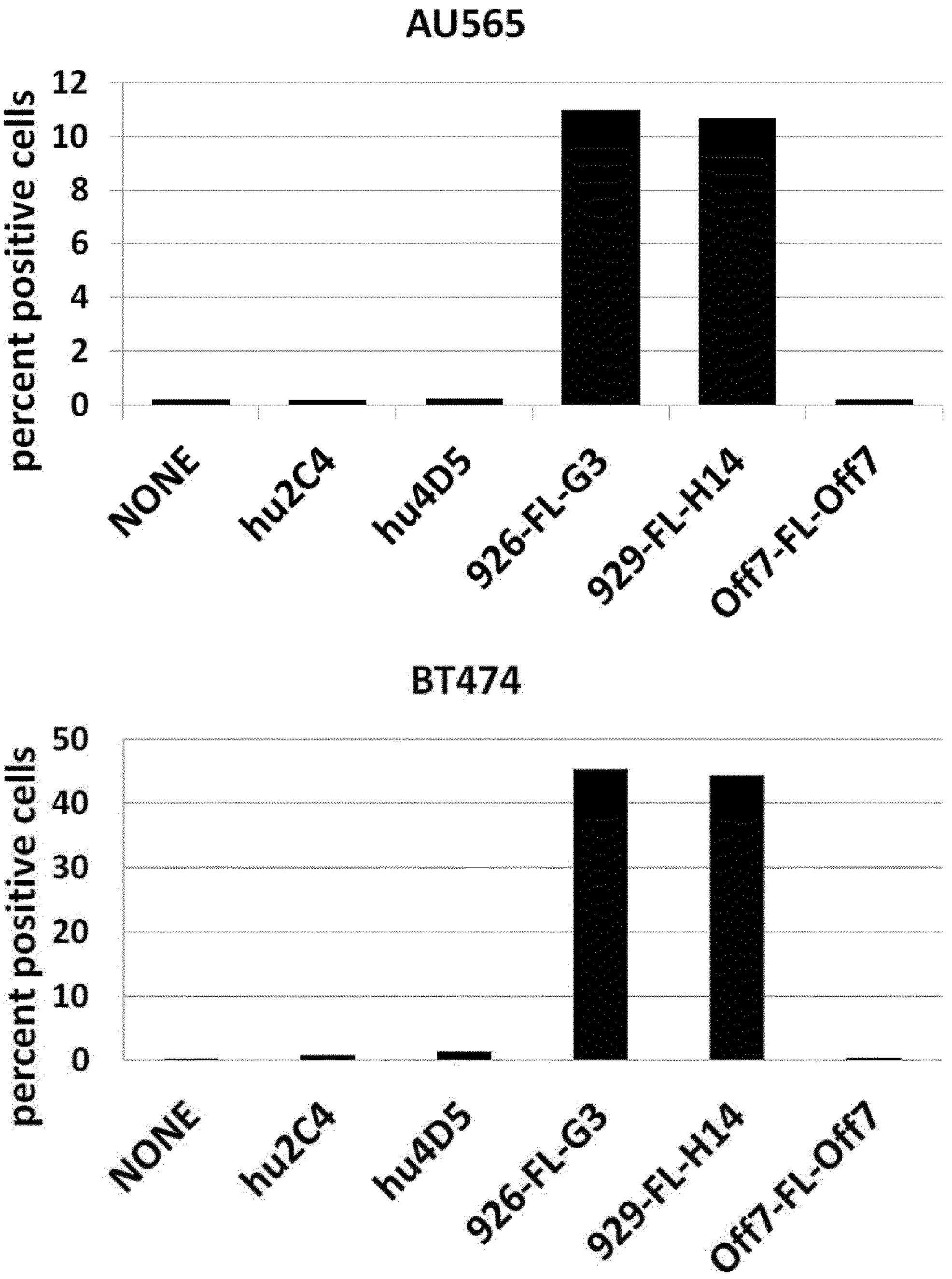
Figure 3B:
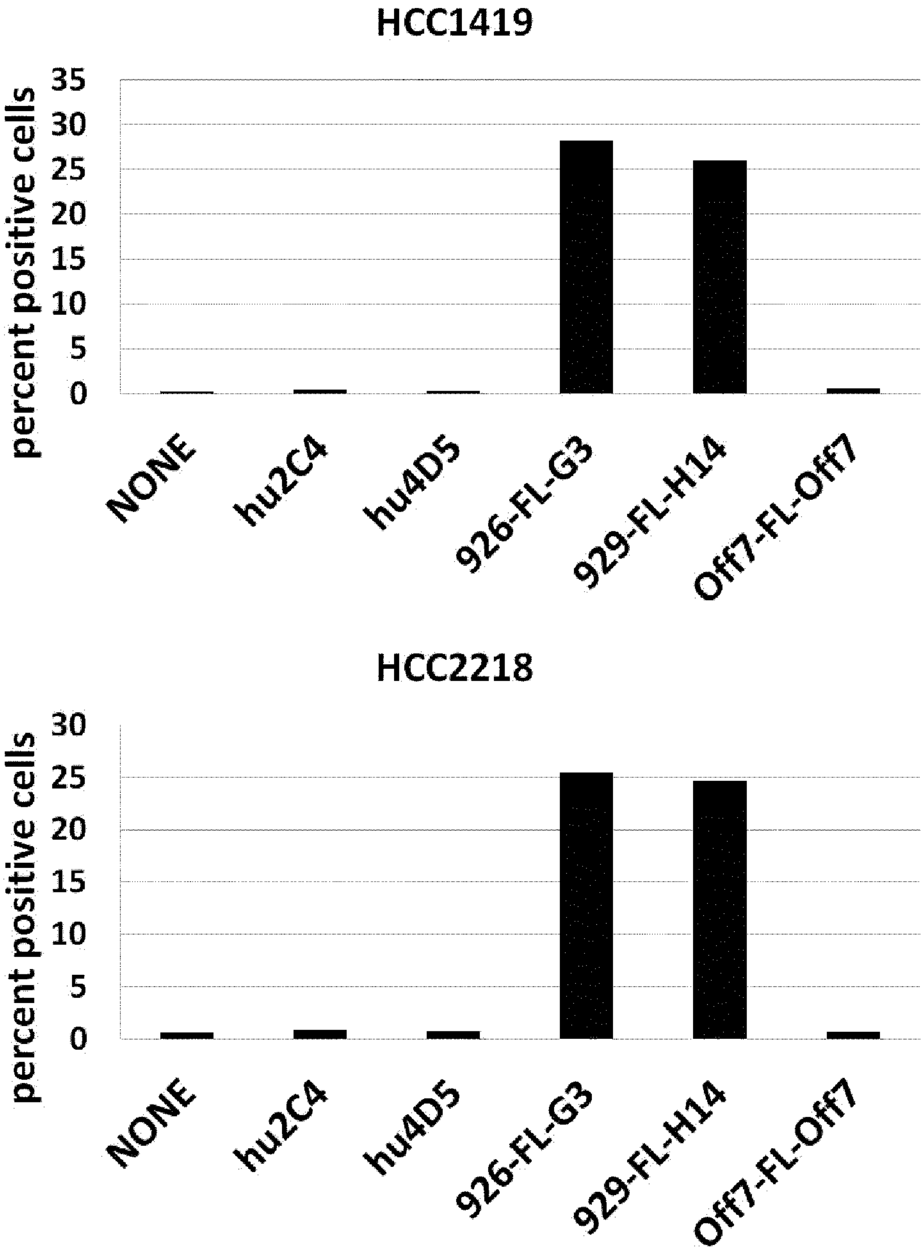

The terminal transferase dUTP nick end labeling (TUNEL) assay and quantification by flow cytometry was used to determine the portion of apoptotic cells upon treatment with anti-HER2 agents (FIG. 3). Cancer cells were seeded 16 h before treatment in RPMI1640 containing 10% FCS. Anti-HER2 agents (pertuzumab: hu2C4; trastuzumab: hu4D5; bispecific targeting agents: 926-FL-G3, 929-FL-H14; mock treatment: Off7-FL-Off7) were added to a final concentration of 100 nM and cells were treated for 3 days. Fractions of adherent and non-adherent cells were pooled. Cells were fixed in 2% paraformaldehyde, permeabilized in cold 0.1% sodium citrate containing 0.1% Triton X-100 for 2 min, washed three times with cold PBS and labeled with fluorescein-conjugated dUTP. FACS measurements were gated to exclude cell debris in a forward vs. side scatter plot and $10^4$ events were recorded. Measurements were plotted as an one parameter FL1 histogram plots (FITC fluorescence on the X-axis and counts on the Y-axis). Population of TUNEL positive (shift towards higher FL1) cells were quantified by one-dimensional regional gates which exclude TUNEL negative cells (auto fluorescence). Gates were applied according to negative control to exclude auto fluorescent cells. Treatment with bispecific targeting agents induces DNA degradation in HER2-dependent cancer cells, which is a hallmark of apoptosis. The number of TUNEL-positive cells correlates with the formation of a Sub-G1 population, as determined by cell cycle analysis (data not shown). The quantification shows 30- to 80-fold higher TUNEL signals for the bispecific binding agents than for trastuzumab or pertuzumab in HER2-dependent cancer cells.

For Western blot analysis of the HER2/HER3 signalling pathway, PI3K/AKT and MAPK pathway and downstream targets of cell cycle and apoptosis, cancer cells were seeded 24 h before treatment in RPMI1640 containing 10% FCS. Anti-HER2 agents were added to a final concentration of 100 nM and cells were treated for 3 days. Afterwards, the fraction of detached apoptotic cells was collected and removed by centrifugation. Remaining attached cells were washed with cold PBS and scraped off into cold PBS_I (PBS containing protease inhibitors (Pefabloc, Leupeptin, Pepstatin, Marimastat) and phosphatase inhibitors (sodium orthovanadate, sodium metavanadate, sodium molybdate, β-glycerol phosphate, sodium fluoride)) on ice. Both cell fractions were pooled and washed in PBS_I. Afterwards, cells were lysed in PBS_I containing 1% Triton X-100 for 30 min at 4° C. on a rocker, and cell lysates were centrifuged at 20,000 g for 20 min at 4° C. Protein concentrations of the respective cell lysates were determined by BCA assays and samples were taken up in lithium dodecyl sulfate (LDS) loading buffer containing β-mercaptoethanol for complete reduction. Samples were heated for 5 min at 80° C. Samples were loaded on 10% SDS-PAGE and afterwards blotted on PVDF_FL membrane (Millipore) according to a BioRad protocol. After incubation with primary detection antibodies, western blots (FIG. 4.) were stained by secondary antibodies labeled with an infrared dye, and membranes were scanned on an Odyssey IR-fluorescence scanning system (LICOR). The following primary detection antibodies were used: Human Epidermal Growth Factor Receptor 2 (HER2); Phospho-Tyr 1248 Human Epidermal Growth Factor Receptor 2 (HER2-Y1248); Human Epidermal Growth Factor Receptor 3 (HER3); Phospho-Tyr 1289 Human Epidermal Growth Factor Receptor 3 (HER3-Y1289); Protein Kinase B (AKT); Phospho-Ser 473 Protein Kinase B (AKT-5473); p44/42 MAPK (ERK1/2); Phospho-Thr202/Tyr204 p44/42 MAPK (ERK1/2-T202/Y204); Cyclin-depended Kinase Inhibitor 1B (p27KIP1); CyclinD1 (CyclinD1); Poly ADP Ribose Polymerase (PARP); Bcl-2 Interacting Mediator of Cell Death (BIM); Glyceraldehyde 3-Phosphate Dehydrogenase (GAPDH).

For quantitative western blot analysis of the time course treatments, BT474 cells were seeded 24 h before treatment in RPMI1640 containing 10% FCS. Anti-HER2 agents were added to a concentration of 100 nM and cells were treated for 3 days. Afterwards, the fraction of only loosely adherent cells was washed away with cold PBS. Attached cells were scraped off in cold PBS_I (PBS containing protease inhibitors (Pefabloc, Leupeptin, Pepstatin, Marimastat) and phosphatase inhibitors (sodium orthovanadate, sodium metavanadate, sodium molybdate, β-glycerol phosphate, sodium fluoride)) on ice. Afterwards, cells were lysed in PBS_I containing 1% Triton X-100 for 30 min at 4° C. on a rocker and cell lysates were centrifuged at 20,000 g for 20 min at 4° C. Protein concentrations of the respective cell lysates were determined by BCA assays. HER2 receptor was immunoprecipitated by 901-FL-zHER2, a DARPin-affibody fusion construct, linked to Biosupport Ultra Link beads. HER2 receptor was depleted from BT474 cell lysate (corresponding to 1 mg protein in the lysate). Beads were washed three times with cold PBS_I. HER2 receptor was eluted from beads by heating to 80° C. for 5 min in LDS loading buffer containing β-mercaptoethanol for complete reduction. HER3 samples were heated for 5 min at 80° C. in LDS loading buffer containing β-mercaptoethanol for complete reduction. Samples were loaded on 10% SDS-PAGE and afterwards blotted on PVDF_FL membrane according to the BioRad protocol. Western blots were stained by secondary antibodies labeled with an infrared dye and membranes were scanned on an Odyssey IR-fluorescence scanning system (LICOR).

Figure 4:
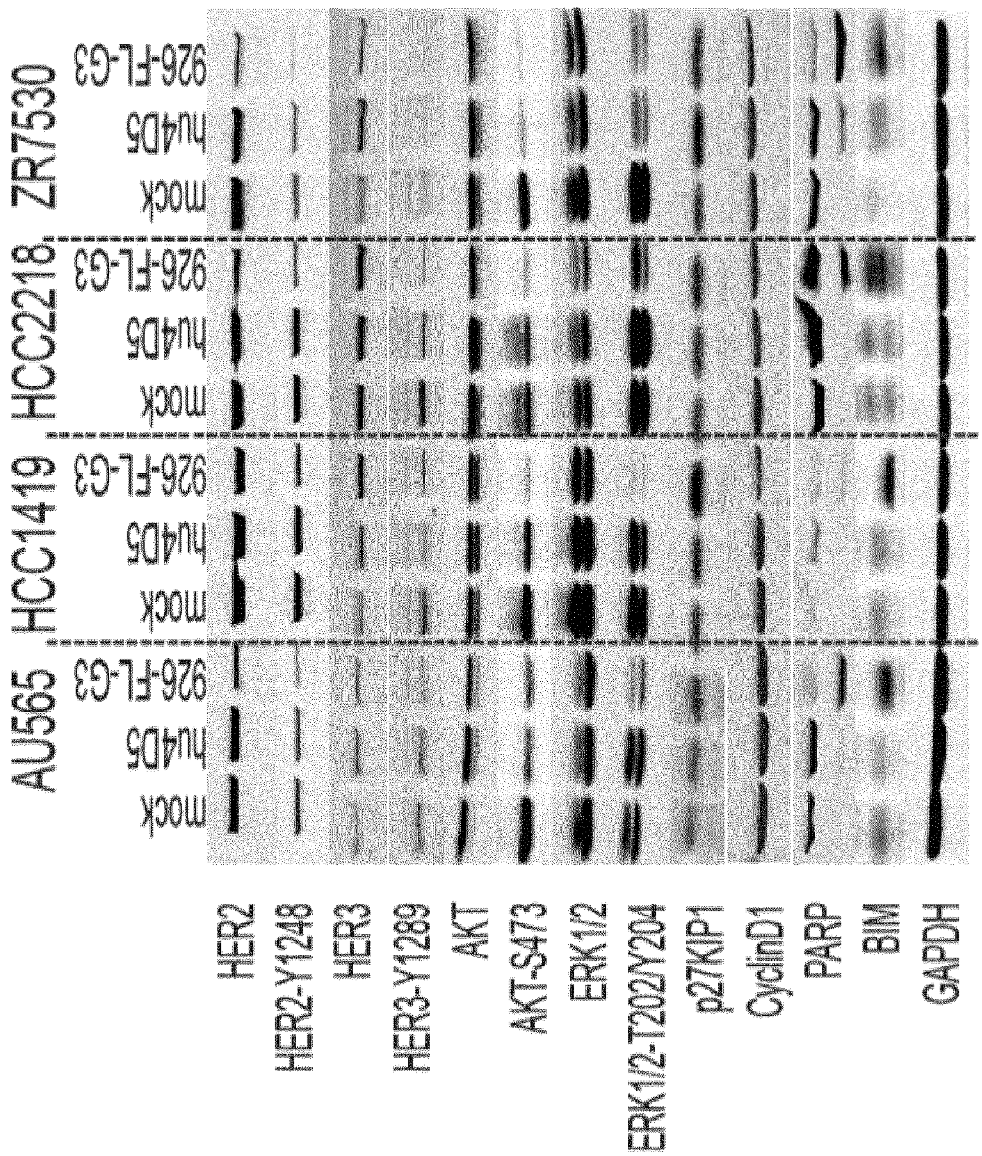
Figure 5A:
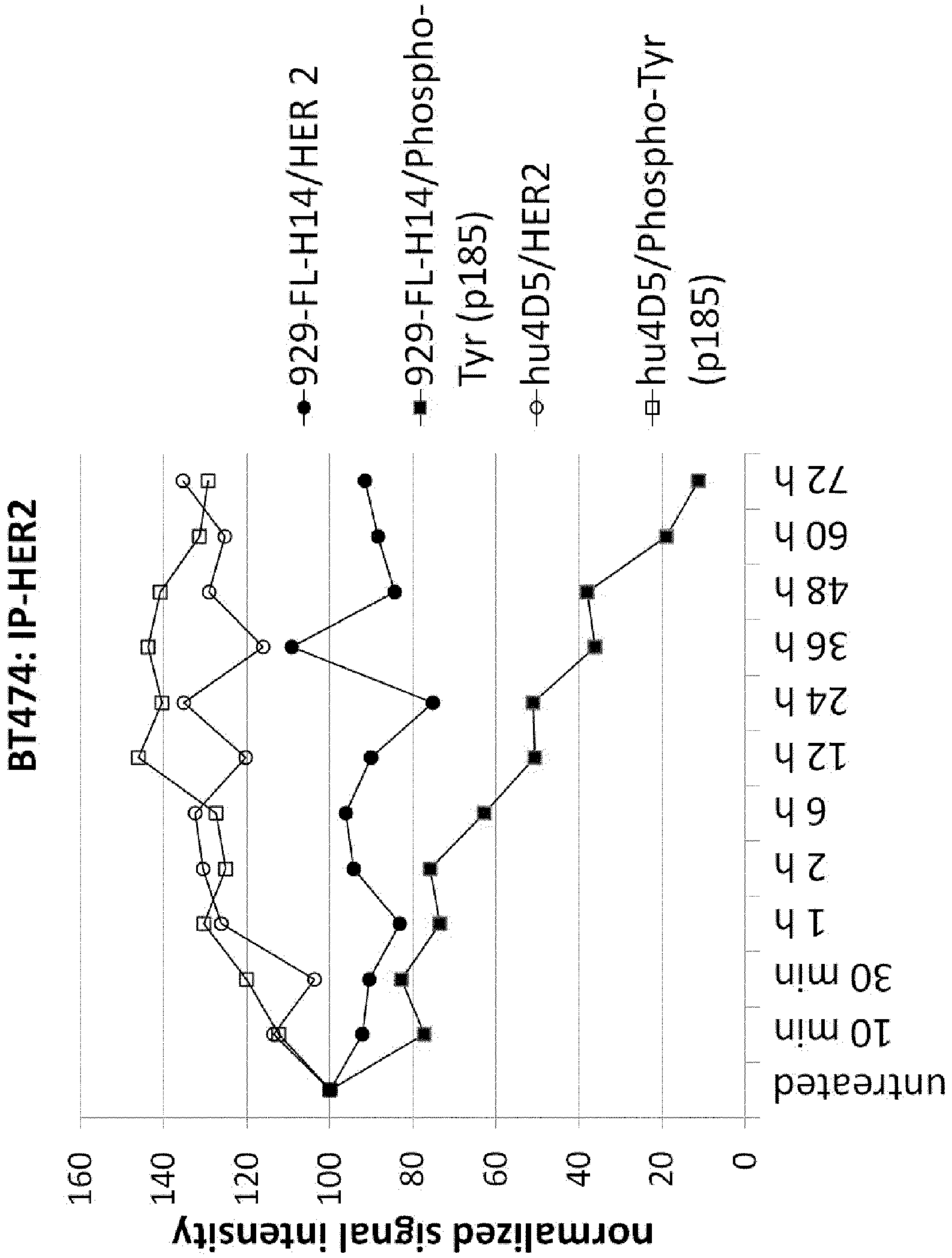
Figure 5B:
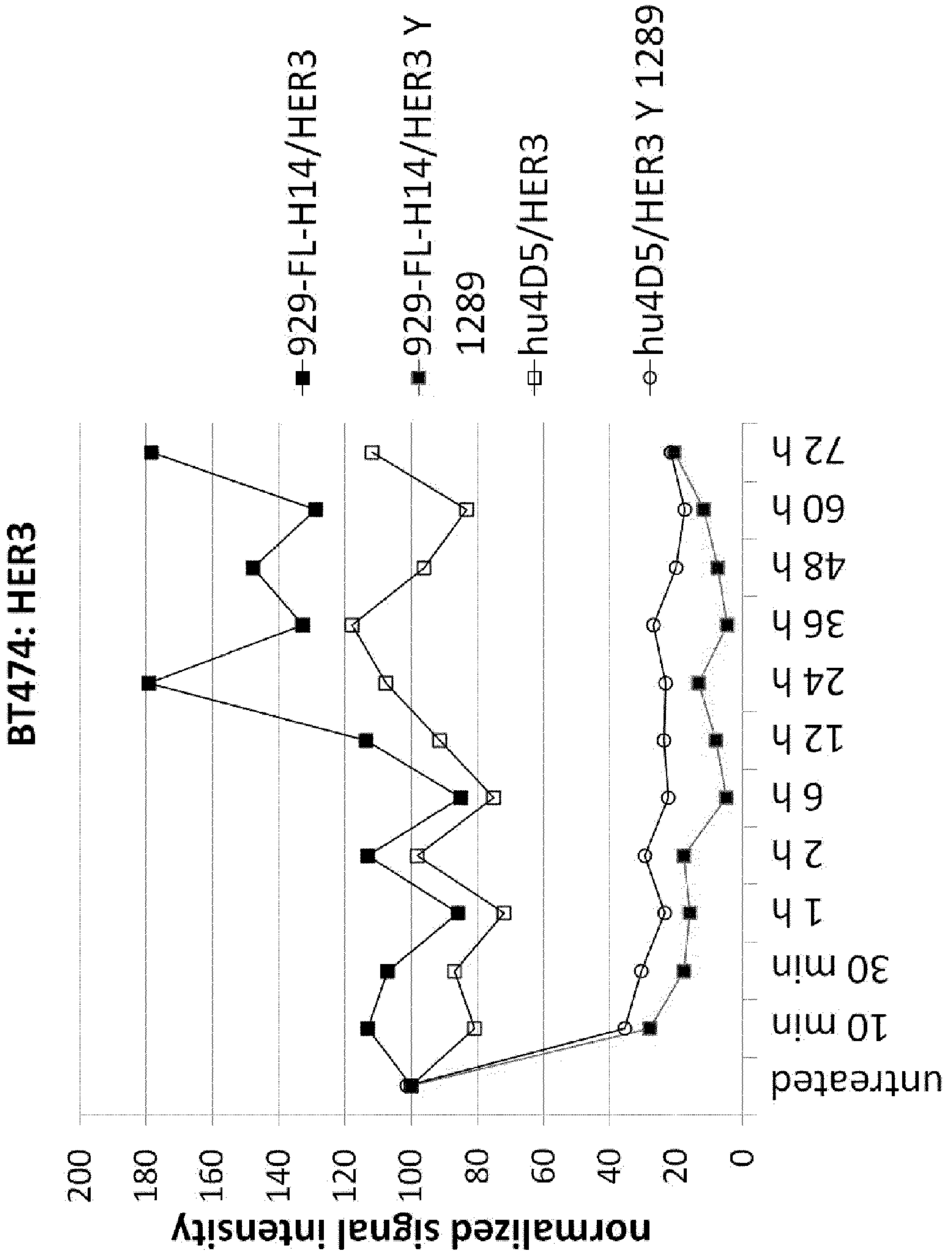

Bispecific agents down-regulate phospho-HER2 levels consistently in all HER2-dependent cancer cells. Down-regulation of phospho-HER2 can correlate with down-regulation of HER2 expression level, which was observed in the fractions of apoptotic cells (FIG. 4). Constant HER2 expression levels were observed in the fraction of attached cells for e.g. BT474 and SkBr3, while phospho-HER2 levels were strongly reduced (FIG. 5). Therefore, down-regulation of HER2 expression can be observed in the apoptotic fraction of HER2-dependent cancer cells but is probably not the cause for induction of apoptosis. Rather, down-regulation of phosho-HER2 simultaneously with reduction of phosho-HER3 is the cause for induction of apoptosis. Down-regulation of phospho-HER3 can be observed after treatment with bispecific targeting agents and trastuzumab. Bispecific targeting agents show stronger down-regulation of phospho-HER3 than trastuzumab. Up-regulation of HER3 expression can be observed after treatment with bispecific targeting agents. A feedback loop sensing inhibition of phospho-AKT and, consequently, up-regulation of HER3 expression has been proposed. Bispecific targeting agents reduce phospho-AKT (downstream HER3) and phospho-ERK (downstream HER2) signaling simultaneously. Trastuzumab treatment mainly down-regulates phospho-AKT, while in ZR7530 cells, trastuzumab treatment leads to a down regulation of phospho-ERK. Cell cycle regulators p27KIP1 (inhibitor of cyclin-dependent kinases) is up-regulated and CyclinD1, which mediates G1/S-phase transition, is down-regulated in several HER2-dependent cancer cell lines. Again, inhibition of the cell cycle is not necessarily observed by bispecific targeting agents, but cell cycle arrest is observed in cell lines which are sensitive to trastuzumab treatment. $BIM_S$ up-regulation and PARP cleavage (up-regulation of PARP p89) is observed in all HER2-dependent cancer cell lines, which show induction of apoptosis after treatment with bispecific targeting agents. ZR7530 and BT474 cells show also PARP cleavage after treatment with trastuzumab, but bispecific targeting agents show consistently stronger signals.

Figure 6:
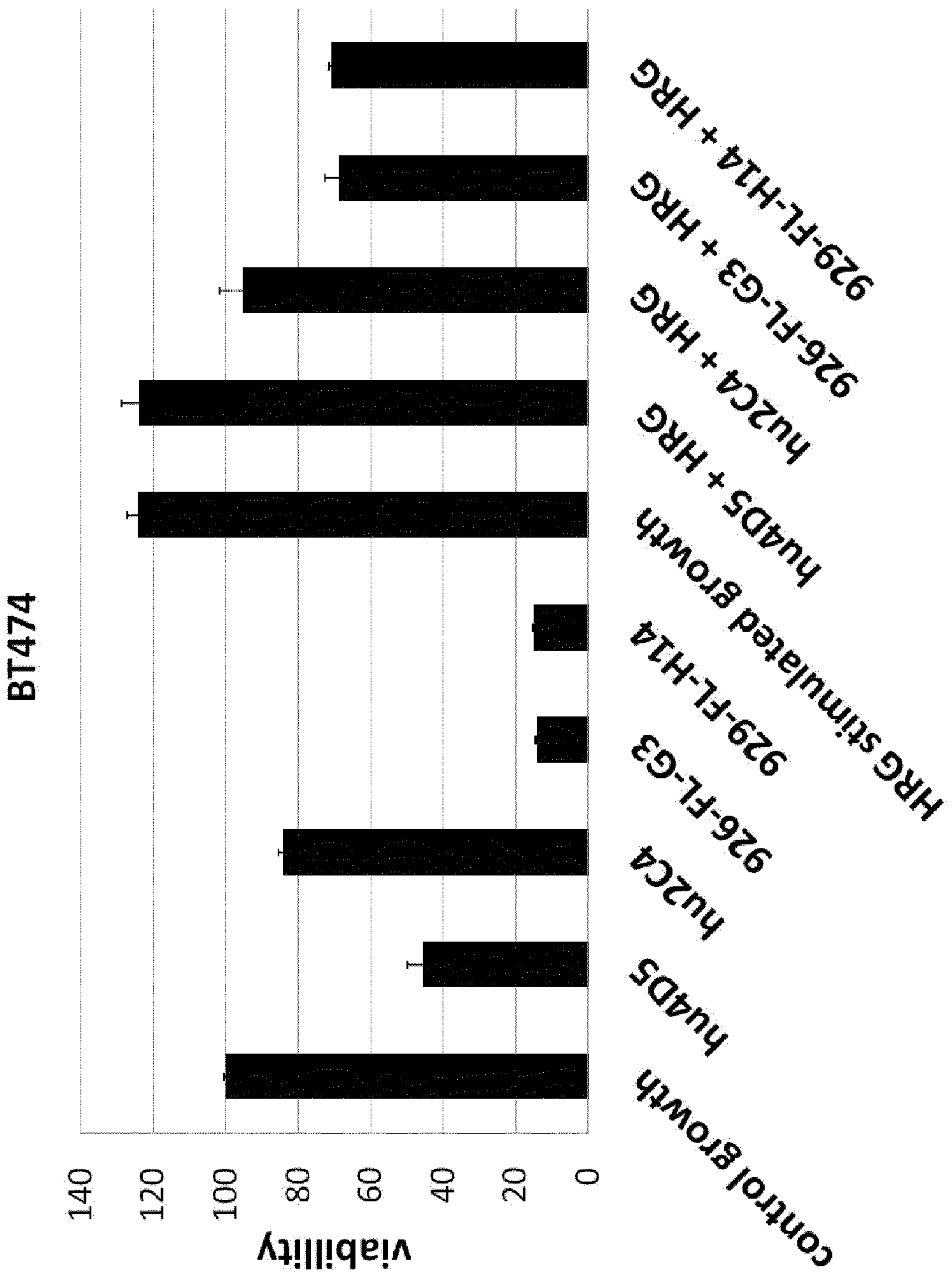
FIG. 6 shows the inhibition of ligand-stimulated growth by bispecific targeting agents in cell proliferation assays.
Figure 7:
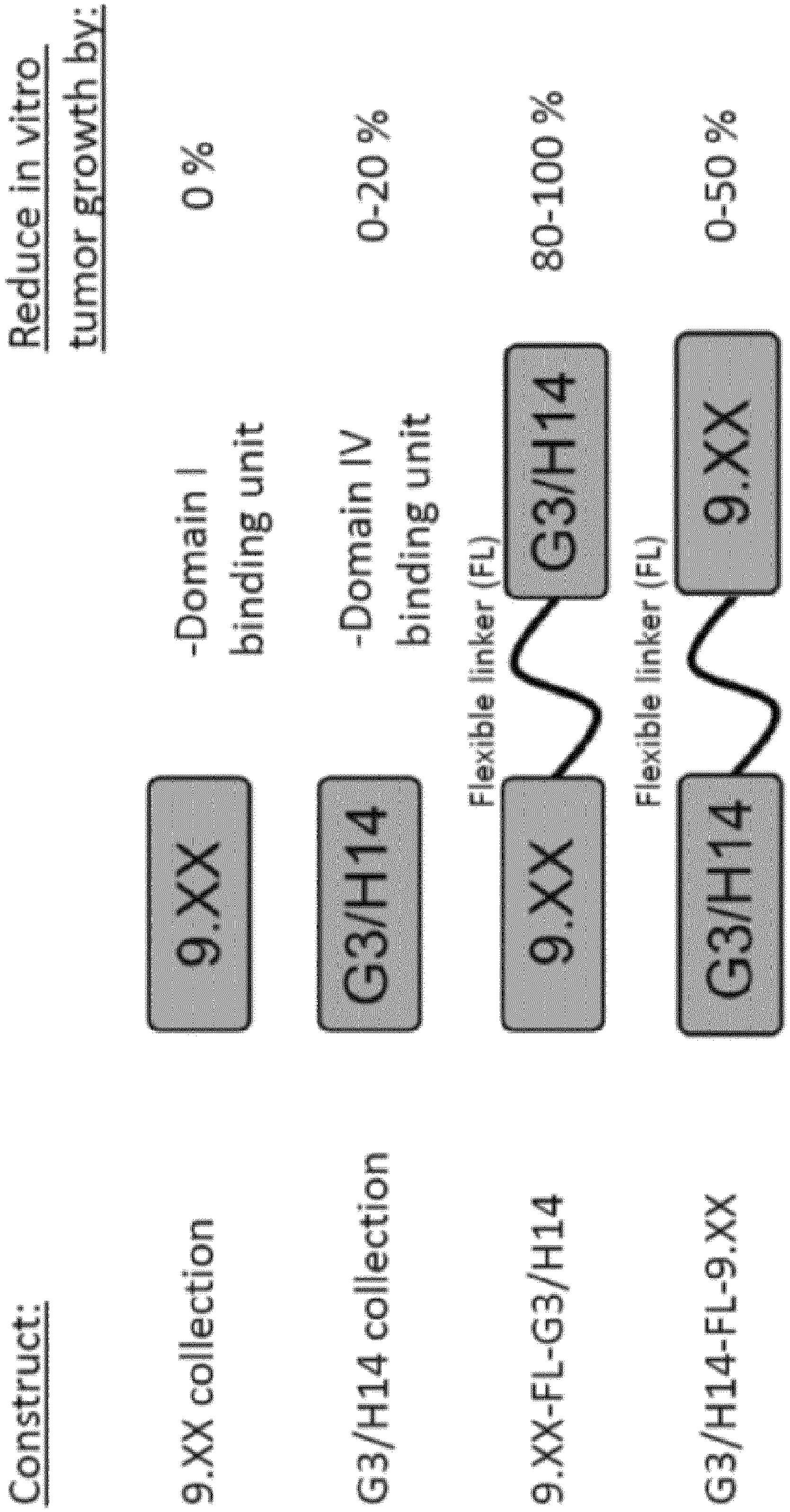
FIG. 7 shows the pictorial summary of anti-HER2 targeting formats.

XTT cell proliferation assays were performed with BT474 cells in 96 well tissue culture plates (FIG. 6). Cells were seeded at a density of $10^4$ cells/$cm^2$16 hours before treatment in RPMI1640 containing 1% FCS (low concentration of additional growth factors). Cells were pre-treated with 100 nM anti-HER2 agents for 2 hours. Afterwards, cells were stimulated by adding heregulin beta-1 (HRG) to a concentration of 1 nM (Recombinant Human NRG1-β1/HRG1-β1: 26.9 kDa). HRG treatment leads to an increase of viable BT474 cells by 20%, compared to the control growth in 1% FCS alone (FIG. 6). The single treatments with anti-HER2 agents are thus compared to the corresponding controls in the absence (100% viability) or presence (120% viability) of HRG. Trastuzumab (hu4D5) treatment reduced viability by 50-60% in the absence of HRG, but did not show anti-tumor activity in ligand-stimulated cancer cells. Trastuzumab completely looses anti-tumor activity in presence of 1 nM HRG. Pertuzumab (hu2C4) treatment reduced viability by 20-30% in the presence or absence of HRG. Bispecific targeting agents reduced the viability by 80-90% in the absence of HRG and also showed 40-50% reduction in the presence of HRG. Therefore, the bispecific targeting agents show strongest anti-tumor activity both in the presence and in the absence of HRG. The additive effect of trastuzumab and pertuzumab resembles the individual maximal anti-tumor activity of the single agents (data not shown), but has no significant mechanistically synergism in in-vitro models. Therefore, the mechanism of action of bispecific targeting agents is superior to the treatment with trastuzumab combined with pertuzumab in in-vitro models. The treatment with the bispecific reagents exceeds the effect of the sum of effects from both antibodies.

A person skilled in the art will appreciate that the XTT-assay is a suitable test for the determination of the cytotoxicity and for the evaluation of the potential of anti-tumor candidate compounds (see Jost et al, (1992) Journal of Immunological Method, 147, 153-165; Scudiero et al. (1988) Cancer Research, 48, 4827-4833; Andjilani et al, (2005) Int. J. Cancer, 117, 68-81; Rubinstein et al. (1990) J Natl Cancer Inst, 82(13), 1113-1117; Monks et al. (1991) J Natl Cancer Inst, 83(11), 757-766).

Example 2: Construction Plan of Bispecific Anti-HER2 Targeting Agents that Induce Apoptosis in HER2 Dependent Cancer Cells Generation of Binding Agents that Form the Components of the Active Molecule Binding molecules were obtained by ribosome display selection of ankyrin repeat protein libraries for specific binding to the full length extracellular domain of HER2 (ECD HER2) by methods previously disclosed (Zahnd et al. (2006) J. Biol. Chem. 279, 18870-18877).

Preparation of the Biotinylated HER2 Target

In order to obtain binders to the individual domains, the different individual domains of HER2 were individually expressed in insect cells, using a baculovirus expression system. Thereby, it is guaranteed that binders selected will be directed towards the domain of interest. Briefly, recombinant ErbB2-ectodomains carrying an N-terminal melittin signal sequence (MKFLVNVALVFMVVYISYIYA, SEQ ID 101) and an N-terminal His6 tag were expressed in *Spodoptera frugiperda* (Sf9) cells using baculoviral vectors. Sf9 cells were grown to a density of $4\times10^6$ cells/mL and co-infected with the respective virus at a MOI of 1. 72 h post-infection, cells were harvested by centrifugation (30 min, 5,000 g, 4° C.) and the cleared medium was subjected to immobilized metal ion affinity chromatography (IMAC) purification with Ni-NTA Superflow purification resin.

To generate binders against any domain of the extracellular region, the extracellular domain (residues 1-621) of HER2 was used as target for the selection with ribosome display (Zahnd et al., J. Biol. Chem. (2006) 281: 35167-35175) or, to generate binders against the first three domains, HER2 residues 1-509 was used.

For immobilization, aliquots of these target proteins (200-600 μg) were chemically biotinylated using EZ-Link Sulfo-NHS-SS-Biotin. Due to the size difference of the target proteins, a variable molar excess of the biotinylating reagent relative to the target protein was used (6-fold for HER2 1-621 or 1-509, 3-fold for the single domains). Reaction conditions were used according to the supplier's manual. Successful biotinylation was confirmed by ELISA and Western blot experiments. The biotinylated HER2 constructs were dialyzed extensively against PBS150.

Target proteins had to be immobilized for selection. To avoid partial protein denaturation of the target proteins that may result from direct immobilization on solid plastic (i.e. polystyrene) surfaces, biotinylated target proteins were bound to neutravidin or streptavidin, which had been immobilized directly on a solid plastic surface, as follows: neutravidin (66 nM, 100 μl/well) or streptavidin (66 nM, 100 μl/well) in PBS was immobilized on MaxiSorp plates (Nunc, Denmark) by incubation at 4° C. overnight. The wells were blocked with 300 μl of PBSTB (PBS containing 0.1% Tween-20, 0.2% BSA) for 1 h at room temperature. Binding of the biotinylated target proteins (100 μl, 100 nM for selection) in PBSTB was allowed to occur for 1 h at 4° C. For the first selection round on immobilized target protein, requiring larger volumes, neutravidin (66 nM, 4 ml/tube) in PBS was immobilized on MaxiSorp Immunotubes by incubation at 4° C. overnight. The tubes were blocked with 4 ml of PBSTB for 1 h at room temperature. Binding of the biotinylated target proteins (4 ml, 100 nM) in PBSTB was allowed to occur for 1 h at 4° C. For selection on immobilized target protein, neutravidin and streptavidin were used alternately in selection rounds to avoid selection of binders against these proteins.

Ribosome Display

Ribosome display followed the published protocols (Dreier et al. (2012) Methods Mol. Biol. 805, 261-286; Zahnd et al. (2007) Nat. Methods 4, 269-279.) Typically 3 or 4 rounds were carried out. The first round was always carried out on plates, the later rounds in some of the selection on plates, in others in solution, where the biotinylated HER2 target is then bound to streptavidin-coated magnetic beads, as described in the protocols in detail (Dreier et al. (2012) Methods Mol. Biol. 805, 261-286; Zahnd et al. (2007) Nat. Methods 4, 269-279.).

In the forth round, the selection pressure was increased by applying off-rate selection. For this purpose, after the in vitro translation was stopped by 5-fold dilution into ice-cold WBT buffer (50 mM Tris acetate, pH 7.5, 150 mM NaCl, 50 mM $Mg(CH3COO^-)_2$, 0.05% Tween 20), biotinylated HER2 construct was added to a final concentration of 10 nM, and the translation was allowed to equilibrate for 2 h at 4° C. The translation reaction was split into two aliquots, and non-biotinylated HER2 construct was added to a final concentration of 1 μM to each aliquot, corresponding to a 100-fold excess over biotinylated antigen. The aliquots were incubated for 2 and 20 h, respectively, to increase the selection stringency for slower off rates. Ribosomal complexes were recovered using 30 μl of streptavidin-coated magnetic beads. In a subsequent round, 175 nM biotinylated HER2 construct was immobilized on a NeutrAvidin-coated Maxisorp plate, i.e. rather non-stringent conditions to collect the binder ("collection round") (Dreier et al. (2012) Methods Mol. Biol. 805, 261-286; Zahnd et al. (2007) Nat. Methods 4, 269-279.)

In all selection rounds on solid-phase immobilized HER2 construct, a prepanning step of 30 min on a neutravidin-coated Maxisorp plate was performed as described (Dreier et al. (2012) Methods Mol. Biol. 805, 261-286; Zahnd et al. (2007) Nat. Methods 4, 269-279.). After prepanning, the translation extracts were allowed to bind for 45 min to HER2 construct-coated Maxisorp plates. Retained complexes were extensively washed with WBT buffer.

Phage Display

Phage display of the DARPin library followed the published protocol (Steiner et al. (2008) J. Mol. Biol. 382, 1211-1227). The immobilization of the various biotinylated HER2 constructs has been described above.

Unless stated otherwise, all steps of the phage display selection were carried out at room temperature. Selection rounds were performed either on biotinylated target protein in solution with subsequent capturing on streptavidin-coated magnetic beads (referred to as: "target protein in solution") or on biotinylated target protein bound to neutravidin or streptavidin, which had been directly immobilized on a solid plastic surface (referred to as: "immobilized target protein"), as described below. Very good results were obtained when performing the first selection round of selection on immobilized target protein, presumably because of the greater efficiency of capturing binders (especially important in the first round), followed by further rounds on target protein in solution, presumably because of the lower enrichment of background binders Selection on Target Proteins in Solution When the first selection cycle was done in solution, about $2.5\times10^{13}$ phage particles of the phage DARPin library were incubated for 1 hour with 100 nM biotinylated target protein in 2 ml PBSTB for the first round of selection. In subsequent selection rounds, about $10^{12}$ phage particles were used (see below). The phage-antigen complexes were then captured on 100 μl streptavidin-coated paramagnetic beads (10 mg/ml) for 20 min. After washing the beads eight times with PBST (PBS, 0.1% Tween-20) the phage particles were eluted with 200 μl of 100 mM triethylamine (Et3N, pH not adjusted) for 6 min, followed by 200 μl of 100 mM glycine-HCl, pH 2, for 10 min. Eluates were neutralized with 100 μl of 1 M Tris-HCl, pH 7, or 18 μl of 2 M Tris-base, respectively, combined and used to infect 5 ml of exponentially growing *E. coli* XL1-Blue cells. After shaking for 1 hour at 37° C., cells were expanded into 50 ml of fresh 2YT medium (5 g NaCl, 10 g yeast extract, 16 g tryptone per liter) containing 10 μg/ml cam and incubated at 37° C. with shaking. After a maximum of 5 h (shorter times if $OD_{600}$=0.5 was reached earlier), isopropyl-β-D-thiogalactoside (IPTG) was added to a final concentration of 0.2 mM and 15 minutes later the phage library was rescued by infection with VCS M13 helper phage at $10^{10}$ pfu (plaque forming units) per ml (multiplicity of infection 20). Cells were grown overnight at 37° C. without the addition of kanamycin. Cells were removed by centrifugation (5600 g, 4° C., 10 min) and 40 ml of the culture supernatant was incubated on ice for 1 hour with one-fourth volume of ice-cold PEG/NaCl solution (20% polyethylene glycol (PEG) 6000, 2.5 M NaCl). The precipitated phage particles were then collected by centrifugation (5600 g, 4° C., 15 min) and redissolved in 2 ml of PBS and used for the second round of selection.

For the subsequent selection rounds, about $10^{12}$ of the amplified phage particles were used as input and incubated with 100 μl of streptavidin-coated paramagnetic beads for 1 h to remove unspecific and streptavidin binding phage particles. After removing the beads, phage particles were incubated for 1 hour with 100 nM biotinylated target protein, complexes were captured on fresh beads, beads were washed 12 times with PBST, phages eluted with 400 μl of 100 mM glycine-HCl, pH 2, for 10 min, the eluate neutralized with 36 μl of 2 M Tris-base and phage particles amplified and purified as described above.

After three rounds, enrichment of phage particles displaying DARPins binding specifically to the HER2 target construct was monitored by phage ELISA. About $5\times10^{10}$ phage particles (estimated spectrophotometrically) of the initial library and the amplified pools of each selection round were pipetted to wells with and without immobilized target protein and incubated at RT for 2 h. After washing the wells four times with 300 μl of PBST, bound phage particles were detected with mouse anti-M13 antibody horseradish peroxidase conjugate and soluble BM Blue peroxidase (POD) substrate.

Selection on Immobilized Target Proteins

For the first selection cycle about $3.5\times10^{13}$ phage particles of the phage DARPin library were added to an immunotube containing the immobilized target protein (biotinylated target protein bound to neutravidin, which had been directly immobilized on the solid plastic surface) and incubated with rotation for 2 h. After rinsing the tube ten times with PBST, the phage particles were eluted with 500 μl of 100 mM $Et_3N$ (pH not adjusted) for 6 min, followed by 500 μl of 100 mM glycine-HCl, pH 2, for 10 min. Eluates were neutralized with 250 μl of 1 M Tris-HCl, pH 7, or 45 μl of 2 M Tris-base, respectively, combined and used to infect 13 ml of exponentially growing *E. coli* XL1-Blue cells. After shaking for 1 hour at 37° C. cells were expanded into 130 ml of fresh 2YT medium containing 10 μg/ml chloramphenicol (cam) and incubated at 37° C. with shaking. Phage amplification and precipitation was done as described above.

In the subsequent selection rounds about $10^{12}$ of the amplified phage particles were first incubated in a blocked immunotube (coated either with neutravidin or streptavidin used for immobilization of the target protein in the previous round of selection and BSA) one hour to remove neutravidin, streptavidin or unspecific binding phage particles. For the binding selection the phage particles were incubated for one hour in four wells containing the immobilized biotinylated target protein (directly coated neutravidin or streptavidin were alternately used in subsequent selection rounds). The wells were washed 12 times with PBST, phages eluted from each well with 100 μl of 100 mM glycine-HCl, pH 2, for 10 min, the combined eluates neutralized with 36 μl of 2 M Tris-base and phage particles amplified and purified as described above. After three rounds, enrichment was determined by phage ELISA as described above.

Phage Display from Antibody Library

Single-chain antibody fragments (scFv) were selected for binding to HER2, which have a molecular weight of 30 kDa, from HuCAL-1 (Knappik et al., 2000), a library of synthetic human antibody fragments. The library has a diversity of about $2\times10^{9}$ members (Knappik et al., JMB, 2000, 296(1), 57-86). M13 phages presenting the HuCAL-1 scFv library as a fusion to the CT domain of g3p coat protein were selected for binding to soluble biotinylated HER2 domain 1 or domain 4, which was immobilized on neutravidin or streptavidin on microtiter wells as described above.

Phage selections were performed by incubating 50 pmol of biotinylated antigen with 1 pmol of phages in 100 μl PBS 0.5% BSA for 1 h at 4° C. The complexes were captured with 1 mg of BSA-blocked streptavidin magnetic particles and washed 10 times with PBS 0.5% BSA. Bound phages were eluted with 100 mM glycine, pH 2.2, and neutralized with the same volume of 1 M Tris, pH 8. *E. coli* TG1 cells were infected with eluted phages and plated on LB agar plates containing 1% glucose and 34 mg/l chloramphenicol. The plates were incubated overnight at 30° C., and bacteria were scraped off to inoculate 2×YT medium containing 1% glucose and 34 mg/l chloramphenicol. The culture was incubated at 37° C. and at $OD_{600}$=0.5 the phage library was rescued by infection with VCS M13 helper phage (Stratagene). The bacteria were harvested by centrifugation and resuspended in 2×YT medium containing 30 mg/l kanamycin, 34 mg/l chloramphenicol, 0.1 mM IPTG and grown overnight at 30° C. Phages were precipitated from the culture supernatant by addition of polyethylene glycol PEG-6000 (3.3% final concentration), NaCl (0.4 M final concentration). Phages were resuspended in $H_2O$, precipitated by addition of polyethylene glycol PEG-6000 (3.3% final concentration), NaCl (0.4 M final concentration) and resuspended in PBS.

After the fourth and fifth round of phage display, pools of selected scFv-encoding sequences were subcloned via restriction sites XbaI and EcoRI into the expression plasmid pMX7 (Knappik et al., JMB, 2000, 296(1), 57-86). *E. coli* SB536 cells were transformed with the constructed vector. Bacteria were grown at 37° C. in 2×YT medium containing 0.1% glucose and 34 mg/l chloramphenicol. At $OD_{600}$=0.5 cultures were induced with 1 mM IPTG. ScFv fragments are secreted to the periplasm of *E. coli*. For small-scale expressions, cultures were incubated for 5 h after induction at 30° C. For periplasmic extracts, cells were collected by centrifugation and incubated overnight in 300 mM boric acid, 150 mM NaCl, 2 mM EDTA, pH 8, at 4° C. After centrifugation, the supernatant was used for enzyme linked immuno-sorbent assay (ELISA) screening.

For large-scale expression of scFv fragments, cultures were incubated for 20 h at 22° C. Bacteria were collected by centrifugation and resuspended in 50 mM $NaH_2PO_4$, 300 mM NaCl, pH 8. After addition of a spatula tip of DNAseI and 2 mM $MgCl_2$, bacteria were lysed in a French pressure cell. The lysate was filtered and purified on Ni-NTA agarose, washing with 16 column volumes of 50 mM $NaH_2PO_4$, 300 mM NaCl, pH 8; 12 column volumes of 50 mM $NaH_2PO_4$, 900 mM NaCl, pH 8; 16 column volumes of 50 mM $NaH_2PO_4$, 300 mM NaCl, 0.1% Triton X-100, pH 8; and 8 column volumes of 50 mM $NaH_2PO_4$, 300 mM NaCl, pH 8. Eluates were concentrated by ultra-centrifugation and buffer-exchanged to PBS using Micro BioSpin P-6 columns. For proliferation assays, samples were additionally purified on Detoxi-Gel endotoxin removal columns and eluted with PBS. When stored at 4° C. under sterile conditions, purified scFv fragments maintained unchanged binding activity for more than 3 months.

Bispecific scFv1-Linker-scFv2 Constructs

Antibody scFv fragments binding to either HER2 domain 1 or HER2 domain 4 were identified by ELISA as described above. From these scFv fragments, a series of bispecific scFv1-linker-scFv2 constructs (bispecific tandem scFv), where always a HER2 domain 1 binder was connected to a HER2 domain 4 binder (in either orientation), was constructed as follows: Since all HuCAL scFv fragments have common internal restriction sites, a vector could be constructed, pHu202, in which the upstream scFv fragment is connected via a flexible linker to the downstream fragment, which does not have a signal sequence, resulting in the arrangement phoA-scFv1-linker-scFv2, where phoA is the secretion signal. The linker segment can be exchanged via unique restriction sites that have been engineered into this fragment at its flanks, NotI and SfiI. Thus, all combinations of potential active bispecific antibodies were conveniently constructed by ligating the linker-scFv2 unit into the secretion vector containing phoA-scFv1, downstream of scFv1. After the active combinations had been identified, the linker was systematically varied in these constructs, by exchanging it into a series of linkers with different length, ligating it via NotI and SfiI.

For large-scale expression of the scFv1-linker-scFv2 fragments, cultures were incubated for 20 h at 22° C. Bacteria were collected by centrifugation and resuspended in 50 mM $NaH_2PO_4$, 300 mM NaCl, pH 8. After addition of a spatula tip of DNAseI and 2 mM $MgCl_2$, bacteria were lysed in a French pressure cell. The lysate was filtered and purified on Ni-NTA agarose, washing with 16 column volumes of 50 mM $NaH_2PO_4$, 300 mM NaCl, pH 8; 12 column volumes of 50 mM $NaH_2PO_4$, 900 mM NaCl, pH 8; 16 column volumes of 50 mM $NaH_2PO_4$, 300 mM NaCl, 0.1% Triton X-100, pH 8; and 8 column volumes of 50 mM $NaH_2PO_4$, 300 mM NaCl, pH 8. Eluates were concentrated by ultra-centrifugation and buffer-exchanged to PBS using Micro BioSpin P-6 columns. For proliferation assays, samples were additionally purified on Detoxi-Gel endotoxin removal columns and eluted with PBS.

Bispecific Diabodies

The cloning of the bispecific diabodies is similar to that of tandem scFvs, but with some important differences. We needed to clone two genes, phoA-VH1-VL2, followed by phoA-VH2-VL1. For simplicity, we opted for two promoters, each driving one of the genes. VH1 and VL1 are the heavy and light chain variable regions of svFv1, and VH2 and VL2 correspondingly of svFv2, but in the diabody arrangement they are now connected to the partner chain of the other scFv. The modularity of the synthetic HuCAL library with its conserved restriction sites within the synthetic genes makes this cloning very convenient. As can be seen, it was only necessary to exchange VH (or VL) between to scFv fragments, using the unique restriction sites by which VH and VL are flanked in the scFv fragment (Knappik et al., 2000). The whole cassette, promoter-phoA-VH1-linker-VH2 had been flanked by Not1 and SfiI sites in the newly created vectors pDia202, while in pDia203, the same sites had been engineered downstream of the scFv expression cassette. Thus, the complete unit promoter-phoA-VH1-linker-VH2 could be cloned into a vector already containing promoter-phoA-VH2-linker-VH1. Thus, both chains of the diabody were encoded on the same plasmid. Both are secreted to the periplasm where they assemble.

For large-scale expression of the diabodies, cultures were incubated for 20 h at 22° C. Bacteria were collected by centrifugation and resuspended in 50 mM $NaH_2PO_4$, 300 mM NaCl, pH 8. After addition of a spatula tip of DNAseI and 2 mM $MgCl_2$, bacteria were lysed in a French pressure cell. The lysate was filtered and purified on Ni-NTA agarose, washing with 16 column volumes of 50 mM $NaH_2PO_4$, 300 mM NaCl, pH 8; 12 column volumes of 50 mM $NaH_2PO_4$, 900 mM NaCl, pH 8; 16 column volumes of 50 mM $NaH_2PO_4$, 300 mM NaCl, 0.1% Triton X-100, pH 8; and 8 column volumes of 50 mM $NaH_2PO_4$, 300 mM NaCl, pH 8. Eluates were concentrated by ultra-centrifugation and buffer-exchanged to PBS using Micro BioSpin P-6 columns. For proliferation assays, samples were additionally purified on Detoxi-Gel endotoxin removal columns and eluted with PBS.

In addition, single-chain diabody constructs were constructed as described in Example 5, (analogous to constructs described by Völkel et al. (2001), Protein Engineering 14, 815-823).

Analysis of Single Binding Agents

Binding agents were characterized by means of enzyme-linked immunosorbent assay (ELISA). ELISAs, using the full length extracellular domain of HER2 (ECD HER2) for coating, were carried out to show binding of all individual binding agents. ELISA, using a truncated form of ECD HER2 (domain 1-3) as target, were performed to show specific binding of the DARPins to this part of HER2 ECD. This was originally applied to the collection of the 9XX series of binders (molecules originating from the HER2_509 selection). Domain 4 binders G3 and H14 were identified by binding to full length ECD HER2 but an absence of binding to the truncated ECD HER2 comprising only domains 1 to 3.

Specific binding experiments were carried out on the surface of viable HER2 overexpressing cancer cells e.g. BT474, SkBr3, SkOv3, using standard flow cytometry methods. Multiple fluorescent detection systems, like e.g. detection of the His-Tag by an anti His-tag antibody, followed by a secondary antibody labeled with Alexa488, or alternatively, genetic superfolder GFP (sfGFP) fusions with the binding molecules or using directly Alexa488-labeled binding reagents, were used to confirm specific binding of all single binding reagents to the surface of HER2 overexpressing cancer cells. The binding to a single epitope was confirmed by the analysis of mean fluorescence intensities, resulting in similar values for all binders at saturation, and more importantly, by complete inhibition of the signal when competed to an unlabeled control binding to said epitope. The single binding reagents also passed different quality control measurements like e.g. size exclusion chromatography, multi-angle light scattering and polyacrylamide gel electrophoresis (PAGE).

Competitive Binding Analysis of Binding Reagents

Competitive binding analysis was performed to characterize the epitopes of the binding agents of the 9XX collection. All binding agents of the 9XX collection compete for binding to a similar epitope on domain 1 of HER2, except binder 9.01. Competitive binding FACS analysis was also performed with domain 4 binding agents versus trastuzumab. Groups of competing and non-competing binding agents were identified. Importantly, binding to the trastuzumab epitope is not a prerequisite for the anti-tumor activity of the bispecific molecules (G3 does not compete with trastuzumab for binding). Binder H14 does compete with G3 and does show competition with trastuzumab.

Competitive binding FACS analysis performed with the 9XX binding molecules versus pertuzumab binding did not show competition. None of the single binding agents binds to the pertuzumab epitope. ELISA, using the domain 1 of the ECD HER2 as target, was performed to show specific binding of the 9XX collection.

Table 1 summarizes properties of preferential binding units (that can be components of bispecific molecules with bioactivity) and control binding units (which do not contribute bioactivity) for the construction of bispecific binding agents with superior anti-tumor activity. Listed are the single domains of the extracellular part of HER2 that are bound by the single agents. The epitope is characterized by inhibition of a binding assay performed in ELISA or on the surface of HER2 overexpressing cancer cells by means of flow cytometry. Crystal structure data are available for the indicated binding agents, which characterize the specific epitopes in detail on the single amino acid level. For the construction of potent bispecific anti-tumor agents, a binding agent which targets domain 1 of HER2 is preferentially fused to a binding agent that targets domain 4 of HER2 from the list of indicated binding agents.

TABLE 1

Summary of single binding agents

| | Binds to HER2 domain: | Competitive Binding to HER2 known with: | Crystal Structure available: | Strong anti-tumor activity in bispecific setup: |
|---|---|---|---|---|
| G3 | IV | H14 | YES | YES |
| H14 | IV | G3; 4D5 | — | YES |
| 902 | I | 929; 926 | — | YES |
| 903 | I | 929; 926 | — | YES |
| 910 | I | 929; 926 | — | YES |
| 916 | I | 929; 926 | — | YES |
| 926 | I | 929; 926 | YES | YES |
| 929 | I | 929; 926 | YES | YES |
| 930 | I | 929; 926 | — | YES |
| H01 | I | 929; 926 | — | YES |
| H03 | I | 929; 926 | — | YES |
| Off7 | none | none | YES | — |
| 4D5, trastuzumab | IV | H14, Nanobody, Zybody | YES | YES |
| 2C4, pertuzumab | II | Nanobody, Zybody | YES | — |
| zHER2 | III | none | YES | — |
| A21 | I | none | YES | YES |

The domain 1-binding scFv A21 is described in example 5.

Expression of Bispecific Binding Agents

The genes or coding sequences of the bispecific molecules were constructed in a vector pQiBi-01- (or -11-; -12-; -22-; -23-; -33-); using conventional restriction digest and ligation techniques with a BamHI/HindIII restriction site for the N-terminal binding molecules and BglII/BsaI restriction sites for the C-terminal binding molecules. This vector is derived from pQE30, but encodes the lacI$^q$ gene and unique restriction sites (BamHI/HindIII and BglII/BsaI, respectively) to clone one binder upstream, the other downstream of a linker via BamHI/HindIII. The numbers indicate the different linker lengths, where each unit is a ($Gly_4$Ser, SEQ ID 51) unit. E.g., the pQiBi-22-vector encodes 4 ($Gly_4$Ser) units (SEQ ID 54 between the binders.

Bispecific constructs were expressed in *E. coli* strains XL1blue or *E. coli* BL21 using the lac-operon induction system by isopropyl-β-D-thiogalactopyranoside (IPTG). Bacteria were lysed by the French press method or by sonification. Filtered bacterial lysates were loaded on NiNTA-agarose bench top columns, washed with TBS_W (50 mM Tris, 400 mM NaCl, 20 mM imidazole, pH 7.5) and in addition washed with 70 CV PBS containing 0.1% Triton X-114 for endotoxin removal. Proteins were eluted in PBS containing 250 mM imidazole. Proteins were further purified by size exclusion chromatography using PBS buffer. Limulus amebocyte lysate (LAL)-assays were performed to assess endotoxin content. Protein concentrations were determined by absorbance spectroscopy at 280 nm and or by a BCA-assay.

Further bispecific agents are described in Examples 5 and 6.

Analysis of Bispecific Binding Reagents

Bispecific binding reagents passed quality control measurements for molecular weight, monomeric status and binding to ECD HER2. Bispecific binding agents comprising trastuzumab-competing binders (in the example, DARPin H14) also compete with trastuzumab in the bispecific setup, as expected. Bispecific binders that do not contain a trastuzumab-competing unit did not show competition in the bispecific setup, also as expected. Competitive binding ELISA, using full length HER2 ECD as target, was performed with all bispecific binding agents also versus pertuzumab. None of the bispecific binding agents competes with pertuzumab for binding to full length ECD HER2 in ELISA. Binding to the surface of viable HER2 overexpressing cancer cells was shown by flow cytometry.

Figure 8:
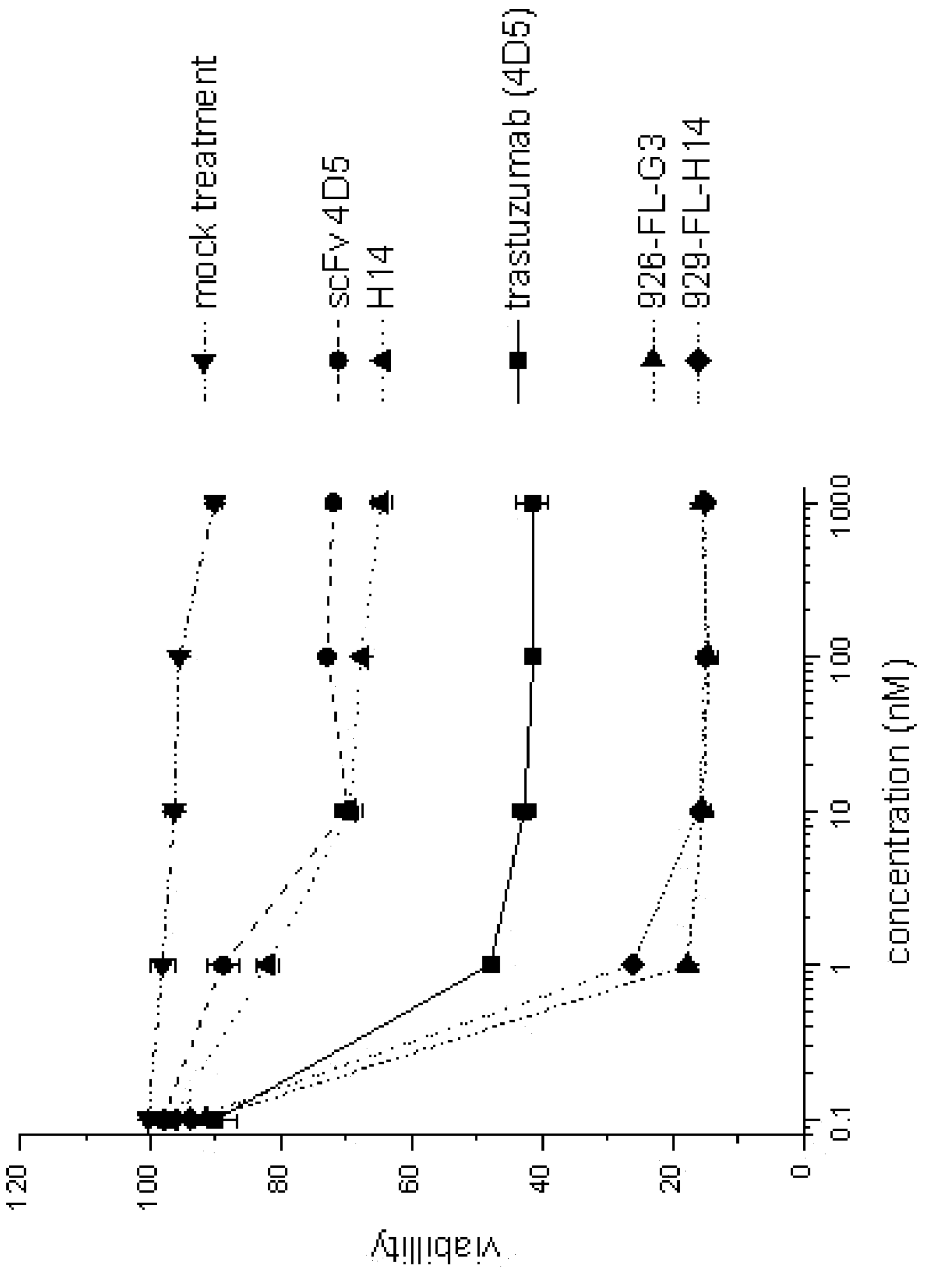
FIG. 8 shows the anti-tumor activity of bispecific binding reagents quantified by cell proliferation assays, shown is the effect of different concentrations of anti-tumor agents on the cell viability.

For determination of the anti-tumor activity of the bispecific agents (FIG. 8), BT474 cells were seeded into 96 well plates 16 h before treatment at a density of $10 \times 10^4$ per $cm^2$ in RPMI1640 containing 10% FCS. Titrations from 100 pM to 1 μM of each agent (final concentrations) were added and cells were treated for 4 days in a cell culture incubator. XTT viability assays were used according to the manufacturer's protocol to assess the remaining viability of the cancer cells. The targeting agents can be grouped according to their anti-tumor activity. The single binding agents scFv 4D5 and DARPin H14 reduced the cell growth by a similar extent, by 20-30%. Trastuzumab reduced the cell growth by an extent of approx. 50%. The flexible bispecific agents 926-FL-G3 and 929-FL-H14 reduced the cell growth by a similar extent of 80-90%.

Figure 9:
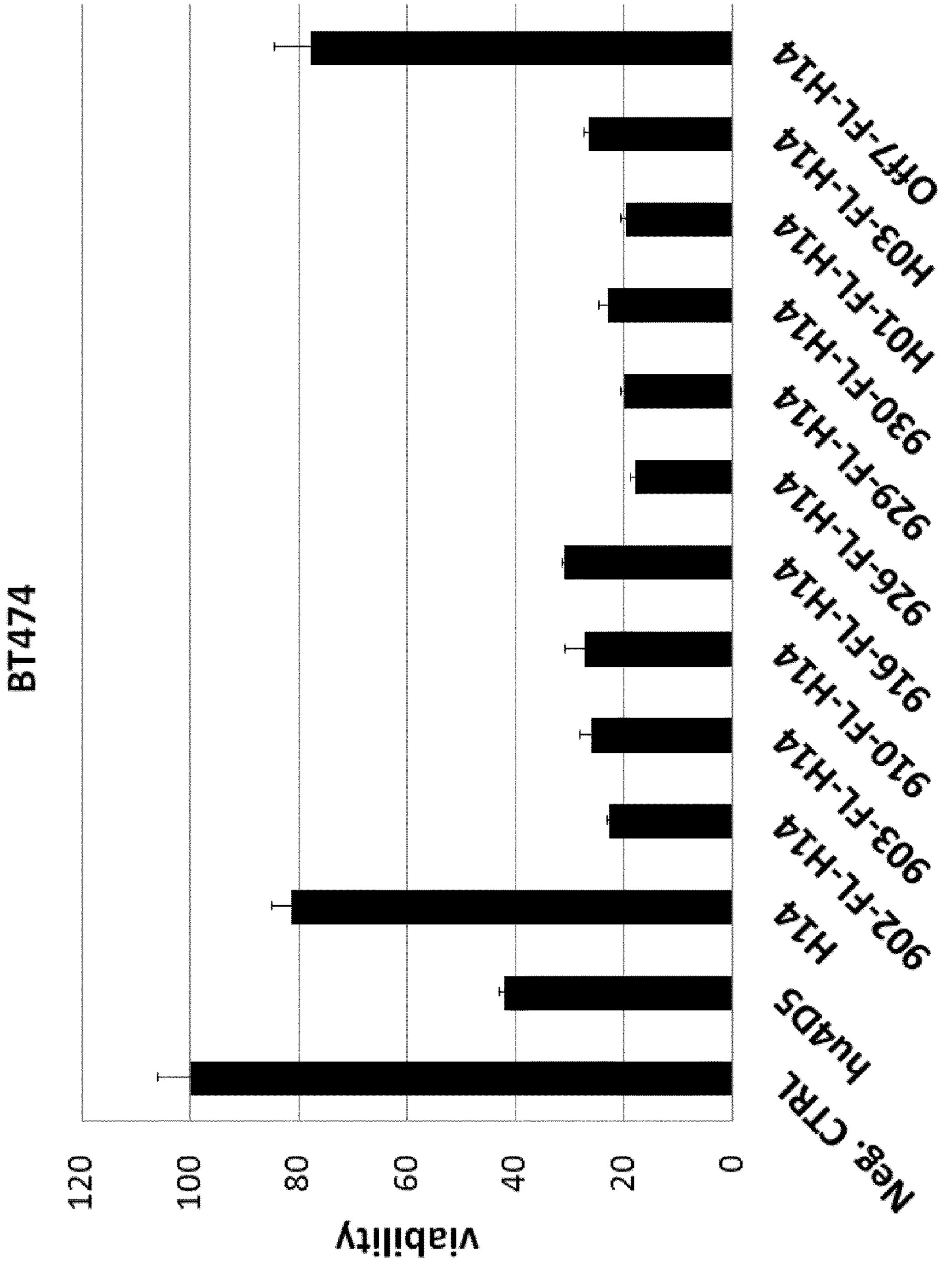
FIG. 9 shows the anti-tumor activity of all constructs that share a similar epitope on domain I of ECD HER2 in a cell proliferation assay, the Y-axis showing the viability of BT474 cells after treatment with any of the agents identified in the legend.

All bispecific constructs that share a similar epitope with e.g. monovalent DARPin 929 on domain 1 of HER2 ECD show strong anti-tumor activity in cell proliferation assays (FIG. 9). BT474 cells were seeded into 96 well plates 16 h before treatment at a density of $10^4$ per $cm^2$ in RPMI1640 containing 10% FCS. Anti-HER2 binding agents were added to a concentration of 100 nM (final concentration), and cells were treated for 4 days. XTT cell proliferation assays were developed according to the manufacturer's protocol. All bispecfic agents containing 9XX at the N-terminus, which showed competitive binding with 926 and 929 in ELISA to ECD HER2, reduced the viability of the cancer cells by 70-80%, i.e. to a higher extent than trastuzumab.

Figure 10:
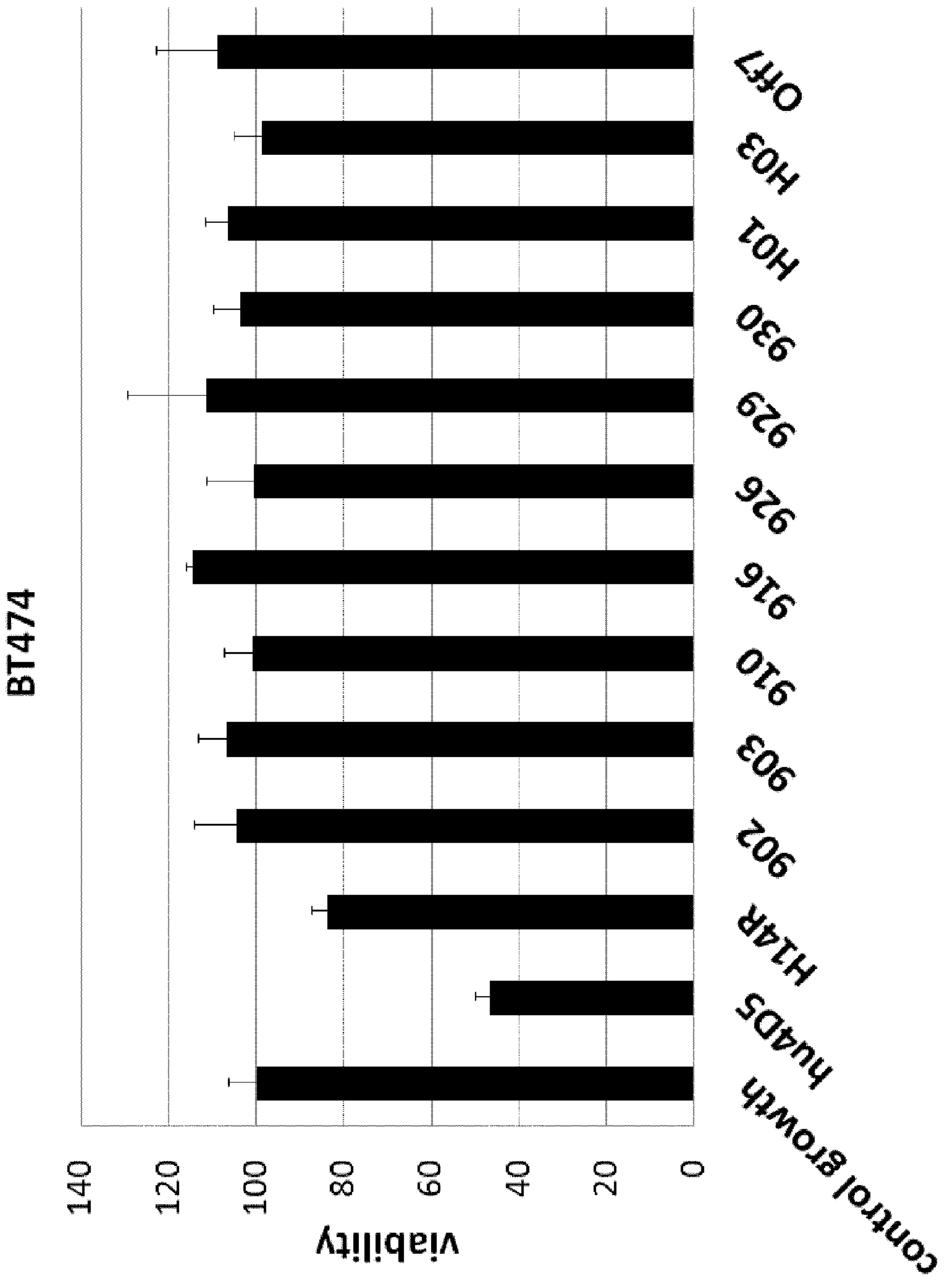
FIG. 10 shows the anti-tumor activity of single binding agents. The Y-axis shows the viability of BT474 cells after treatment with any of the agents identified in the legend.

For determination of the anti-tumor activity of single binding agents, BT474 cells were seeded into 96 well plates 16 h before treatment at a density of $10^4$ per $cm^2$ in RPMI1640 containing 10% FCS. Anti-HER2 binding agents were added to a concentration of 100 nM, and cells were treated for 4 days. XTT cell proliferation assays were developed according to the manufacturer's protocol. H14, the HER2 domain 4 binding agents which competes for binding with trastuzumab (hu4D5), reduces tumor growth by 20%. The 9XX domain 1 binding agents do not show any anti-tumor activity as single binding agents (FIG. 10).

Figure 11:
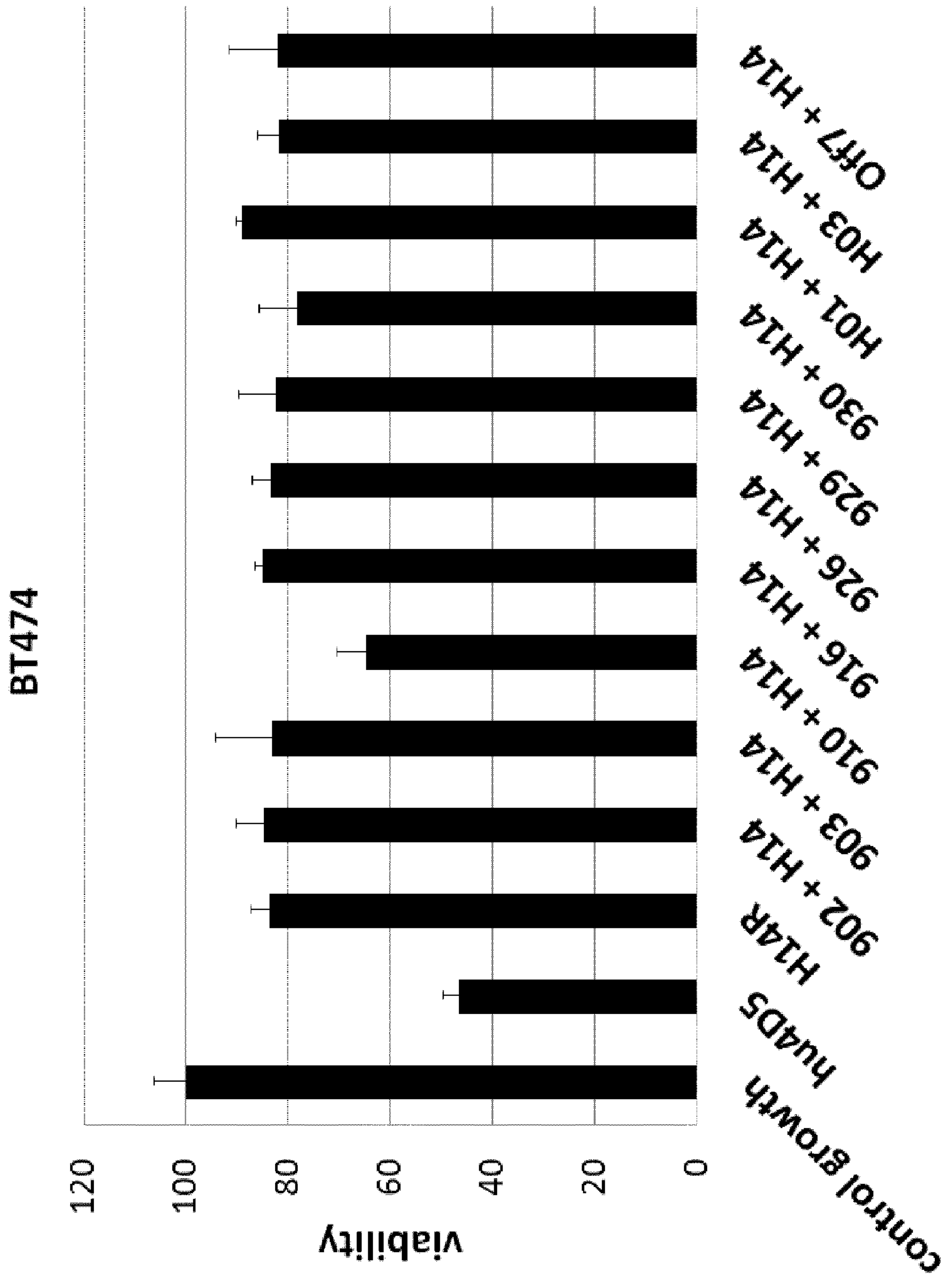
FIG. 11 shows the effect of combination treatment of the single anti-HER2 binding agents on the cell viability (Y-axis) of BT474 cells after treatment with any of the agents identified in the legend.
Figure 12A:
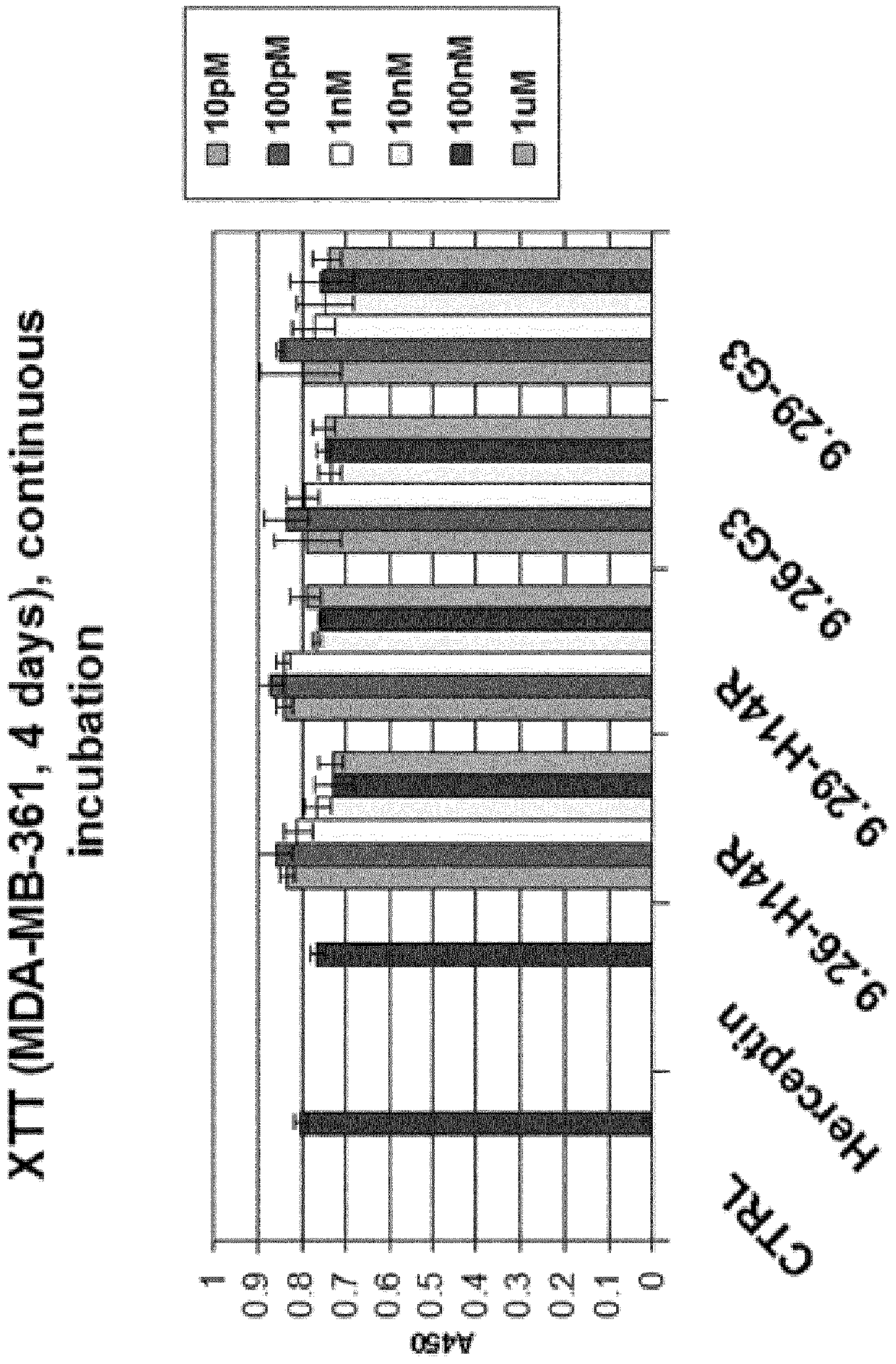
Figure 12B:
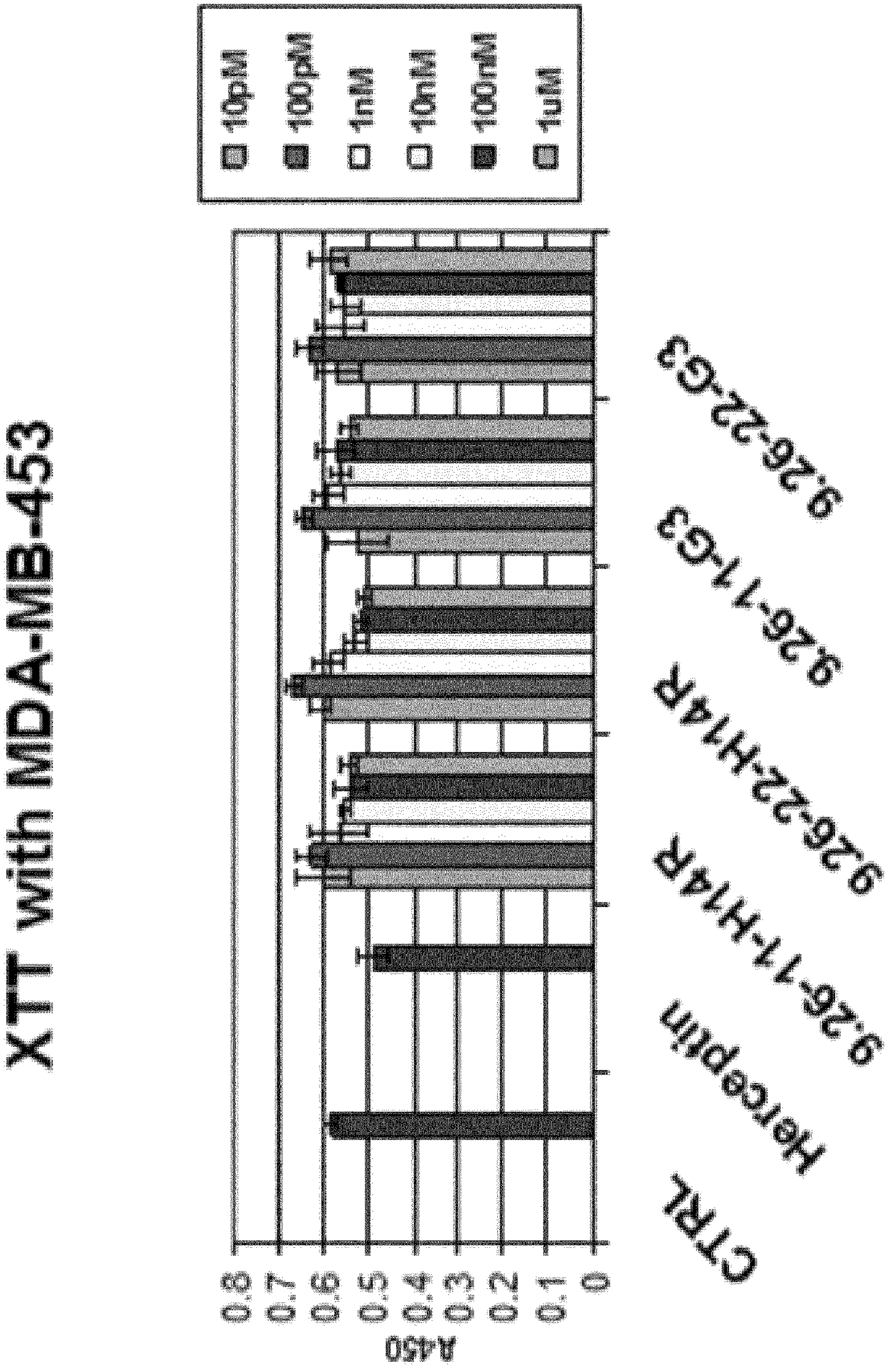
Figure 12C:
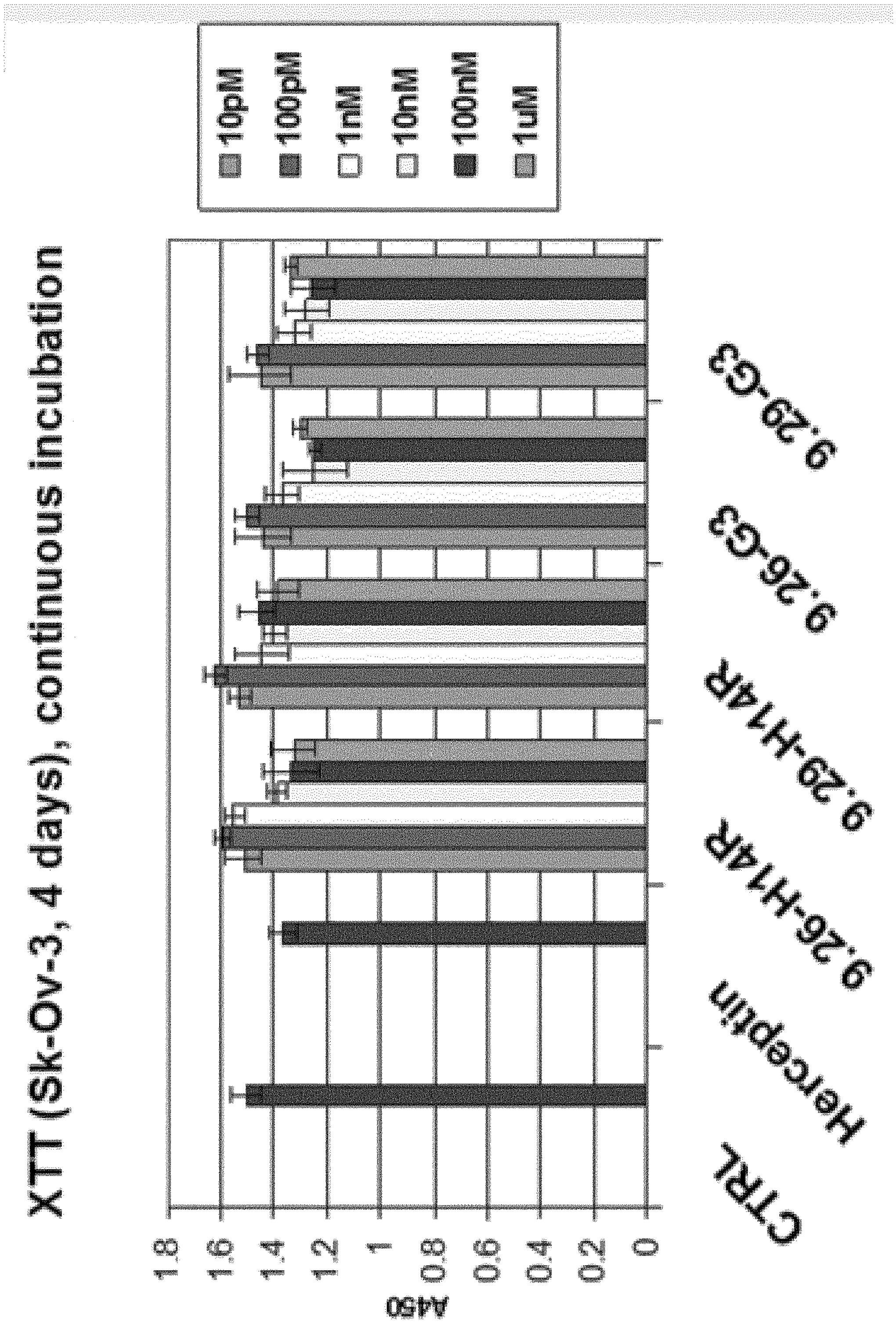
Figure 12D:
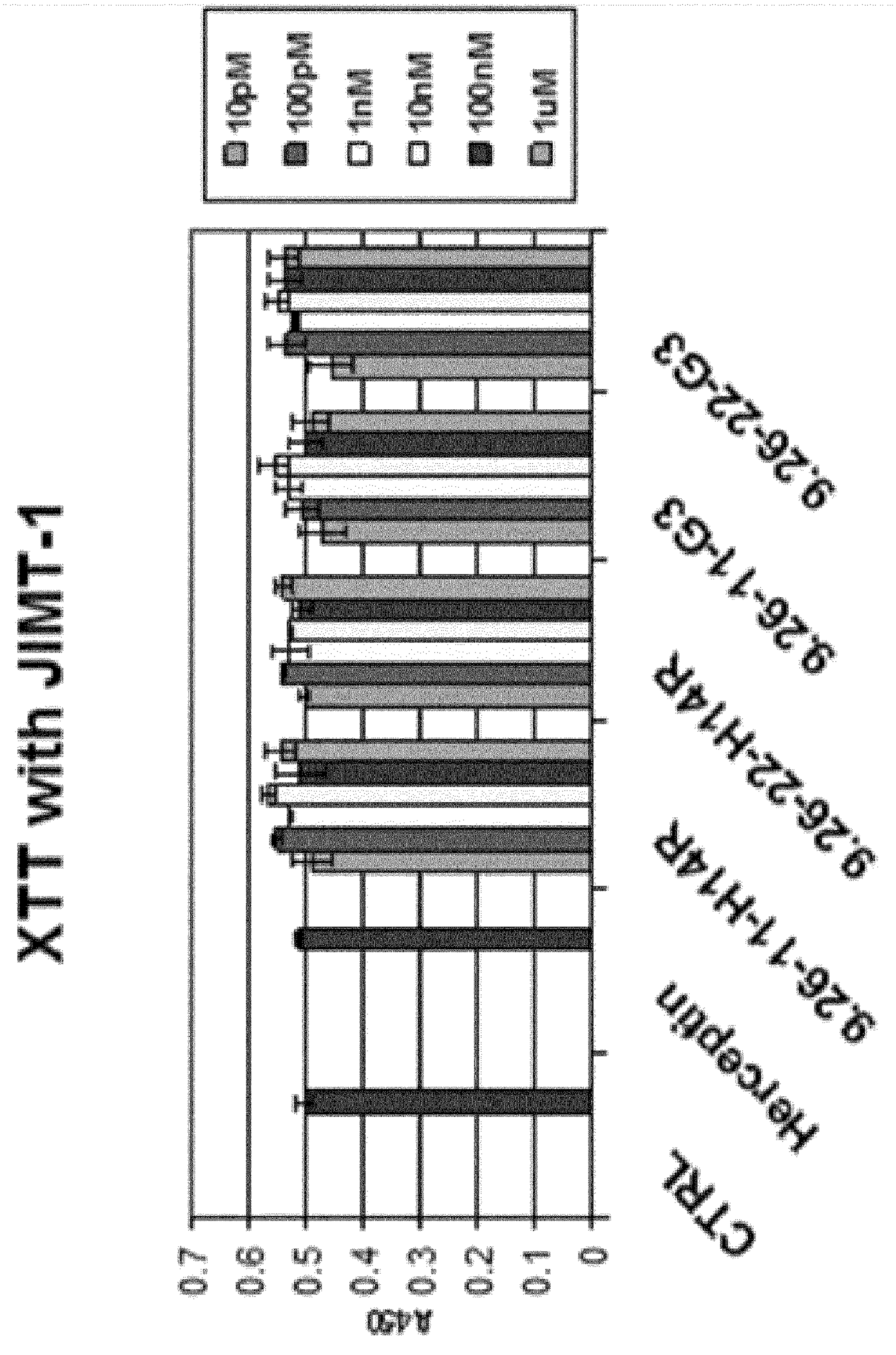
Figure 12E:
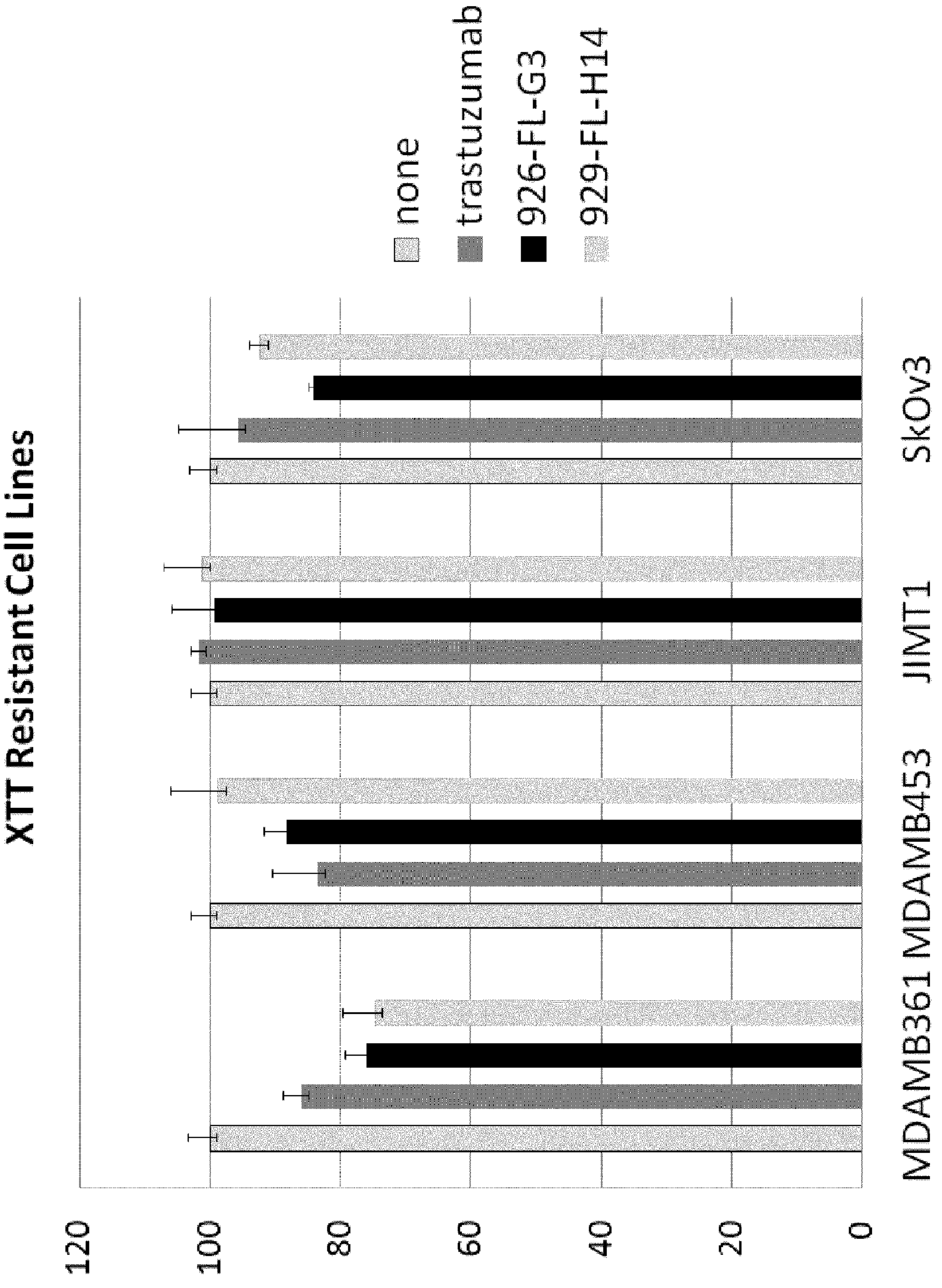

The combination treatment of the single anti-HER2 binding agents is shown in FIG. 11. BT474 cells were seeded into 96 well plates 16 h before treatment at a density of $10^4$ per $cm^2$ in RPMI1640 containing 10% FCS. Anti-HER2 binding agents were added to a concentration of 100 nM, and cells were treated for 4 days. XTT cell proliferation assays were developed according to the manufacturer's protocol. The 9XX domain 4 binding agents do not show an additive effect to anti-tumor activity of H14. Thus, the strong anti-tumor activity requires that the binding agents are connected into a bispecific molecule.

Cell proliferation assays with trastuzumab-resistant cell lines are shown in FIG. 12. Cancer cells were seeded into 96 well plates 16 h before treatment. A serial dilution of anti-HER2 binding agents was added and cells were treated for 4 days. XTT cell proliferation assays were developed according to the manufacturer's protocol. The anti-tumor activity of bispecific targeting agents is similarly modest to trastuzumab in trastuzumab-resistant cell lines.

Example 3: Differentiation from Prior Art Constructs: Comparison of Apoptosis Induced by 7C2 in Combination with 4D5 Versus Bispecific Targeting Agents As was demonstrated in the patent (U.S. Pat. No. 7,371,376 B1; US20110033460 (A1) ANTI-ErbB2 ANTIBODIES), the antibody 7C2 is competent as a single agent to induce apoptosis in the following cell lines BT474, SkBr3, SkOv3 or Calu-3. The epitopes on domain 1 of the ECD HER2 bound by 7C2 and 7F3 are different from the epitopes bound by the 9XX collection (see below), and are also different from those of scFv fragment A21 (see example 5 below) The bispecific targeting agents disclosed here induce apoptosis in BT474 and SkBr3 cells, but not in SkOv3 cells. The absence of anti-tumor activity in SkOv3 cells can be explained by the activating mutation H1047R of the PI3-Kinase. The induction of apoptosis by the bispecific targeting agents is thus correlated with a non-mutated, wild-type downstream signaling pathway of HER2 and HER3.

The absence of anti-tumor activity is another difference to the antibodies 7C2 and 7F3, which show anti-tumor activity as single agents. In US20110033460A1, an additive effect of 7C2 and 4D5 (trastuzumab) to anti-tumor activity is shown. In contrast, the anti-tumor activities of bispecific targeting agents disclosed here are significantly reduced in combination with trastuzumab (FIG. 13).

Even more importantly, the monospecific, bivalent constructs made in analogy to the targeting agents disclosed here, are not active when mixed (FIG. 14; see detailed description of this experiment below). This is in contradistinction to the mixture of the antibody 7C2 with 4D5 and 7F3 with 4D5. This underlines that the mechanism of action of said antibody mixtures is completely different to the bispecific targeting reagents disclosed herein. For the bispecific targeting reagents disclosed herein, the covalent linking of a domain I binding unit to a domain IV binding unit is essential for the mode of action.

In the case of H14 fusions this reduced activity can be explained by simple competition for binding to the same epitope, while in the case of G3 fusions, trastuzumab and G3 do not compete for binding to domain 4. Hence, trastuzumab blocks the formation of inactive HER2 homodimers that are induced by the bispecific molecules according to the invention. Therefore, the modes of action of 7C2 in combination with 4D5, in comparison to the bispecific targeting agents according to our invention, are different. Furthermore, the concept for induction of apoptosis in HER2 overexpressing cancer cells is completely different. Here it is shown that through the strong inhibition of the internal cell signalling in these HER2-dependent cancer cells, apoptosis is induced by the bispecific binding molecules. In contrast, 7C2, a homobivalent IgG, is shown to induce apoptosis but not inhibition of cell growth. This mode of action uncouples signalling from apoptosis and is therefore more similar to e.g. death receptor signaling (FAS or TNF receptor). The inventors believe, without wishing to be bound by theory, that the bispecific reagents according to the present invention work mainly by preventing formation of active dimers and act thus at the level of signaling. Downregulation of receptors is not likely to form an intrinsic part of the mechanism of the bispecific molecules disclosed here. In contrast, it may be part of the mechanism of action of the combination of 7C2 in combination with 4D5.

The antibodies trastuzumab (TT, 4D5) and pertuzumab (PER, 2C4) disrupt the inactive HER2 homodimers formed by bispecific targeting agents (FIG. 13). BT474 cells were seeded into 96 well plates more than 16 h before treatment at a density of $10^4$ per $cm^2$ in RPMI1640 containing 10% FCS. The bispecific targeting agents 926-G3 and 929-H14 were added at a concentration of 100 nM. Subsequently, titration from 10 pM to 1 μM of an anti-HER2 antibody, either trastuzumab (TT, 4D5) or pertuzumab (PER, 2C4), was added. BT474 cells were treated for 4 days in a cell culture incubator at 37° C. and 5% $CO_2$. XTT cell viability assays were performed according to manufacturer's protocol. The absorbance at 450 nm correlates with the number of viable cells. By increasing concentrations of trastuzumab or pertuzumab in the presence of the bispecific agents 926-G3 and 929-H14, the antitumor activity of the bispecific targeting agents is significantly reduced. This indicates that the anti-tumor effect of the bispecific molecules according to this invention is greater than that of trastuzumab or pertuzumab.

The anti-tumor activity of bispecific targeting agents is not caused by random cross-linking of receptors (FIG. 14; A—control; C—926-22-926/H14R-22-H14R; D—926AvantE-22-926AventE/H14R-22-H14R; E—926AvantE-22-926AventE/H14AvantE-22-H14AventE; F—926-22-926/G3-22-G3; first column=10 pM, second column=100 pM, third column=1 nM, forth column=10 nM, fifth column=100 nM and sixth column=1 μM of C, D, E and F, respectively). BT474 cells were seeded into 96 well plates more than 16 h before treatment at a density of $10^4$ per $cm^2$ in RPMI1640 containing 10% FCS. Combinations of homo-bivalent targeting agents were titrated from 10 pM to 1 μM. The combination of both homo-bivalent targeting agents did not show any signification reduction in the viability of the cancer cells.

Bispecific targeting agents do not compete for binding with pertuzumab in ELISA (FIG. 15, A-pertuzumab, 2ndAb (no competitor), B-2nd Ab, C-pertuzumab, 2nd Ab (no ErbB2), D-2nd Ab (no ErbB2)). Wells of the MaxiSorp plate were coated with 100 μl PBS containing 66 nM streptavidin for 12 hours at 4° C. Liquids were removed completely after each step. The plastic surface was blocked by PBS_TB (PBS containing 0.1% Tween20, 0.2% BSA) for 1 hour at room temperature with continuous shaking. Afterwards, 20 nM of truncated ErbB2-avidin conjugate was added in 100 μl PBS_TB and incubated for 1 hour. The plate was washed four times with PBS_TB. Then, bivalent DARPins were added to 1 μM in PBS_TB, and binding took place for 3 hours on a shaker. Next, 1 nM of pertuzumab was added and incubated for 30 min. The plate was washed four times in PBS_TB. The secondary anti-human antibody coupled to alkaline phosphatase was incubated in 100 μl PBS_TB for 1 hour. The plate was washed four times with PBS_TB. Finally, 100 μl of freshly prepared and filtered pNPP buffer (3 mM pNPP, 50 mM $NaHCO_3$, 50 mM $MgCl_2$) was added and the color reaction was developed for 5 min at room temperature. Absorbance was detected on an ELISA plate reader at the wavelength of 405 nm.

Analysis of competitive binding to domain 4 of HER2 was measured by flow cytometry (FIG. 16). $10^5$ BT474 cells were incubated with either 1 μM of G3 or H14 for 30 min at room in 100 μl PBS_BA (PBS, 0.2% $NaN_3$, 1% BSA). Subsequently, Alexa$4_{88}$-trastuzumab, which had been labeled with $Alexa_{488}$-succinimidyl ester, was added to a concentration of 100 nM and incubated for 30 min at room temperature. Afterwards, cells were washed twice using PBS_BA. Flow cytometry measurements were performed on a Cyflow space system. $10^4$ events were recorded in a FSC/SSC gate to measure cells with proper size. Mean fluorescence intensities were calculated by FlowJo software and data were normalized to the MFI of $Alexa_{488}$-trastuzumab binding. G3 does not compete with the binding of trastuzumab, while H14 and trastuzumab bind to a very similar epitope and therefore show 100% competition for binding.

Bivalent binding of the bispecific targeting agent to HER2 at the surface of cancer cells is a prerequisite for strong anti-tumor activity. To confirm the binding of bispecific agents, the association rate constant $k_{on}$ and dissociation rate constant $k_{off}$ on intact cells can be measured by flow cytometry (FIG. 17) (Tamaskovic et al. (2012) Methods Enzymol. 503, 101-134).

The following tables show the determined binding affinities of single and bispecific binding agents and certain DARPins.

| | average $k_{on}$ ($M^{-1}s^{-1}$) | average $k_{obs}$ ($s^{-1}$) | average $k_{off}$ ($s^{-1}$) | average $K_d$ (M) |
|---|---|---|---|---|
| 929 | 68977 | 0.0035 | $2.21 \times 10^{-3}$ | $33.47 \times 10^{-9}$ |
| H14 | 196244 | 0.0037 | $1.79 \times 10^{-4}$ | $0.97 \times 10^{-9}$ |
| 929-FL-H14 | 77959 | 0.0015 | $3.99 \times 10^{-5}$ | $0.52 \times 10^{-9}$ |

| DARPin | $K_D$ (nM) | $k_{on}$ ($10^5$ $M^{-1}s^{-1}$) | $k_{off}$ ($10^{-3}$ $s^{-1}$) |
|---|---|---|---|
| 916 (domain 1 binder) | 6.9 | 1.2 | 0.9 |
| 926 (domain 1 binder) | 1.4 | 0.7 | 0.1 |
| 929 (domain 1 binder) | 3.8 | 2.0 | 0.8 |
| H14 (domain 4 binder) | 0.2 | 4.1 | 0.1 |

Preparation of Cancer Cells for Flow Cytometry Measurements

Cells were detached by collagenase and EDTA for 5 min at 37° C. The solution was quenched by addition of medium and centrifuged at 300 g for 3 min. Cells were washed twice in warm PBS. Cell densities were determined with a CASY cell analyzer and adjusted to $10^6$ cells per sample. Internalization was blocked by incubation in PBS containing 0.2% $NaN_3$ and 1% BSA for 30 min at 37° C.

Flow Cytometry Measurements

Samples were resuspended in 1 ml cold PBS and measured on flow cytometer. 10,000 cells per sample were recorded. Results were gated for FSC vs SSC of the cells. Green fluorescence was detected with the FL1 detector. Data were processed by the FlowJo 7.2.5 software.

Measuring Association of Binding Agents on the Surface of Cancer Cells

For on-rate determinations, BT474 cells are incubated at a concentration of $1\times10^6$ cells/ml with 2.5, 7.5, and 22.5 nM DARPin-Alexa Fluor-488 conjugates in PBSBA at room temperature for defined time intervals, ranging from 1 to 60 min. For each time point, a 1 ml aliquot of cells is withdrawn and subjected to FACS. Since the applied concentrations of the labeled ligand conjugates are very low, and since the time resolution of the measurement is to be maintained to ensure the accuracy of the on-rate determination, the samples are processed without further washing. For each time point, at least $10^4$ intact cells (gated as a uniform population on a FSC/SSC scatter plot) are counted, and the MFI (mean fluorescence intensity) is recorded.

Measuring Dissociation of Binding Agents on the Surface of Cancer Cells $10^6$ cells per time point were incubated with 1 μM Alexa488 labeled binding agents in 100 μl PBS (0.2% $NaN_3$, 1% BSA) for 1 hour at 4° C. on the shaker. Corresponding to 100 μl cell suspension, samples were washed twice in 1 ml PBS (0.2% $NaN_3$, 1% BSA) and centrifuged at 600 g for 30 sec at room temperature. Cells were resuspended in 1 ml PBS (0.2% $NaN_3$, 1% BSA) containing 100 nM of equivalent unlabeled binding agent. The dissociation reaction was incubated for the indicated times (15, 30, 60, 120, 180 and 240 min) at room temperature while continuously stirring in the dark. Dissociation was stopped by placing the cell pellets on ice. Each sample was washed once with 1 ml cold PBS.

Example 4: Additional Data Regarding Construction and the Effects of Mono- and Bivalent Constructs on Cell Proliferation and Cell Death DARPins that had been selected by phage display or ribosome display to target the full-length ectodomain of HER2 without showing any cross-specificity against other EGFR-family members were characterized concerning which of the four HER2-subdomains forms the epitope. Since DARPins typically recognize conformational epitopes, subdomains were expressed alone and in combination in insect cells using a baculovirus system. To minimize glycosylation for subsequent crystallization, the Asn residues were replaced in predicted N-linked glycosylation sites by Asp. ELISAs on these proteins showed that the epitopes recognized by DARPins 9_26 and 9_29 are located on HER2-I, while DARPin G3 bound to HER2-IV. Competition for binding to HER2-overexpressing cells measured by flow cytometry revealed that DARPins 9_26 and 9_29 compete for the same epitope. DARPin G3, which binds to HER2 subdomain IV, did not compete with trastuzumab but competed with a different HER2-specific DARPin, H.14, which in turn competed with trastuzumab.

Various bivalent and bispecific constructs were generated by genetically fusing two DARPins by $(G_4S)_n$ linkers of different lengths. To target two non-overlapping epitopes with a single molecule, DARPins 9_29 or 9_26 were connected to DARPin G3 by a 20 amino acid linker, with either an ECD-I binder at the N-terminal end and the ECD-IV binder at the C-terminus or in opposite orientation. The four different bispecific binders (e.g., 9_26-$(G_4S)_4$-G3, abbreviated "6_20_G" for the two DARPins and the linker length of 20 amino acids) were tested regarding their binding to HER2-overexpressing cells. G3 with a KD of 90 pM has the highest affinity of the three HER2-binders used in this study, compared to a KD of 1 nM for 9_26 and 1 nM for 9_29. Kinetic experiments on cells in the presence of a competing DARPin (to prevent rebinding) revealed that the off-rates of the bispecific binders were 10 times lower than the off-rates of monovalent G3 (FIG. 18A). The slower off-rate and higher KD of the bispecific constructs, compared to their monovalent building blocks, can be attributed to an avidity effect and indicates bispecific binding to HER2 on the cell.

The influence of the different DARPin constructs on cell proliferation and cell survival were tested in XTT assays, using BT474 cells as an example of a HER2-addicted cell line. MCF7-cells, which express HER2 at much lower levels than BT474 cells, were used as a control. Calibration experiments showed that a signal decrease by 60%, compared to untreated cells, corresponded to lack of cell proliferation over the 4 days of cell growth before the XTT assay—a larger decrease indicated cell death. The XTT assay were performed as described in example 1.

None of the characterized monovalent DARPins affected the number of viable cells measured by the XTT assay (FIG. 18B). Mixtures of two different DARPins proved to be equally inert, as did control constructs in which one of the two DARPins in the bispecific molecule had been replaced by a non-HER2-binding DARPin (DARPin off7, targeting maltose-binding-protein) (FIG. 18C). A monospecific bivalent DARPin G_20_G even stimulated cell proliferation (FIG. 18C).

Bispecific constructs composed of a subdomain I binder at the N- and the subdomain IV binder at the C-terminus (6_20_G or 9_20_G) showed a concentration-dependent decrease of cell viability by up to 75%, while treatment with trastuzumab decreased viability by ~50% (FIG. 18D). The constructs with reverse orientation (G_20_9) either lacked any effect on cell-growth (G_20_6) or even slightly promoted cell growth. Similar to trastuzumab, bispecific constructs did not affect the cell-proliferation of MCF7-cells (FIG. 18E), suggesting the restriction of the observed effects to HER2-addicted cells. Comparison of constructs with 5, 10, 20, 30 and 40 amino acid linkers showed that for 9_x_G constructs, specific activity and potency decreases with increasing linker length. The most potent constructs proved to be 6_5_G and 9_5_G, with $(G_4S)$-linkers of only five amino acids. They decreased the cell viability in XTT-assays after four days of growth by more than 80% as compared to untreated cells, and showed a half-maximal effect already at a concentration of less than 100 pM compared to ca. 1 nM for 6_20_G and 9_20_G. Conversely, increasing the linker length to forty amino acids, as in 6_40_G and 9_40_G, decreased the biological activity (growth reduction of only 40%) (FIG. 18F). The constructs with inverse orientation, G_x_6 and G_x_9, inactive or even stimulatory at a linker length of 20 amino acids, gained anti-proliferative activity at short linker lengths, but the best construct was found to be only as active as trastuzumab (FIG. 18G).

Neither the single DARPins nor the bispecific constructs affected internalization or degradation of HER2, as determined by flow cytometry.

Example 5: Bispecific HER2 Bindings Agent with One or Two Antibody Fragments To demonstrate the cytotoxic activity of bispecific HER2 binding agents constructed from antibody fragments, bispecific constructs of the type scFv1-linker-scFv2; DARPin-linker-scFv; and scFv-linker-DARPin constructs were constructed. Here, in each fusion protein, one of the units (scFv1, scFv2, scFv or DARPin) binds to domain 1, the other one binds to domain 4.

For a description of scFv1-linker-scFv2 constructs, cf. p. 37.

To generate a domain 1-binding scFv, the scFv chA21 (A21) was used described in Hu S. et al., (2008) Proteins 70:938-949.). The crystal structure in complex with HER2 had been determined, verifying the binding of this scFv to domain 1. The protein sequence of the heavy and light chain of the scFv A21 was obtained from the PDB file (PDB ID: 2GJJ). A flexible glycine serine linker of 4×GGGGS units (GGGGS GGGGS GGGGS GGGGS, SEQ ID 54) was introduced to connect the heavy and the light chain in either orientation: Two orientations were thus obtained, by either fusing the N-terminal heavy chain to the light chain (A21HL, SEQ ID 65) or the N-terminal light chain to the heavy chain (A21LH, SEQ ID 66 or SEQ ID 93) within one single protein sequence connected by the said glycine-serine linker.

The respective gene sequences were synthesized by Genescript Inc., and they additionally contain a BamHI/HindIII cloning site for directional cloning (see below).

To generate a domain 4-binding scFv, the scFv of the antibody hu4D5 was constructed. The crystal structure of the corresponding Fab fragment (hu4D5, trastuzumab; Herceptin) in complex with HER2 had been determined, verifying the binding of this scFv to domain 4, as described in Cho et al., (2003) Nature 421:756-760. The protein sequence of the heavy and light chain for the construction of the scFv 4D5 was obtained from the PDB file (PDB ID: 1N8Z). A flexible glycine serine linker of 4×GGGGS units (GGGGS GGGGS GGGGS GGGGS, SEQ ID 54) was introduced to connect the heavy and the light chain in either orientation: Two orientations were thus obtained, by either fusing the N-terminal heavy chain to the light chain (4D5HL, SEQ ID 67) or the N-terminal light chain to the heavy chain (4D5LH, SEQ ID 68 or SEQ ID 92) within one single protein sequence connected by the said glycine-serine linker. Also, an additional scFv 4D5LH (SEQ ID 69) with an alternative has been created.

The respective gene sequences were synthesized by Genescript Inc., and they additionally contain a BamHI/HindIII cloning site for directional cloning (see below).

Construction of scFv1-Linker-scFv2; DARPin-Linker-scFv; and scFv-Linker-DARPin Fusion Proteins For the gene construction of bispecific fusions proteins, which contain a HER2 domain 1 and a domain 4 binding moiety, a generic vector (pMxAC) was used. This vector is based on pMx9 (Rauchenberger, R. et al. (2003) J. Biol. Chem. 278, 38194-38205), and contains an OmpA signal sequence for periplasmic expression in *E. coli*. The OmpA signal sequence was exchanged by a DsbA signal sequence taken from the vector pDSt066 (see description in Steiner et al. (2008) J. Mol. Biol., 382:1211-1127). In addition, a new multiple cloning site was introduced into the vector pMx9 containing the DsbA signal sequence, in which restriction sites allowed specific cloning on either side of the flexible gly-ser linker. These cloning cassettes therefore allowed the preparation of fusion proteins with different lengths of linkers originating from the plasmid pQiBi-22- (4×GGGGs flexible linker, SEQ ID 54); pQiBi-11- (2×GGGGs flexible linker, SEQ ID 52) and pQiBi-01- (1×GGGGs flexible linker, SEQ ID 51) (Boersma et al. (2011), J. Biol. Chem. 286, 41273-41285.)

The new vectors were termed pMxAC-22- (4×GGGGs flexible linker, SEQ ID 54); pMxAC-11-(2×GGGGs flexible linker, SEQ ID 52) or pMxAC-01- (1×GGGGs flexible linker SEQ ID 51) respectively.

These pMxAC vectors contain a BamHI/HindIII cloning site for inserting the N-terminal binding construct (upstream of the linker) and a BglII/BsaI site (compatible with BamHI/HindIII cloning sites) cloning site for introducing the C-terminal binding moiety (downstream of the linker). In addition, the construct contains a C-terminal 6×His-tag for purification and detection and a FLAG-tag M1 for detection of periplasmic export (Knappik et al. (1994) Biotechniques 17, 754-761.).

Map of the ORF in the pMxAC-22-Vector

```
                                    (SEQ ID 94)
MKKIWLALAGLVLAFSASADYKDDIGS-

                                    (SEQ ID 95)
N-terminal_scFv/DARPin-KLGGGGSGGGGSGGGGSGGGGSRS-

                                    (SEQ ID 96)
C-terminal scFv/DARPin-KLGSHHHHHH
```

Legend, Explaining the Different Elements:

MKKIWLALAGLVLAFSASA (SEQ ID 112): DsbA-signal sequence, which gets cleaved off

DYKDDI (SEQ ID 113): FLAG-Tag M1

GS: BamHI cloning site

N-terminal_scFv/DARPin N-terminal protein of interest, either scFv or DARPin

KL: HindIII cloning site

GGGGSGGGGSGGGGSGGGGS: Flexible linker (-22-/FL4, SEQ ID 54)

RS: BgIII cloning site

C-terminal_scFv/DARPin C-terminal protein of interest, either scFv or DARPin

KL: Bsa1 cloning site

GS: flexible spacer

HHHHHH: 6xHis-Tag (SEQ ID 114)

Alternative Vectors for scFv/DARPin Fusion Proteins

In addition to the periplasmic expression in *E. coli* described above, expression of the scFv/DARPin fusion proteins was performed by secretion from *Spodoptera frugiperda* (Sf9) cells using the Multibac system as described previously (Fitzgerald et al. (2006) Nature Methods 3:1021-32.). In brief, the coding sequences of the fusion proteins were subcloned via ligation-independent cloning (LIC) into the donor vector pFLmLIC introducing an N-terminal melittin signal sequence (SEQ ID 99). The donor vectors were used to introduce the fusion protein coding sequences into the bacmid EmBacY. Baculoviruses for infection of Sf9 cells were generated through transfection of the bacmid DNA into Sf9 cells. For expression, Sf9 cells were grown to a density of $4\times10^6$ cells/mL and co-infected with the respective virus at a MOI of 1. 72 h post infection, cells were harvested by centrifugation (30 min, 5000 g, 4° C.) and the cleared medium was subjected to immobilized metal ion affinity chromatography (IMAC) purification with Ni-NTA Superflow (Qiagen) purification resin.

The following table shows the scFv/DARPin fusion proteins which were expressed in Sf9 cells or in *E. coli*. Note that the N-terminal melittin signal sequence (MVVYISYIY, SEQ ID 99) is cleaved upon protein secretion and not present in the secreted and purified proteins.

| scFv/DARPin fusion protein | SEQ ID |
|---|---|
| A21HL_L4_G3 | 70 |
| A21LH_L4_G3 | 71 |
| A21HL_L4_H14 | 72 |
| H14_L4_A21LH | 73 |
| H14_L4_A21HL | 74 |
| G3_L4_A21LH | 75 |
| G3_L4_A21HL | 76 |
| A21HL_L1_G3 | 77 |
| 9.29_L1_4D5LH | 78 |
| 926E-L4-4D5HL | 88 |
| 926E-L4-4D5LH | 89 |
| 929-L4-4D5HL | 90 |
| 929-L4-4D5LH | 91 |

Expression scFv1-Linker-scFv2 Constructs in the Periplasm of *E. coli*

ScFv1-linker-scFv2 constructs were co-expressed with periplasmic chaperones in the periplasm of *E. coli*. For this purpose, the pMxAC scFv1-linker-scFv2 plasmids were co-transformed with the plasmid pCH-A1 (Schaefer and Plückthun (2010) Improving expression of scFv fragments by co-expression of periplasmic chaperones, in: Antibody Engineering, Kontermann, and Dübel, eds., Vol. 2, 2nd edit., pp. 345-361, Springer Verlag, Berlin Heidelberg, Germany) into *E. coli* SF130 (Meerman and Georgiou (1994); Biotechnology (N Y) 12:1107-1110). After transformation, single clones of *E. coli* were adapted to Terrific Broth growth medium (TB; Cold Spring Harbor Protocols) overnight and transferred to 1 L TB expression culture to an initial $OD_{600}$ of 0.1. ScFv fusion construct expression was induced by isopropyl-β-D-thiogalactopyranoside (IPTG), and expression was performed overnight at 25° C.

Purification of scFv1-Linker-scFv2 Constructs from *E. coli* Expression Culture

Expression cultures were pelleted by centrifugation, washed with Tris buffer (50 mM Tris base, 150 mM NaCl, pH 7.5) and resuspended in cold Tris buffer containing protease inhibitors (Roche—complete protease inhibitor cocktail) and DNaseI (Roche) and kept at 4° C. during the entire process. *E. coli* were lysed with a French press and centrifuged for 30 min at 20,000 g. The supernatant was adjusted to a final concentration of 20 mM imidazole, 400 mM NaCl, 10% glycerol, pH 7.5, and applied to Ni-NTA bench-top columns. Columns were washed with 30 CV of Tris buffer containing 20 mM imidazole, 400 mM NaCl and 10% glycerol, high-salt washed with 30 CV Tris buffer containing 1 M NaCl, low-salt washed with 30 CV Tris buffer containing 10 mM NaCl. The bound fraction was eluted with Tris buffer containing 300 mM imidazole. Ni-NTA-eluted protein was loaded on a protein-A bench-top column, and endotoxin-washed with 80 CV phosphate buffer saline (Dulbecco's PBS) containing 0.1% Triton X-114, washed with 30 CV PBS and eluted with 4 CV 100 mM glycine buffer pH 3.6 into 4 CV of 1.5 M Tris buffer pH 8, 150 mM NaCl. Proteins were concentrated and dialyzed against HEPES buffer (25 mM HEPES, 150 mM NaCl, pH 7.5).

The following table shows the scFv1-linker-scFv2 constructs that have been expressed in *E. coli*:

| scFv1-linker-scFv2 | SEQ ID |
|---|---|
| 4D5HL-L1-A21HL | 80 |
| 4D5HL-L4-A21LH | 81 |
| 4D5LH-L1-A21HL | 82 |
| 4D5LH-L4-A21HL | 83 |
| 4D5LH-L4-A21LH | 84 |
| A21HL-L4-4D5LH | 85 |
| A21LH-L1-4D5LH | 86 |
| A21LH-L4-4D5LH | 87 |
| 4D5LH-L1-A21LH | 100 |

Diabody A21H_4D5LH_A21L

The gene of the diabody construct (analogous to constructs described by Völkel et al. (2001), Protein Engineering 14, 815-823), consisting domains from scFv fragments of 4D5 and A21, was synthesized at Genescript Inc. and carries additionally BamHI/HindIII cloning sites for directional cloning into pcDNA3 (see below).

The diabody construct A21H_4D5LH_A21L (SEQ ID 79) consists of a first moiety consisting of the A21 heavy chain connected to the 4D5 light chain by a glycine/serine linker characterized by SEQ ID 51, and second moiety consisting of the 4D5 heavy chain connected to the A21 light chain by a glycine/serine linker characterized by SEQ ID 51, wherein the first moiety is connected to the second moiety by a glycine/serine linker characterized by SEQ ID 54 (FIG. 19A).

Expression of Diabody Constructs in CHO Cells

For the expression of the diabody construct A21H_4D5LH_A21L a vector plasmid based on pcDNA3.1 (+) Hygro has been constructed. A poly linker (multiple cloning site) was synthesized that carries a N-terminal signal sequence of the mouse Ig Kappa light chain followed by BamHI/HindIII cloning site and a C-terminal 6×His-tag (FIG. 19B). The vector was termed pcDNA3.1 Seq mIgκ.

```
METDTLLLWVLLLWVPGSTGS (SEQ ID 97)-

diabody A21H_4D5LH_A21L- KLHHHHHH

(SEQ ID 98)

METDTLLLWVLLLWVPGST: mouse Ig Kappa light chain
signal sequence (SEQ ID 115)

GS: BamHI site

KL: HindIII site

HHHHHH: 6xHis Tag (SEQ ID 114)
```

Chinese hamster ovarian cells (CHO) FreeStyle from Invitrogen adapted for serum free suspension growth have been used for transient expression of the diabody construct. The diabody plasmid (pcDNA3.1 Seq mIgκ A21H_4D5LH_A21L) was transfected into CHO cells by TransIT-PRO (Mirus) transfection reagent using the manufacturer's protocol. Expression was performed in bioreactors (Sigma) for 1 week in CHO-FreeStyle medium (Invitrogen).

Purification of Diabody Constructs from Supernatant of CHO Cells

After expression, the supernatant was collected by centrifugation, filtered and concentrated to a small volume. The supernatant was dialyzed against Tris buffer (50 mM Tris base, 150 mM NaCl, pH 7.5) and afterwards adjusted to 20 mM imidazole, 400 mM NaCl, 10% glycerol and loaded on a Ni-NTA bench top column. The column was washed with 30 CV of Tris buffer containing 20 mM imidazole, 400 mM NaCl, 10% glycerol, pH 7.5, 30 CV of Tris buffer and eluted in 2 CV Tris buffer pH 7.5 containing 300 mM imidazole. Samples were concentrated and dialyzed against HEPES buffer (25 mM HEPES, 150 mM NaCl, pH 7.5).

Anti-Tumor Activity of the Bispecific HER2 Binding Agents in Comparison to Trastuzumab To test the cytotoxic activity of the bispecific HER2 binding agents described above, XTT-viability assay were performed as described in example 1. FIG. 20 show the results of the tests in BT474 cells, and FIG. 21 the results of the tests in HCC1419 cells, wherein CTRL means control, no addition; A21 the scFv fragment A21, 4D5 the scFv fragment 4D5; A21+4D5, a mixture of scFv fragment A21 and scFv fragment 4D5; and TZB trastuzumab. Note that the diabody (SEQ ID 79) was used at only 10 nM in the experiments shown in FIG. 21, while all other agents were used at 100 nM.

These results show that the principle of connecting a binder of domain 1 of HER to a binder of domain of HER2 by a linker leads in order to obtain a compound with strong cytotoxic and/or anti-proliferative effects does work, no matter whether the binder is or comprises an antibody fragment or a DARPin.

Additionally TUNEL assays as described in example 1 were performed with the above mentioned bispecific HER2 binding agents. As shown in FIG. 22, the percentage of TUNEL-positive cells is significantly higher for the tested bispecific agents than for trastuzumab. These results were verified by Western blot analysis, wherein the apoptosis was detected by the cleavage of Poly ADP Ribose Polymerase (FIG. 23). The Western blot analysis was performed as described in example 1.

In summary, it could be shown that the bispecific HER2 binding agents comprising one or two antibody fragments are able to trigger apoptosis of the targeted cell much better than trastuzumab.

Example 6: Bispecific HER2 Bindings Agent Comprising Two DARPins Connected by a Shared Helix The principle of the bispecific constructs, namely that an HER2_I and an HER2_IV binder are fused in order to bring the respective domains of two different HER2-molecules into proximity, does in principle work with flexible linkers of different lengths. As an alternative to this, DARPin constructs have been created in which the two DARPins have been fused rigidly in different angles and tested in cell viability assay as described in example 1.

All 9 tested constructs 9.29_SH_G3 #2 (SEQ ID 102), 9.29_SH_G3 #6 (SEQ ID 103), 9.29_SH_G3 #9 (SEQ ID 104), 9.29_SH_G3 #10 (SEQ ID 105), 9.29_G3 #11 (SEQ ID 106), 9.29_SH_G3 #12 (SEQ ID 107), 9.29_SH_G3 #13 (SEQ ID 108), 9.29_SH_G3 #14 (SEQ ID 109), and 9.29_SH_G3 #15 (SEQ ID 110) have strong anti-proliferative activity in cell viability assays with HER2-dependent cancer cells (BT474), however to varying degrees.

Without wishing to be bound by theory, it is supposed that the target (HER2) can orient in various orientations over the membrane insertion point. Still, in all different orientations, the two transmembrane helices of the bound receptors will be kept at a distance sufficient to inactivate the kinase activity. This blueprint allows some flexibility in the epitopes bound on HER2_I and HER2_IV and in the orientation with which these epitopes are bound.

The invention claimed is:

1. A bispecific HER2 targeting agent comprising an amino acid sequence as set forth in SEQ ID 03, SEQ ID 04, SEQ ID 05, SEQ ID 06, SEQ ID 07, SEQ ID 08, SEQ ID 09, SEQ ID 58, or SEQ ID 59.

2. A method of treating a HER2-expressing cancer, comprising administering a bispecific HER2 targeting agent of claim 1 to a patient with a HER2-expressing cancer, thereby treating the HER2 cancer.

3. The bispecific HER2 targeting agent of claim 1, which comprises the amino acid sequence as set forth in SEQ ID 03.

4. A method of treating a HER2-expressing cancer, comprising administering a bispecific HER2 targeting agent of claim 3 to a patient with a HER2-expressing cancer, thereby treating the HER2 cancer.

5. The bispecific HER2 targeting agent of claim 1, which comprises the amino acid sequence as set forth in SEQ ID 04.

6. A method of treating a HER2-expressing cancer, comprising administering a bispecific HER2 targeting agent of claim 5 to a patient with a HER2-expressing cancer, thereby treating the HER2 cancer.

7. The bispecific HER2 targeting agent of claim 1, which comprises the amino acid sequence as set forth in SEQ ID 05.

8. A method of treating a HER2-expressing cancer, comprising administering a bispecific HER2 targeting agent of claim 7 to a patient with a HER2-expressing cancer, thereby treating the HER2 cancer.

9. The bispecific HER2 targeting agent of claim 1, which comprises the amino acid sequence as set forth in SEQ ID 06.

10. A method of treating a HER2-expressing cancer, comprising administering a bispecific HER2 targeting agent of claim 9 to a patient with a HER2-expressing cancer, thereby treating the HER2 cancer.

11. The bispecific HER2 targeting agent of claim 1, which comprises the amino acid sequence as set forth in SEQ ID 07.

12. A method of treating a HER2-expressing cancer, comprising administering a bispecific HER2 targeting agent of claim 11 to a patient with a HER2-expressing cancer, thereby treating the HER2 cancer.

13. The bispecific HER2 targeting agent of claim 1, which comprises the amino acid sequence as set forth in SEQ ID 08.

14. A method of treating a HER2-expressing cancer, comprising administering a bispecific HER2 targeting agent of claim 13 to a patient with a HER2-expressing cancer, thereby treating the HER2 cancer.

15. The bispecific HER2 targeting agent of claim 1, which comprises the amino acid sequence as set forth in SEQ ID 09.

16. A method of treating a HER2-expressing cancer, comprising administering a bispecific HER2 targeting agent of claim 15 to a patient with a HER2-expressing cancer, thereby treating the HER2 cancer.

17. The bispecific HER2 targeting agent of claim 1, which comprises the amino acid sequence as set forth in SEQ ID 58.

18. A method of treating a HER2-expressing cancer, comprising administering a bispecific HER2 targeting agent of claim 17 to a patient with a HER2-expressing cancer, thereby treating the HER2 cancer.

19. The bispecific HER2 targeting agent of claim 1, which comprises the amino acid sequence as set forth in SEQ ID 59.

20. A method of treating a HER2-expressing cancer, comprising administering a bispecific HER2 targeting agent of claim 19 to a patient with a HER2-expressing cancer, thereby treating the HER2 cancer.

21. A bispecific HER2 targeting agent comprising an amino acid sequence as set forth in SEQ ID 102, SEQ ID 103, SEQ ID 104, SEQ ID 105, SEQ ID 106, SEQ ID 107, SEQ ID 108, SEQ ID 109, or SEQ ID 110.

22. A method of treating a HER2-expressing cancer, comprising administering a bispecific HER2 targeting agent of claim 21 to a patient with a HER2-expressing cancer, thereby treating the HER2 cancer.

* * * * *